(12) United States Patent
Goldblum et al.

(10) Patent No.: US 8,524,689 B2
(45) Date of Patent: Sep. 3, 2013

(54) ANTIBACTERIAL AMINOGLYCOSIDE ANALOGS

(75) Inventors: Adam Aaron Goldblum, Berkeley, CA (US); Paola Dozzo, San Francisco, CA (US); James Bradley Aggen, Burlingame, CA (US); Martin Sheringham Linsell, San Mateo, CA (US)

(73) Assignee: Achaogen, Inc., South San Francisco, CA (US)

( * ) Notice: Subject to any disclaimer, the term of this patent is extended or adjusted under 35 U.S.C. 154(b) by 5 days.

(21) Appl. No.: 13/295,247

(22) Filed: Nov. 14, 2011

(65) Prior Publication Data

US 2012/0135948 A1  May 31, 2012

Related U.S. Application Data

(63) Continuation of application No. PCT/US2010/034884, filed on May 14, 2010.

(60) Provisional application No. 61/312,349, filed on Mar. 10, 2010, provisional application No. 61/178,809, filed on May 15, 2009.

(51) Int. Cl.
*C07H 15/20* (2006.01)
*A01N 43/04* (2006.01)
*A61K 31/715* (2006.01)

(52) U.S. Cl.
USPC ............................ 514/61; 536/13.7; 536/13.8

(58) Field of Classification Search
None
See application file for complete search history.

(56) References Cited

U.S. PATENT DOCUMENTS

| | | | |
|---|---|---|---|
| 3,872,079 A | 3/1975 | Naito et al. | |
| 3,940,382 A | 2/1976 | Umezawa et al. | |
| 3,997,524 A | 12/1976 | Nagabhushan | |
| 4,000,261 A | 12/1976 | Daniels | |
| 4,000,262 A | 12/1976 | Daniels | |
| 4,002,742 A | 1/1977 | Wright et al. | |
| 4,029,882 A | 6/1977 | Wright | |
| 4,055,715 A | 10/1977 | Tomioka et al. | |
| 4,085,208 A | 4/1978 | Mallams et al. | |
| 4,091,202 A | 5/1978 | Umezawa et al. | |
| 4,107,424 A | 8/1978 | Umezawa et al. | |
| 4,117,221 A | 9/1978 | Daniels | |
| 4,120,955 A * | 10/1978 | Umezawa et al. | 514/41 |
| 4,136,254 A | 1/1979 | Nagabhushan et al. | |
| 4,166,114 A | 8/1979 | Igarashi | |
| 4,169,141 A | 9/1979 | Topliss et al. | |
| 4,178,437 A * | 12/1979 | Thomas | 536/13.8 |
| 4,190,722 A | 2/1980 | Voss et al. | |
| 4,195,171 A | 3/1980 | Tomioka et al. | |
| 4,199,570 A | 4/1980 | Igarashi et al. | |
| 4,199,572 A | 4/1980 | Schröder et al. | |
| 4,200,628 A | 4/1980 | Igarashi et al. | |
| 4,201,774 A | 5/1980 | Igarashi et al. | |
| 4,212,859 A | 7/1980 | Daniels et al. | |

(Continued)

FOREIGN PATENT DOCUMENTS

| | | |
|---|---|---|
| CA | 1 034 573 | 7/1978 |
| CA | 1 105 452 | 7/1981 |

(Continued)

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Adachi et al., "Synthesis and Evaluation of Aminoglycosides as Inhibitors for Rev binding to Rev Responsive Element," *Letters in Drug Design & Discovery* 3:71-75, 2006.

(Continued)

*Primary Examiner* — Traviss C McIntosh, III
(74) *Attorney, Agent, or Firm* — Cooley LLP

(57) ABSTRACT

Compounds having antibacterial activity are disclosed. The compounds have the following structure (I) or (II):

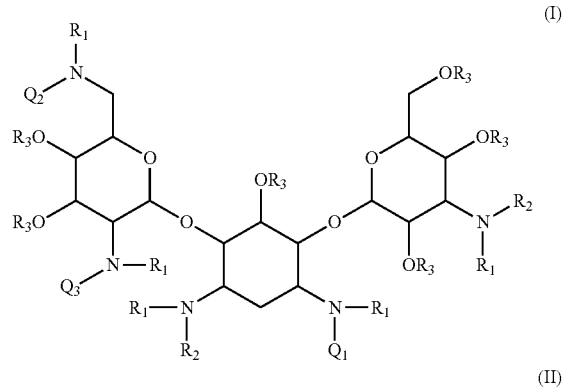

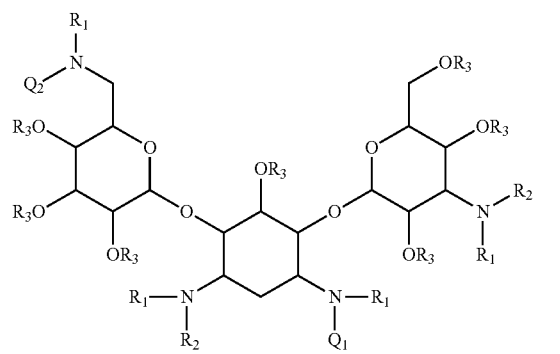

including stereoisomers, pharmaceutically acceptable salts and prodrugs thereof, wherein $Q_1$, $Q_2$, $Q_3$, $R_1$, $R_2$ and $R_3$ are as defined herein. Methods associated with preparation and use of such compounds, as well as pharmaceutical compositions comprising such compounds, are also disclosed.

20 Claims, No Drawings

(56) References Cited

U.S. PATENT DOCUMENTS

| | | |
|---|---|---|
| 4,214,074 A | 7/1980 | Richardson et al. |
| 4,224,315 A | 9/1980 | Stadler et al. |
| 4,230,847 A | 10/1980 | Nagabhushan et al. |
| 4,234,572 A | 11/1980 | Petersen et al. |
| 4,235,888 A | 11/1980 | Stadler |
| 4,248,865 A | 2/1981 | Igarashi et al. |
| 4,273,923 A | 6/1981 | Igarashi et al. |
| 4,282,350 A | 8/1981 | Wright |
| 4,312,859 A | 1/1982 | Petersen et al. |
| 4,335,114 A | 6/1982 | Voss et al. |
| 4,337,335 A | 6/1982 | Nagabhushan et al. |
| 4,347,354 A | 8/1982 | Cron et al. |
| 4,380,625 A | 4/1983 | Stadler et al. |
| 4,393,051 A | 7/1983 | Stadler et al. |
| 4,438,260 A | 3/1984 | Petersen et al. |
| 4,617,293 A | 10/1986 | Wahlig et al. |
| 5,534,408 A | 7/1996 | Green et al. |
| 5,696,244 A | 12/1997 | Kim et al. |
| 5,900,406 A | 5/1999 | von Ahsen et al. |
| 5,935,776 A | 8/1999 | Green et al. |
| 6,541,456 B1 | 4/2003 | Swayze et al. |
| 6,759,523 B2 | 7/2004 | Swayze et al. |
| 6,967,242 B2 | 11/2005 | Swayze et al. |
| 7,893,039 B2 | 2/2011 | Swayze et al. |
| 7,943,749 B2 | 5/2011 | Hanessian et al. |
| 8,114,856 B2 | 2/2012 | Swayze et al. |
| 2004/0072798 A1 | 4/2004 | Naggi et al. |
| 2007/0161581 A1 | 7/2007 | Minowa et al. |
| 2008/0045468 A1 | 2/2008 | Hanessian et al. |
| 2008/0214845 A1 | 9/2008 | Migawa et al. |
| 2008/0293649 A1 | 11/2008 | Swayze et al. |
| 2008/0300199 A1 | 12/2008 | Linsell et al. |
| 2010/0099661 A1 | 4/2010 | Aggen et al. |
| 2011/0245476 A1 | 10/2011 | Migawa et al. |
| 2011/0275586 A1 | 11/2011 | Aggen et al. |
| 2011/0288041 A1 | 11/2011 | Aggen et al. |
| 2012/0122809 A1 | 5/2012 | Goldblum et al. |
| 2012/0135945 A1 | 5/2012 | Dozzo et al. |
| 2012/0135946 A1 | 5/2012 | Goldblum et al. |
| 2012/0165282 A1 | 6/2012 | Dozzo et al. |
| 2012/0172332 A1 | 7/2012 | Aggen et al. |
| 2012/0184501 A1 | 7/2012 | Dozzo et al. |
| 2012/0196791 A1 | 8/2012 | Armstrong et al. |
| 2012/0208781 A1 | 8/2012 | Bruss et al. |
| 2012/0214759 A1 | 8/2012 | Bruss et al. |
| 2012/0214760 A1 | 8/2012 | Bruss et al. |
| 2012/0258925 A1 | 10/2012 | Aggen et al. |
| 2012/0283207 A1 | 11/2012 | Maianti et al. |
| 2012/0283208 A1 | 11/2012 | Aggen et al. |
| 2012/0283209 A1 | 11/2012 | Dozzo et al. |

FOREIGN PATENT DOCUMENTS

| | | |
|---|---|---|
| CA | 1 105 454 | 7/1981 |
| CN | 1 397 562 A | 2/2003 |
| DE | 24 37 160 A1 | 2/1975 |
| DE | 24 40 956 A1 | 3/1975 |
| DE | 24 58 921 A1 | 6/1975 |
| DE | 25 55 405 A1 | 6/1976 |
| DE | 27 48 257 A1 | 5/1978 |
| DE | 28 18 822 A1 | 11/1978 |
| DE | 29 36 120 A1 | 3/1980 |
| DE | 31 00 739 A1 | 8/1982 |
| DE | 31 08 068 A1 | 9/1982 |
| DE | 34 05 326 A13 | 8/1985 |
| EP | 0 001 643 A2 | 5/1979 |
| EP | 0 002 450 A1 | 6/1979 |
| EP | 0 009 670 A1 | 4/1980 |
| EP | 0 056 575 A1 | 7/1982 |
| GB | 1 470 329 | 4/1977 |
| GB | 1 473 733 | 5/1977 |
| GB | 1 494 129 | 12/1977 |
| GB | 1 535 215 | 12/1978 |
| GB | 2 030 141 A | 4/1980 |
| GB | 1 583 366 | 1/1981 |
| GB | 1 598 294 | 9/1981 |
| JP | 54-46770 A | 4/1979 |
| JP | 54-61151 A | 5/1979 |
| JP | 55-000329 A | 5/1980 |
| JP | 55-17397 A | 6/1980 |
| JP | 56-15298 A | 2/1981 |
| JP | 1-254694 A | 10/1989 |
| SU | 623524 | 12/1975 |
| WO | WO 2005/070945 A1 | 8/2005 |
| WO | WO 2006/052930 A1 | 5/2006 |
| WO | WO 2007/028012 A2 | 3/2007 |
| WO | WO 2007/064954 A2 | 6/2007 |
| WO | WO 2008/124821 A1 | 10/2008 |
| WO | WO 2009/067692 A1 | 5/2009 |
| WO | WO 2010/030690 A1 | 3/2010 |
| WO | WO 2010/030704 A2 | 3/2010 |
| WO | WO 2010/042850 A1 | 4/2010 |
| WO | WO 2010/042851 A1 | 4/2010 |
| WO | WO 2010/132757 A2 | 11/2010 |
| WO | WO 2010/132759 A1 | 11/2010 |
| WO | WO 2010/132760 A1 | 11/2010 |
| WO | WO 2010/132765 A2 | 11/2010 |
| WO | WO 2010/132768 A1 | 11/2010 |
| WO | WO 2010/132770 A1 | 11/2010 |
| WO | WO 2010/132777 A2 | 11/2010 |
| WO | WO 2010/132839 A2 | 11/2010 |
| WO | WO 2010/147836 A1 | 12/2010 |
| WO | WO 2011/044498 A1 | 4/2011 |
| WO | WO 2011/044501 A1 | 4/2011 |
| WO | WO 2011/044502 A1 | 4/2011 |
| WO | WO 2011/044503 A1 | 4/2011 |
| WO | WO 2011/044538 A1 | 4/2011 |
| WO | WO 2012/067978 A1 | 5/2012 |

OTHER PUBLICATIONS

Afonso et al., "Synthesis of 1-N-Peptidyl Derivatives of Sisomicin," *Current Chemotherapy and Infectious Disease, Proceedings of the 11th International Congress of Chemotherapy and the 19th Interscience Conference on Antimicrobial Agents and Chemotherapy* 1:405-406, 1980 (7 pages total).

Aggen et al., "Synthesis, Structure, and In Vitro Activity of the Neoglycoside ACHN-490," Poster No. FI-840 presented at 49th Interscience Conference on Antimicrobial Agents and Chemotherapy (ICAAC), San Francisco, California, Sep. 12-15, 2009 (+ Abstract 085(F1) p. 185) (3 pages).

Ahsen et al., "Non-competitive Inhibition of Group I Intron RNA Self-splicing by Aminoglycoside Antibiotics," *J. Mot. Biol.* 226(4):935-941, 1992.

Alhambra et al., "In vitro susceptibility of recent antibiotic-resistant urinary pathogens to ertapenem and 12 other antibiotics," *Journal of Antimicrobial Chemotherapy* 53:1090-1094, 2004.

Alper et al., "Probing the Specificity of Aminoglycoside—Ribosomal RNA Interactions with Designed Synthetic Analogs," *J. Am. Chem. Soc.* 120(9):1965-1978, 1998.

Andes et al., "Pharmacodynamics of the New Fluoroquinolone Gatifloxacin in Murine Thigh and Lung Infection Models," *Antimicrobial Agents and Chemotherapy* 46(6):1665-1670, Jun. 2002.

Armstrong et al., "Surveying Aminoglycoside-Resistance Mechanisms: A Tool For The Development of Neoglycosides," Presented at 19th European Congress of Clinical Microbiology and Infectious Diseases (ECCMID), Helsinki, Finland, May 16-19, 2009 (+ Abstract P643, p. S149).

Bailey et al., "Comparison of single dose netilmicin with a five-day course of co-trimoxazole for uncomplicated urinary tract infections," *New Zealand Medical Journal* 97:262-264, 1984.

Bassaris et al., "Once-Daily High-Dose Netilmicin—A New Short-Term Treatment Regimen for Patients with Moderate to Severe Gram-Negative Infections," *Clin. Drug Invest.* 15(3):205-216, 1998.

Beauchamp et al., "Pharmacologic Basis for the Treatment of Pyelonephritis," *Current infectious Disease Reports* 1:371-378, 1999.

Benenson et al., "Carbapenem-resistant *Klebsiella pneumoniae* endocarditis in a young adult Successful treatment with gentamicin and colistin," *International Journal of Infectious Diseases* 13:e295-e298, 2009.

Bergeron, "Treatment of Pyelonephritis in Adults," *Medical Clinics of North America* 79(3):619-649, May 1995.

Biedenbach et al., "Ten Year Trend in Aminoglycoside Resistance from a Worldwide Collection of Gram-Negative Pathogens (1998-2007)," Poster No. 636 presented at 19th European Congress of Clinical Microbiology and Infectious Diseases (ECCMID), Helsinki, Finland, May 16-19, 2009 (+ Abstract P636, p. S147).

Biedenbach et al., "Activity of ACHN-490 Against Complicated Urinary Tract Infection (cUTI) Pathogens From the United States and Europe," ICAAC 2009, Poster # F1-843, 1 page.

Blaser et al., "Multicenter Quality Control Study of Amikacin Assay for Monitoring Once-Daily Dosing Regimens," *Therapeutic Drug Monitoring* 17:133-136, 1995.

Bonfiglio et al., "In vitro Activity of Piperacillin/Tazobactam against 615 *Pseudomonas aeruginosa* Strains Isolated in Intensive Care Units," *Chemotherapy* 44:305-312, 1998.

Boxler et al., "Semisynthetic Aminoglycoside Antibacterials. Part 9. Synthesis of Novel 1- and 3-Substituted and 1- and 3-*epi*-Substituted Derivatives of Sisomicin and Gentamicin from the 1- and 3-Oxo-derivatives," *J.C.S. Perkin I*:2168-2185, 1981.

Bratu et al., "Carbapenemase-producing *Klebsiella pneumoniae* in Brooklyn, NY: molecular epidemiology and in vitro activity of polymyxin B and other agents," *Journal of Antimicrobial Chemotherapy* 56:128-132, 2005.

Brummett et al., "Ototoxicity of tobramycin, gentamicin, amikacin and sisomicin in the guinea pig," *Journal of Antimicrobial Chemotherapy* 4(Suppl. A):73-83, 1978.

Buijk et al., "Experience with a once-daily dosing program of aminoglycosides in critically ill patients," *Intensive Care Med.* 28:936-942, 2002.

Carapetis et al., "Randomized, controlled trial comparing once daily and three times daily gentamicin in children with urinary tract infections," *Pediatr. Infect. Dis. J.* 20(3):240-246, 2001.

Cass et al., "Pharmacokinetics of the Novel Neoglycoside ACHN-490 in Mouse, Rat, and Dog," ICAAC 2009, Poster # F1-846, 1 page.

Centrón et al., "Characterization of the 6'-N-Aminoglycoside Acetyltransferase Gene *aac*(6')-*Iq* from the Integron of a Natural Multiresistance Plasmid," *Antimicrobial Agents and Chemotherapy* 42(6):1506-1508, Jun. 1998.

Chambers, H. F., Goodman & Gilman's The Pharmcological Basis of Therapeutics, Eleventh Edition, Brunton et al. (ed.), McGraw-Hill, Inc., New York, 2006, Chapter 45, "Aminoglycosides," pp. 1155-1171 (+ 3 cover pages).

Chanal et al., "Comparative Study of a Novel Plasmid-Mediated β-Lactamase, CAZ-2, and the CTX-1 and CAZ-1 Enzymes Conferring Resistance to Broad-Spectrum Cephalosporins," *Antimicrobial Agents and Chemotherapy* 32(11):1660-1665, Nov. 1988.

Chow et al., "A Structural Basis for RNA-Ligand Interactions," *Chem. Rev.* 97(5):1489-1513, Jul./Aug. 1997.

Christenson et al., "In vitro activity of meropenem, imipenem, cefepime and ceftazidime against *Pseudomonas aeruginosa* isolates from cystic fibrosis patients," *Journal of Antimicrobial Chemotherapy* 45:899-901, 2000.

Conil et al., "Increased amikacin dosage requirements in burn patients receiving a once-daily regimen," *International Journal of Antimicrobial Agents* 28:226-230, 2006.

Credito et al., "Activity of Daptomycin Alone and in Combination with Rifampin and Gentamicin against *Staphylococcus aureus* Assessed by Time-Kill Methodology," *Antimicrobial Agents and Chemotherapy* 51(4):1504-1507, Apr. 2007.

Cunha, B.A., "Aminoglycosides in Urology," *Urology* 36(1):1-14, Jul. 1990.

Daniels et al., "Semisynthetic Aminoglycoside Antibacterials. Part 11. Solution Conformations of Semisynthetic and Naturally Occurring Aminoglycoside Antibiotics," *J. Chem. Soc., Perkin Trans.* 1:2209-2227, 1981.

Daniels et al., "Some Recent Advances in the Chemistry of Antibiotics of the Gentamicin Series," *The Japanese Journal of Antibiotics* 32(S-195) (11 pages), Dec. 1979.

Davies et al., "Semisynthetic Aminoglycoside Antibacterials. 6. Synthesis of Sisomicin, Antibiotic G-52, and Novel 6'-Substituted Analogues of Sisomicin from Aminoglycoside 66-40C," *Journal of Medicinal Chemistry* 21(2):189-193, 1978.

De Broe et al., "Influence of dosage schedule on renal cortical accumulation of amikacin and tobramycin in man," *Journal of Antimicrobial Chemotherapy* 27(Suppl. C):41-47, 1991.

de Vries et al., "Prospective Randomized Study of Once-Daily versus Thrice-Daily Netilmicin Regimens in Patients with Intraabdominal Infections," *Eur. J. Clin. Microbiol. Infect. Dis.* 9(3):161-168, Mar. 1990.

Doi et al., "16S Ribosomal RNA Methylation: Emerging Resistance Mechanism against Aminoglycosides," Clinical Infectious Diseases 45:88-94, Jul. 1, 2007.

Dozzo et al., "New aminoglycoside antibiotics," *Expert Opin. Ther. Patents* 20(10):1-21, 2010.

Drusano et al., "Back to the Future: Using Aminoglycosides Again and How to Dose Them Optimally," *Clinical Infectious Diseases* 45:753-760, Sep. 15, 2007.

Echols et al., "Demographic, Clinical, and Treatment Parameters Influencing the Outcome of Acute Cystitis," *Clinical Infectious Diseases* 29(1):113-119, Jul. 1999.

Endimiani et al., "Presence of Plasmid-Mediated Quinolone Resistance in *Klebsiella pneumoniae* Isolates Possessing $bla_{KPC}$ in the United States," *Antimicrobial Agents and Chemotherapy* 52(7):2680-2682, Jul. 2008.

Endimiani et al., "Characterization of $bla_{KPC}$-containing *Klebsiella pneumoniae* isolates detected in different institutions in the Eastern USA," *Journal of Antimicrobial Chemotherapy* 63:427-437, 2009.

Endiamiani et al., "ACHN-490, a Neoglycoside with Potent In Vitro Activity against Multidrug-Resistant *Klebsiella pneumoniae* Isolates," *Antimicrobial Agents and Chemotherapy* 53(10):4504-4507, Oct. 2009.

Etra et al., "Sisomicin in Urinary Tract Infection. Tolerance and Efficacy Study," *Urology* 7(2):160-164, Feb. 1976.

Food & Drug Administration, Center for Drug Evaluation and Research (CDER), U.S. Department of Health and Human Services, *Guidance for Industry, Complicated Urinary Tract Infections and Pyelonephritis—Developing Antimicrobial Drugs for Treatment*, Draft Guidance, Jul. 1998, 11 pages.

Forge et al., "Aminoglycoside Antibiotics," *Audiol. Neurootol.* 5:3-22, 2000.

Freeman et al., "Once-daily dosing of aminoglycosides: review and recommendations for clinical practice," *Journal of Antimicrobial Chemotherapy* 39:677-686, 1997.

French, G. L., "Bactericidal agents in the treatment of MRSA infections—the potential role of daptomycin," *Journal of Antimicrobial Chemotherapy* 58:1107-1117, 2006.

Gaynes et al., "Overview of Nosocomial Infections Caused by Gram-Negative Bacilli," *Clinical Infectious Diseases* 41:848-854, Sep. 15, 2005.

Georgescu et al., "Activity of ACHN-490, a Novel Neoglycoside Antibiotic, Against Contemporary Gram-Negative Clinical Isolates from Brooklyn, NY Hospitals," ICAAC 2009, Poster # F1-842, 1 page.

Giuliano et al., "The Effect of Dosing Strategy on Kidney Cortical Accumulation of Aminoglycosides in Rats," *American Journal of Kidney Diseases* 8(5):297-303, Nov. 1986.

Giuliano et al., "In Vivo Uptake Kinetics of Aminoglycosides in the Kidney Cortex of Rats," *The Journal of Pharmacology and Experimental Therapeutics* 236(2):470-475, 1986.

Goldfarb et al., "Detection of Plasmid-Mediated KPC-Producing *Klebsiella pneumoniae* in Ottawa, Canada: Evidence of Intrahospital Transmission," *Journal of Clinical Microbiology* 47(6):1920-1922, Jun. 2009.

Goossens et al., "Prevalence and antimicrobial susceptibility data for extended-spectrum β-lactamase- and AmpC-producing Enterobacteriaceae from the MYSTIC Program in Europe and the United States (1997-2004)," *Diagnostic Microbiology and Infectious Disease* 53:257-264, 2005.

Griebling, T. L., "Urinary Tract Infection in Women," in Litwin et al. (eds.), *Urologic Diseases in America*, DHHS, PHS, NIH, NIDDK, Washington, D.C.: GPO, 2007, NIH Publication 07-5512:587-619.

Grohs et al., "In Vitro Bactericidal Activities of Linezolid in Combination with Vancomycin, Gentamicin, Ciprofloxacin, Fusidic Acid, and Rifampin against *Staphylococcus aureus*," *Antimicrobial Agents and Chemotherapy* 47(1):418-420, Jan. 2003.

Guan et al., "A biochemical basis for the inherited susceptibility to aminoglycoside ototoxicity," *Human Molecular Genetics* 9(12):1787-1793, 2000.

Gülmez et al., "Carbapenem-resistant *Escherichia coil* and *Klebsiella pneumoniae* isolates from Turkey with OXA-48-like carbapenemases and outer membrane protein loss," *International Journal of Antimicrobial Agents 31*:523-526, 2008.

Hanessian et al., "Probing the functional requirements of the L-haba side-chain of amikacin—synthesis, 16S A-site rRNA binding, and antibacterial activity," *Tetrahedron 59*:995-1007, 2003.

Hare et al., "Evaluation of New 1-*N*-Substituted Aminoglycosides Against Strains with Known Resistance Mechanisms," Current Chemotherapy and Infectious Disease, Proceedings of the 11th International Congress of Chemotherapy and the 19th Interscience Conference on Antimicrobial Agents and Chemotherapy 1:403-405, 1980 (7 pages total).

Harrison, L. H., "Treatment of Complicated Urinary Tract Infections With Amikacin," *Urology 10*(2):110-113, Aug. 1977.

Hawkey et al., "The changing epidemiology of resistance," *Journal of Antimicrobial Chemotherapy 64*(Suppl 1):i3-i10, 2009.

Hawser et al., "In vitro susceptibilities of aerobic and facultative anaerobic Gram-negative bacilli from patients with intra-abdominal infections worldwide from 2005-2007: results from the Smart study," *International Journal of Antimicrobial Agents 34*:585-588, 2009.

Hermann, T., "Biomedicine & Diseases: Review. Aminoglycoside antibiotics: old drugs and new therapeutic approaches," *Cell. Mol. Life. Sci. 64*:1841-1852, 2007.

Hiraiwa et al., "Synthesis and antibacterial activity of 5-deoxy-5-episubstituted arbekacin derivatives," *Bioorganic & Medicinal Chemistry Letters 17*:3540-3543, 2007.

Hirakata et al., "Regional variation in the prevalence of extended-spectrum β-lactamase—producing clinical isolates in the Asia-Pacific region (SENTRY 1998-2002)," *Diagnostic Microbiology and Infectious Disease 52*:323-329, 2005.

Hottendorf et al., "Nonparallel Nephrotoxicity Dose-Response Curves of Aminoglycosides," *Antimicrobial Agents and Chemotherapy 19*(6):1024-1028, Jun. 1981.

Hujer et al., "Analysis of Antibiotic Resistance Genes in Multidrug-Resistant *Acinetobacter* sp. Isolates from Military and Civilian Patients Treated at the Walter Reed Army Medical Center," *Antimicrobial Agents and Chemotherapy 50*(12):4114-4123, Dec. 2006.

International Preliminary Report on Patentability, for International Application No. PCT/US2008/084399, mailed May 25, 2010, 6 pages.

International Preliminary Report on Patentability, for International Application No. PCT/US2010/038138, mailed Jan. 5, 2012, 11 pages.

International Preliminary Report on Patentability, for International Application No. PCT/US2010/035006, mailed Nov. 24, 2011, 26 pages.

International Preliminary Report on Patentability, for International Application No. PCT/US2010/034898, mailed Nov. 24. 2011, 13 pages.

International Preliminary Report on Patentability, for International Application No. PCT/US2010/034909, mailed Nov. 24, 2011. 17 pages.

International Preliminary Report on Patentability, for International Application No. PCT/US2010/034896, mailed Nov. 24, 2011, 14 pages.

International Preliminary Report on Patentability, for International Application No. PCT/US2010/034893, mailed Nov. 24, 2011, 14 pages.

International Preliminary Report on Patentability, for International Application No. PCT/US2010/034888, mailed Nov. 24, 2011, 15 pages.

International Preliminary Report on Patentability, for International Application No. PCT/US2010/034886, mailed Nov. 24, 2011, 15 pages.

International Preliminary Report on Patentability, for International Application No. PCT/US2010/034884, mailed Nov. 24, 2011, 12 pages.

International Search Report and Written Opinion, for International Application No. PCT/US2008/084399, mailed Apr. 21, 2009, 8 pages.

International Search Report and Written Opinion, for International Application No. PCT/US2010/034886, mailed Aug. 25, 2010, 19 pages.

International Search Report and Written Opinion, for International Application No. PCT/US2010/034888, mailed Aug. 25, 2010, 21 pages.

International Search Report and Written Opinion, for International Application No. PCT/US2010/034893, mailed May 3, 2011, 20 pages.

International Search Report and Written Opinion for International Application no. PCT/US2010/034896, mailed Sep. 6, 2010, 21 pages.

International Search Report and Written Opinion for International Application no. PCT/US2010/034909, mailed Dec. 2, 2010, 31 pages.

International Search Report and Written Opinion, for International Application No. PCT/US2010/034898, mailed Oct. 8, 2010, 23 pages.

International Search Report and Written Opinion for PCT/US2010/035006, mailed Dec. 8, 2010, 39 pages.

International Search Report and Written Opinion for PCT/US2010/038138, mailed Aug. 20, 2010, 18 pages.

International Search Report and Written Opinion for PCT/US2010/034884, mailed Mar. 1, 2011, 19 pages.

Invitation to Pay Additional Fees and Partial International Search Report for PCT/US2010/034884, mailed Oct. 26, 2010, 7 pages.

Invitation to Pay Additional Fees, and Partial International Search Report, for International Application No. PCT/US2010/034886, mailed Jul. 2, 2010, 4 pages.

Invitation to Pay Additional Fees, and Partial International Search Report, for International Application No. PCT/US2010/034888, mailed Jun. 30, 2010, 5 pages.

Invitation to Pay Additional Fees and, Where Applicable, Protest Fee, for International Application No. PCT/US2010/034893, mailed Mar. 2, 2011, 9 pages.

Invitation to Pay Additional Fees, and Partial International Search Report, for International Application No. PCT/US2010/034896, mailed Jul. 12, 2010, 6 pages.

Invitation to Pay Additional Fees, and Partial International Search Report, for International Application No. PCT/US2010/034898, mailed Aug. 4, 2010, 5 pages.

Invitation to Pay Additional Fees, and Partial International Search Report, for International Application No. PCT/US2010/034909, mailed Aug. 25, 2010, 7 pages.

Invitation to Pay Additional Fees, and Partial International Search Report, for International Application No. PCT/US2010/035006, mailed Aug. 18, 2010, 8 pages.

Jana et al., "Molecular understanding of aminoglycoside action and resistance," *Appl Microbiol Biotechnol 70*:140-150, 2006.

Johnson et al., "Urinary Tract Infections in Women: Diagnosis and Treatment," *Annals of Internal Medicine 111*:906-917, 1989.

Jones et al., "Antimicrobial Activity of ACHN-490, a Neoglycoside, Tested Against a Contemporary Collection of Clinical Isolates Including Problematic Antimicrobial-Resistant Phenotypes," ICAAC 2009, Poster # F1-846a, 1 page.

Jones et al., "Spectrum and activity of three contemporary fluoroquinolones tested against *Pseudomonas aeruginosa* isolates from urinary tract infections in the SENTRY Antimicrobial Surveillance Program (Europe and the Americas; 2000): More alike than different!" *Diagnostic Microbiology and Infectious Disease 41*:161-163, 2001.

Kahlmeter et al., "Aminoglycoside toxicity—a review of clinical studies published between 1975 and 1982," *J. Antimicrob. Chemo. 13*(Suppl. A):9-22, 1984.

Kahlmeter et al., "Cross-resistance and associated resistance in 2478 *Escherichia coli* isolates from the Pan-European ECO•SENS Project surveying the antimicrobial susceptibility of pathogens from uncomplicated urinary tract infections," *J. Antimirob. Chemo. 52*(1):128-131, 2003.

Karlowsky et al., "Trends in Antimicrobial Resistance among Urinary Tract Infection Isolates of *Escherichia coil* from Female Outpatients in the United States," *Antimicrobial Agents and Chemotherapy* 46(8):2540-2545, Aug. 2002.

Karlowsky et al., "Fluoroquinolone-Resistant Urinary Isolates of *Escherichia coil* from Outpatients Are Frequently Multidrug Resistant: Results from the North American Urinary Tract Infection Collaborative Alliance-Quinolone Resistance Study," *Antimicrobial Agents and Chemotherapy* 50(6):2251-2254, Jun. 2006.

Kishi et al., "Comparative Study on Intravenous Drip Infusion of Dibekacin Once Daily and Twice Daily in Treatment of Complicated Urinary Tract Infections," *Hinyokika Kiyo* 30(1):103-120, 1984.

Kitasato et al., "Reduction of Dibekacin-Induced Nephrotoxicty in the Rat by the Formation of N-Alkylsulfonate Derivatives," *Drugs Exptl. Clin. Res.* 15(6/7):239-247, 1989.

Kitasato et al., "Comparative Ototoxicity of Ribostamycin, Dactimicin, Dibekacin, Kanamycin, Amikacin, Tobramycin, Gentamicin, Sisomicin and Netilmicin in the Inner Ear of Guinea Pigs," *Chemotherapy* 36:155-168, 1990.

Klastersky et al., "Clinical Significance of In Vitro Synergism Between Antibiotics in Gram-Negative Infections," *Antimicrobial Agents and Chemotherapy* 2(6):470-475, Dec. 1972.

Klevens et al., "Estimating Health Care-Associated Infections and Deaths in U.S. Hospitals, 2002," *Public Health Reports* 122:160-166, Mar.-Apr. 2007.

Kondo et al., "Synthesis of 2"-Amino-2"-Deoxyarbekacin and Its Analogs Having Potent Activity Against Methicillin-Resistant *Staphylococcus aureus*," *The Journal of Antibiotics* 47(7):821-832, Jul. 1994.

Kondo et al., "Semisynthetic aminoglycoside antibiotics: Development and enzymatic modifications," *J. Infect. Chemother.* 5:1-9, 1999.

Kotretsou et al., "Synthesis and Antimicrobial and Toxicological Studies of Amino Acid and Peptide Derivatives of Kanamycin A and Netilmicin," *J. Med. Chem.* 38:4710-4719, 1995.

Kotretsou et al., "Synthesis of Amino Acid and Peptide Derivatives of Aminoglycosides Targeted Against Resistance of Bacteria," *Topics in Molecular Organization and Engineering* 11:277-280, 1994.

Kostrub et al., "Quantitative Comparison of Aminoglycoside Nephrotoxicity in Rats for Effective Screening and Evaluation of New Derivatives, and Dosing Rationales That Minimise Toxicity," ECCMID 2009, Poster # P-1979, 1 page.

Kostrub et al., "Ototoxic Potential of ACHN-490 Compared to Gentamicin and Amikacin in the Guinea Pig," ECCMID 2010, Poster # P-1249, 1 page.

Lee et al., "Decreased Susceptibility to Polymyxin B during Treatment for Carbapenem-Resistant *Klebsiella pneumoniae* Infection," *Journal of Clinical Microbiology* 47(5):1611-1612, May 2009.

Lee et al., "Selective reactions of reactive amino groups in polyamino compounds by metal-chelated or -mediated methods," *Tetrahedron* 57:4801-4815, 2001.

Li et al., "Tuning the Regioselectivity of the Staudinger Reaction for the Facile Synthesis of Kanamycin and Neomycin Class Antibiotics with N-1 Modification," *Organic Letters* 7(14):3061-3064, 2005.

Li et al., "Colistin: the re-emerging antibiotic for multidrug-resistant Gram-negative bacterial infections," *Lancet Infect. Dis.* 6:589-601, Sep. 2006.

Lin et al., "Activity of ACHN-490 in Combination with Daptomycin, Ceftobiprole, or Linezolid against 47 Methicillin-resistant *Staphylococcus aureus* by Synergy Time-kill," ICAAC 2009, Poster # F1-844, 1 page.

Lin et al., "Antistaphylococcal Activity of ACHN-490 Tested Alone and in Combination With Other Agents by Time-Kill Assay," *Antimicrobial Agents and Chemotherapy* 54(5):2258-2261, May 2010.

Liu et al., Database WPI Accession No. 2003-713635 [68], retrieved Feb. 23, 2011, 1 page.

Madsen et al., "Treatment of Complicated Urinary Tract Infections, Comparative Study of Sisomicin and Gentamicin," *Urology* 9(6):635-638, Jun. 1977.

Magnet et al., "Molecular Insights into Aminoglycoside Action and Resistance," *Chem. Rev.* 105:477-497, 2005.

Maigaard et al., "Comparison of Netilmicin and Amikacin in Treatment of Complicated Urinary Tract Infections," *Antimicrobial Agents and Chemotherapy* 14(4):544-548, Oct. 1978.

Mallams et al., "Synthesis of Novel 1-*N* Aminoalkyloxycarbonyl and 1-*N*-Aminoalkylcarboxamido Derivatives of Sisomicin, Gentamicin B, Gentamicin C-1a, and Kanamycin A," Current Chemotherapy and Infectious Disease: Proceedings of the 11th International Congress of Chemotherapy and the 19th Interscience Conference on Antimicrobial Agents & Chemotherapy, Boston, MA, Oct. 1-5, 1979, vol. 1, Jan. 1, 1980, pp. 406-408.

Mallams et al., "Semisynthetic Aminoglycoside Antibacterials. Part 10. Synthesis of Novel 1-*N*-Aminoalkoxycarbonyl and 1-*N*-Aminoalkylcarboxamido Derivatives of Sisomicin,Gentamicin B, Gentamicin C, and Kanamycin A," *J. Chem. Soc., Perkin Trans.* 1:2186-2208, 1981.

Maller et al., "Once—versus twice-daily amikacin regimen: efficacy and safety in systemic Gram-negative infections," *Journal of Antimicrobial Chemotherapy* 31:939-948, 1993.

Maltezou et al., "Outbreak of infections due to KPC-2-producing *Klebsiella pneumoniae* in a hospital in Crete (Greece)," *Journal of Infection* 58:213-219, 2009.

Marrie et al., "Clinical and laboratory study of tobramycin in the treatment of infections due to gram-negative organisms," *Canadian Medical Association Journal* 117(2):138,141-143, Jul. 23, 1977.

Martino et al., "N-Formimidoyl-Thienamycin and Norfloxacin Against Multiple-Resistant *Pseudomonas aeruginosa* Strains. Combined In Vitro Activity and Comparison With 14 Other Antibiotics," *Drugs Exptl. Clin. Res.* 11(4):247-251, 1985.

Mentec et al., "Piperacillin, Tazobactam, and Gentamicin Alone or Combined in an Endocarditis Model of Infection by a TEM-3-Producing Strain of *Klebsiella pneumoniae* or Its Susceptible Variant," *Antimicrobial Agents and Chemotherapy* 36(9):1883-1889, Sep. 1992.

Miller et al., "The Most Frequent Aminoglycoside Resistance Mechanisms—Changes with Time and Geographic Area: A Reflection of Aminoglycoside Usage Patterns?" *Clinical Infectious Diseases* 24(Suppl 1):S46-S62, 1997.

Miller et al., "The Most Frequently Occurring Aminoglycoside Resistance Mechanisms—Combined Results of Surveys in Eight Regions of the World," *Journal of Chemotherapy* 7(Supplement n. 2):17-30, 1995.

Moazed et al., "Interaction of antibiotics with functional sites in 16S ribosomal RNA," *Nature* 327:389-394, Jun. 4, 1987.

Mori et al., Database WPI Accession No. 1980-11681C [07], retrieved Apr. 27 2011, 1 page.

Nagabhushan et al., "Interaction of Vicinal and Nonvicinal Amino-Hydroxy Group Pairs in Aminoglycoside—Aminocyclitol Antibiotics with Transition Metal Cations. Selective N Protection," *Journal of the American Chemical Society* 100(16):5253-5254, Aug. 2, 1978.

Nagabhushan et al., "Chemical Modification of Some Gentamicins and Sisomicin at the 3"-Position," *The Journal of Antibiotics* 31(1):43-54, Jan. 1978.

Nagabhushan et al., "The Syntheses and Biological Properties of 1-*N*-(*S*-4-Amino-2-Hydroxybutyryl)-Gentamicin B and 1-*N*-(*S*-3-Amino-2-Hydroxypropionyl)-Gentamicin B," *The Journal of Antibiotics* 31(7):681-687, Jul. 1978.

Nam et al., "An Efficient and Selective 1-*N*-Monoethylation of Sisomicin: Process Development of Netilmicin," *Organic Process Research & Development* 6(1):78-81, 2002.

National Center for Health Statistics. National Hospital Discharge Survey: 2004 Annual Summary with Detailed Diagnosis and Procedure Data. DHHS, Centers for Disease Control and Prevention, Hyattsville, MD: GPO; 2006. DHHS publication 2006-1733, 218 pages.

Nicolau et al., "Experience with a Once-Daily Aminoglycoside Program Administered to 2,184 Adult Patients," *Antimicrobial Agents and Chemotherapy* 39(3):650-655, Mar. 1995.

Nishimura et al., "A proof of the specificity of kanamycin-ribosomal RNA interaction with designed synthetic analogs and the antibacterial activity," *Bioorganic & Medicinal Chemistry Letters* 15:2159-2162, 2005.

Nordmann et al., "The real threat of *Klebsiella pneumoniae* carbapenemase-producing bacteria," *Lancet Infect. Dis.* 9:228-236, Apr. 2009.

Odds, F.C., "Synergy, antagonism, and what the chequerboard puts between them," *Journal of Antimicrobial Chemotherapy* 52:1, 2003.

O'Shea et al., "Physiochemical Properties of Antibacterial Compounds: Implications for Drug Discovery," *Journal of Medicinal Chemistry* 51(10):2871-2878, May 22, 2008.

Pavez et al., "Early Dissemination of KPC-2-Producing *Klebsiella pneumoniae* Strains in Brazil," *Antimicrobial Agents and Chemotherapy* 53(6):2702, Jun. 2009.

Peloquin et al., "Aminoglycoside Toxicity: Daily versus Thrice-Weekly Dosing for Treatment of Mycobacterial Diseases," *Clinical Infectious Diseases* 38:1538-1544, Jun. 1, 2004.

Peterson, "A review of tigecycline—the first glycylcycline," *International Journal of Antimicrobial Agents* 32(S4):S215-S222, 2008.

Queenan et al., "Carbapenemases: the Versatile β-Lactamases," *Clinical Microbiology Reviews* 20(3):440-458, Jul. 2007.

Rai et al., "Novel Method for the Synthesis of 3', 4'-Dideoxygenated Pyranmycin and Kanamycin Compounds, and Studies of Their Antibacterial Activity Against Aminoglycoside-Resistant Bacteria," *Journal of Carbohydrate Chemistry* 24:131-143, 2005.

Rane et al., "Synthesis and In Vitro Microbiological Properties of the 1-*N*-(3-Amino-2-Hydroxypropionyl) Derivatives of Sisomicin and 5-Episisomicin," Current Chemotherapy and Infectious Disease, Proceedings of the 11th International Congress of Chemotherapy and the 19th Interscience Conference on Antimicrobial Agents and Chemotherapy 1:408-410, 1980 (7 pages total).

Reyes et al., "In Vivo Efficacy of the Neoglycoside ACHN-490 Against Enterobacteriaceae and MRSA," ICAAC 2009, Poster # F1-845, 1 page.

Rodriguez-Baño et al., "Clinical significance of extended-spectrum β-lactamases," *Expert Rev. Anti Infect. Ther.* 6(5):671-683, 2008.

Rossi et al., "In vitro susceptibilities of aerobic and facultatively anaerobic Gram-negative bacilli isolated from patients with intra-abdominal infections worldwide: 2004 results from SMART (Study for Monitoring Antimicrobial Resistance Trends)," *Journal of Antimicrobial Chemotherapy* 58:205-210, 2006.

Rybak et al., "Combination Antimicrobial Therapy for Bacterial Infections," *Drugs* 52(3):390-405, Sep. 1996.

*The Sanford Guide to Antimicrobial Therapy*, 37th Edition, Gilbert et al. (eds.), Antimicrobial Therapy: Sperryville, VA, 2007, p. 93.

Santucci et al., "Gentamicin for the Practicing Urologist: Review of Efficacy, Single Daily Dosing and "Switch" Therapy," *The Journal of Urology* 163:1076-1084, Apr. 2000.

Selimoglu, E., "Aminoglycoside-Induced Ototoxicity," *Current Pharmaceutical Design* 13:119-126, 2007.

Sepulchre et al., "The Chemical Ionisation Mass Spectrometry of Aminocyclitol-Aminoglycoside Antibiotics," *Nouveau Journal de Chimie* 2(4):405-409, Jul. 1978.

Shaw et al., "Molecular Genetics of Aminoglycoside Resistance Genes and Familial Relationships of the Aminoglycoside-Modifying Enzymes," *Microbiological Reviews* 57(1):138-163, Mar. 1993.

Singh et al., "Microwave-Assisted Synthesis of Substituted Tetrahydropyrans Catalyzed by $ZrCl_4$ and Its Application in the Asymmetric Synthesis of exo- and endo-brevicomin," *J. Org. Chem.* 74:5758-5761, 2009.

Stamm, W. E. "Urinary Tract Infections and Pyelonephritis," in Braunwald et al. (eds.), *Harrison's 15th Edition Principles of Internal Medicine*, McGraw-Hill, New York, 2001, pp. 1620-1626.

Streicher et al., "Synthesis and Structure/Activity Relationships of New Guanidino Derivatives of Aminoglycoside Antibiotics," *Drugs Exptl. Clin. Res.* IX(8/9):591-598, 1983.

Talan et al., "Prevalence and Risk Factor Analysis of Trimethoprim-Sulfamethoxazole—and Fluoroquinolone-Resistant *Escherichia coli* Infection among Emergency Department Patients with Pyelonephritis," *Clinical Infectious Diseases* 47:1150-1158, 2008.

Tanabe et al., "Aminoglycoside Antibiotics: Synthesis of Nebramine, Tobramycin and 4"-Epi-Tobramycin," *Tetrahedron Letters* 41:3607-3610, 1977.

Theuretzbacher, Ursula, "Future antibiotics scenarios: is the tide starting to turn?" *International Journal of Antimicrobial Agents* 34:15-20, 2009.

Traczewski et al., "In Vitro Activity of Doripenem against *Pseudomonas aeruginosa* and *Burkholderia cepacia* Isolates from both Cystic Fibrosis and Non-Cystic Fibrosis Patients," *Antimicrobial Agents and Chemotherapy* 50(2):819-821, Feb. 2006.

Urban et al., "Daily Dosage of Aminoglycosides," *Current Clinical Topics in Infectious Diseases* 17:236-255, 1997.

Van der Auwera et al., "Pharmacodynamic Parameters and Toxicity of Netilmicin (6 Milligrams/Kilogram/Day) Given Once Daily or in Three Divided Doses to Cancer Patients with Urinary Tract Infection," *Antimicrobial Agents and Chemotherapy* 35(4):640-647, Apr. 1991.

Van Schepdael et al., "New Derivatives of Kanamycin B Obtained by Modifications and Substitutions in Position 6". 1. Synthesis and Microbiological Evaluation, *J. Med. Chem.* 34:1468-1475, 1991.

Van Schepdael et al., "New Derivatives of Kanamycin B Obtained by Combined Modifications in Positions 1 and 6". Synthesis, Microbiological Properties, and in Vitro and Computer-Aided Toxicological Evaluation, *J. Med. Chem.* 34:1483-1492, 1991.

Verpooten et al., "Once-daily dosing decreases renal accumulation of gentamicin and netilmicin," *Clin. Pharmacol. Ther.* 45:22-27, Jan. 1989.

Wachino et al., "Novel Plasmid-Mediated 16S rRNA $m^1$ A1408 Methyltransferase, NpmA, Found in a Clinically Isolated *Escherichia coli* Strain Resistant to Structurally Diverse Aminoglycosides," *Antimicrobial Agents and Chemotherapy* 51(12):4401-4409, Dec. 2007.

Waitz et al., "Chemotherapeutic Evaluation of 5-Episisomicin (Sch 22591), a New Semisynthetic Aminoglycoside," *Antimicrobial Agents and Chemotherapy* 13(1):41-48, Jan. 1978.

Wallis et al., "The Binding of Antibiotics to RNA," *Prog. Biophys. Molec. Biol.*, 67(2/3):141-154, 1997.

Wang et al., "Design, Chemical Synthesis, and Antibacterial Activity of Kanamycin and Neomycin Class Aminoglycoside Antibiotics," in Dev P. Arya (ed.), *Aminoglycoside Antibiotics, From Chemical Biology to Drug Discovery*, Wiley-Interscience, 2007, pp. 141-180.

Warren et al., "Guidelines From the Infectious Diseases Society of America: Guidelines for Antimicrobial Treatment of Uncomplicated Acute Bacterial Cystitis and Acute Pyelonephritis in Women," *Clinical Infectious Diseases* 29:745-758, Oct. 1999.

Widmer, Andreas F., "Ceftobiprole: A New Option for Treatment of Skin and Soft-Tissue Infections due to Methicillin-Resistant *Staphylococcus aureus*," *Clinical Infectious Diseases* 46:656-658, Mar. 1, 2008.

Woodford et al., "Arrival of *Klebsiella pneumoniae* producing KPC carbapenemase in the United Kingdom," *Journal of Antimicrobial Chemotherapy* 62:1261-1264, 2008.

Wright, Gerard D., "Aminoglycoside-modifying enzymes," *Current Opinion in Microbiology* 2(5):499-503, Oct. 1, 1999.

Wright et al., "Selective *N*-Acylation of Gentamicin Antibiotics—Synthesis of 1-*N*-Acyl Derivatives," *The Journal of Antibiotics* 29(7):714-719, Jul. 1976.

Yamane et al., "Antimicrobial susceptibilities of organisms isolated from patients with complicated urinary tract infections in 2004 and 2005," *Japanese Journal of Chemotherapy* 55(6):473-478, Nov. 2007 (with English Abstract).

Yamasaki et al., "Synthesis and Biological Activity of 1-*N*-[4-(Substituted)Amidino and Guanidino-2-Hydroxybutyryl]Kanamycins A and B," *The Journal of Antibiotics* 44(6):646-658, Jun. 1991.

Office Action for U.S. Appl. No. 12/487,427, dated Aug. 29, 2012 (10 pages).

Office Action for U.S. Appl. No. 13/295,238, dated Aug. 28, 2012 (8 pages).

Office Action for U.S. Appl. No. 13/295,233, dated Aug. 28, 2012 (8 pages).

Office Action for U.S. Appl. No. 13/295,231, dated Sep. 13, 2012 (7 pages).

Office Action for U.S. Appl. No. 13/295,227, dated Nov. 7, 2012 (8 pages).

Office Action (Restriction Requirement) for U.S. Appl. No. 13/327,377, dated Aug. 30, 2012 (9 pages).

Zurenko et al., "The Bactericidal Activity of the Neoglycoside ACHN-490 Against Aminoglycoside-Resistant Bacteria," ICAAC 2009, Poster # F1-841, 2 pages.

* cited by examiner

ANTIBACTERIAL AMINOGLYCOSIDE ANALOGS

CROSS-REFERENCE TO RELATED APPLICATIONS

This application is a continuation of International PCT Application No. PCT/US2010/034884, filed May 14, 2010, now pending, which claims the benefit under 35 U.S.C. §119(e) of U.S. Provisional Patent Application No. 61/178,809 filed May 15, 2009 and U.S. Provisional Patent Application No. 61/312,349 filed Mar. 10, 2010. The foregoing applications are incorporated herein by reference in their entireties.

BACKGROUND

1. Field

The present invention is directed to novel aminoglycoside compounds, more specifically, novel kanamycin derivatives, and methods for their preparation and use as therapeutic or prophylactic agents.

2. Description of the Related Art

A particular interest in modern drug discovery is the development of novel low molecular weight drugs that work by binding to RNA. RNA, which serves as a messenger between DNA and proteins, was thought to be an entirely flexible molecule without significant structural complexity. Recent studies have revealed a surprising intricacy in RNA structure. RNA has a structural complexity rivaling proteins, rather than simple motifs like DNA. Genome sequencing reveals both the sequences of the proteins and the mRNAs that encode them. Since proteins are synthesized using an RNA template, such proteins can be inhibited by preventing their production in the first place by interfering with the translation of the mRNA. Since both proteins and the RNAs are potential drug targeting sites, the number of targets revealed from genome sequencing efforts is effectively doubled. These observations unlock a new world of opportunities for the pharmaceutical industry to target RNA with small molecules.

Classical drug discovery has focused on proteins as targets for intervention. Proteins can be extremely difficult to isolate and purify in the appropriate form for use in assays for drug screening. Many proteins require post-translational modifications that occur only in specific cell types under specific conditions. Proteins fold into globular domains with hydrophobic cores and hydrophilic and charged groups on the surface. Multiple subunits frequently form complexes, which may be required for a valid drug screen. Membrane proteins usually need to be embedded in a membrane to retain their proper shape. The smallest practical unit of a protein that can be used in drug screening is a globular domain. The notion of removing a single alpha helix or turn of a beta sheet and using it in a drug screen is not practical, since only the intact protein may have the appropriate 3-dimensional shape for drug binding. Preparation of Biologically Active Proteins for Screening is a Major Limitation in Classical high throughput screening. Quite often the limiting reagent in high throughput screening efforts is a biologically active form of a protein which can also be quite expensive.

For screening to discover compounds that bind RNA targets, the classic approaches used for proteins can be superceded with new approaches. All RNAs are essentially equivalent in their solubility, ease of synthesis or use in assays. The physical properties of RNAs are independent of the protein they encode. They may be readily prepared in large quantity through either chemical or enzymatic synthesis and are not extensively modified in vivo. With RNA, the smallest practical unit for drug binding is the functional subdomain. A functional subdomain in RNA is a fragment that, when removed from the larger RNA and studied in isolation, retains its biologically relevant shape and protein or RNA-binding properties. The size and composition of RNA functional subdomains make them accessible by enzymatic or chemical synthesis. The structural biology community has developed significant experience in identification of functional RNA subdomains in order to facilitate structural studies by techniques such as NMR spectroscopy. For example, small analogs of the decoding region of 16S rRNA (the A-site) have been identified as containing only the essential region, and have been shown to bind antibiotics in the same fashion as the intact ribosome.

The binding sites on RNA are hydrophilic and relatively open as compared to proteins. The potential for small molecule recognition based on shape is enhanced by the deformability of RNA. The binding of molecules to specific RNA targets can be determined by global conformation and the distribution of charged, aromatic, and hydrogen bonding groups off of a relatively rigid scaffold. Properly placed positive charges are believed to be important, since long-range electrostatic interactions can be used to steer molecules into a binding pocket with the proper orientation. In structures where nucleobases are exposed, stacking interactions with aromatic functional groups may contribute to the binding interaction. The major groove of RNA provides many sites for specific hydrogen bonding with a ligand. These include the aromatic N7 nitrogen atoms of adenosine and guanosine, the 04 and 06 oxygen atoms of uridine and guanosine, and the amines of adenosine and cytidine. The rich structural and sequence diversity of RNA suggests to us that ligands can be created with high affinity and specificity for their target.

Although our understanding of RNA structure and folding, as well as the modes in which RNA is recognized by other ligands, is far from being comprehensive, significant progress has been made in the last decade (see, e.g., Chow, C. S.; Bogdan, F. M., *Chem. Rev.,* 1997, 97, 1489 and Wallis, M. G.; Schroeder, R., *Prog. Biophys. Molec. Biol.* 1997, 67, 141). Despite the central role RNA plays in the replication of bacteria, drugs that target these pivotal RNA sites of these pathogens are scarce. The increasing problem of bacterial resistance to antibiotics makes the search for novel RNA binders of crucial importance.

Certain small molecules can bind and block essential functions of RNA. Examples of such molecules include the aminoglycoside antibiotics and drugs such as erythromycin which binds to bacterial rRNA and releases peptidyl-tRNA and mRNA. Aminoglycoside antibiotics have long been known to bind RNA. They exert their antibacterial effects by binding to specific target sites in the bacterial ribosome. For the structurally related antibiotics neamine, ribostamycin, neomycin B, and paromomycin, the binding site has been localized to the A-site of the prokaryotic 16S ribosomal decoding region RNA (see Moazed, D.; Noller, H. F., *Nature,* 1987, 327, 389). Binding of aminoglycosides to this RNA target interferes with the fidelity of mRNA translation and results in miscoding and truncation, leading ultimately to bacterial cell death (see Alper, P. B.; Hendrix, M.; Sears, P.; Wong, C., *J. Am. Chem. Soc.,* 1998, 120, 1965).

There is a need in the art for new chemical entities that work against bacteria with broad-spectrum activity. Perhaps the biggest challenge in discovering RNA-binding antibacterial drugs is identifying vital structures common to bacteria that can be disabled by small molecule drug binding. A challenge in targeting RNA with small molecules is to develop a chemical strategy which recognizes specific shapes of RNA.

There are three sets of data that provide hints on how to do this: natural protein interactions with RNA, natural product antibiotics that bind RNA, and man-made RNAs (aptamers) that bind proteins and other molecules. Each data set, however, provides different insights to the problem.

Several classes of drugs obtained from natural sources have been shown to work by binding to RNA or RNA/protein complexes. These include three different structural classes of antibiotics: thiostreptone, the aminoglycoside family and the macrolide family of antibiotics. These examples provide powerful clues to how small molecules and targets might be selected. Nature has selected RNA targets in the ribosome, one of the most ancient and conserved targets in bacteria. Since antibacterial drugs are desired to be potent and have broad-spectrum activity, these ancient processes, fundamental to all bacterial life, represent attractive targets. The closer we get to ancient conserved functions the more likely we are to find broadly conserved RNA shapes. It is important to also consider the shape of the equivalent structure in humans, since bacteria were unlikely to have considered the therapeutic index of their RNAs while evolving them.

A large number of natural antibiotics exist, these include the aminoglycosides, such as, kirromycin, neomycin, paromomycin, thiostrepton, and many others. They are very potent, bactericidal compounds that bind RNA of the small ribosomal subunit. The bactericidal action is mediated by binding to the bacterial RNA in a fashion that leads to misreading of the genetic code. Misreading of the code during translation of integral membrane proteins is thought to produce abnormal proteins that compromise the barrier properties of the bacterial membrane.

Antibiotics are chemical substances produced by various species of microorganisms (bacteria, fungi, actinomycetes) that suppress the growth of other microorganisms and may eventually destroy them. However, common usage often extends the term antibiotics to include synthetic antibacterial agents, such as the sulfonamides, and quinolines, that are not products of microbes. The number of antibiotics that have been identified now extends into the hundreds, and many of these have been developed to the stage where they are of value in the therapy of infectious diseases. Antibiotics differ markedly in physical, chemical, and pharmacological properties, antibacterial spectra, and mechanisms of action. In recent years, knowledge of molecular mechanisms of bacterial, fungal, and viral replication has greatly facilitated rational development of compounds that can interfere with the life cycles of these microorganisms.

At least 30% of all hospitalized patients now receive one or more courses of therapy with antibiotics, and millions of potentially fatal infections have been cured. At the same time, these pharmaceutical agents have become among the most misused of those available to the practicing physician. One result of widespread use of antimicrobial agents has been the emergence of antibiotic-resistant pathogens, which in turn has created an ever-increasing need for new drugs. Many of these agents have also contributed significantly to the rising costs of medical care.

When the antimicrobial activity of a new agent is first tested, a pattern of sensitivity and resistance is usually defined. Unfortunately, this spectrum of activity can subsequently change to a remarkable degree, because microorganisms have evolved the array of ingenious alterations discussed above that allow them to survive in the presence of antibiotics. The mechanism of drug resistance varies from microorganism to microorganism and from drug to drug.

The development of resistance to antibiotics usually involves a stable genetic change, inheritable from generation to generation. Any of the mechanisms that result in alteration of bacterial genetic composition can operate. While mutation is frequently the cause, resistance to antimicrobial agents may be acquired through transfer of genetic material from one bacterium to another by transduction, transformation or conjugation.

For the foregoing reasons, while progress has been made in this field, there is a need for new chemical entities that possess antibacterial activity. Further, in order to accelerate the drug discovery process, new methods for synthesizing aminoglycoside antibiotics are needed to provide an array of compounds that are potentially new drugs for the treatment of bacterial infections. The present invention fulfills these needs and provides further related advantages.

BRIEF SUMMARY

In brief, the present invention is directed to novel aminoglycoside compounds, more specifically, novel kanamycin derivatives, having antibacterial activity, including stereoisomers, pharmaceutically acceptable salts and prodrugs thereof, and the use of such compounds in the treatment of bacterial infections.

In one embodiment, compounds having the following structure (I) are provided:

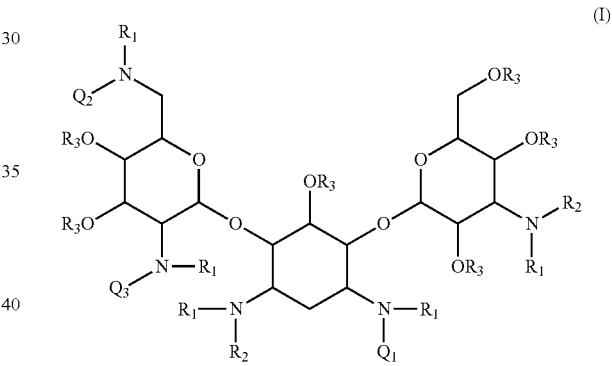

or a stereoisomer, pharmaceutically acceptable salt or prodrug thereof, wherein:

$Q_1$ is alkyl optionally substituted with hydroxyl or amino,

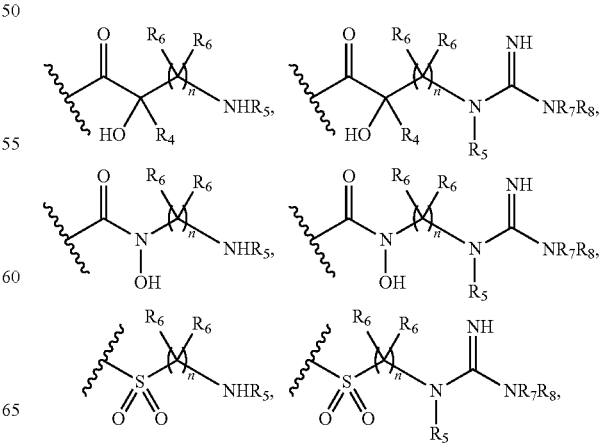

-continued

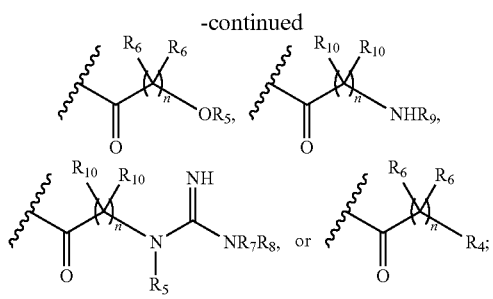

$Q_2$ is hydrogen, optionally substituted alkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_7$R$_8$,

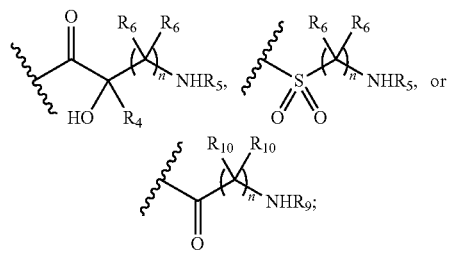

$Q_3$ is hydrogen, optionally substituted alkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_7$R$_8$,

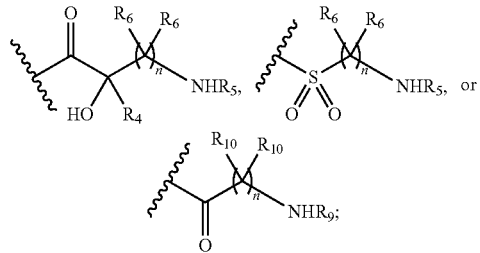

each $R_1$ and $R_2$ is, independently, hydrogen or an amino protecting group;

each $R_3$ is, independently, hydrogen or a hydroxyl protecting group;

each $R_4$, $R_5$, $R_7$ and $R_8$ is, independently, hydrogen or $C_1$-$C_6$ alkyl optionally substituted with one or more halogen, hydroxyl or amino;

each $R_6$ is, independently, hydrogen, halogen, hydroxyl, amino or $C_1$-$C_6$ alkyl;

or $R_4$ and $R_5$ together with the atoms to which they are attached can form a heterocyclic ring having from 4 to 6 ring atoms, or $R_5$ and one $R_6$ together with the atoms to which they are attached can form a heterocyclic ring having from 3 to 6 ring atoms, or $R_4$ and one $R_6$ together with the atoms to which they are attached can form a carbocyclic ring having from 3 to 6 ring atoms, or $R_7$ and $R_8$ together with the atom to which they are attached can form a heterocyclic ring having from 3 to 6 ring atoms;

each $R_9$ is, independently, hydrogen, hydroxyl, amino or $C_1$-$C_6$ alkyl optionally substituted with one or more halogen, hydroxyl or amino;

each $R_{10}$ is, independently, hydrogen, halogen, hydroxyl, amino or $C_1$-$C_6$ alkyl;

or $R_9$ and one $R_{10}$ together with the atoms to which they are attached can form a heterocyclic ring having from 3 to 6 ring atoms; and each n is, independently, an integer from 0 to 4, and wherein (i) at least one of $Q_2$ and $Q_3$ are other than hydrogen, and (ii) if $Q_1$ is —C(=O)OC(CH$_3$)$_3$, —C(=O)CH(OH)CH$_2$NH$_2$, —C(=O)CH(OH)(CH$_2$)$_2$NH$_2$, or —C(=O)CH(OH)(CH$_2$)$_3$NH$_2$, then $Q_2$ is not methyl or —C(=O)OC(CH$_3$)$_3$, and (iii) if $Q_1$ is —C(=O)OC(CH$_3$)$_3$, —C(=O)CH(OH)CH$_2$NH$_2$ or —C(=O)CH(OH)(CH$_2$)$_2$NH$_2$, then $Q_3$ is not —C(=O)OC(CH$_3$)$_3$, —C(=O)OCH$_2$Ph, —C(=O)CH(OH)CH$_2$NH$_2$ or —C(=O)CH(OH)(CH$_2$)$_2$NH$_2$.

In another embodiment, compounds having the following structure (II) are provided:

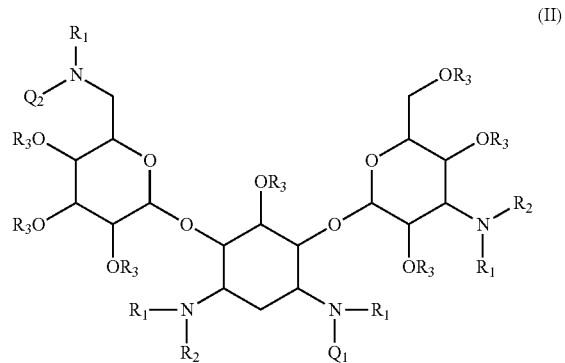

(II)

or a stereoisomer, pharmaceutically acceptable salt or prodrug thereof, wherein:

$Q_1$ is alkyl optionally substituted with hydroxyl or amino,

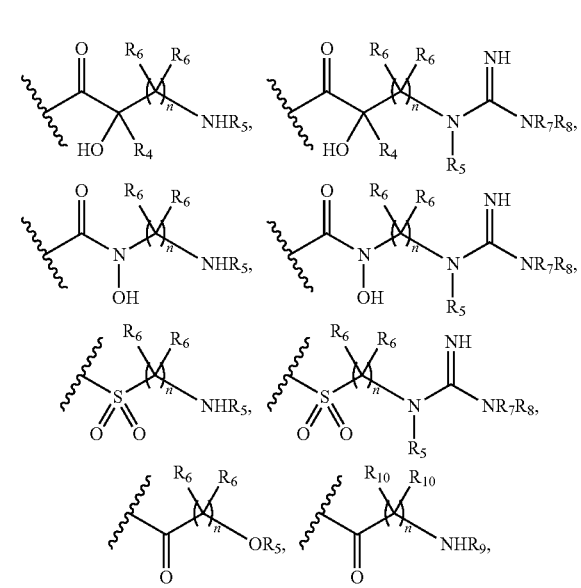

-continued

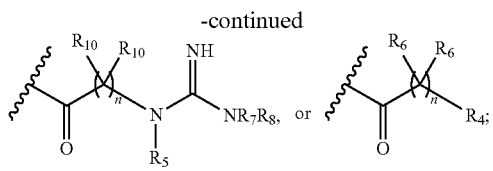 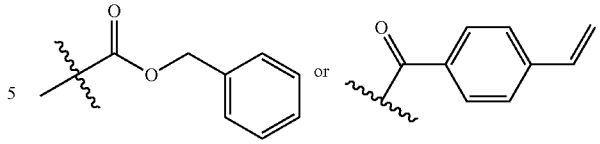

Q₂ is optionally substituted alkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR₇R₈,

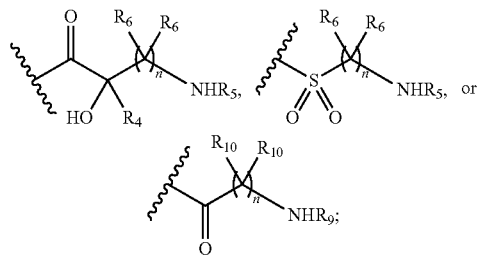

each $R_1$ and $R_2$ is, independently, hydrogen or an amino protecting group;

each $R_3$ is, independently, hydrogen or a hydroxyl protecting group;

each $R_4$, $R_5$, $R_7$ and $R_8$ is, independently, hydrogen or $C_1$-$C_6$ alkyl optionally substituted with one or more halogen, hydroxyl or amino;

each $R_6$ is, independently, hydrogen, halogen, hydroxyl, amino or $C_1$-$C_6$ alkyl;

or $R_4$ and $R_5$ together with the atoms to which they are attached can form a heterocyclic ring having from 4 to 6 ring atoms, or $R_5$ and one $R_6$ together with the atoms to which they are attached can form a heterocyclic ring having from 3 to 6 ring atoms, or $R_4$ and one $R_6$ together with the atoms to which they are attached can form a carbocyclic ring having from 3 to 6 ring atoms, or $R_7$ and $R_8$ together with the atom to which they are attached can form a heterocyclic ring having from 3 to 6 ring atoms;

each $R_9$ is, independently, hydrogen, hydroxyl, amino or $C_1$-$C_6$ alkyl optionally substituted with one or more halogen, hydroxyl or amino;

each $R_{10}$ is, independently, hydrogen, halogen, hydroxyl, amino or $C_1$-$C_6$ alkyl;

or $R_9$ and one $R_{10}$ together with the atoms to which they are attached can form a heterocyclic ring having from 3 to 6 ring atoms; and each n is, independently, an integer from 0 to 4, and wherein (i) if $Q_1$ is —C(=O)CHOH(CH₂)₂NHR₅, then $Q_2$ is not optionally substituted alkyl, and (ii) if $Q_1$ is —C(=O)CH(OH)(CH₂)₂NHC(=NH)NH₂, —C(=O)CH(CH₃)CH₂NH₂, —CH₂CH(OH)(CH₂)₂NH₂, —C(=O)CH(OH)CH₂NH₂, —C(=O)CH(OH)(CH₂)₂NH₂, —C(=O)CH(OH)(CH₂)₃NH₂, —C(=O)CHF(CH₂)₂NH₂ or —C(=O)CH₃, then $Q_2$ is not methyl, ethyl, —CH(=NH), —C(CH₃)(=NH), —C(=NH)NH₂, —C(=O)CH₃, —C(=O)(CH₂)₂CO₂H, —C(=O)CH(OH)(CH₂)₂NH₂, In another embodiment, a pharmaceutical composition is provided comprising a compound having structure (I) or (II), or a stereoisomer, pharmaceutically acceptable salt or prodrug thereof, and a pharmaceutically acceptable carrier, diluent or excipient.

In another embodiment, a method of using a compound having structure (I) or (II) in therapy is provided. In particular, the present invention provides a method of treating a bacterial infection in a mammal comprising administering to the mammal an effective amount of a compound having structure (I) or (II), or a stereoisomer, pharmaceutically acceptable salt or prodrug thereof.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the specification and appended claims, unless specified to the contrary, the following terms have the meaning indicated.

"Amino" refers to the —NH₂ radical.
"Cyano" refers to the —CN radical.
"Hydroxy" or "hydroxyl" refers to the –01-1 radical.
"Imino" refers to the =NH substituent.
"Nitro" refers to the —NO₂ radical.
"Oxo" refers to the =O substituent.
"Thioxo" refers to the =S substituent.
"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl(iso-propyl), n-butyl, n-pentyl, 1,1-dimethylethyl(t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_b$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_d$ is an alkylene chain as defined above and $R_g$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkyl arylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gC(=NR_g)NR_gR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The term "protecting group," as used herein, refers to a labile chemical moiety which is known in the art to protect reactive groups including without limitation, hydroxyl and amino groups, against undesired reactions during synthetic procedures. Hydroxyl and amino groups which protected with a protecting group are referred to herein as "protected hydroxyl groups" and "protected amino groups", respectively. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999). Groups can be selectively incorporated into aminoglycosides of the invention as precursors. For example an amino group can be placed into a compound of the invention as an azido group that can be chemically converted to the amino group at a desired point in the synthesis. Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72. Examples of "hydroxyl protecting groups" include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Examples of "amino protecting groups" include, but are not limited to, carbamate-protecting groups, such as 2-trimethylsilylethoxycarbonyl(Teoc), 1-methyl-1-(4-biphenylyl)ethoxy-carbonyl (Bpoc), t-butoxycarbonyl (BOC), allyloxycarbonyl(Alloc), 9-fluorenylmethyloxycarbonyl(Fmoc), and benzyloxycarbonyl(Cbz); amide protecting groups, such as formyl, acetyl, trihaloacetyl, benzoyl, and nitrophenylacetyl; sulfonamide-protecting groups, such as 2-nitrobenzenesulfonyl; and imine and cyclic imide protecting groups, such as phthalimido and dithiasuccinoyl.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxyl, amino or mercapto group is bonded to any group that, when the prodrug of the compound of the invention is administered to a mammalian subject, cleaves to form a free hydroxyl, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of structure (I) or (II) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I) or (II), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) or (II) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethyl amine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment, as defined below, of a bacterial infection in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

As noted above, in one embodiment of the present invention, compounds having antibacterial activity are provided, the compounds having the following structure (I):

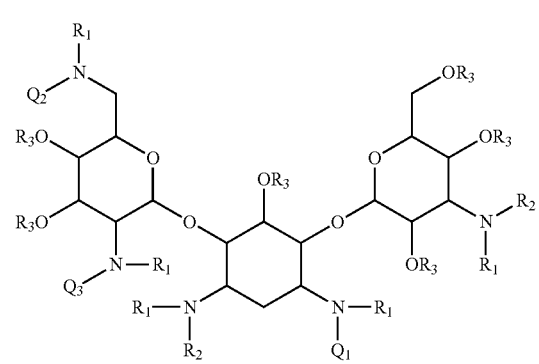

or a stereoisomer, pharmaceutically acceptable salt or prodrug thereof, wherein:

$Q_1$ is alkyl optionally substituted with hydroxyl or amino,

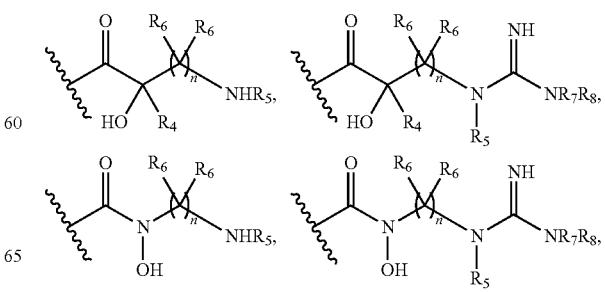

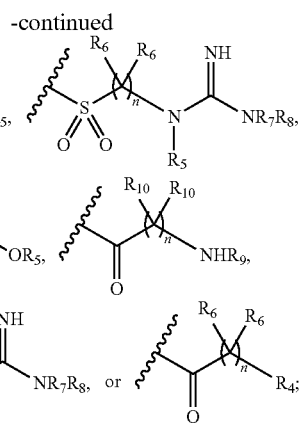

$Q_2$ is hydrogen, optionally substituted alkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_7$R$_8$,

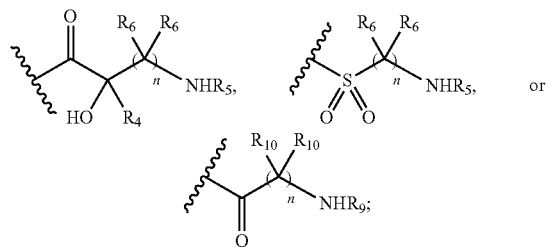

$Q_3$ is hydrogen, optionally substituted alkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_7$R$_8$,

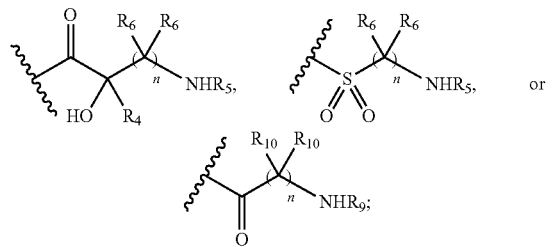

each $R_1$ and $R_2$ is, independently, hydrogen or an amino protecting group;

each $R_3$ is, independently, hydrogen or a hydroxyl protecting group;

each $R_4$, $R_5$, $R_7$ and $R_8$ is, independently, hydrogen or $C_1$-$C_6$ alkyl optionally substituted with one or more halogen, hydroxyl or amino;

each $R_6$ is, independently, hydrogen, halogen, hydroxyl, amino or $C_1$-$C_6$ alkyl;

or $R_4$ and $R_5$ together with the atoms to which they are attached can form a heterocyclic ring having from 4 to 6 ring atoms, or $R_5$ and one $R_6$ together with the atoms to which they are attached can form a heterocyclic ring having from 3 to 6 ring atoms, or $R_4$ and one $R_6$ together with the atoms to which they are attached can form a carbocyclic ring having from 3 to 6 ring atoms, or $R_7$ and $R_8$ together with the atom to which they are attached can form a heterocyclic ring having from 3 to 6 ring atoms;

each $R_9$ is, independently, hydrogen, hydroxyl, amino or $C_1$-$C_6$ alkyl optionally substituted with one or more halogen, hydroxyl or amino;

each $R_{10}$ is, independently, hydrogen, halogen, hydroxyl, amino or $C_1$-$C_6$ alkyl;

or $R_9$ and one $R_{10}$ together with the atoms to which they are attached can form a heterocyclic ring having from 3 to 6 ring atoms; and each n is, independently, an integer from 0 to 4, and wherein (i) at least one of $Q_2$ and $Q_3$ are other than hydrogen, and (ii) if $Q_1$ is —C(=O)OC(CH$_3$)$_3$, —C(=O)CH(OH)CH$_2$NH$_2$, —C(=O)CH(OH)(CH$_2$)$_2$NH$_2$, or —C(=O)CH(OH)(CH$_2$)$_3$NH$_2$, then $Q_2$ is not methyl or —C(=O)OC(CH$_3$)$_3$, and (iii) if $Q_1$ is —C(=O)OC(CH$_3$)$_3$, —C(=O)CH(OH)CH$_2$NH$_2$ or —C(=O)CH(OH)(CH$_2$)$_2$NH$_2$, then $Q_3$ is not —C(=O)OC(CH$_3$)$_3$, —C(=O)OCH$_2$Ph, —C(=O)CH(OH)CH$_2$NH$_2$ or —C(=O)CH(OH)(CH$_2$)$_2$NH$_2$.

In further embodiments:

$Q_1$ is alkyl optionally substituted with hydroxyl or amino, —C(=O)H,

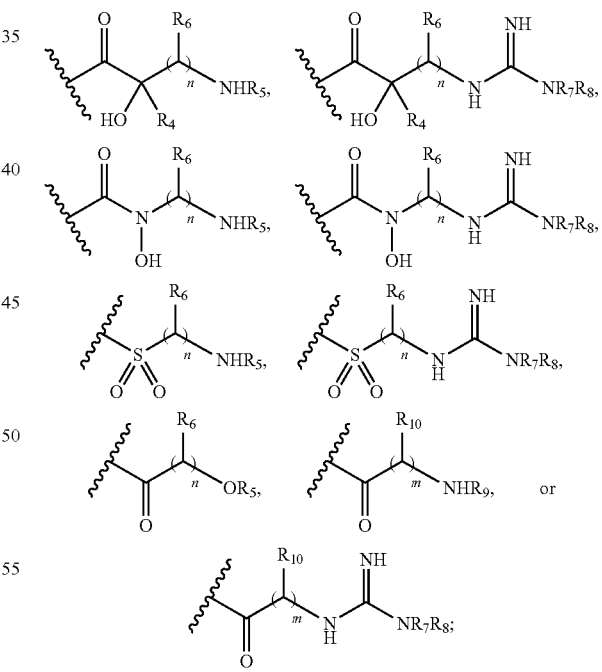

$Q_2$ is hydrogen, optionally substituted alkyl, optionally substituted aryl, optionally substituted aralkyl, optionally substituted cycloalkyl, optionally substituted cycloalkylalkyl, optionally substituted heterocyclyl, optionally substituted heterocyclyl alkyl, optionally substituted heteroaryl, optionally substituted heteroarylalkyl, —C(=NH)NR$_7$R$_8$,

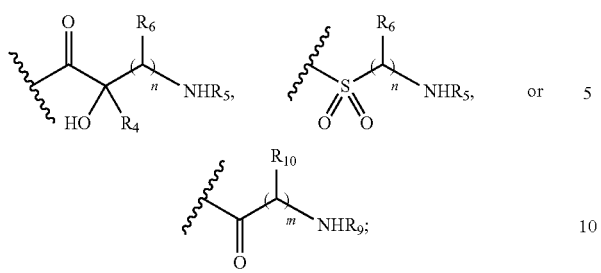

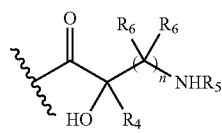

Q₃ is hydrogen, optionally substituted alkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(═NH)NR₇R₈,

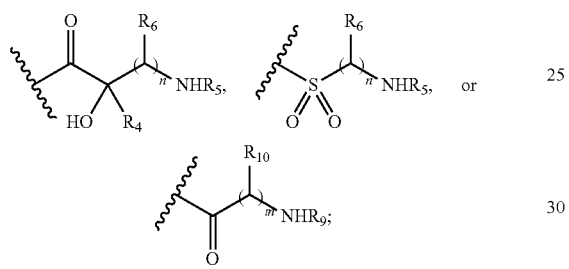

each R₁ and R₂ is, independently, hydrogen or an amino protecting group;

each R₃ is, independently, hydrogen or a hydroxyl protecting group;

each R₄, R₅, R₆, R₇ and R₈ is, independently, hydrogen or C₁-C₆ alkyl, or R₄ and R₅ together with the atoms to which they are attached can form a heterocyclic ring having from 4 to 6 ring atoms, or R₅ and R₆ together with the atoms to which they are attached can form a heterocyclic ring having from 4 to 6 ring atoms, or R₄ and R₆ together with the atoms to which they are attached can form a carbocyclic ring having from 3 to 6 ring atoms, or R₇ and R₈ together with the atom to which they are attached can form a heterocyclic ring having from 4 to 6 ring atoms;

each R₉ and R₁₀ is, independently, hydrogen, hydroxyl, amino or C₁-C₆ alkyl, or R₉ and R₁₀ together with the atoms to which they are attached can form a heterocyclic ring having from 4 to 6 ring atoms;

each n is, independently, an integer from 0 to 4; and each m is, independently, an integer from 0 to 4, and wherein (i) at least one of Q₂ and Q₃ are other than hydrogen, and (ii) if Q₁ is —C(═O)OC(CH₃)₃, —C(═O)CH(OH)CH₂NH₂, —C(═O)CH(OH)(CH₂)₂NH₂, or —C(═O)CH(OH)(CH₂)₃NH₂, then Q₂ is not methyl or —C(═O)OC(CH₃)₃, and (iii) if Q₁ is —C(═O)OC(CH₃)₃, —C(═O)CH(OH)CH₂NH₂ or —C(═O)CH(OH)(CH₂)₂NH₂, then Q₃ is not —C(═O)OC(CH₃)₃, —C(═O)OCH₂Ph, —C(═O)CH(OH)CH₂NH₂ or —C(═O)CH(OH)(CH₂)₂NH₂.

In other further embodiments, Q₁ is:

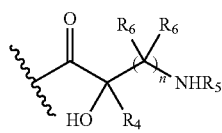

wherein: R₄ is hydrogen; R₅ is hydrogen; and n is an integer from 1 to 4. In further embodiments, each R₆ is hydrogen. For example, in more specific embodiments of the foregoing, Q₁ is:

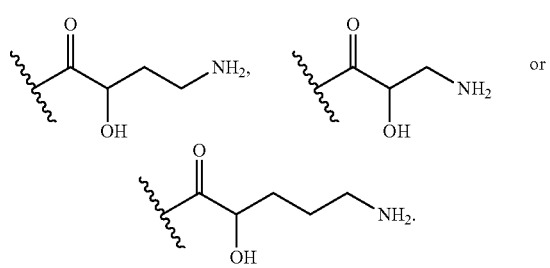

In other further embodiments, at least one R₆ is halogen.

In other further embodiments, Q₁ is:

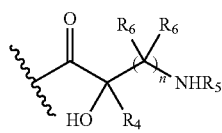

wherein: R₄ is hydrogen; R₅ and one R₆ together with the atoms to which they are attached form a heterocyclic ring having from 3 to 6 ring atoms; and n is an integer from 1 to 4. For example, in more specific embodiments of the foregoing, Q₁ is:

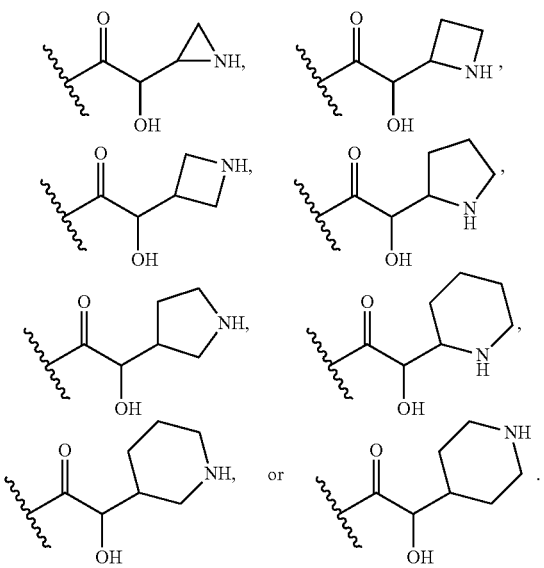

In other further embodiments, at least one R₆ is halogen.

In other further embodiments, $Q_1$ is:

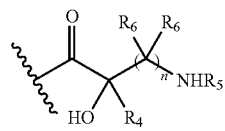

wherein: $R_4$ and $R_5$ together with the atoms to which they are attached form a heterocyclic ring having from 4 to 6 ring atoms; and n is an integer from 1 to 4. In further embodiments, each $R_6$ is hydrogen. For example, in more specific embodiments of the foregoing, $Q_1$ is:

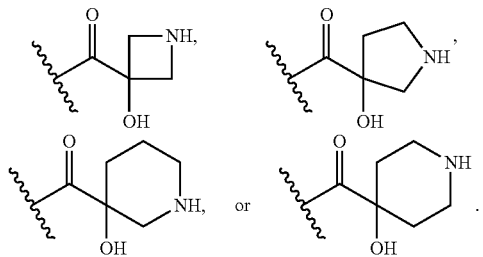

In other further embodiments, at least one $R_6$ is halogen.
In other further embodiments, $Q_1$ is:

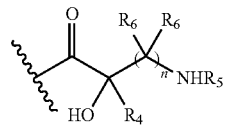

wherein: $R_5$ is hydrogen; $R_4$ and one $R_6$ together with the atoms to which they are attached form a carbocyclic ring having from 3 to 6 ring atoms; and n is an integer from 1 to 4. For example, in more specific embodiments of the foregoing, $Q_1$ is:

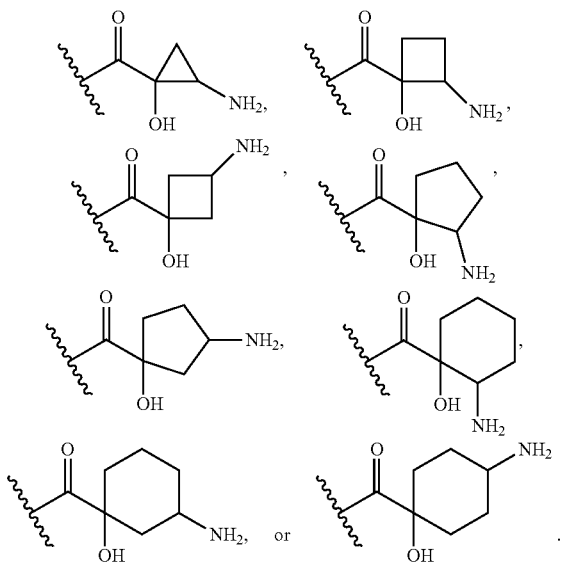

In other further embodiments, at least one $R_6$ is halogen.
In other further embodiments, $Q_1$ is:

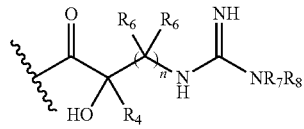

wherein: $R_4$ is hydrogen; $R_7$ is hydrogen; $R_8$ is hydrogen; and n is an integer from 1 to 4. In further embodiments, each $R_6$ is hydrogen. For example, in more specific embodiments of the foregoing, $Q_1$ is:

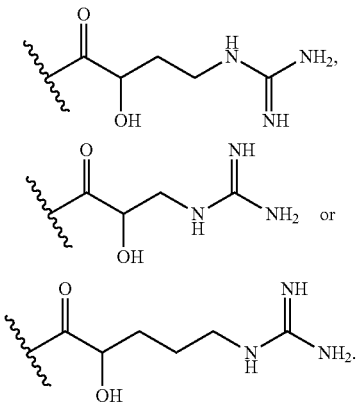

In other further embodiments, at least one $R_6$ is halogen.
In other further embodiments, $Q_1$ is:

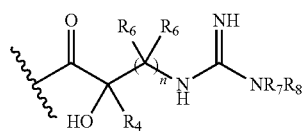

wherein: $R_4$ and one $R_6$ together with the atoms to which they are attached form a carbocyclic ring having from 3 to 6 ring atoms; $R_7$ is hydrogen; $R_8$ is hydrogen; and n is an integer from 1 to 4. For example, in more specific embodiments of the foregoing, $Q_1$ is:

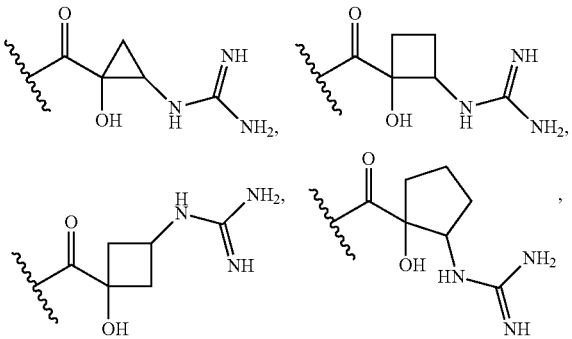

-continued

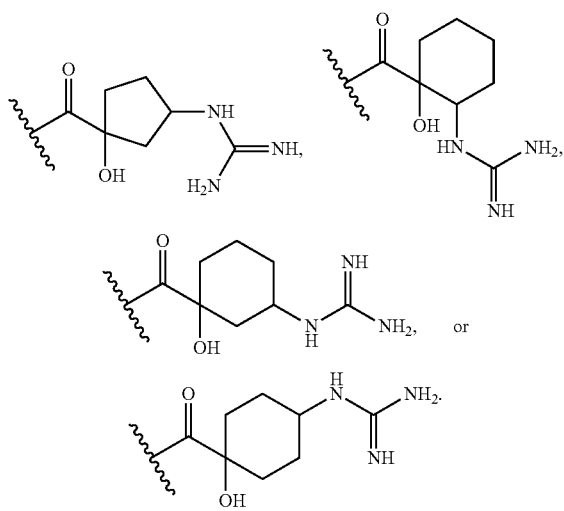

In other further embodiments, at least one $R_6$ is halogen.

In other further embodiments, $Q_1$ is:

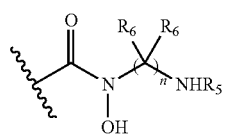

wherein $R_5$ is hydrogen. In further embodiments, each $R_6$ is hydrogen. For example, in more specific embodiments of the foregoing, $Q_1$ is:

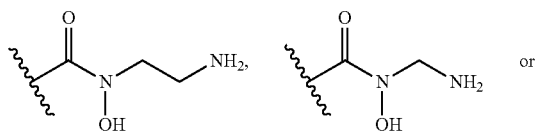

In other further embodiments, at least one $R_6$ is halogen.

In other further embodiments, $Q_1$ is:

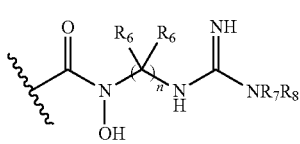

wherein: $R_7$ is hydrogen; and $R_8$ is hydrogen. In further embodiments, each $R_6$ is hydrogen. For example, in more specific embodiments of the foregoing, $Q_1$ is:

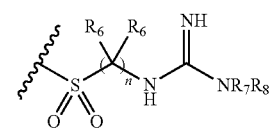

In other further embodiments, at least one $R_6$ is halogen.

In other further embodiments, $Q_1$ is:

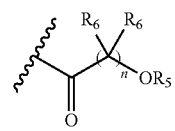

wherein $R_5$ is hydrogen. In further embodiments, each $R_6$ is hydrogen. In other further embodiments, at least one $R_6$ is halogen.

In other further embodiments, $Q_1$ is:

wherein: $R_7$ is hydrogen; and $R_8$ is hydrogen. In further embodiments, each $R_6$ is hydrogen. In other further embodiments, at least one $R_6$ is halogen.

In other further embodiments, $Q_1$ is:

wherein $R_5$ is hydrogen. In further embodiments, each $R_6$ is hydrogen. In other further embodiments, at least one $R_6$ is halogen.

In other further embodiments, $Q_1$ is:

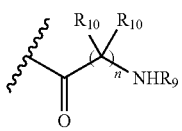

wherein $R_9$ is hydrogen. In further embodiments, each $R_{10}$ is hydrogen. In other further embodiments, at least one $R_{10}$ is halogen.

In other further embodiments, $Q_1$ is:

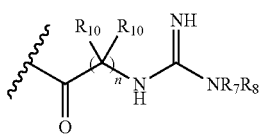

wherein: $R_7$ is hydrogen; and $R_8$ is hydrogen. In further embodiments, each $R_{10}$ is hydrogen. In other further embodiments, at least one $R_{10}$ is halogen.

In other further embodiments, $Q_1$ is:

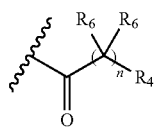

wherein $R_4$ is hydrogen. In further embodiments, each $R_6$ is hydrogen. In other further embodiments, at least one $R_6$ is halogen. In other further embodiments, $Q_1$ is —C(=O)H.

In other further embodiments, $Q_1$ is alkyl optionally substituted with hydroxyl or amino. For example, in more specific embodiments, $Q_1$ is unsubstituted. In other more specific embodiments, $Q_1$ is substituted with hydroxyl or amino.

In other further embodiments, $Q_2$ is other than hydrogen.

In other further embodiments, $Q_2$ is optionally substituted alkyl. For example, in more specific embodiments, $Q_2$ is unsubstituted. In other more specific embodiments, $Q_2$ is substituted with hydroxyl or amino.

In other further embodiments, $Q_2$ is optionally substituted cycloalkyl. For example, in more specific embodiments, $Q_2$ is unsubstituted. In other more specific embodiments, $Q_2$ is substituted with hydroxyl or amino.

In other further embodiments, $Q_2$ is optionally substituted cycloalkylalkyl. For example, in more specific embodiments, $Q_2$ is unsubstituted. In other more specific embodiments, $Q_2$ is substituted with hydroxyl or amino.

In other further embodiments, $Q_2$ is optionally substituted heterocyclyl. For example, in more specific embodiments, $Q_2$ is unsubstituted. In other more specific embodiments, $Q_2$ is substituted with hydroxyl or amino.

In other further embodiments, $Q_2$ is optionally substituted heterocyclylalkyl. For example, in more specific embodiments, $Q_2$ is unsubstituted. In other more specific embodiments, $Q_2$ is substituted with hydroxyl or amino.

In other further embodiments, $Q_2$ is hydrogen.

In other further embodiments, $Q_3$ is other than hydrogen.

In other further embodiments, $Q_3$ is optionally substituted alkyl. For example, in more specific embodiments, $Q_3$ is unsubstituted. In other more specific embodiments, $Q_3$ is substituted with hydroxyl or amino.

In other further embodiments, $Q_3$ is optionally substituted cycloalkyl. For example, in more specific embodiments, $Q_3$ is unsubstituted. In other more specific embodiments, $Q_3$ is substituted with hydroxyl or amino.

In other further embodiments, $Q_3$ is optionally substituted cycloalkylalkyl. For example, in more specific embodiments, $Q_3$ is unsubstituted. In other more specific embodiments, $Q_3$ is substituted with hydroxyl or amino.

In other further embodiments, $Q_3$ is optionally substituted heterocyclyl. For example, in more specific embodiments, $Q_3$ is unsubstituted. In other more specific embodiments, $Q_3$ is substituted with hydroxyl or amino.

In other further embodiments, $Q_3$ is optionally substituted heterocyclylalkyl. For example, in more specific embodiments, $Q_3$ is unsubstituted. In other more specific embodiments, $Q_3$ is substituted with hydroxyl or amino.

In other further embodiments, $Q_3$ is —C(=NH)NH$_2$.

In other further embodiments, $Q_3$ is hydrogen.

In other further embodiments, each $R_1$, $R_2$ and $R_3$ is hydrogen.

As also noted above, in another embodiment of the present invention, compounds having antibacterial activity are provided, the compounds having the following structure (II):

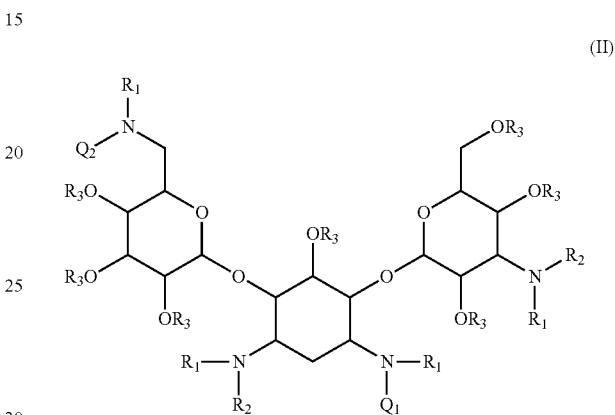

(II)

or a stereoisomer, pharmaceutically acceptable salt or prodrug thereof,
wherein:
$Q_1$ is alkyl optionally substituted with hydroxyl or amino,

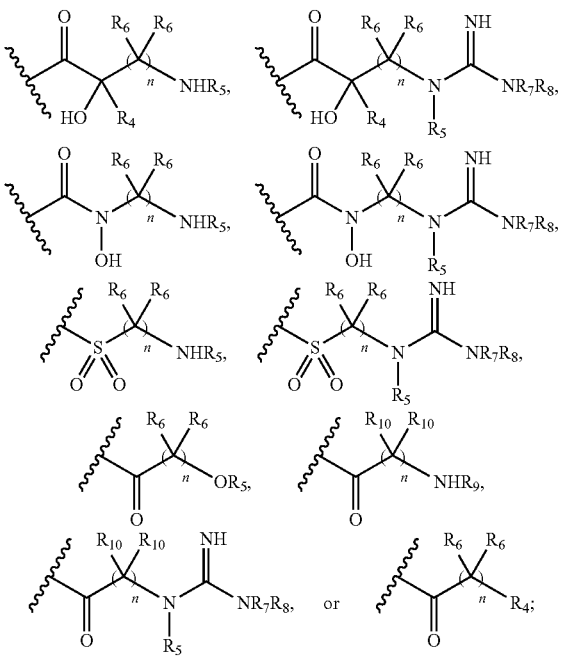

$Q_2$ is optionally substituted alkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_7$R$_8$,

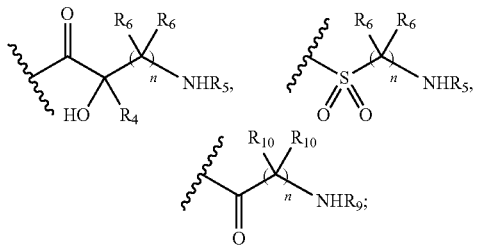

each R$_1$ and R$_2$ is, independently, hydrogen or an amino protecting group;

each R$_3$ is, independently, hydrogen or a hydroxyl protecting group;

each R$_4$, R$_5$, R$_7$ and R$_8$ is, independently, hydrogen or C$_1$-C$_6$ alkyl optionally substituted with one or more halogen, hydroxyl or amino;

each R$_6$ is, independently, hydrogen, halogen, hydroxyl, amino or C$_1$-C$_6$ alkyl;

or R$_4$ and R$_5$ together with the atoms to which they are attached can form a heterocyclic ring having from 4 to 6 ring atoms, or R$_5$ and one R$_6$ together with the atoms to which they are attached can form a heterocyclic ring having from 3 to 6 ring atoms, or R$_4$ and one R$_6$ together with the atoms to which they are attached can form a carbocyclic ring having from 3 to 6 ring atoms, or R$_7$ and R$_8$ together with the atom to which they are attached can form a heterocyclic ring having from 3 to 6 ring atoms;

each R$_9$ is, independently, hydrogen, hydroxyl, amino or C$_1$-C$_6$ alkyl optionally substituted with one or more halogen, hydroxyl or amino;

each R$_{10}$ is, independently, hydrogen, halogen, hydroxyl, amino or C$_1$-C$_6$ alkyl;

or R$_9$ and one R$_{10}$ together with the atoms to which they are attached can form a heterocyclic ring having from 3 to 6 ring atoms; and each n is, independently, an integer from 0 to 4, and wherein (i) if Q$_1$ is —C(=O)CHOH(CH$_2$)$_2$NHR$_5$, then Q$_2$ is not optionally substituted alkyl, and (ii) if Q$_1$ is —C(=O)CH(OH)(CH$_2$)$_2$NHC(=NH)NH$_2$, —C(=O)CH(CH$_3$)CH$_2$NH$_2$, —CH$_2$CH(OH)(CH$_2$)$_2$NH$_2$, —C(=O)CH(OH)CH$_2$NH$_2$, —C(=O)CH(OH)(CH$_2$)$_2$NH$_2$, —C(=O)CH(OH)(CH$_2$)$_3$NH$_2$, —C(=O)CHF(CH$_2$)$_2$NH$_2$ or —C(=O)CH$_3$, then Q$_2$ is not methyl, ethyl, —CH(=NH), —C(CH$_3$)(=NH), —C(=NH)NH$_2$, —C(=O)CH$_3$, —C(=O)(CH$_2$)$_2$CO$_2$H, —C(=O)CH(OH)(CH$_2$)$_2$NH$_2$,

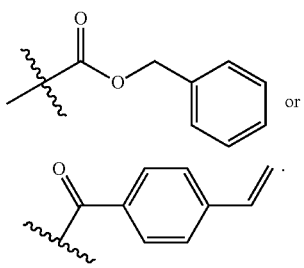

In further embodiments:

Q$_1$ is alkyl optionally substituted with hydroxyl or amino, —C(=O)H,

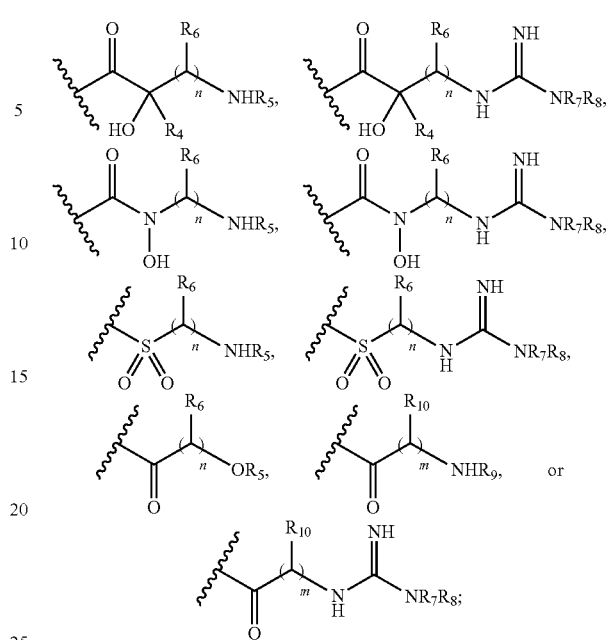

Q$_2$ is optionally substituted alkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_7$R$_8$,

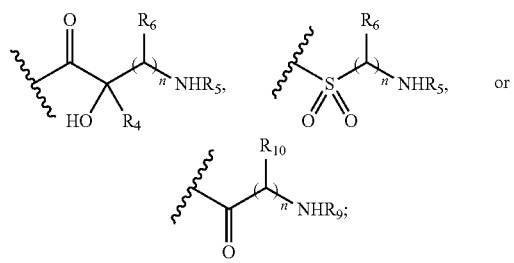

each R$_1$ and R$_2$ is, independently, hydrogen or an amino protecting group;

each R$_3$ is, independently, hydrogen or a hydroxyl protecting group;

each R$_4$, R$_5$, R$_6$, R$_7$ and R$_8$ is, independently, hydrogen or C$_1$-C$_6$ alkyl, or R$_4$ and R$_5$ together with the atoms to which they are attached can form a heterocyclic ring having from 4 to 6 ring atoms, or R$_5$ and R$_6$ together with the atoms to which they are attached can form a heterocyclic ring having from 4 to 6 ring atoms, or R$_4$ and R$_6$ together with the atoms to which they are attached can form a carbocyclic ring having from 3 to 6 ring atoms, or R$_7$ and R$_8$ together with the atom to which they are attached can form a heterocyclic ring having from 4 to 6 ring atoms;

each R$_9$ and R$_{10}$ is, independently, hydrogen, hydroxyl, amino or C$_1$-C$_6$ alkyl, or R$_9$ and R$_{10}$ together with the atoms to which they are attached can form a heterocyclic ring having from 4 to 6 ring atoms;

each n is, independently, an integer from 0 to 4; and each m is, independently, an integer from 0 to 4, and wherein if Q$_1$ is —C(=O)CH(OH)(CH$_2$)$_2$NHC(=NH)NH$_2$, —C(=O)CH(CH$_3$)CH$_2$NH$_2$, —CH$_2$CH(OH)(CH$_2$)$_2$ NH$_2$, —C(=O)CH(OH)CH$_2$NH$_2$, —C(=O)CH(OH)(CH$_2$)$_2$ NH$_2$, or —C(=O)CH(OH)(CH$_2$)$_3$NH$_2$, then Q$_2$ is not methyl, ethyl, —CH(=NH), —C(CH$_3$)(=NH), —C(=NH)NH$_2$, —C(=O)CH$_3$, —C(=O)(CH$_2$)$_2$CO$_2$H, —C(=O)CH(OH)(CH$_2$)$_2$NH$_2$,

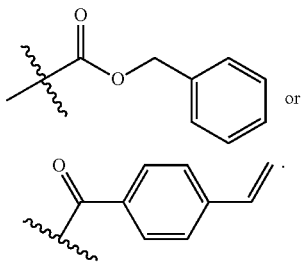

or

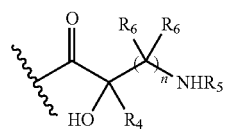

In other further embodiments, Q$_1$ is:

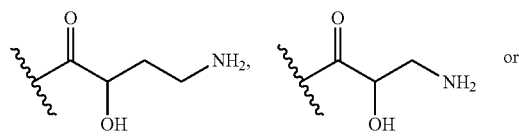

wherein: R$_4$ is hydrogen; R$_5$ is hydrogen; and n is an integer from 1 to 4. In further embodiments, each R$_6$ is hydrogen. For example, in more specific embodiments of the foregoing, Q$_1$ is:

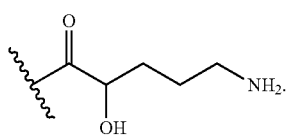

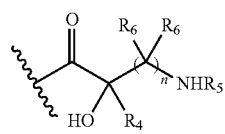

In other further embodiments, at least one R$_6$ is halogen.
In other further embodiments, Q$_1$ is:

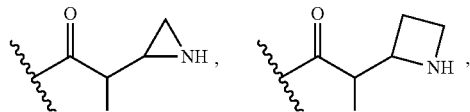

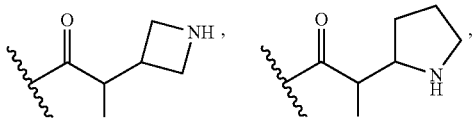

wherein: R$_4$ is hydrogen; R$_5$ and one R$_6$ together with the atoms to which they are attached form a heterocyclic ring having from 3 to 6 ring atoms; and n is an integer from 1 to 4. For example, in more specific embodiments of the foregoing, Q$_1$ is:

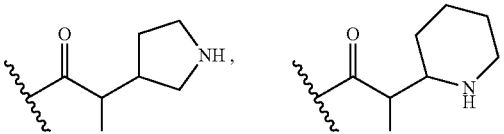

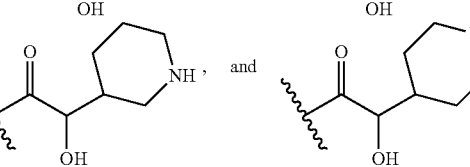

In other further embodiments, at least one R$_6$ is halogen.
In other further embodiments, Q$_1$ is:

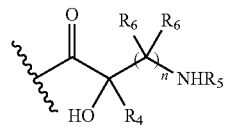

wherein: R$_4$ and R$_5$ together with the atoms to which they are attached form a heterocyclic ring having from 4 to 6 ring atoms; and n is an integer from 1 to 4. In further embodiments, each R$_6$ is hydrogen. For example, in more specific embodiments of the foregoing, Q$_1$ is:

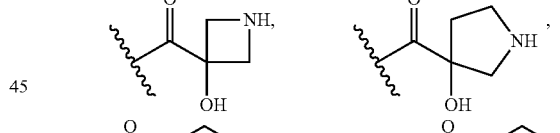

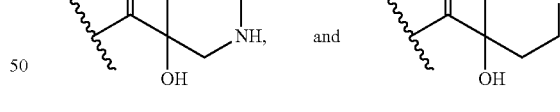

In other further embodiments, at least one R$_6$ is halogen.
In other further embodiments, Q$_1$ is:

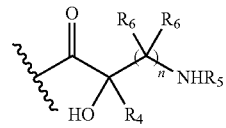

wherein: R$_5$ is hydrogen; R$_4$ and one R$_6$ together with the atoms to which they are attached form a carbocyclic ring having from 3 to 6 ring atoms; and n is an integer from 1 to 4. For example, in more specific embodiments of the foregoing, Q$_1$ is:

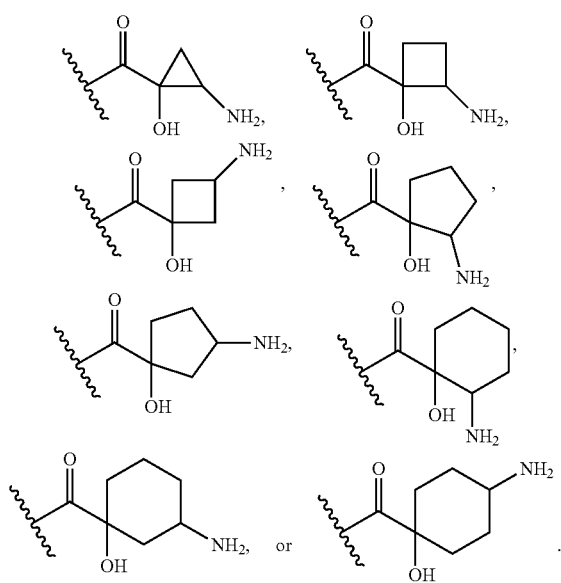

In other further embodiments, at least one $R_6$ is halogen.

In other further embodiments, $Q_1$ is:

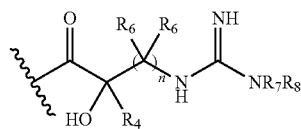

wherein: $R_4$ is hydrogen; $R_7$ is hydrogen; $R_8$ is hydrogen; and n is an integer from 1 to 4. In further embodiments, each $R_6$ is hydrogen. For example, in more specific embodiments of the foregoing, $Q_1$ is:

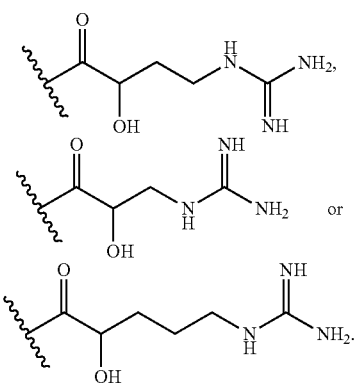

In other further embodiments, at least one $R_6$ is halogen.

In other further embodiments, $Q_1$ is:

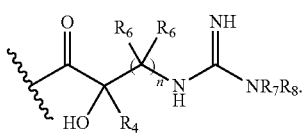

wherein: $R_4$ and one $R_6$ together with the atoms to which they are attached form a carbocyclic ring having from 3 to 6 ring atoms; $R_7$ is hydrogen; $R_8$ is hydrogen; and n is an integer from 1 to 4. For example, in more specific embodiments of the foregoing, $Q_1$ is:

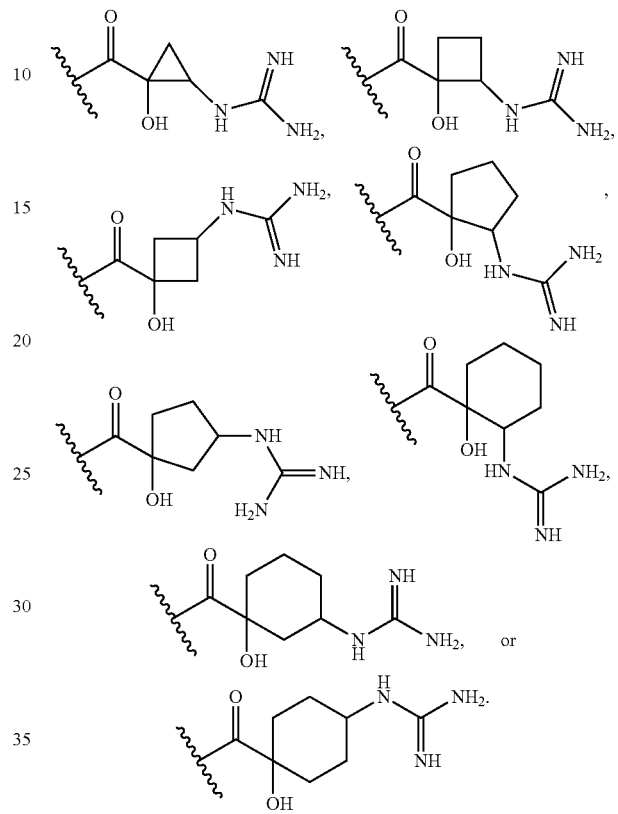

In other further embodiments, at least one $R_6$ is halogen.

In other further embodiments, $Q_1$ is:

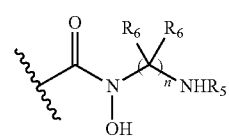

wherein $R_5$ is hydrogen. In further embodiments, each $R_6$ is hydrogen. For example, in more specific embodiments of the foregoing, $Q_1$ is:

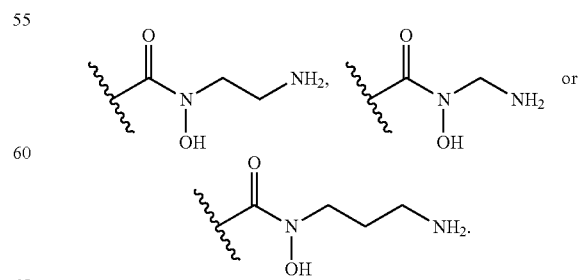

In other further embodiments, at least one $R_6$ is halogen.

In other further embodiments, $Q_1$ is:

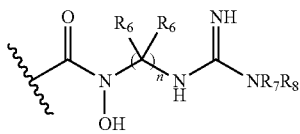

wherein: $R_7$ is hydrogen; and $R_8$ is hydrogen. In further embodiments, each $R_6$ is hydrogen. For example, in more specific embodiments of the foregoing, $Q_1$ is:

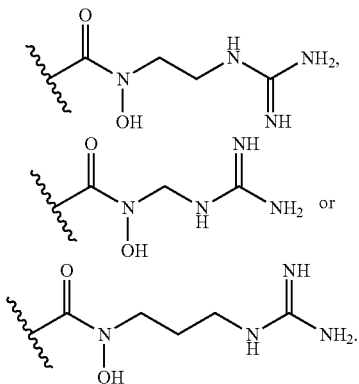

In other further embodiments, at least one $R_6$ is halogen.
In other further embodiments, $Q_1$ is:

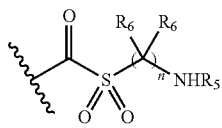

wherein $R_5$ is hydrogen. In further embodiments, each $R_6$ is hydrogen. In other further embodiments, at least one $R_6$ is halogen.
In other further embodiments, $Q_1$ is:

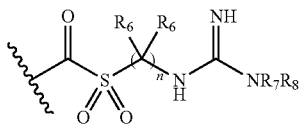

wherein: $R_7$ is hydrogen; and $R_8$ is hydrogen. In further embodiments, each $R_6$ is hydrogen. In other further embodiments, at least one $R_6$ is halogen.
In other further embodiments, $Q_1$ is:

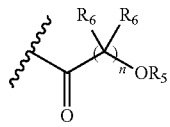

wherein $R_5$ is hydrogen. In further embodiments, each $R_6$ is hydrogen. In other further embodiments, at least one $R_6$ is halogen.

In other further embodiments, $Q_1$ is:

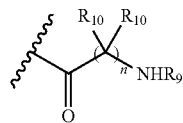

wherein $R_9$ is hydrogen. In further embodiments, each $R_{10}$ is hydrogen. In other further embodiments, at least one $R_{10}$ is halogen.
In other further embodiments, $Q_1$ is:

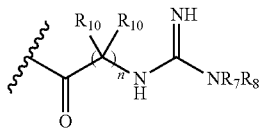

wherein: $R_7$ is hydrogen; and $R_8$ is hydrogen. In further embodiments, each $R_{10}$ is hydrogen. In other further embodiments, at least one $R_{10}$ is halogen.
In other further embodiments, $Q_1$ is:

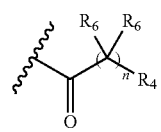

wherein $R_4$ is hydrogen. In further embodiments, each $R_6$ is hydrogen. In other further embodiments, at least one $R_6$ is halogen. In other further embodiments, $Q_1$ is —C(=O)H.

In other further embodiments, $Q_1$ is alkyl optionally substituted with hydroxyl or amino. For example, in more specific embodiments, $Q_1$ is unsubstituted. In other more specific embodiments, $Q_1$ is substituted with hydroxyl or amino.

In other further embodiments, $Q_2$ is optionally substituted alkyl. For example, in more specific embodiments, $Q_2$ is unsubstituted. In other more specific embodiments, $Q_2$ is substituted with hydroxyl or amino.

In other further embodiments, $Q_2$ is optionally substituted cycloalkyl. For example, in more specific embodiments, $Q_2$ is unsubstituted. In other more specific embodiments, $Q_2$ is substituted with hydroxyl or amino.

In other further embodiments, $Q_2$ is optionally substituted cycloalkylalkyl. For example, in more specific embodiments, $Q_2$ is unsubstituted. In other more specific embodiments, $Q_2$ is substituted with hydroxyl or amino.

In other further embodiments, $Q_2$ is optionally substituted heterocyclyl. For example, in more specific embodiments, $Q_2$ is unsubstituted. In other more specific embodiments, $Q_2$ is substituted with hydroxyl or amino.

In other further embodiments, $Q_2$ is optionally substituted heterocyclylalkyl. For example, in more specific embodiments, $Q_2$ is unsubstituted. In other more specific embodiments, $Q_2$ is substituted with hydroxyl or amino.

In other further embodiments, each $R_1$, $R_2$ and $R_3$ is hydrogen.

It is understood that any embodiment of the compounds of structure (I) or (II), as set forth above, and any specific substituent set forth herein for a $Q_1$, $Q_2$, $Q_3$, $R_1$, $R_2$ and $R_3$ group in the compounds of structure (I) or (II), as set forth above, may be independently combined with other embodiments and/or substituents of compounds of structure (I) or (II) to form embodiments of the invention not specifically set forth above. In addition, in the event that a list of substitutents is listed for any particular substituent group in a particular embodiment and/or claim, it is understood that each individual substituent may be deleted from the particular embodiment and/or claim and that the remaining list of substituents will be considered to be within the scope of the invention.

For the purposes of administration, the compounds of the present invention may be administered as a raw chemical or may be formulated as pharmaceutical compositions. Pharmaceutical compositions of the present invention comprise a compound of structure (I) or (II) and a pharmaceutically acceptable carrier, diluent or excipient. The compound of structure (I) or (II) is present in the composition in an amount which is effective to treat a particular disease or condition of interest—that is, in an amount sufficient to treat a bacterial infection, and preferably with acceptable toxicity to the patient. The antibacterial activity of compounds of structure (I) or (II) can be determined by one skilled in the art, for example, as described in the Examples below. Appropriate concentrations and dosages can be readily determined by one skilled in the art.

The compounds of the present invention possess antibacterial activity against a wide spectrum of gram positive and gram negative bacteria, as well as enterobacteria and anaerobes. Representative susceptible organisms generally include those gram positive and gram negative, aerobic and anaerobic organisms whose growth can be inhibited by the compounds of the invention such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella, Francisella, Anthracis, Yersinia, Corynebacterium, Moraxella, Enterococcus*, and other organisms.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: *The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

It is understood that in the present description, combinations of substituents and/or variables of the depicted formulae are permissible only if such contributions result in stable compounds.

It will also be appreciated by those skilled in the art that in the synthetic processes described herein the functional groups of intermediate compounds may need to be protected by suitable protecting groups. Such functional groups include hydroxyl, amino, mercapto and carboxylic acid. Suitable protecting groups for hydroxyl include trialkylsilyl or diaryalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although a protected derivative of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The following Examples illustrate various methods of making compounds of this invention, i.e., compounds of structure (I) or (II):

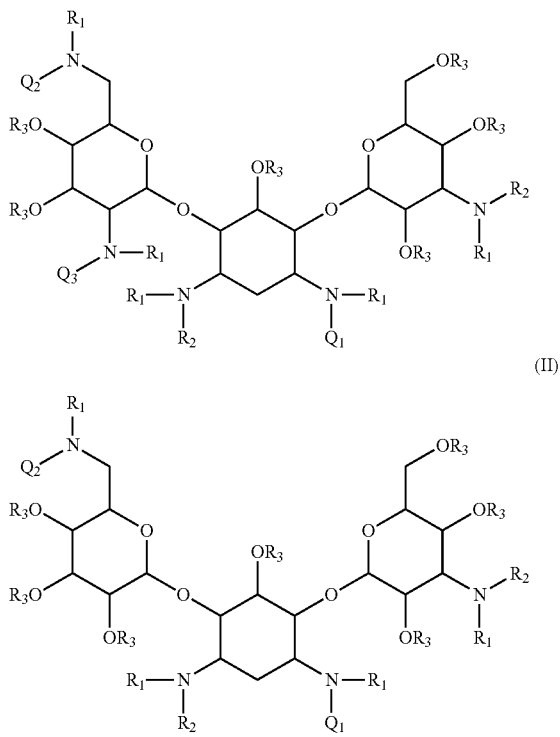

wherein $Q_1$, $Q_2$, $Q_3$, $R_1$, $R_2$ and $R_3$ are as defined herein. It is understood that one skilled in the art may be able to make these compounds by similar methods or by combining other methods known to one skilled in the art. It is also understood that one skilled in the art would be able to make, in a similar manner as described below, other compounds of structure (I) or (II) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described herein.

The following examples are provided for purposes of illustration, not limitation.

EXAMPLES

Kanamycin B Analogs

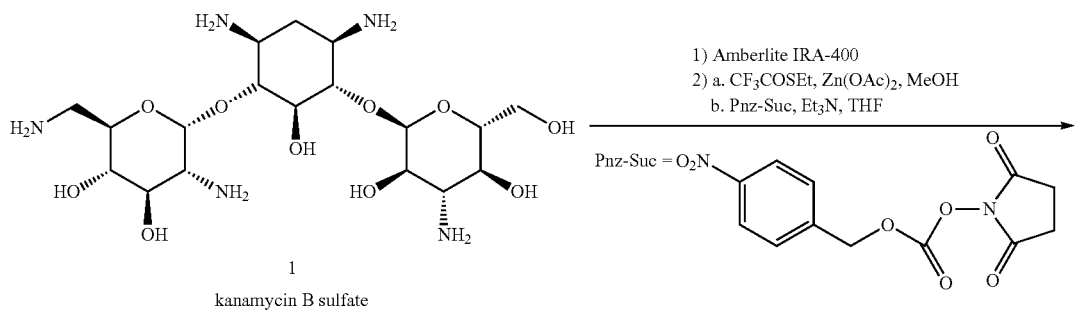

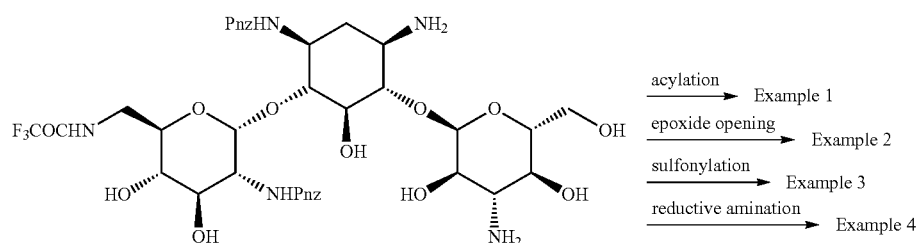

-continued
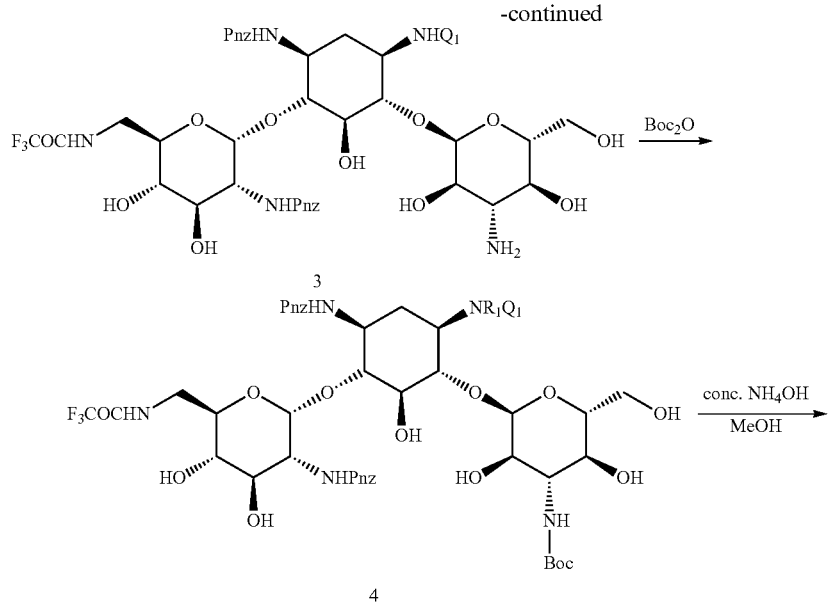
3
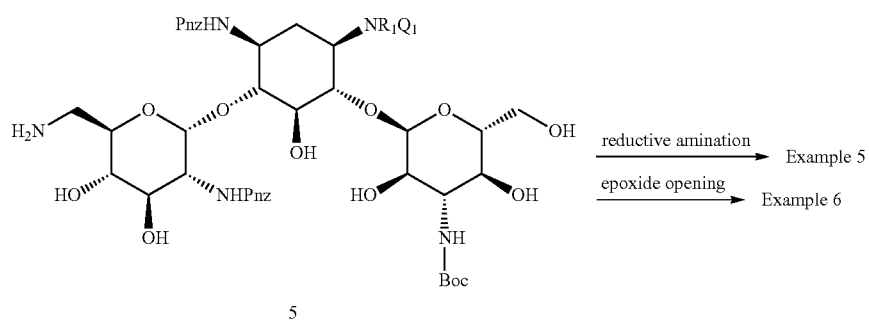
4
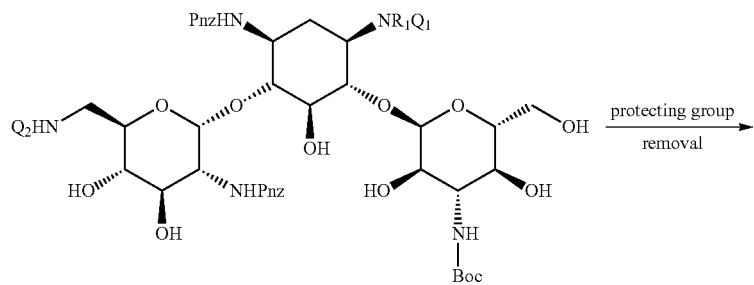
5
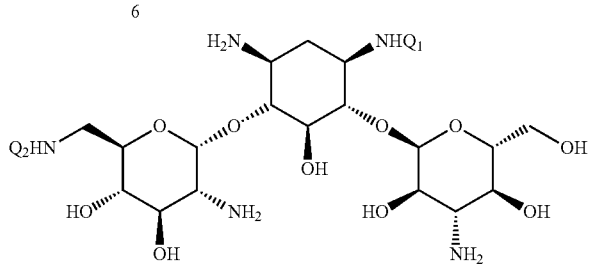
6
7
N-1, N-6′-bis-substituted kanamycin B

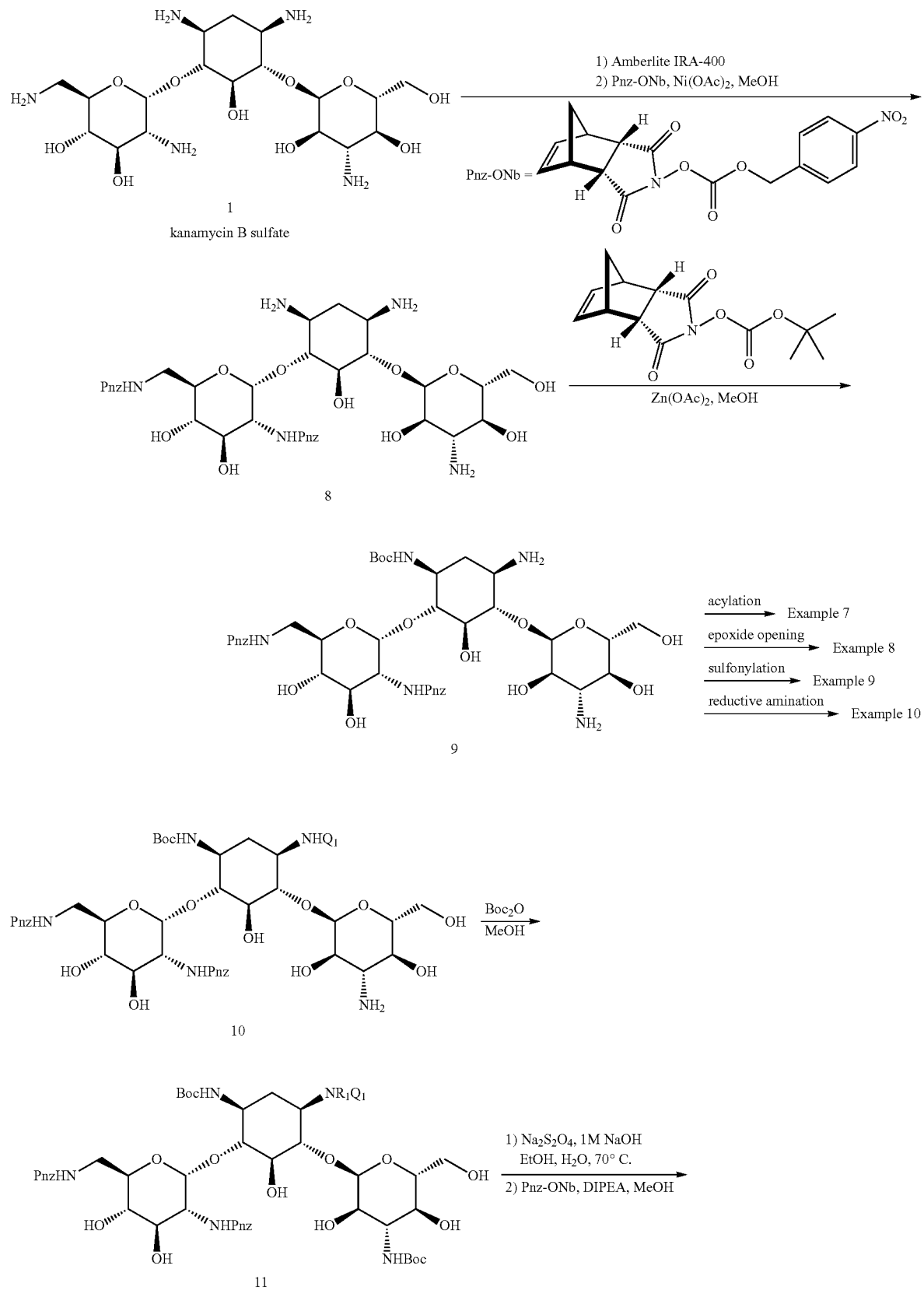

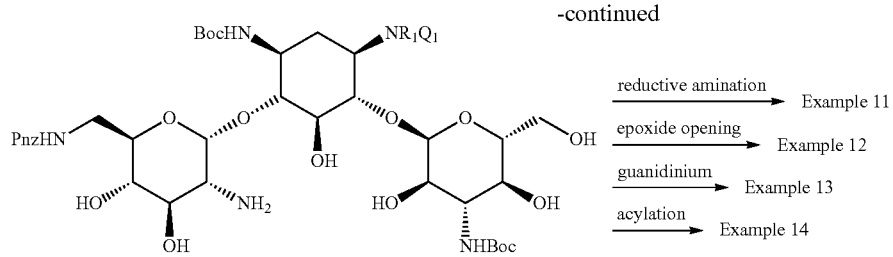
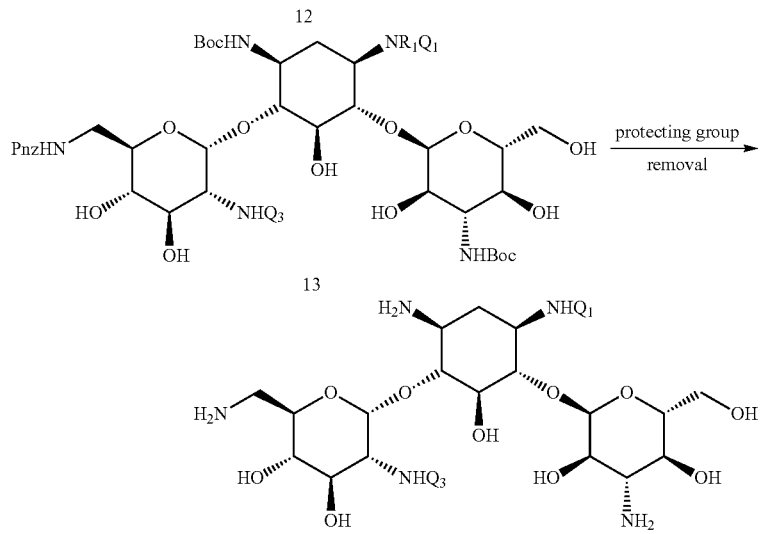
N-1, N-2′-bis-substituted kanamycin B
Example 1
N-1 Acylation
Method A:
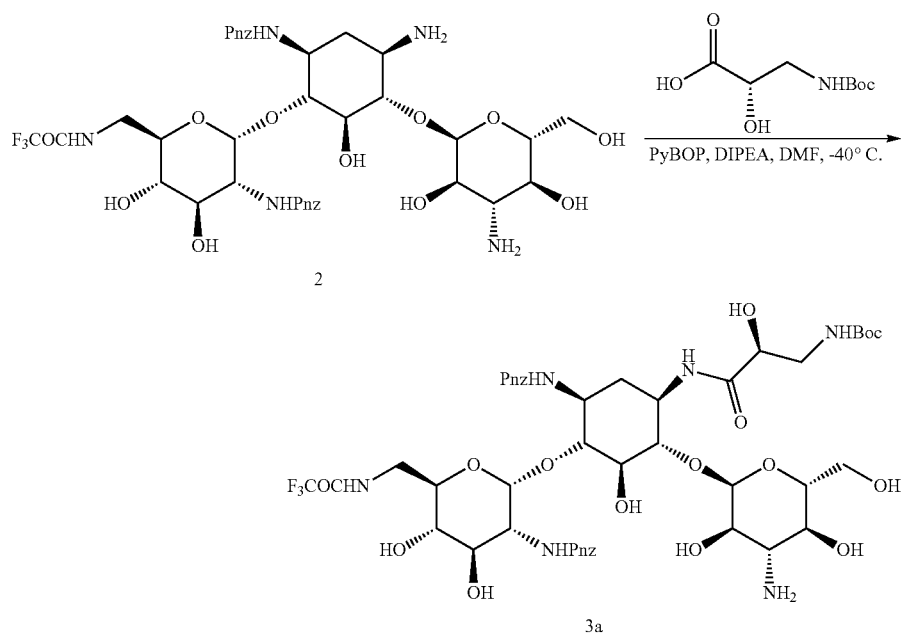

Method B:
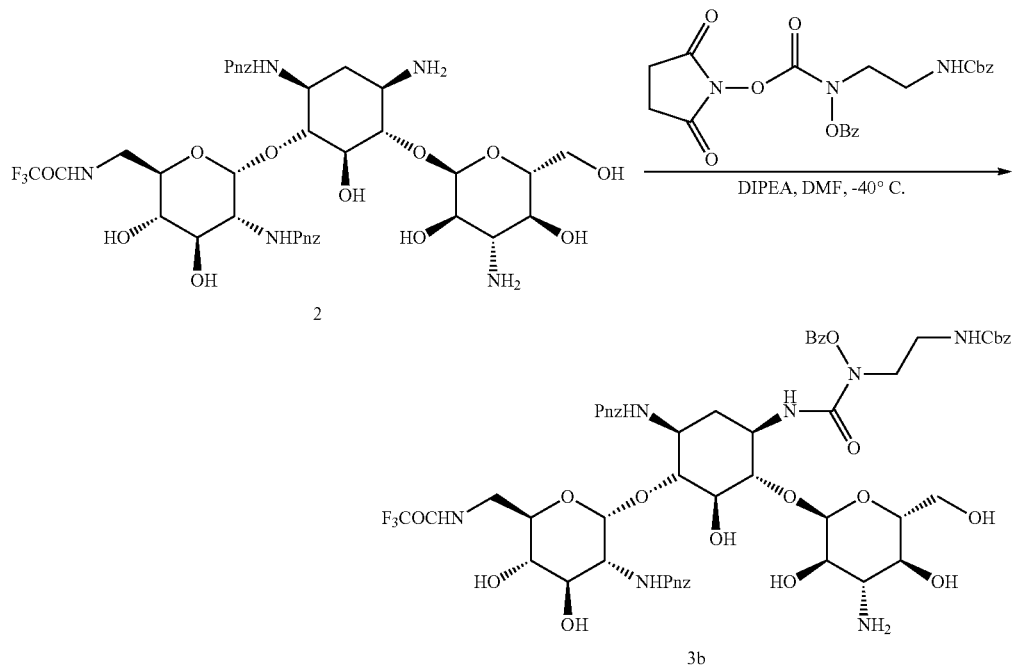
Example 2
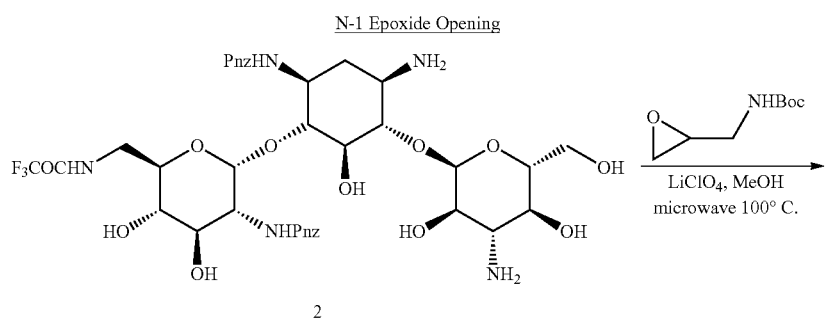
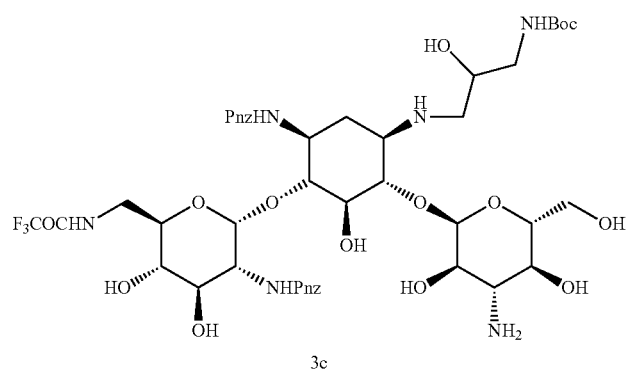

Example 3
N-1 Sulfonylation
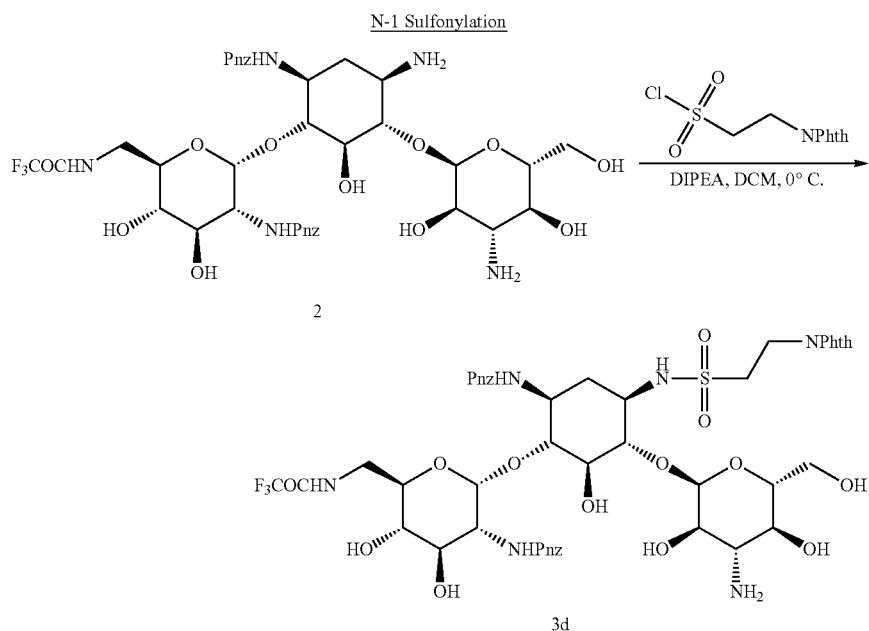
Phth = phthalimido
Example 4
N-1 Reductive Amination
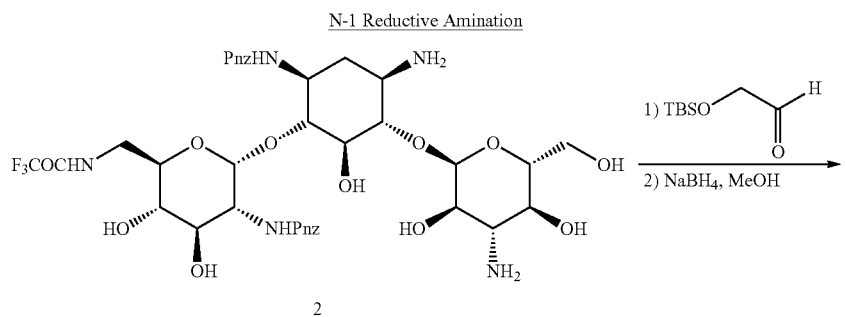
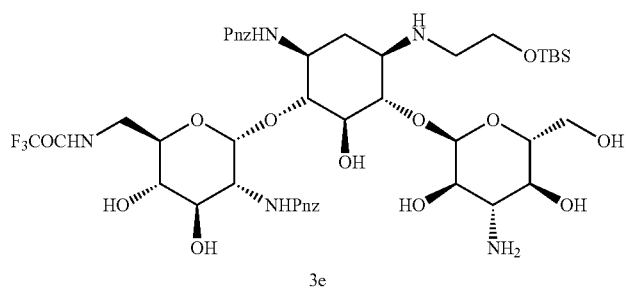

Example 5
N-6' Reductive Amination
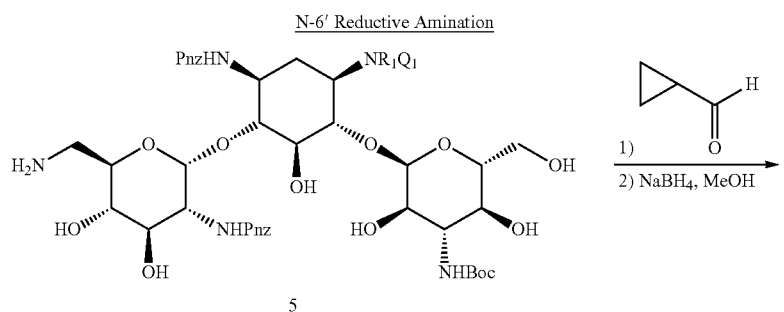
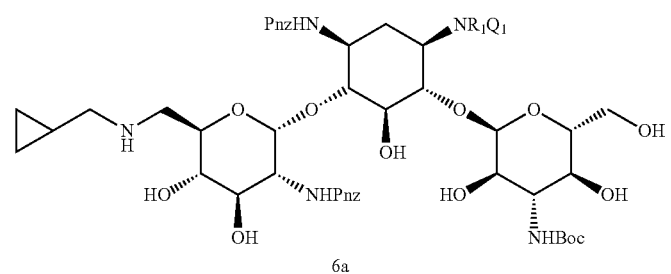
Example 6
N-6' Epoxide Opening
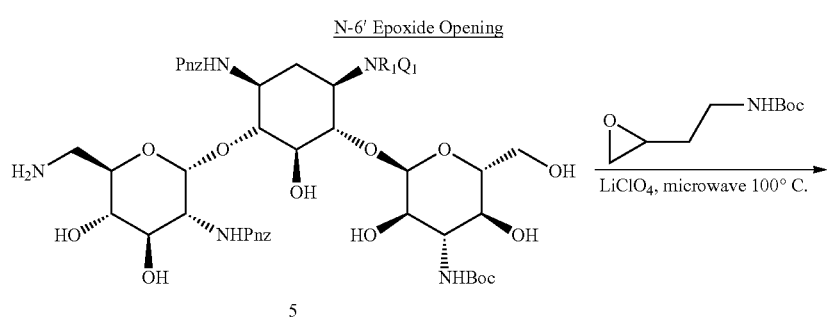
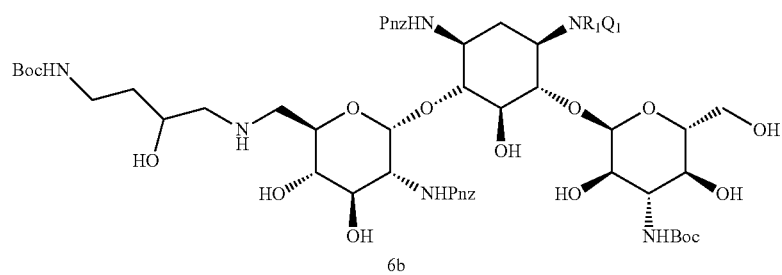

Example 7
N-1 Acylation
Method A:
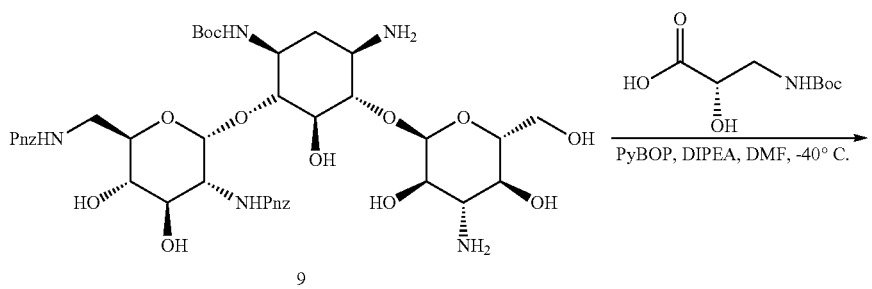
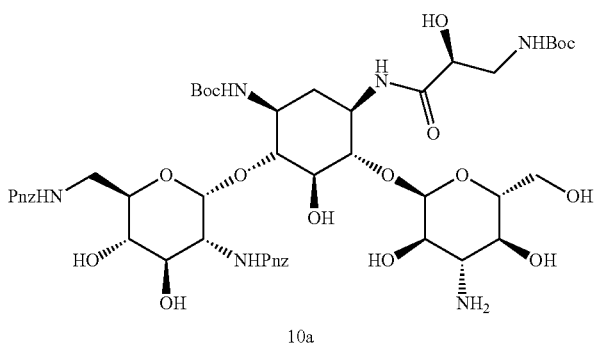
10a
Method B:
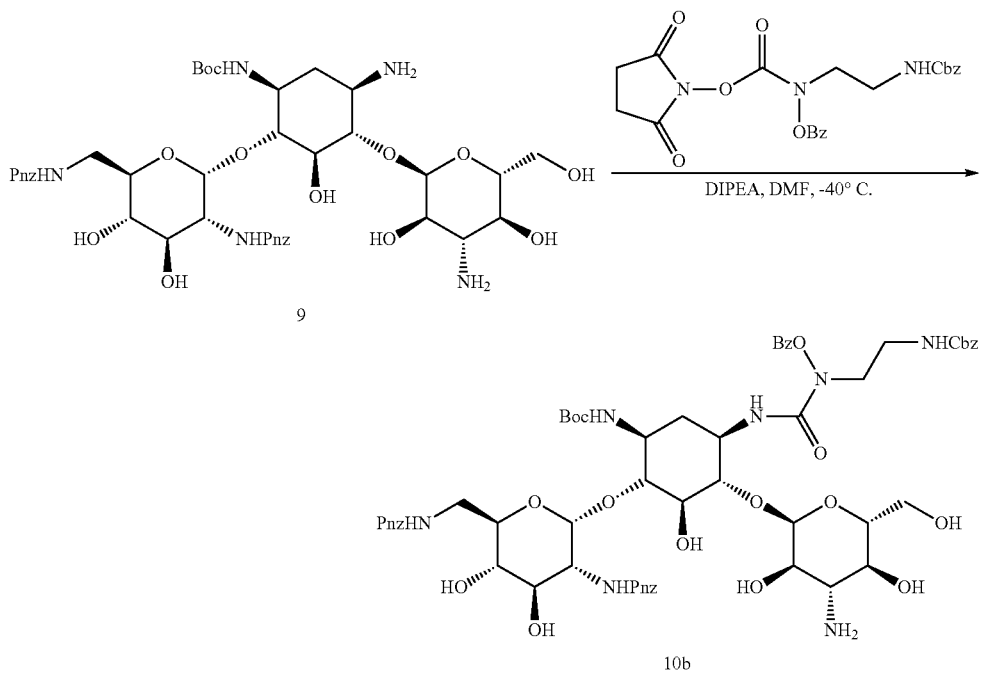
10b

Example 8
N-1 Epoxide Opening
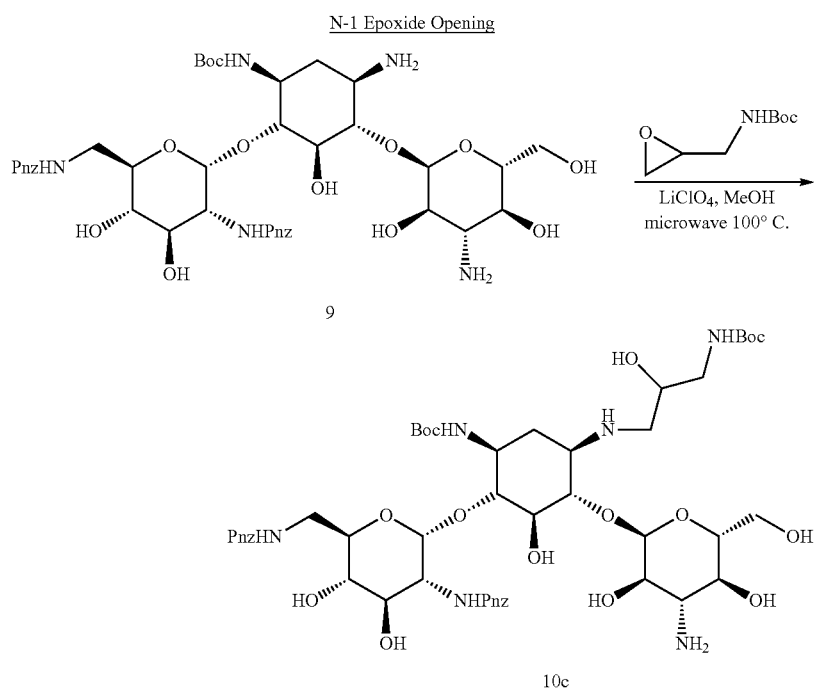
Example 9
N-1 Sulfonylation
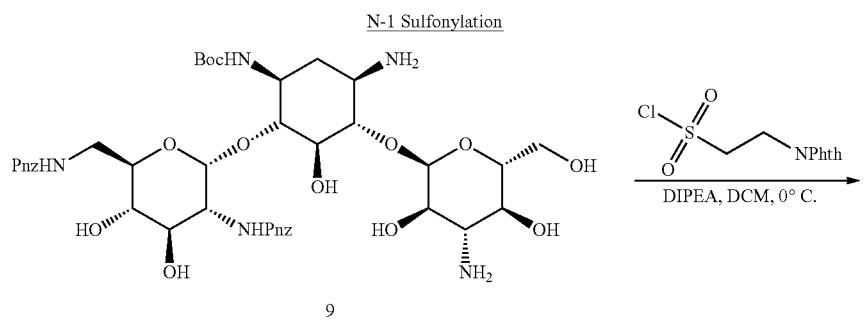
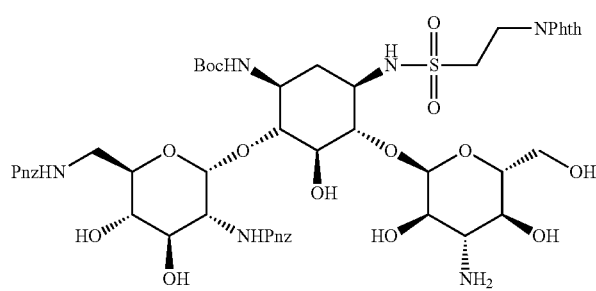
Phth = phthalimido

Example 10
N-1 Reductive Amination
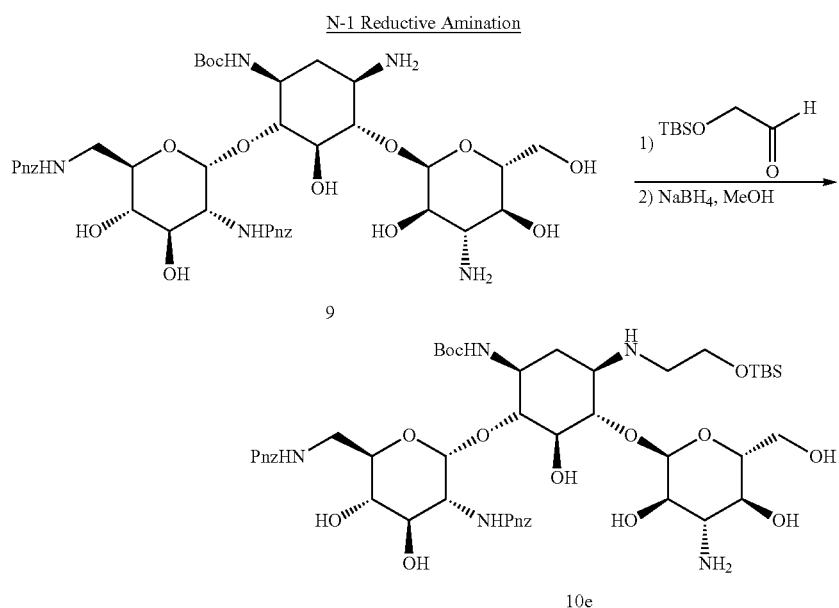
Example 11
N-2' Reductive Amination
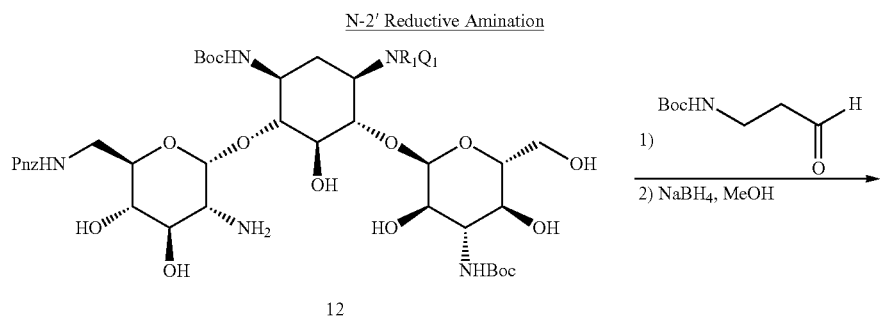
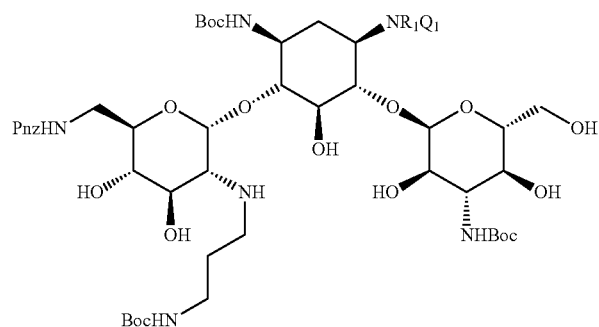

Example 12
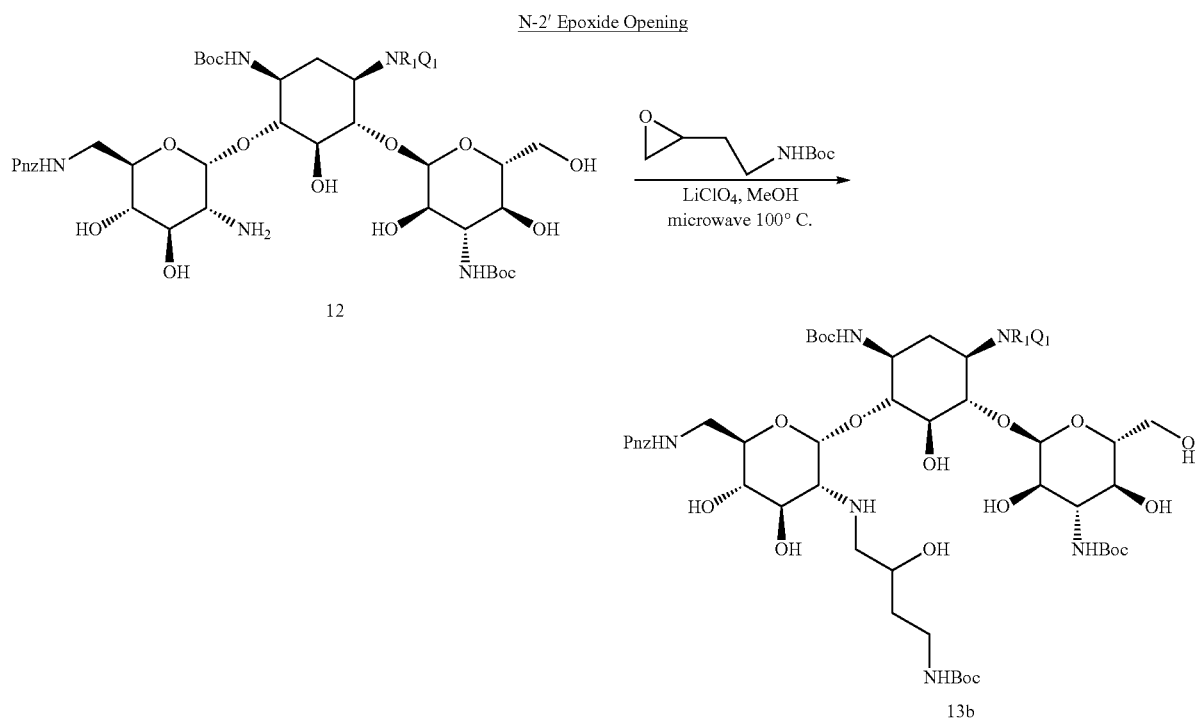
Example 13
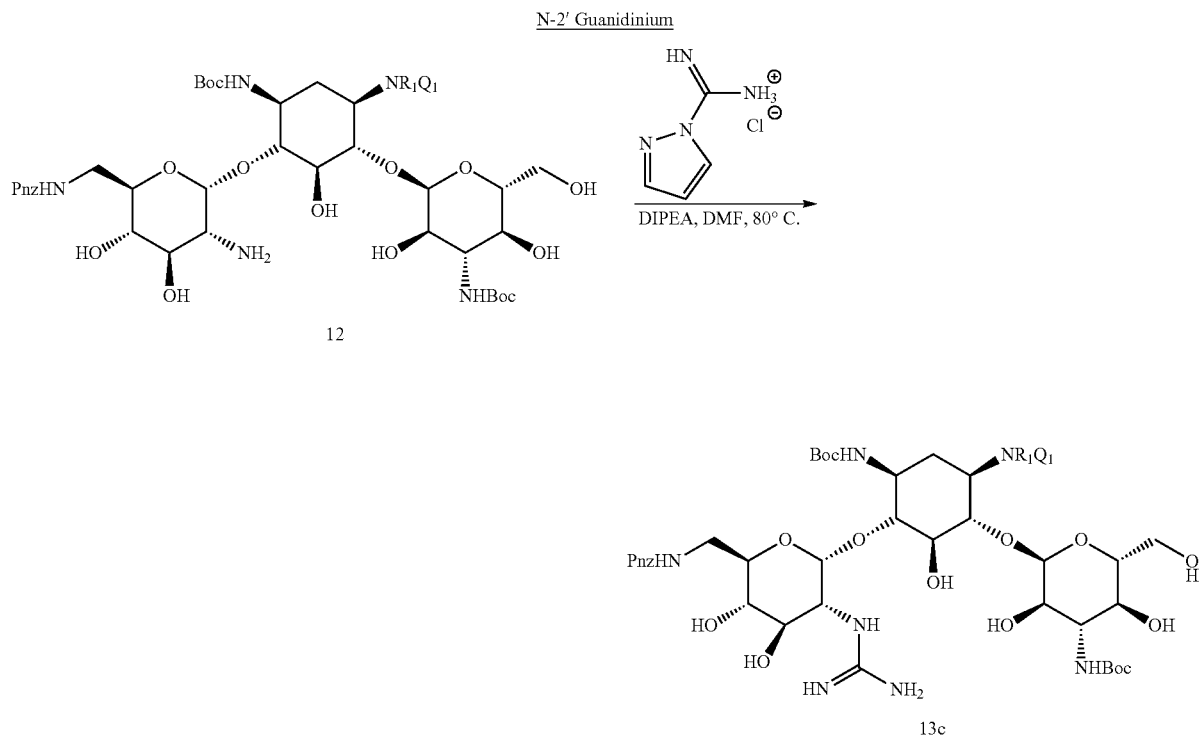

Example 14
N-2' Acylation
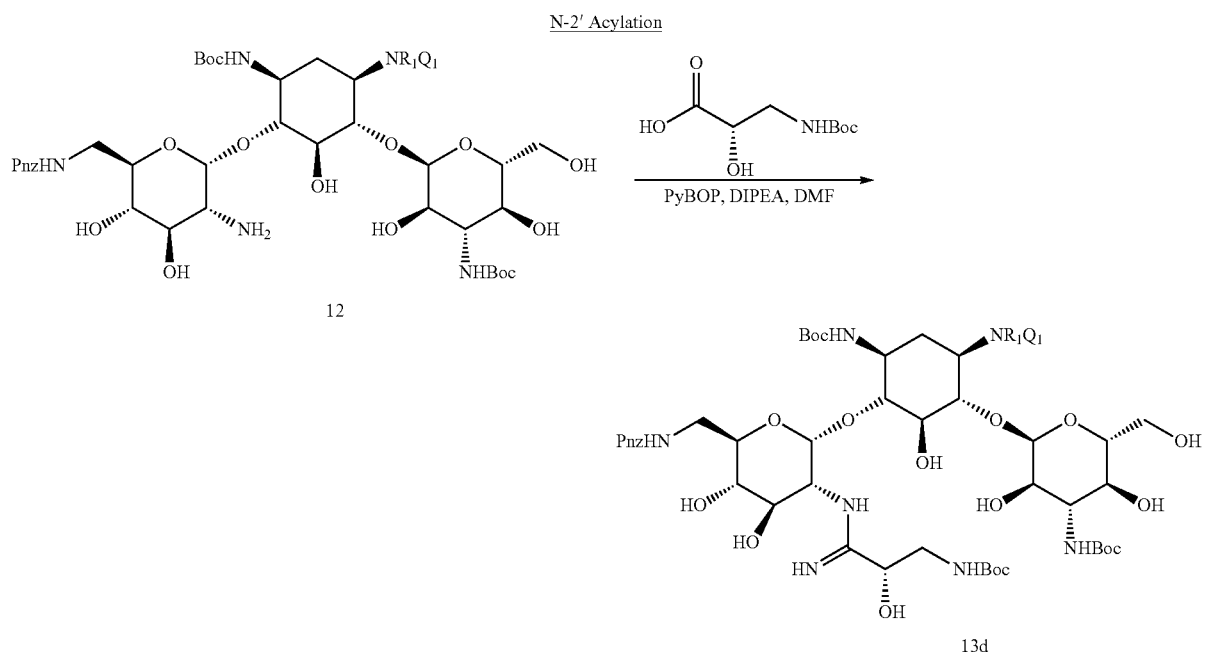
Kanamycin A Analogs
Scheme 1
N-6', N-1 Bis-substituted Kanamycin A Analogs
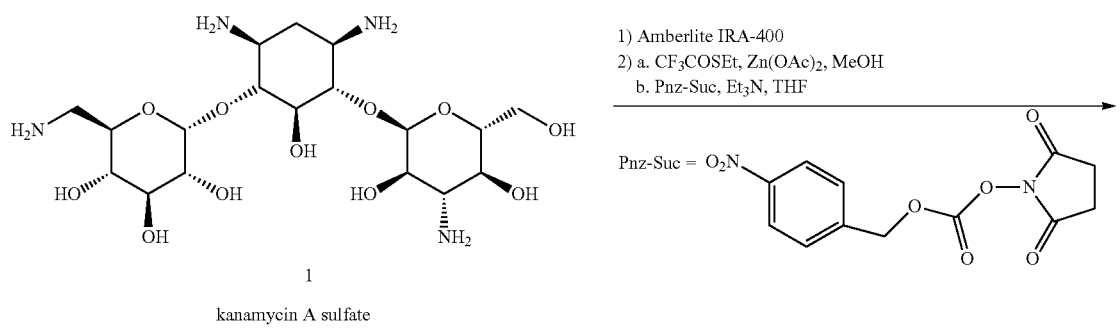
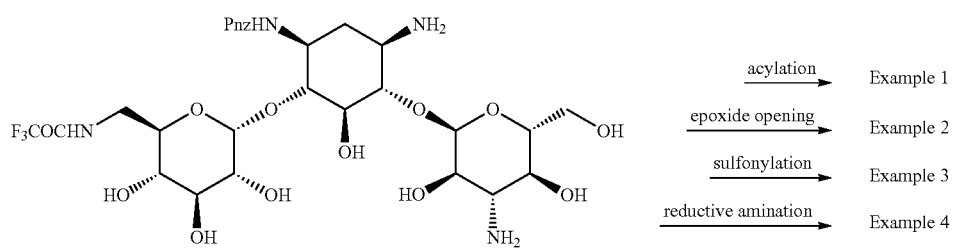

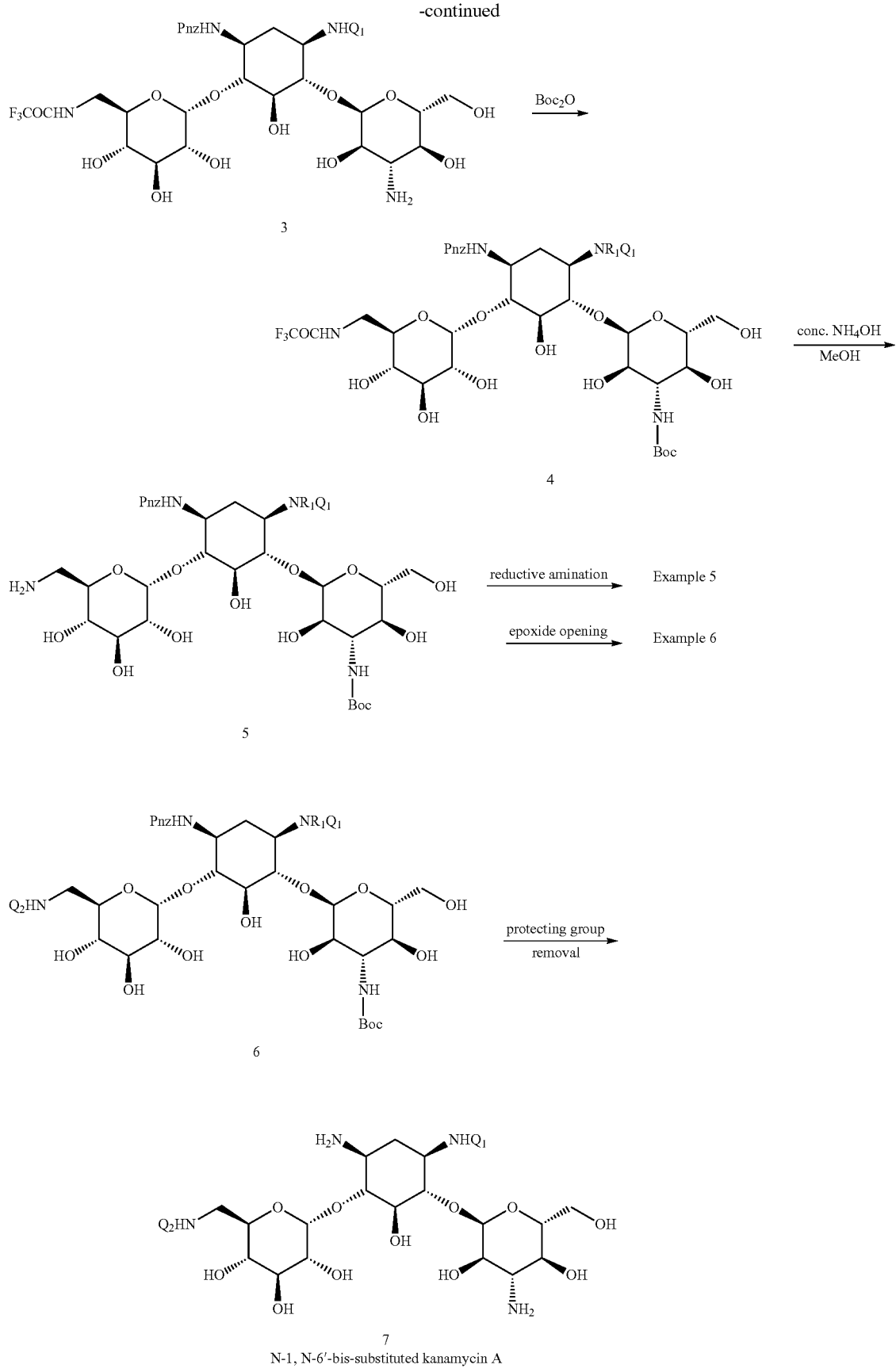
N-1, N-6'-bis-substituted kanamycin A

Example 1
N-1 Acylation
Method A:
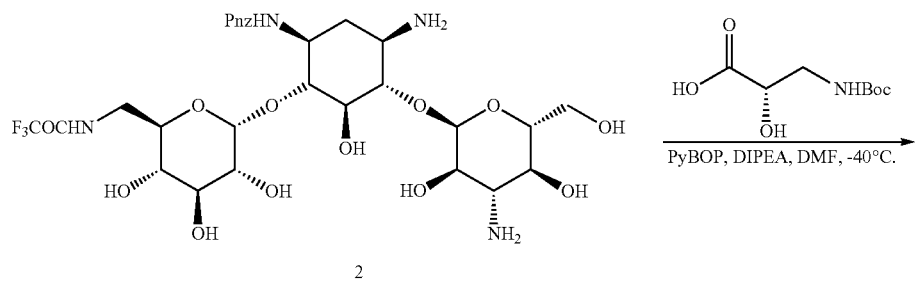
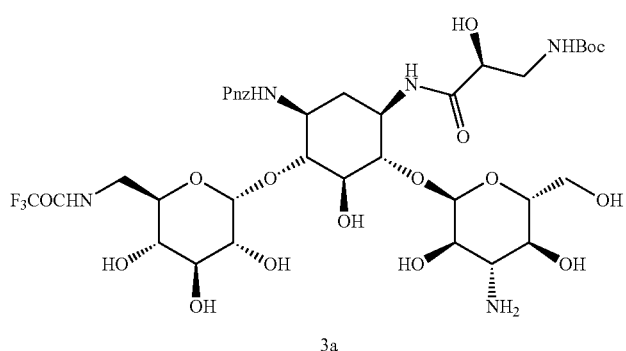
Method B:
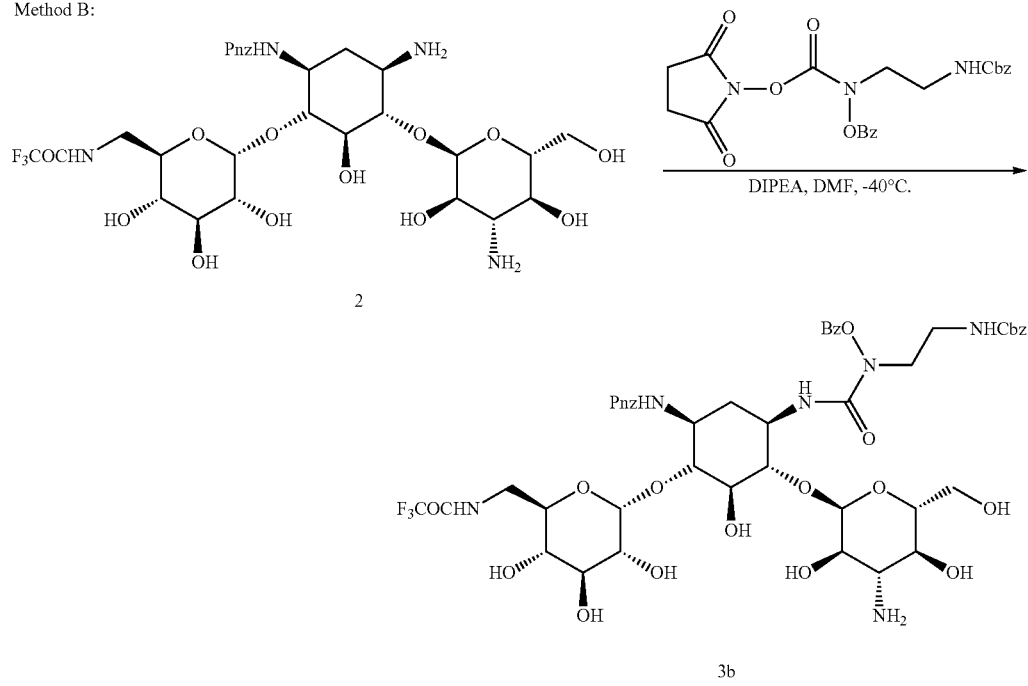

Example 2
N-1 Epoxide Opening
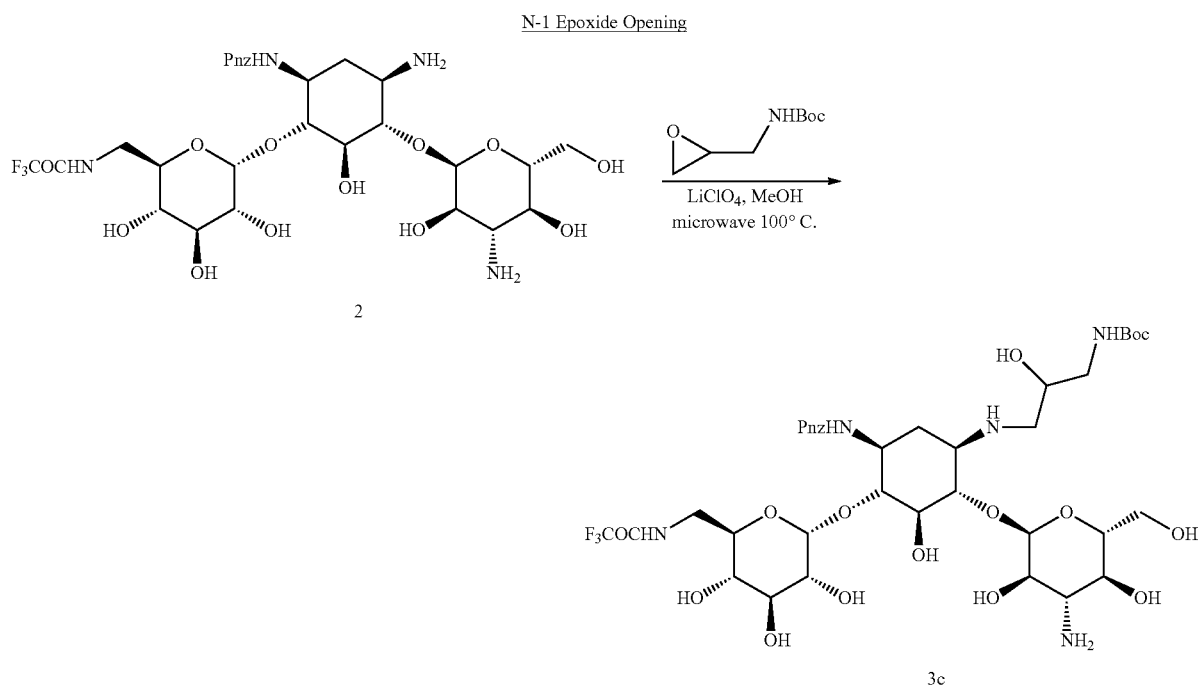
Example 3
N-1 Sulfonylation
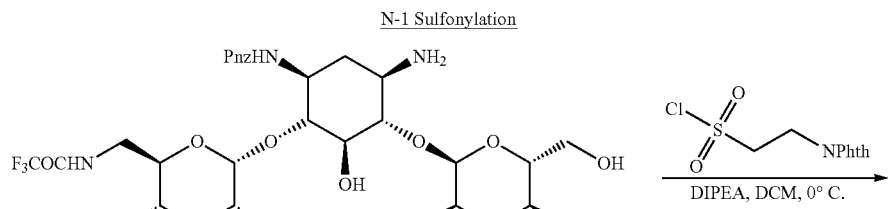
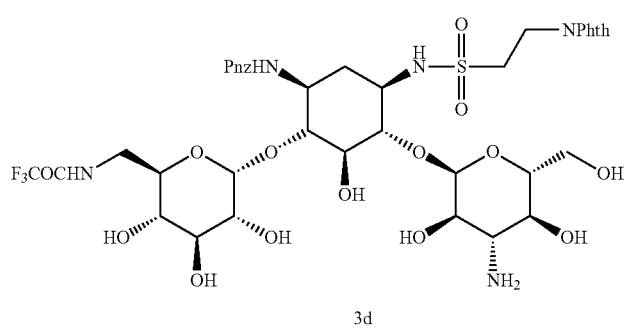
Phth = phthalimido

Example 4
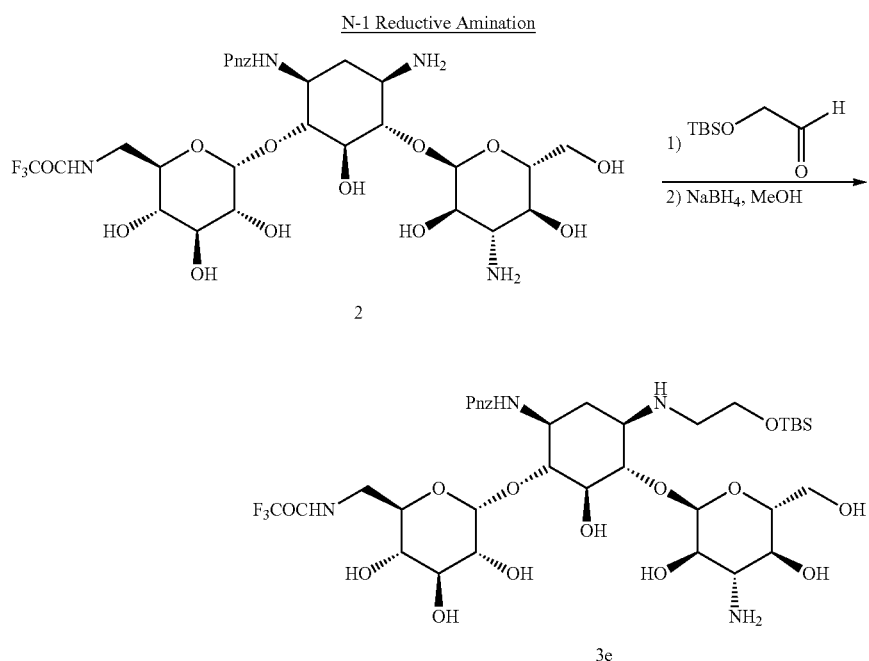
Example 5
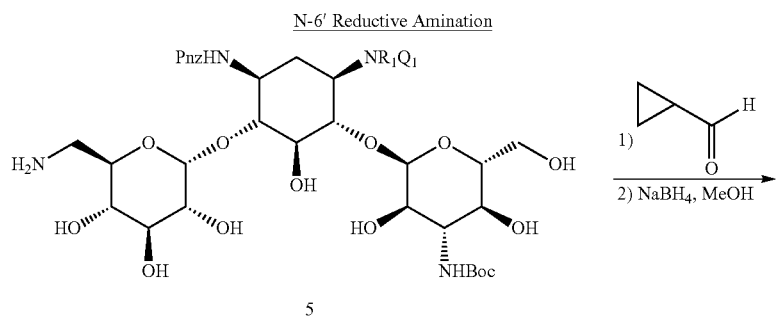
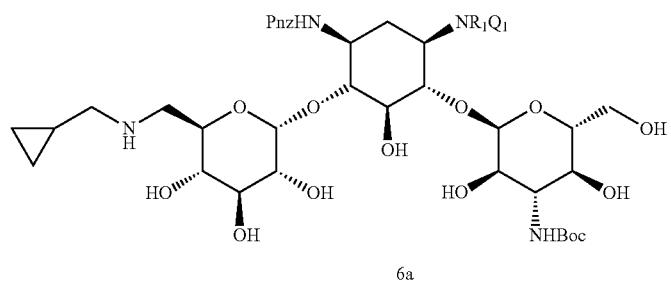

Example 6
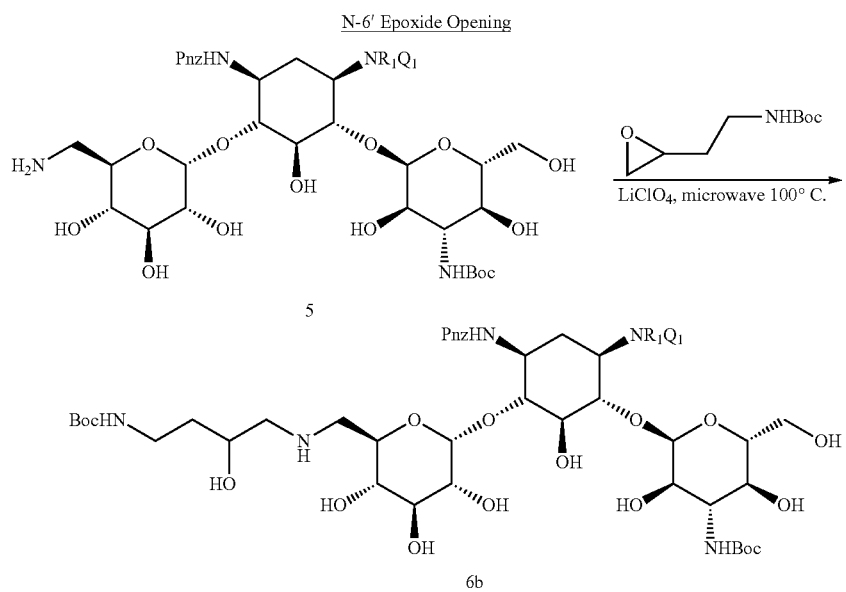
Representative Coupling Agents
As one of skill in the art will appreciate, other representative coupling agents that may be utilized in the above examples include, but are not limited to, the following.
Representative N-1 Coupling Reagents
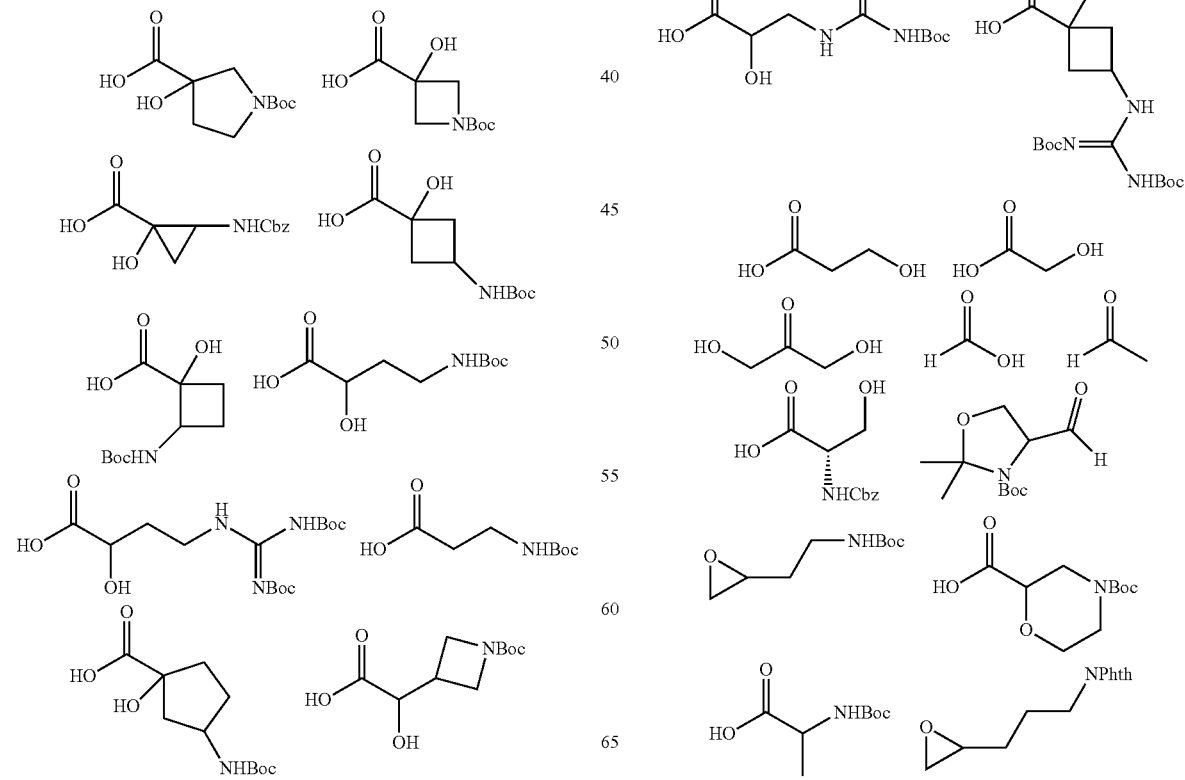

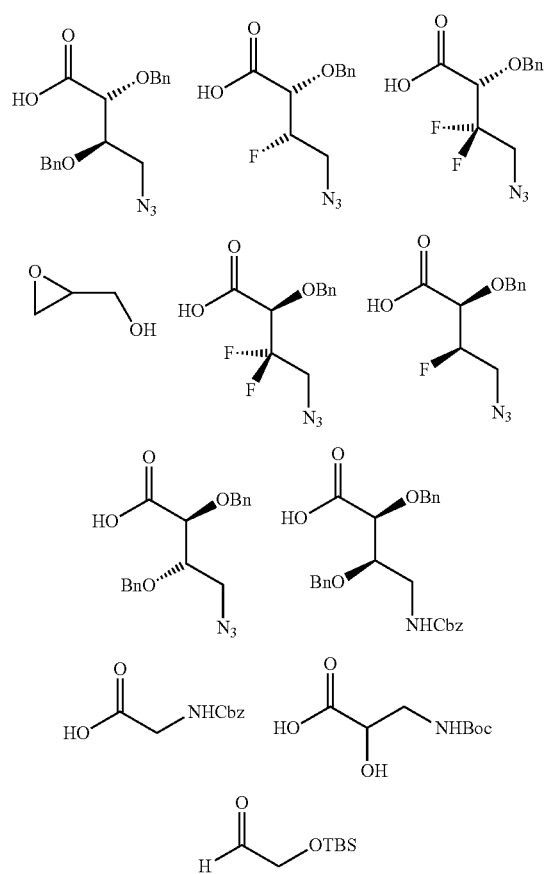
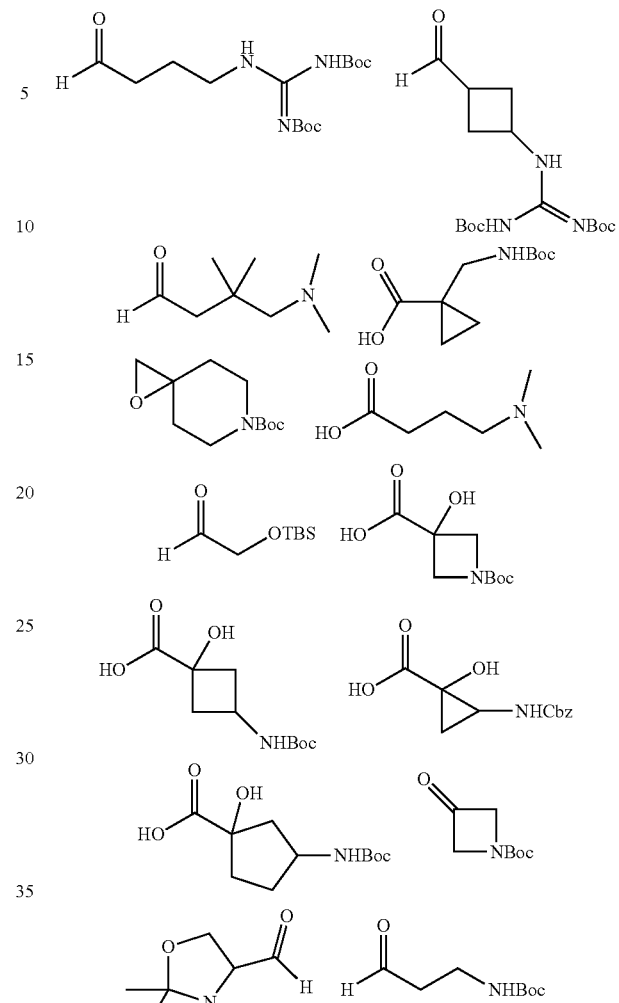
Representative N-2' Coupling Reagents
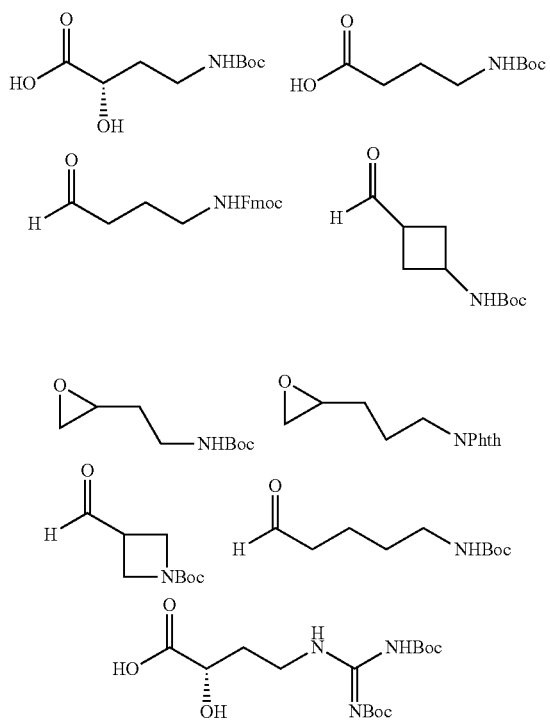
Representative N-6' Coupling Reagents
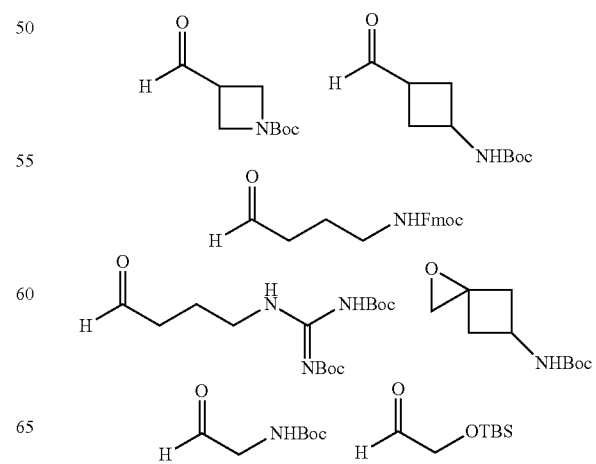

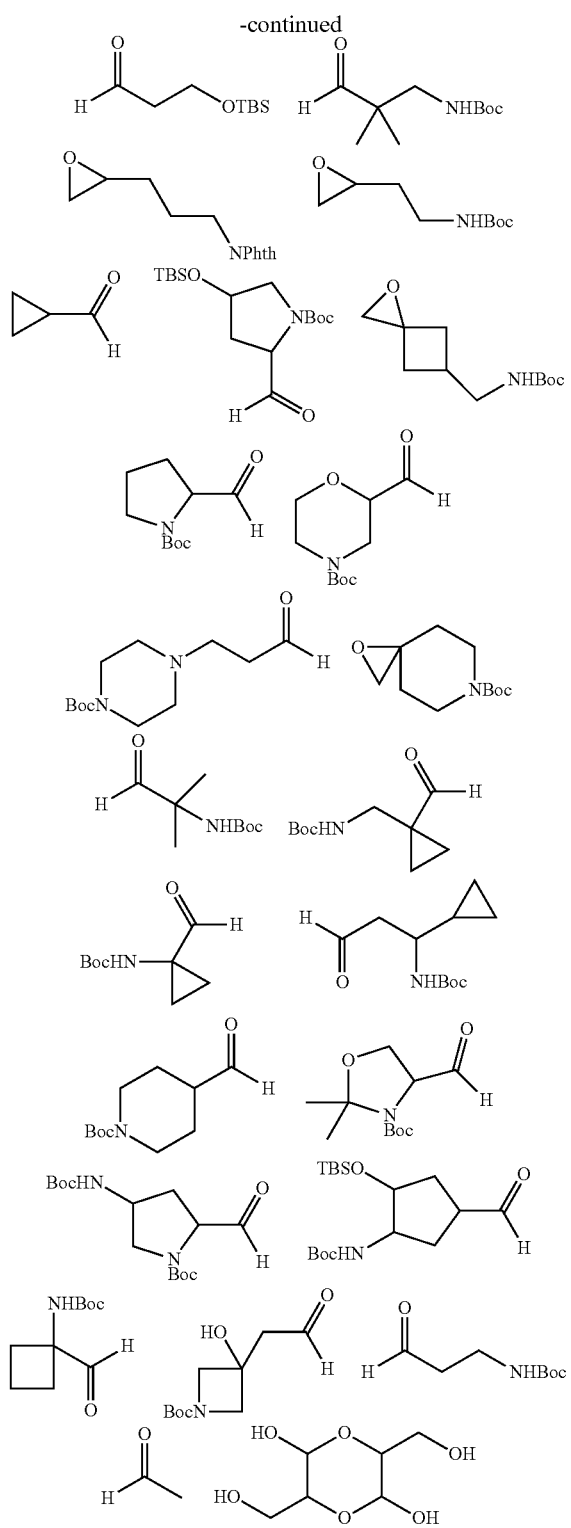

General Synthetic Procedures

Procedure 1: Reductive Amination

Method A: To a stirring solution of the aminoglycoside derivative (0.06 mmol) in MeOH (2 mL) was added the aldehyde (0.068 mmol), silica supported cyanoborohydride (0.1 g, 1.0 mmol/g), and the reaction mixture was heated by microwave irradiation to 100° C. (100 watts power) for 15 minutes. The reaction was checked by MS for completeness, and once complete all solvent was removed by rotary evaporation. The resulting residue was dissolved in EtOAc (20 ml), and washed with 5% NaHCO$_3$ (2×5 mL), followed by brine (5 mL). The organic phase was then dried over Na$_2$SO$_4$, filtered and the solvent was removed by rotary evaporation.

Method B: To a solution of aminoglycoside derivative (0.078 mmol) in DMF (1 ml) were added 3 Å molecular sieves (15-20), followed by the aldehyde (0.15 mmol) and the reaction was shaken for 2.5 hours. The reaction was checked by MS for completeness and, if needed, more aldehyde (0.5 eq) was added. The reaction mixture was then added dropwise to a stirring solution of NaBH$_4$ (0.78 mmol) in MeOH (2 mL) at 0° C., and the reaction was stirred for 1 hour. The reaction was diluted with H$_2$O (2 mL) and EtOAc (2 ml). The organic layer was separated and the aqueous layer was extracted with EtOAc (3×3 mL). The combined organic layers were dried over Na$_2$SO$_4$, filtered and concentrated to dryness.

Procedure 2: PNZ Deprotection

To a stirring solution of the PNZ protected aminoglycoside derivative (0.054 mmol) in EtOH (1.5 mL) and H$_2$O (1 mL) was added 1N NaOH (0.3 mL), followed by Na$_2$S$_2$O$_4$ (0.315 mmol), and the reaction mixture was heated at 70° C. for 12 hours. The reaction progress was monitored by MS. Once complete, the reaction mixture was diluted with H$_2$O (5 mL) and then extracted with EtOAc (2×10 mL). The combined organic layers were washed with H$_2$O (2×5 mL), brine (5 mL), dried over Na$_2$SO$_4$, filtered and concentrated to dryness.

Procedure 3: Boc Deprotection (tert-butyl dimethyl silyl Protecting Group is Removed Under These Conditions)

Important: Before Boc deprotection a sample must be dried well by pumping at high vacuum for 3 h.

Method A: To a stirring solution of the Boc protected aminoglycoside (0.054 mmol) in DCM (1 mL) were added 3 Å molecular sieves (4-6), and trifluoroacetic acid (0.6 mL). The reaction was stirred at room temperature for 1 h, and checked for completeness by MS. Upon completion the reaction mixture was diluted with ether (15 mL) to induce precipitation. The vial was centrifuged and the supernatant was decanted. The precipitate was washed with ether (2×15 ml), decanted and dried under vacuum.

Method B: To a stirring solution of Boc-protected aminoglycoside derivative (0.078 mmol) in DCM (1.5 mL) at 0° C. was added trifluoroacetic acid (1.5 mL). The reaction was stirred for 45 minutes, and checked for completeness by MS. Upon completion, the reaction was diluted with dichloroethane (10 ml) and concentrated to dryness. The last dilution/concentration step was repeated twice.

Procedure 4: PyBOP Coupling

To a stirring solution of aminoglycoside derivative (0.078 mmol) in DMF (1 mL) at −40° C. was added the acid (0.16 mmol), followed by PyBOP (0.16 mmol) and DIPEA (0.31 mmol) and the reaction was stirred. The reaction mixture was diluted with EtOAc (3 mL) and H$_2$O (3 mL), and the aqueous layer was separated and extracted with EtOAc (3×3 mL). The combined organic layers were dried over Na$_2$SO$_4$, filtered and concentrated to dryness.

Procedure 5: Epoxide Opening

To a stirring solution of the aminoglycoside derivative (0.06 mmol) in MeOH (2 mL) was added the epoxide (0.07 mmol), LiClO$_4$ (0.15 mmol), and the reaction mixture was heated by microwave irradiation to 100° C. for 90 minutes. The reaction progress was monitored by MS. Upon completion, the solvent was removed by rotary evaporation. The resulting residue was dissolved in EtOAc (20 mL), washed with H$_2$O (2×5 mL) and brine (5 mL), dried over Na$_2$SO$_4$, filtered and concentrated to dryness.

Procedure 6: Phthalimido Deprotection

To a stirring solution of the phthalimido protected aminoglycoside (0.064 mmol) in EtOH (3 mL) was added hydrazine (0.32 mmol), and the reaction mixture was heated to reflux for 2 h. The reaction progress was monitored by MS. Upon cooling to room temperature, the cyclic by-product precipitated and was removed by filtration. The filtrate was concentrated to dryness to yield a residue, which was dissolved in EtOAc (20 mL), washed with 5% NaHCO$_3$ (2×5 mL) and brine (5 mL), dried over Na$_2$SO$_4$, filtered and concentrated to dryness.

Procedure 7: Addition of Guanidinium Group

To a stirring solution of the aminoglycoside derivative (0.063 mmol) in DMF (1 mL) was added 1H-pyrazole-1-carboxamidine hydrochloride (0.09 mmol), followed by DIPEA (0.862 ml) and the reaction mixture was heated to 80° C. and stirred overnight. The reaction progress was monitored by MS. Upon completion, the reaction mixture was cooled to room temperature and diluted with water (3 mL). The aqueous phase was separated and extracted with EtOAc (2×5 mL), and the combined organics were washed with brine (5 mL), dried over Na$_2$SO$_4$, filtered and concentrated to dryness.

Procedure 8: Sulfonylation

To a stirring solution of the aminoglycoside (0.067 mmol) in DCM (3 mL) was added DIPEA (0.128 mol) and the sulfonyl chloride (0.07 mmol). The reaction mixture was stirred at room temperature and its progress was monitored by MS. Once complete, the solvent was removed by rotary evaporation and the residue was dissolved in ethyl acetate (20 mL), washed with 5% NaHCO$_3$ (2×5 mL) and brine (5 mL), dried over Na$_2$SO$_4$, filtered and concentrated to dryness.

Procedure 9: N-Boc Protection

To a stirring solution of the amine (4.64 mmol) in THF (10 mL) was added 1N NaOH (10 mL), followed by Boc-anhydride (5.57 mmol) and the reaction progress was checked by MS. Once complete, the THF was removed by rotary evaporation and water (40 mL) was added. The aqueous phase was separated and extracted with Et$_2$O (2×30 ml). The aqueous phase was acidified to pH 3 by the addition of dilute H$_3$PO$_4$ and was then extracted with EtOAc (2×60 ml). The combined organic layers were washed with H$_2$O (2×30 mL) and brine (30 mL), dried over Na$_2$SO$_4$, filtered and concentrated to dryness.

Procedure 10: Syntheses of Epoxides

To a stirring solution of the alkene (5.16 mmol) in chloroform (20 mL) at 0° C. was added m-chloroperbenzoic acid (8.0 mmol) and the reaction mixture was stirred for 30 minutes at 0° C. and was then allowed to warm to room temperature. The reaction progress was monitored by MS and TLC, and additional portions of m-CPBA were added as needed. Upon completion, the reaction mixture was diluted with chloroform (50 mL) and washed with 10% aq. Na$_2$SO$_3$ (2×30 mL), 10% aq. NaHCO$_3$ (2×50 mL) and brine (50 mL). The organic layer was dried over Na$_2$SO$_4$, filtered and concentrated to yield a crude product, which was purified by flash chromatography (silica gel/hexanes:ethyl acetate 0-25%).

Procedure 11: General Procedure for Synthesis of α-Hydroxy Carboxylic Acids

Step #1. O-(Trimethylsilyl)cyanohydrines: A 50-mL flask equipped with a magnetic stirring bar and drying tube was charged with the ketone or aldehyde (0.010 mmol), followed by THF (50 mL), trimethylsilyl cyanide (1.39 g, 14 mmol), and zinc iodide (0.090 g, 0.28 mmol), and the reaction mixture was stirred at room temperature for 24 hr. Solvent evaporation gave a residue, which was dissolved in EtOAc (60 mL), washed with 5% aq. NaHCO$_3$ (2×30 mL), H$_2$O (30 mL), and brine (30 mL), dried over Na$_2$SO$_4$, filtered and concentrated to dryness to yield a crude, which was carried through to the next step without further purification.

Step #2. Acid hydrolysis to a hydroxy carboxylic acid: AcOH (25 ml) and conc. HCl (25 ml) were added to the unpurified material from step #1 and the reaction mixture was refluxed for 2-3 hr. The reaction mixture was then concentrated to dryness to give a white solid, which was carried through to the next step without further purification.

Step #3. Boc protection: To a stirring solution of solid from step #2 in 2 M NaOH (20 mL) and i-PrOH (20 mL) at 0° C. was added Boc$_2$O (6.6 g, 3 mmol) in small portions, and the reaction mixture was allowed to warm to room temperature over 4 h. i-PrOH was then evaporated, and H$_2$O (50 mL) was added, and the aqueous phase was separated and extracted with Et$_2$O (2×30 ml). The aqueous layer was acidified to pH 3 by addition of dilute H$_3$PO$_4$ and was extracted with EtOAc (2×60 ml). The combined organic layers were washed with H$_2$O (2×30 mL) and brine (30 mL), dried over Na$_2$SO$_4$, filtered and concentrated to yield the desired N-Boc-α-hydroxy carboxylic acids in 56-72% yield.

Procedure 12: Protection of Amine by Fmoc Group

To a stirring solution of the amine (0.049 mol) in DCM (100 mL), was added DIPEA (16 mL, 0.099 mol) and the reaction mixture was cooled to 0° C. Fmoc-Cl (12.8 g, 0.049 mol) was then added portion-wise over several minutes, and the reaction was allowed to warm to room temperature for 2 hr. The organic layer was washed with water (2×50 mL) and brine (50 mL), dried over Na$_2$SO$_4$, filtered and concentrated to dryness to yield the Fmoc protected amine (90-95% yield).

Procedure 13: Synthesis of Aldehydes via TEMPO/Bleach Oxidation

To a vigorously stirring solution of the alcohol (1.54 mmol) in DCM (4 mL) was added TEMPO (0.007 g, 0.045 mmol, 0.03 mol %) and a 2M aqueous KBr solution (75 mL, 0.15 mmol, 10 mol %) and the reaction mixture was cooled to −10° C. In a separate flask NaHCO$_3$ (0.5 g, 9.5 mmol) was dissolved in bleach (25 mL, Chlorox 6.0% NaOCl) to yield a 0.78 M buffered NaOCl solution. This freshly prepared 0.78 M NaOCl solution (2.3 mL, 1.8 mmol, 117 mol %) was added to the reaction mixture over 5 min and the reaction was stirred for an additional 30 min at 0° C. The organic phase was separated and the aqueous layer was extracted with dichloromethane (2×4 mL). The combined organic layers were washed with 10% aq. Na$_2$S$_2$O$_3$ (4 mL), sat. aq. NaHCO$_3$ (2×4 mL), brine (5 mL), dried over Na$_2$SO$_4$ and concentrated to dryness.

Procedure 14: Synthesis of Alcohols Via Borane Reduction

To a stirring solution of the acid (1.5 mmol) in THF (5 mL) at −10° C. was slowly added 1.0 M BH$_3$-THF (2.98 mL, 2.98 mmol). The reaction mixture was stirred vigorously for an additional 3 min at −10° C., and was then allowed to warm to room temperature overnight. The reaction was quenched by the dropwise addition of a solution of HOAc/H$_2$O (1:1 v/v, 2.0 mL). The THF was removed by rotary evaporation and sat. aq. NaHCO$_3$ (15 mL) was added. The aqueous layer was extracted with DCM (3×5 mL) and the combined organic layers were washed with sat. aq. NaHCO$_3$ (2×5 mL), brine (10 mL), dried over Na$_2$SO$_4$, filtered and concentrated to dryness.

Procedure 15: Ozonolysis and Pinnick Oxidation

The substrate olefin (0.5 to 0.75 mmol) was dissolved in DCM (30 mL) and the reaction was cooled to −78° C. Ozone was bubbled through until a blue color persisted (3 to 5 min), and the reaction was stirred for 1 hr. Argon was then bubbled through to remove excess ozone for 10 minutes. The reaction was further quenched by the addition of dimethyl sulfide (10 equiv.), and was stirred for 30 min with warming to rt. The solvent was reduced under vacuum to yield the crude aldehyde, which was dried under high-vacuum for 10 min, and used without further purification. To a stirring solution of the aldehyde in THF, tBuOH and H₂O (3:3:2, 10 mL), was added NaH₂PO₄ (4 equiv.) followed by 2-methyl-2-butene (10 equiv.) and sodium chlorite (2 equiv.), and the reaction was stirred for 4 hr. The reaction mixture was then added to sat. aq. NaCl (10 mL) and extracted with DCM (3×). The combined organic layers were dried over Na₂SO₄, filtered and reduced under vacuum to yield a crude, which was purified by flash chromatography (silica gel, 0→0.5 or 1% MeOH/DCM).

Procedure 16: Hydrogenolysis

To a stirring solution of aminoglycoside (0.031 mmol) in AcOH (2 mL), was added H₂O (1 mL), followed by Pd(OH)₂/C (40 mg) and the reaction was stirred under a hydrogen atmosphere for 3 hours. The catalyst was removed by filtration, and the reaction was diluted with water and lyophilized to yield a crude, which was purified on a 1-inch reverse phase HPLC column (buffered with 10 mM NH₄OH) to yield the desired product.

General Purification Procedures

Method #1: Purification by Basic Condition
Mobile Phases:
    A—Water with 10 mM NH₄OH
    B—Acetonitrile with 10 mM NH₄OH
Columns:
    A: Waters-XBridge Prep Shield RP18 Column
    19×250 mm, 5 μm
    Gradient: 20 min at 0%, then 0-20% in 200 min at a flow of 20 ml/min
    B: Waters-XBridge Prep Shield RP18 Column
    50×100 mm, 5 μm
    Gradient: 20 min at 0%, then 0-20% in 200 min at a flow of 20 ml/min
Method #2: Purification by Acidic Condition
Mobile Phases:
    A—Water with 0.1% TFA
    B—Acetonitrile with 0.1% TFA
Columns:
    A: Phenomenex Luna C18
    21.4×250 mm, 10 μm
    Gradient: 0-100%, flow 25 ml/min
    B: Phenomenex Luna C18
    50×250 mm, 10 μm
    Gradient: 0-100%, flow 45 ml/min Representative Intermediates Aminoglycoside Freebasing Amberlite IRA-400 (OH form) (200 g) was washed with MeOH (3×200 ml). To a stirring suspension of the washed resin in MeOH (150 mL) was added aminoglycoside sulfate (20 g) and the mixture was stirred overnight. The resin was then filtered and washed with MeOH (100 mL) and the combined organic layers were concentrated to dryness to yield the desired aminoglycoside.

(N-Hydroxy-5-norbornene-2,3-dicarboxyl-imido)-4-nitro-benzoate

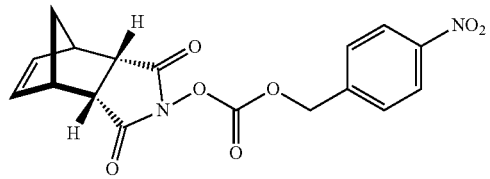

To a stirring solution of 4-nitrobenzyl chloroformate (5.0 g, 0.023 mol) in THF (90 mL) at 0° C. was added N-hydroxy-5-norbornene-2,3-dicarboximide (4.16 g, 0.023 mol), followed by the dropwise addition of a solution of Et₃N (3.2 mL, 0.02 mol) in THF (50 mL) and the reaction was stirred for 4 hours with gradual warming to room temperature. The reaction vessel was then placed in the freezer (−5° C.) for 1 hour to induce precipitation of triethylamine hydrochloride, which was removed by filtration. The filtrate was concentrated to dryness to yield a residue, which was vigorously stirred in MeOH (80 mL) for 1 h and then filtered to yield (N-hydroxy-5-norbornene-2,3-dicarboxyl-imido)-4-nitro-benzoate as a white solid (7.98 g, 0.022 mol, 96% yield): TLC (hexanes:EtOAc v/v 1:1) Rf=0.35.

2,5-Dioxo-pyrrolidin-1-yl-4-nitrobenzyl carbonate (PNZ-succinimide)

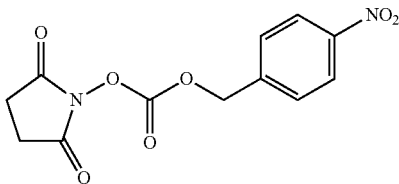 [SMILES: O=C(OCc1ccc([N+](=O)[O-])cc1)ON1C(=O)CCC1=O]

To a stirring solution of N-hydroxysuccinimide (5.35 g, 46.5 mmol) in anhydrous THF (100 mL) was added para-nitrobenzylchloroformate (10.0 g, 46.5 mmol), and the solution was cooled in an ice bath. Triethylamine (6.5 mL, 4.89 g, 46.5 mmol) was added over 10 minutes, and, after 30 minutes, the reaction mixture was allowed to warm to room temperature and stir overnight. The slurry was cooled in an ice-bath, and was filtered, followed by rinsing with ethyl acetate. The filtrate was concentrated in vacuo, and the residue was triturated with methanol. The solids were isolated by filtration to give 2,5-dioxopyrrolidin-1-yl-4-nitrobenzyl carbonate.

N,N'-bis-Cbz-2(S)-hydroxy-4-guanidino-butyric acid

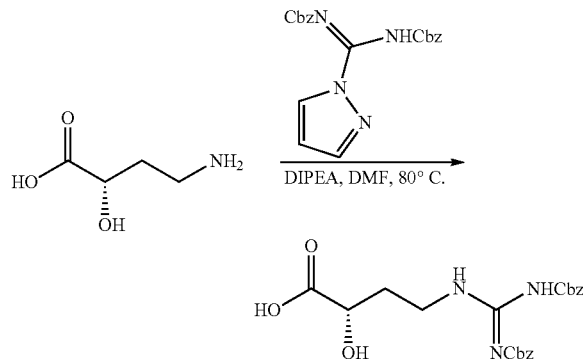

To a stirring solution of 2(S)-hydroxy-4-amino-butyric acid (0.059 g, 0.50 mmol) in DMF (2 ml) was added N,N'-bis(benzyloxycarbonyl)-1H-pyrazole-1-carboxamidine (0.26 g, 0.70 mmol) followed by DIPEA (0.87 mL, 4.99 mmol) and the reaction was heated to 80° C. and stirred overnight. The crude mixture was purified on a 2-inch reverse-phase HPLC column to yield N,N'-bis-Cbz-2(S)-hydroxy-4-guanidino-butyric acid: MS: m/z (M+H)+ calcd. 430.15, found 430.1.

Benzyl-2-(benzoyloxyamino)ethyl carbamate

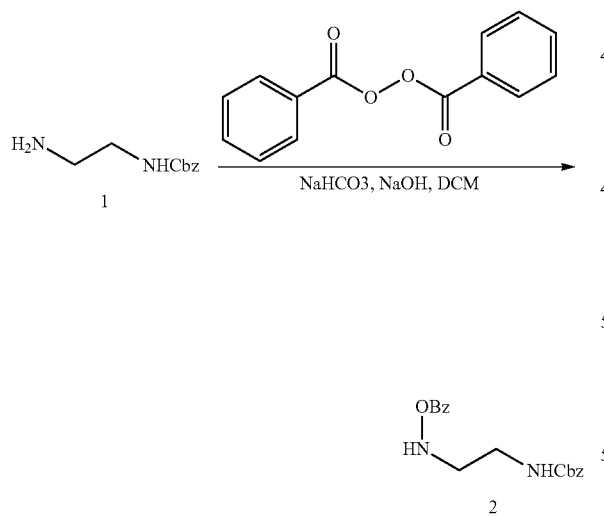

To a solution of benzyl-N-(2-aminoethyl)carbamate chloride salt (1, 540 mg, 2.34 mmol) in sat. aq. NaHCO$_3$ (45 mL) was added 1 M NaOH (15 mL) and the reaction was stirred vigorously. DCM (30 mL) was added, followed by benzoylperoxide (1.13 g, 4.68 mmol) and the reaction was stirred overnight. The organic layer was separated and washed with brine, dried over MgSO$_4$, filtered and concentrated to a crude, which was purified on a 1-inch reverse-phase HPLC column to yield benzyl-2-(benzoyloxyamino)ethyl carbamate (2, 252 mg, 0.80 mmol, 34.2%): MS: m/z (M+H)+ calc. 315.13, obs. 315.0.

Succinimidyl benzoyloxy(2-Cbz-aminoethyl)carbamate

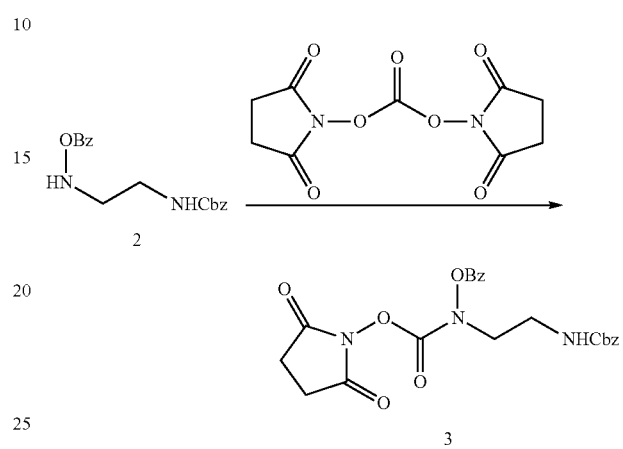

To a stirring solution of disuccinimidyl carbonate (525 mg, 2.05 mmol) in CH$_3$CN (16 mL) was added benzyl-2-(benzoyloxyamino)ethyl carbamate (2, 252 mg, 0.80 mmol) as a solution in CH$_3$CN (12 mL) over 4 hours, and the reaction was stirred overnight. Additional disuccinimidyl carbonate (251 mg, 0.98 mmol) was added and the reaction was heated at 60° C. overnight. Solvent removal gave a crude, which was purified on a 2-inch reverse-phase HPLC column to yield succinimidyl benzoyloxy(2-Cbz-aminoethyl)carbamate (3, 81 mg, 0.18 mmol, 22.5% yield).

N-Boc-3-amino-2(S)-hydroxy-propionic acid

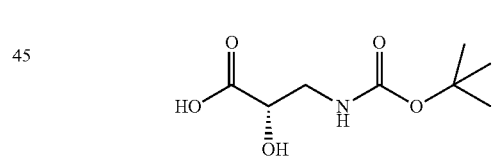

To a stirring solution of S-isoserine (4.0 g, 0.038 mol) in dioxane: H$_2$O (100 mL, 1:1 v/v) at 0° C. was added N-methylmorpholine (4.77 mL, 0.043 mol), followed by Boc$_2$O (11.28 mL, 0.049 mol) and the reaction was stirred overnight with gradual warming to room temperature. Glycine (1.0 g, 0.013 mol) was then added and the reaction was stirred for 20 min. The reaction was cooled to 0° C. and sat aq. NaHCO$_3$ (75 mL) was added. The aqueous layer was washed with ethyl acetate (2×60 mL) and then acidified to pH 1 with NaHSO$_4$. This solution was then extracted with ethyl acetate (3×70 mL) and these combined organic layers were dried over Na$_2$SO$_4$, filtered and concentrated to dryness to give the desired N-Boc-3-amino-2(S)-hydroxy-propanoic acid (6.30 g, 0.031 mmol, 81.5% yield): $^1$H NMR (400 MHz, CDCl$_3$) δ 7.45 (bs, 1 H), 5.28 (bs, 1 H), 4.26 (m, 1 H), 3.40-3.62 (m, 2 H), 2.09 (s, 1 H), 1.42 (s, 9 H);

$^{13}$C NMR (100 MHz, CDCl$_3$) δ 174.72, 158.17, 82, 71.85, 44.28, 28.45.

(N-Hydroxy-5-norbornene-2,3-dicarboxyl-imido)-tert-butyl-carbonate

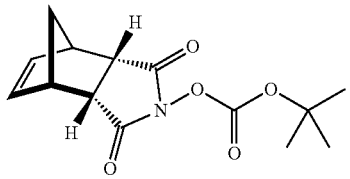

To a stirring solution of N-hydroxy-5-norbornene-2,3-dicarboximide (20.0 g, 0.112 mol) in THF (200 mL) at 0° C. was added triethylamine (0.65 mL, 4.8 mmol), followed by the dropwise addition of a solution of Boc$_2$O (29.23 g, 0.134 mol) in THF (30 mL) and the reaction was allowed to stir overnight with gradual warming to room temperature. A precipitate formed, which was filtered and washed with cold THF (200 mL). The crude solid was then vigorously stirred in MeOH (100 mL) for 1 hour, before being filtered, washed with MeOH (50 mL), and dried under high vacuum to yield the desired (N-hydroxy-5-norbornene-2,3-dicarboxyl-imido)-tert-butylcarbonate as a white solid (28.0 g, 0.1 mol, 89.3% yield): TLC (hexanes:ethyl acetate, 1:1 v/v) R$_f$=0.44; NMR (400 MHz, DMSO-d$_6$) δ 6.10 (bs, 2 H), 3.48 (bs, 2 H), 3.29-3.32 (m, 2 H), 1.58-1.62 (m, 1 H), 1.50-1.55 (m, 1 H), 1.47 (s, 9 H).

N-Boc-4-amino-2(S)-hydroxy-butyric acid

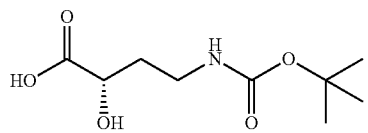

To a stirring solution of S-4-amino-2-hydroxy-butyric acid (51.98 g, 0.44 mol) in dioxane: H$_2$O (2 L, 1:1 v/v) was added K$_2$CO$_3$ (106 g, 0.91 mol) followed by a solution of Boc-anhydride (100 g, 0.46 mol) in dioxane (100 mL), and the reaction was stirred overnight. The reaction was washed with DCM (2×300 mL), and the aqueous layer was acidified to pH 2 with H$_3$PO$_4$. The aqueous layer was extracted with DCM (2×300 mL), and the combined organic layers were dried over MgSO$_4$, filtered and concentrated to dryness to yield the desired N-Boc-4-amino-2(S)-hydroxybutyric acid (48.2 g, 50% yield).

N-Boc-3-amino-propanal

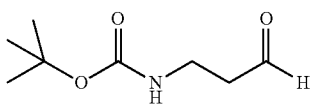

To a stirring solution of 3-(Boc-amino)-1-propanol (25 mL, 0.144 mol) in water saturated DCM (1.0 L) was added Dess-Martin reagent (99.2 g, 233.9 mmol) and the reaction mixture was stirred for 1 hour. The reaction was then diluted with ether (1.0 L), followed by a solution of Na$_2$S$_2$O$_3$ (250 g) in 80% NaHCO$_3$ (450 g in 1.0 L H$_2$O). The reaction was stirred vigorously for 30 minutes until two layers formed, the top layer was clear. The reaction was filtered to remove the precipitated solids and the aqueous layer was extracted with ether (1.0 L). The organic layer was washed with sat. NaHCO$_3$ (1.0 L), H$_2$O (1.0 L), and brine (1 L), dried over Na$_2$SO$_4$ and concentrated to a clear oil. The crude oil was dissolved in EtOAc:hexanes (1:1 v/v, 1.0 L) and filtered through a short silica gel column to yield the desired N-Boc-3-amino-propanal (21.7 g, 0.125 mol, 85.6% yield): $^1$H NMR (400 MHz, CDCl$_3$) δ 9.77 (s, 1H, CHO), 4.85 (bs, 1 H, NH), 3.36-3.42 (m, 2H, CH$_2$), 2.67 (t, 2H, CH$_2$), 1.39 (s, 9H, (CH$_3$)$_3$).

N-Boc-1-oxa-6-azaspiro[2.5]octane

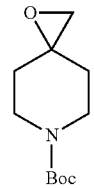

4-Methylene-piperidine (0.222 g, 1.12 mmol) was submitted to Procedure 10 to form the desired N-Boc-1-oxa-6-azaspiro[2.5]octane (0.215 g, 1.01 mmol, 90.2% yield): $^1$H NMR (250 MHz, DMSO-d$_6$) δ 3.29-3.61 (m, 6 H), 1.56-1.70 (m, 2 H), 1.30-1.54 (m, 11 H).

2-(Pent-4-enyl)-isoindoline-1,3-dione

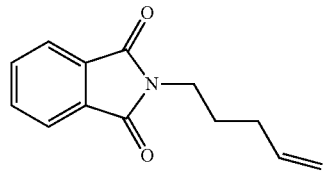 [SMILES: C=CCCCN1C(=O)c2ccccc2C1=O]

To a stirring solution of 5-bromo-pentene (6.0 g, 0.040 mol) in DMF (30 mL) was added K$_2$CO$_3$ (4.7 g, 0.034 mol) and potassium phthalimide (6.21 g, 0.033 mmol) and the reaction mixture was heated at 100° C. for 1 hr. The reaction mixture was cooled to room temperature, and water (50 mL) was added. The aqueous layer was then extracted with ethyl acetate (2×50 mL), and the combined organic layers were washed with 5% aq. NaHCO$_3$ (2×20 mL), brine (30 mL) and dried over Na$_2$SO$_4$. Filtration and solvent evaporation gave an oil, which was purified by flash chromatography (silica gel/hexanes:ethyl acetate 0-35%) to yield the desired 2-(pent-4-enyl)-isoindoline-1,3-dione as a solid (6.36 g, 0.029 mmol, 72.5% yield): MS m/e [M+H]$^+$ calcd 216.1, found 216.1;

NMR (250 MHz, DMSO-d$_6$) δ 7.79-7.95 (m, 4 H), 5.70-5.91 (m, 1 H), 4.90-5.11 (m, 2 H), 3.58 (t, 2 H), 1.98-2.10 (m, 2 H), 1.59-1.78 (m, 2 H).

2-(3-(Oxiran-2-yl)-propyl)-isoindoline-1,3-dione

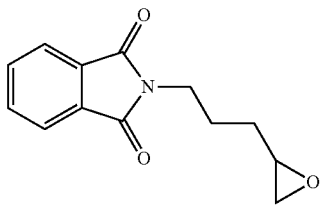 [SMILES: O=C1c2ccccc2C(=O)N1CCCC1CO1]

2-(Pent-4-enyl)-isoindoline-1,3-dione (6.36 g, 0.029 mmol) was submitted to Procedure 10 for epoxide formation to yield 2-(3-(oxiran-2-yl)-propyl-isoindoline-1,3-dione (5.8 g, 0.025 mmol, 86.2% yield): MS m/e [M+H]$^+$ calcd 232.1, found 232.1; $^1$H NMR (250 MHz, DMSO-d$_6$) δ 7.75-7.90 (m, 4H, Ar), 3.52 (t, 2H, CH$_2$), 2.87-2.96 (m, 1H, CH), 2.70 (t, 1 H), 2.30-2.45 (m, 1 H), 1.36-1.80 (m, 4 H).

N-Boc-3-hydroxypyrrolidine-3-carboxylic acid

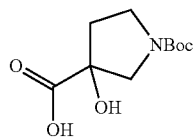 [SMILES: CC(C)(C)OC(=O)N1CCC(O)(C(=O)O)C1]

N-Boc-3-pyrrolidone (0.010 mmol) was submitted to Procedure 11 to yield the desired N-Boc-3-hydroxy-pyrrolidine-3-carboxylic acid.

N-Boc-1-amino-but-3-ene

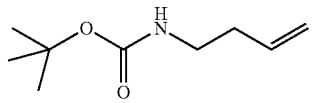

3-Buten-1-amine (4.93 g, 0.069 mol) was submitted to Procedure 9 for Boc protection to yield a crude, which was purified by flash chromatography (silica gel/hexanes:ethyl acetate 0-30%) to yield N-Boc-1-amino-but-3-ene (6.47 g, 0.038 mol, 55.1% yield).

N-Boc-2-(oxiran-2-yl)-ethyl carbamate

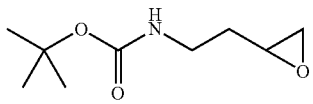

N-Boc-1-amino-but-3-ene (6.47 g, 0.038 mol) was submitted to Procedure 10 for epoxide formation to yield a crude, which was purified by flash chromatography (silica gel/hexanes:ethyl acetate 0-45%) to yield N-Boc-2-(oxiran-2-yl)-ethyl carbamate (6.0 g, 0.032 mol, 84.2% yield): $^1$H NMR (250 MHz, DMSO-d$_6$) δ 2.98-3.09 (m, 2 H), 2.83-2.92 (m, 1 H), 2.65 (t, 1 H), 2.42 (dd, 1 H), 1.44-1.66 (m, 2 H), 1.36 (s, 9H, (CH$_3$)$_3$).

N-Boc-3-hydroxy-azetidin-3-carboxylic acid

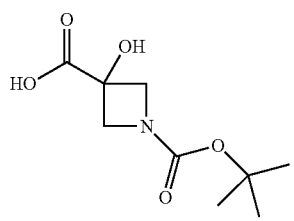

N-Boc-3-azetidinone (21.9 g, 0.128 mol) was submitted to Procedure 11 to yield the desired N-Boc-3-hydroxy-azetidin-3-carboxylic acid (18.7 g, 0.086 mol, 67.0% yield): MS m/e [M+H]$^+$ calcd 218.1, found 218.2.

3-Methylene-1-methylamino-cyclobutane

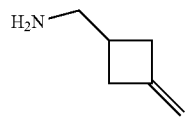

To a stirring solution of 3-methylene-1-cyano-cyclobutane (2.5 g, 0.026 mol) in THF (35 ml) at 0° C. was slowly added 2M LiAlH$_4$ (22 mL, 0.044 mmol) and the reaction was allowed to warm to room temperature. The reaction was then quenched by the addition of sat. aq. NH$_4$Cl (10 mL), and THF (10 mL). The organic layer was separated and concentrated to dryness to yield a residue, which was dissolved in ethyl acetate (100 mL). The organic layer was washed with 5% NaHCO$_3$ (2×20 mL), brine (20 mL), dried over Na$_2$SO$_4$, filtered and concentrated to yield the desired 3-methylene-1-methylamino-cyclobutane as an oil, which was carried through to the next step without further purification.

3-Methylene-1-N-Boc-methylamino-cyclobutane

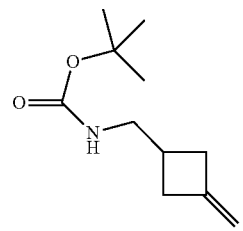

To a stirring solution of 3-methylene-1-methylamino-cyclobutane (2.52 g, 0.026 mol) in 1N NaOH (15 ml) and THF (15 mL), was added Boc$_2$O (6.7 g, 0.030 mol) and the reaction mixture was stirred overnight. THF was evaporated and the aqueous layer was extracted with ethyl acetate (2×40 mL). The combined organic layers were washed with 5% NaHCO$_3$ (2×20 mL) brine (20 mL), dried over Na$_2$SO$_4$, filtered and concentrated to dryness to yield a crude, which was purified by flash chromatography (silica gel/hexanes:ethyl acetate 0%-60%) to yield the desired 3-methylene-1-N-Boc-methylamino-cyclobutane (1.9 g, 0.0096 mol, 36.9% yield): $^1$H NMR (250 MHz, DMSO-d$_6$) δ 6.88 (bs, 1 H), 4.72 (s, 2 H), 2.95-3.05 (m, 2 H), 2.56-2.71 (m, 2 H), 2.21-2.40 (m, 3 H), 1.20 (s, 9 H).

N-Boc-1-oxaspiro[2.3]hexan-5-yl-methanamine

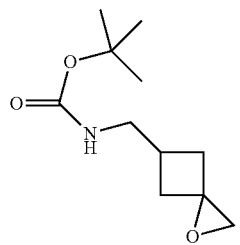

3-Methylene-1-N-Boc-methylamino-cyclobutane (1.9 g, 0.0096 mol) was submitted to Procedure 10 for epoxide formation to yield N-Boc-1-oxaspiro[2.3]hexan-5-yl-methanamine (1.34 g, 6.27 mol, 65.3% yield): $^1$HNMR (250 MHz, DMSO-d$_6$) δ 2.99-3.10 (m, 2 H), 2.60-2.66 (m, 2 H), 1.99-2.47 (m, 5 H), 1.40 (s, 9 H).

N-Fmoc-4-amino-butyraldehyde diethyl acetal

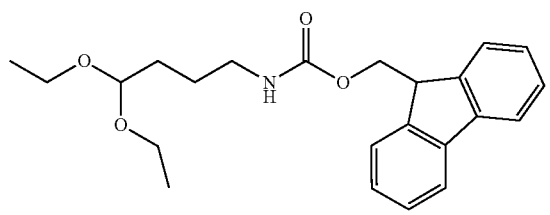 [SMILES: CCOC(CCCNC(=O)OCC1c2ccccc2-c2ccccc21)OCC]

4-Amino-butyraldehyde diethyl acetal (8.0 g, 0.050 mol) was Fmoc protected following Procedure 12 to give the desired N-Fmoc-4-amino-butyraldehyde diethyl acetal (22.08 g, MS m/e [M+Na]$^+$ calcd 406.2, found 406.1), which was carried through to the next step without further purification.

N-Fmoc-4-amino-butyraldehyde

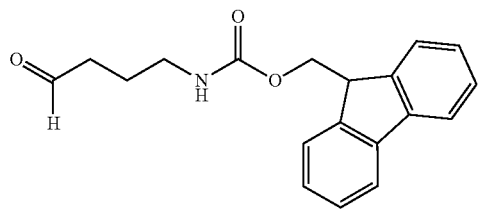 [SMILES: O=CCCCNC(=O)OCC1c2ccccc2-c2ccccc21]

To a stirring solution of N-Fmoc-4-amino-butyraldehyde diethyl acetal (0.050 mmol) in 1,4-dioxane (100 mL) was added aq. HCl (100 ml, 1:1 v/v, H$_2$O: conc. HCl) and the reaction progress was monitored by MS. Upon completion, the organic solvent was removed by rotary evaporation, and the aqueous layer was extracted with ethyl acetate (2×200 mL). The combined organic layers were washed with 5% NaHCO$_3$ (2×75 mL), brine (75 mL), dried over Na$_2$SO$_4$, filtered and concentrated to dryness to yield the desired N-Fmoc-4-amino-butyraldehyde (15.35 g, 0.049 mol, 90.0% yield), which was carried through to the next step without further purification: MS m/e [M+Na]$^+$ calcd 332.1, found 332.0.

3-Methylene-cyclobutane carboxylic acid

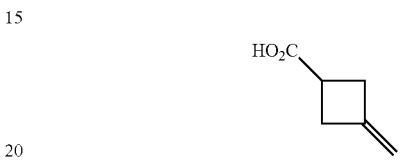

To a stirring solution of KOH (70.0 g, 1.25 mol) in EtOH/H$_2$O (500 mL, 1:1 v/v) was added 3-methylenecyclobutane carbonitrile (25.0 g, 0.26 mol) and the reaction mixture was refluxed for 6 h. The reaction progress was monitored by TLC and, upon completion, the mixture was cooled and acidified to pH 3-4 with HCl. The ethanol was evaporated, and the remaining aqueous layer was extracted with Et$_2$O (200 mL). The organic layer was washed with water (2×20 mL), brine (30 ml), dried over Na$_2$SO$_4$, filtered and concentrated to dryness to yield 3-methylene-cyclobutane carboxylic acid, which was carried through to the next step without further purification:
$^1$H NMR (250 MHz, CDCl$_3$) δ 10.75 (bs, 1 H), 4.80 (s, 2 H), 2.85-3.26 (m, 5 H).

N-Boc-3-Methylene-cyclobutanamine

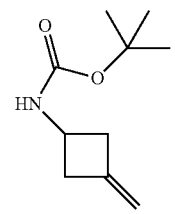

To a stirring solution of 3-methylene-cyclobutane carboxylic acid (1.0 g, 8.9 mmol) in THF (90 mL) was added NaN$_3$ (2.0 g, 31.1 mmol), followed by tetrabutyl ammonium bromide (0.48 g, 1.5 mmol) and Zn(OTf)$_2$ (0.1 g, 0.3 mmol), and the reaction mixture was heated to 40° C. Boc$_2$O (2.1 g, 9.8 mmol) was then added at once, and the reaction was heated at 45° C. overnight. The reaction was then cooled to 0° C. and was quenched with 10% aq. NaNO$_2$ (180 mL). The THF was evaporated and the aqueous layer was extracted with EtOAc (180 mL). The organic layer was washed with 5% aq. NaHCO$_3$ (2×20 mL), brine (30 ml), dried over Na$_2$SO$_4$, filtered and concentrated to dryness to yield a crude, which was purified by flash chromatography (silica gel/hexanes:ethyl acetate: 0-90%) to yield the desired N-Boc-3-methylene-cyclobutanamine (0.57 g, 3.1 mmol, 34.9% yield): $^1$H NMR (250 MHz, CDCl$_3$) δ 4.83 (s, 2 H), 4.79 (bs, 1 H), 4.05-4.23 (m, 1 H), 2.92-3.11 (m, 2 H), 2.50-2.65 (m, 2 H), 1.44 (s, 9 H).

N-Boc-1-oxaspiro[2.3]hexan-5-amine

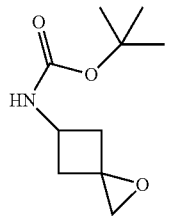

N-Boc-3-methylene-cyclobutanamine (1.65 g, 9.0 mmol) was submitted to Procedure 10 for epoxide formation to yield N-Boc-1-oxaspiro[2.3]hexan-5-amine (1.46 g, 7.33 mmol, 81.5% yield): $^1$H NMR (250 MHz, CDCl$_3$) δ 4.79 (bs, 1 H), 4.13-4.31 (m, 1 H), 2.66-2.83 (m, 4 H), 2.31-2.47 (m, 2 H), 1.45 (s, 9 H).

N-Boc-2,2-dimethyl-3-amino-propionaldehyde

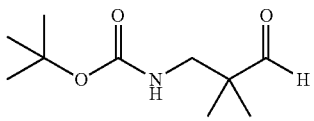

N-Boc-3-amino-2,2-dimethyl propanol (0.415 g, 2.04 mmol) was submitted to Procedure 13 to yield N-Boc-2,2-dimethyl-3-amino-propionaldehyde (0.39 g, 1.94 mmol, 95.1% yield): $^1$H NMR (250 MHz, CDCl$_3$) δ 9.42 (s, 1 H), 4.80 (bs, 1 H), 3.11 (d, 2 H), 1.39 (s, 9 H), 1.06 (s, 6 H).

N-Boc-3-amino-3-cyclopropyl propionaldehyde

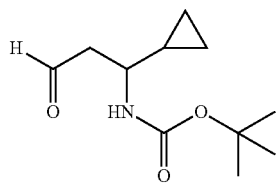

N-Boc-3-amino-propanol (0.130 g, 0.60 mmol) was submitted to Procedure 13 for oxidation to the corresponding N-Boc-3-amino-3-cyclopropyl propionaldehyde, which was carried through to the next step without further purification.

4(S)-tert-Butyldimethylsilyloxy-N-Boc-pyrrolidin-2 (R)-carboxaldehyde

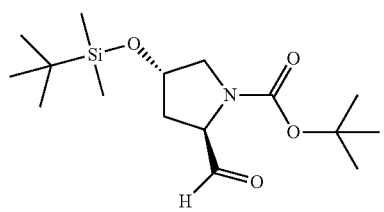 [SMILES: CC(C)(C)OC(=O)N1C[C@@H](O[Si](C)(C)C(C)(C)C)C[C@@H]1C=O]

4(S)-tert-Butyldimethylsilyloxy-N-Boc-pyrrolidin-2(R)-methanol (0.50 g, 1.50 mmol) was submitted to Procedure 13 for oxidation to the corresponding 4(S)-tert-butyldimethylsilyloxy-N-Boc-pyrrolidin-2(R)-carboxaldehyde, which was carried through to the next step without further purification.

3-tert-Butyldimethylsilyloxy-propanal

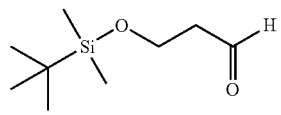

3-tert-Butyldimethylsilyloxy-propanol (0.50 g, 2.62 mmol) was submitted to Procedure 13 for oxidation to the corresponding 3-tert-butyldimethylsilyloxy-propanal, which was carried through to the next step without further purification.

2-Methyl-N-Boc-2-amino-propanal

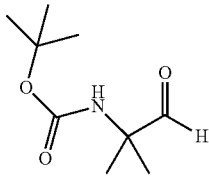

2-Methyl-N-Boc-2-amino-propanol (0.83 g, 4.38 mmol) was submitted to Procedure 13 for oxidation to the corresponding 2-methyl-N-Boc-2-amino-propanal (0.706 g, 3.77 mmol, 86.1% yield): $^1$H NMR (250 MHz, CDCl$_3$) δ 9.40 (s, 1 H), 1.57 (s, 1 H), 1.41 (s, 9 H), 1.30 (s, 6 H).

N-Boc-1-amino-cyclobutane carboxylic acid

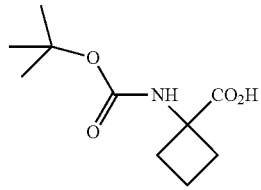

1-Amino-cyclobutane carboxylic acid ethyl ester (1.0 g, 6.28 mmol) was dissolved in 1N HCl (10 mL) and the reaction was heated to a reflux for 2 hours. The reaction mixture was then concentrated to dryness to yield a crude which was submitted to Procedure 9 for Boc protection to yield the desired N-Boc-1-Amino-cyclobutane carboxylic acid.

N-Boc-1-amino-cyclobutyl-methanol

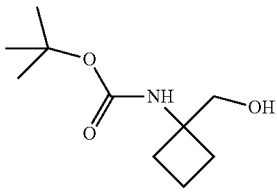

N-Boc-1-amino-cyclobutane carboxylic acid (6.28 mmol) was submitted to Procedure 14 for reduction to the corresponding N-Boc-1-Amino-cyclobutyl-methanol.

N-Boc-1-amino-cyclobutane carboxaldehyde

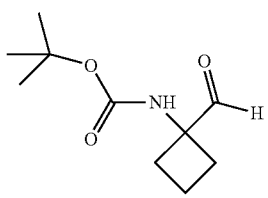

N-Boc-1-amino-cyclobutyl-methanol (0.25 g, 1.24 mmol) was submitted to Procedure 13 to yield the corresponding N-Boc-1-amino-cyclobutane carboxaldehyde (0.24 g, 1.20 mmol, 96.8% yield): $^1$H NMR (250 MHz, CDCl$_3$) δ 9.0 (s, 1 H), 4.91 (bs, 1 H), 3.74 (bs, 2 H), 1.71-2.20 (m, 4 H), 1.42 (s, 9 H).

N-Boc-3-amino-cyclobutanone

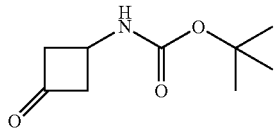

To a vigorously stirring solution of N-Boc-3-methylene-cyclobutanamine (9.8 g, 53.5 mmol) in DCM (160 mL) and H$_2$O (160 mL) was added K$_2$CO$_3$ (3 g, 21.7 mmol), followed by NaIO$_4$ (35 g, 163.5 mmol), tetrabutylammonium chloride (0.2 g, 0.72 mmol) and RuCl$_3$ (0.6 g, 7.6 mmol). During the course of the reaction, the organic solution turned dark brown, the catalyst turned black, while the upper aqueous layer turned white. The reaction was monitored by TLC, and upon completion, the reaction mixture was filtered through a pad of celite. The filtrates were transferred to a separatory funnel, and the aqueous layer was extracted with DCM (2×50 mL). The combined organic layers were washed with 5% NaHCO$_3$ (2×30 mL), brine (30 mL), dried over Na$_2$SO$_4$, filtered and evaporated to dryness to yield a crude, which was purified by flash chromatography (silica gel/hexanes:ethyl acetate 0-60%) to yield the desired N-Boc-3-amino-cyclobutanone (7.13 g, 38.53 mmol, 72% yield): NMR (250 MHz, CDCl$_3$) δ 4.88 (bs, 1 H), 4.13-4.29 (m, 1 H), 3.23-3.41 (m, 2 H), 2.9-3.05 (m, 2 H), 1.39 (s, 9 H).

N-Boc-1-hydroxy-3-amino-cyclobutyl-carboxylic acid

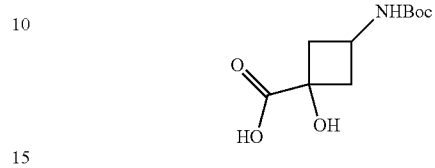

N-Boc-3-amino-cyclobutanone (7.13 g, 38.53 mmol) was submitted to Procedure 11 to yield the desired N-Boc-1-hydroxy-3-amino-cyclobutyl-carboxylic acid (MS m/e [M+E]$^+$ calcd 232.1, found 232.2.

N,N-diBoc-4(S)-amino-2(S)-methanol-pyrrolidine

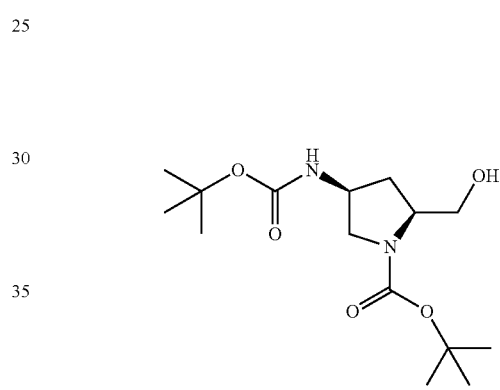

N,N-diBoc-4(S)-amino-pyrrolidine-2(S)-carboxylic acid (1.03 g, 3.12 mmol) was submitted to Procedure 14 to yield the corresponding N,N-diBoc-4(S)-amino-2(S)-methanol pyrrolidine (0.605 g, 1.91 mmol, 61.2% yield), which was carried through to the next step without further purification.

N,N-diBoc-4(S)-amino-pyrrolidine-2(S)-carbaldehyde

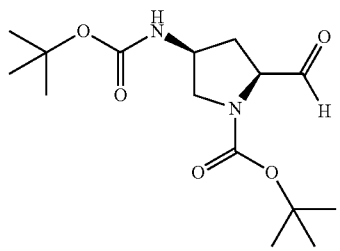 [SMILES: CC(C)(C)OC(=O)N[C@H]1C[C@@H](C=O)N(C(=O)OC(C)(C)C)C1]

N,N-diBoc-4(S)-amino-2(S)-methanol pyrrolidine (0.486 g, 1.53 mmol) was submitted to Procedure 13 for oxidation to the corresponding N,N-diBoc-4(S)-amino-pyrrolidine-2(S)-carbaldehyde, which was carried through to the next step without further purification.

N-Boc-1-aminomethyl-cyclopropyl-methanol

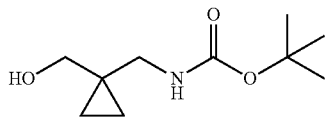

N-Boc-1-aminomethyl-cyclopropane carboxylic acid (1.0 g, 4.64 mmol) was submitted to Procedure 14 to yield the corresponding N-Boc-1-aminomethyl-cyclopropyl-methanol (0.99 g, MS m/e [M+H][30] calcd 202.1, found 202.1), which was carried through to the next step without further purification.

N-Boc-1-aminomethyl-cyclopropane carboxaldehyde

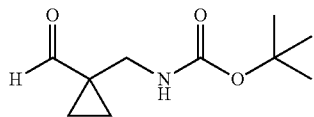

N-Boc-1-aminomethyl-cyclopropyl-methanol (0.87 g, 4.32 mmol) was submitted to Procedure 13 for oxidation to the corresponding N-Boc-1-aminomethyl-cyclopropane carboxaldehyde, which was carried through to the next step without further purification.

N-Boc-1-amino-cyclopropyl-methanol

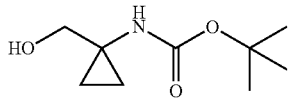

N-Boc-1-amino-cyclopropane carboxylic acid (0.25 g, 1.24 mmol) was submitted to Procedure 14 to yield the corresponding N-Boc-1-amino-cyclopropyl-methanol (0.051 g, 0.27 mmol, 21.8% yield), which was carried through to the next step without further purification.

N-Boc-1-amino-cyclopropane carboxaldehyde

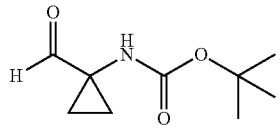

N-Boc-1-amino-cyclopropyl-methanol (0.051 g, 0.27 mmol) was submitted to Procedure 13 for oxidation to the corresponding N-Boc-1-amino-cyclopropane carboxaldehyde, which was carried through to the next step without further purification.

N-Boc-1(R)-amino-2(S)-tert-butyldimethylsilyloxy-cyclopentane-4(S)-carboxylic acid

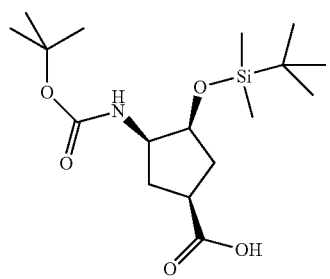 [SMILES: CC(C)(C)OC(=O)N[C@@H]1C[C@H](C(=O)O)C[C@@H]1O[Si](C)(C)C(C)(C)C]

To a stirring solution of N-Boc-1(R)-amino-2(S)-hydroxy-cyclopentane-4(S)-carboxylic acid methyl ester (0.622 g, 2.40 mmol) in DCM (1.9 mL) was added imidazole (0.164 g, 2.41 mmol), DMAP (0.047 g, 0.35 mmol) and TBSCl (0.363 g, 2.40 mmol) and the reaction was stirred at room temperature for 18 hours, followed by heating at 40° C. for 1 hour. The reaction mixture was cooled to room temperature, and was quenched with $H_2O$ (3 mL). The organic layer was separated and was concentrated to dryness to yield a residue, which was dissolved in isopropanol (6 mL) and 1M NaOH (2.9 mL), and the reaction was heated at 60° C. for 1 hour. The reaction was cooled to 0° C. and slowly acidified to pH 3 with 1M HCl (3 mL). After adding chloroform (18 mL), the organic layer was separated, dried over $Na_2SO_4$, and concentrated to dryness to yield the desired acid (0.75 g, 2.09 mmol, 87.1% yield).

N-Boc-1(R)-amino-2(S)-tert-butyldimethylsilyloxy-4(S)-hydroxymethyl-cyclopentane

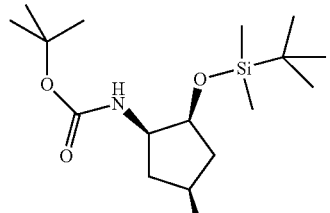

N-Boc-1(R)-amino-2(S)-tert-butyldimethylsilyloxy-cyclopentane-4(S)-carboxylic acid (0.53 g, 1.47 mmol) was submitted to Procedure 14 for reduction to the corresponding N-Boc-1(R)-amino-2(S)-tert-butyldimethylsilyloxy-4(S)-hydroxymethyl-cyclopentane (0.44 g, 1.27 mmol, 86.4% yield): $^1$H NMR (250 MHz, $CDCl_3$) δ 4.69-4.79 (m, 1 H), 4.08-4.13 (m, 1 H), 3.88 (bs, 1 H), 3.52-3.61 (m, 2 H), 2.16-

2.30 (m, 2 H), 1.96-2.14 (m, 2 H), 1.48-1.53 (m, 2 H), 1.47 (s, 9 H), 0.91 (s, 9 H), 0.09 (s, 6 H).

N-Boc-1(R)-amino-2(S)-tert-butyldimethylsilyloxy-cyclopentane-4(S)-carboxaldehyde

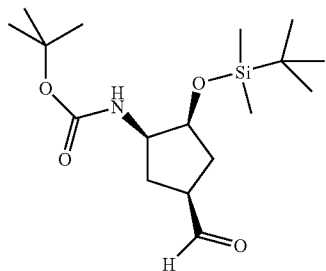 [SMILES: CC(C)(C)OC(=O)N[C@@H]1C[C@H](C=O)C[C@@H]1O[Si](C)(C)C(C)(C)C]

N-Boc-1(R)-amino-2(S)-tert-butyldimethylsilyloxy-4(S)-hydroxymethyl-cyclopentane (0.44 g, 1.27 mmol) was submitted to Procedure 13 for oxidation to the corresponding N-Boc-1(R)-amino-2(S)-tert-butyldimethylsilyloxy-cyclopentane-4(S)-carboxaldehyde (0.42 g, 1.22 mmol, 96.1% yield).

tert-Butyl-2-(N-Boc-3-hydroxy-azetidin-3-yl)acetate

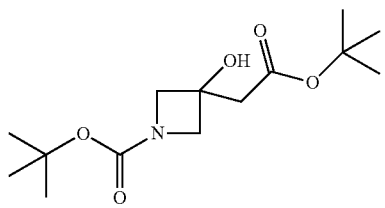 [SMILES: CC(C)(C)OC(=O)CC1(O)CN(C(=O)OC(C)(C)C)C1]

To a stirring solution of N-Boc-3-azetidinone (0.45 g, 2.64 mmol) in THF (5 mL) was slowly added a 0.5 M solution of 2-tert-butoxy-2-oxoethyl-zinc chloride in Et$_2$O (10 mL, 5.0 mmol), and the reaction mixture was stirred for 5 h. The reaction was then quenched with sat. aq. NH$_4$Cl (10 mL), and the aqueous layer was separated and extracted with ethyl acetate (2×30 mL). The combined organic layers were washed with 5% aq. NaHCO$_3$ (2×10 mL), brine (15 mL), dried over Na$_2$SO$_4$, filtered and concentrated to dryness to yield tert-butyl-2-(N-Boc-3-hydroxy-azetidin-3-yl)-acetate (MS m/e [M+H]$^+$ calcd 288.2, found 287.7).

2-(N-Boc-3-hydroxy-azetidin-3-yl)-acetic acid

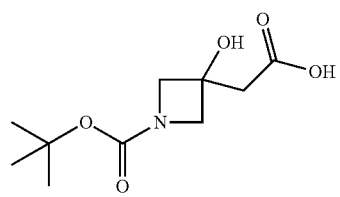 [SMILES: CC(C)(C)OC(=O)N1CC(O)(CC(=O)O)C1]

To a stirring solution of tert-butyl-2-(N-Boc-3-hydroxy-azetidin-3-yl)-acetate (0.86 g, 2.99 mmol) in dioxane (18 mL) was added 3M HCl (5 mL), and the mixture was heated at 70° C. for 1 h. The reaction mixture was then cooled to 0° C. and it was basified with 2 M NaOH (8 mL), followed by addition of BOC$_2$O (1.0 g, 4.6 mmol). The reaction mixture was allowed to warm to room temperature for 2 h, and was then concentrated to half its total volume on the rotary evaporator. Isopropanol (3 mL) and chloroform (12 mL) were then added and the mixture was cooled to 0° C. and slowly acidified to pH 3 with 1M HCl. The organic layer was then separated, dried over Na$_2$SO$_4$, and concentrated to dryness to yield 2-(N-Boc-3-hydroxy-azetidin-3-yl)-acetic acid (0.65 g, 2.81 mmol, 94.0% yield).

N-Boc-3-(2-hydroxy-ethyl)-azetidin-3-ol

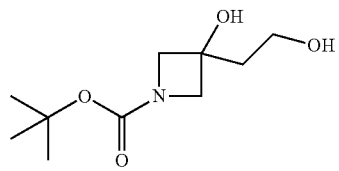

2-(N-Boc-3-hydroxy-azetidin-3-yl)-acetic acid (0.44 g, 1.90 mmol) was submitted to Procedure 14 for reduction to yield the corresponding N-Boc-3-(2-hydroxy-ethyl)-azetidin-3-ol (0.29 g, 1.33 mmol, 70.0% yield).

2-(N-Boc-3-hydroxy-azetidin-3-yl)-acetaldehyde

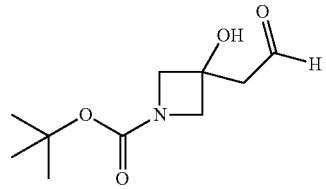

N-Boc-3-(2-hydroxy-ethyl)-azetidin-3-ol (0.29 g, 1.33 mmol) was submitted to Procedure 13 for oxidation to the corresponding 2-(N-Boc-3-hydroxy-azetidin-3-yl)-acetaldehyde, which was carried through to the next step without further purification.

N-Boc-3-hydroxymethyl-azetidine

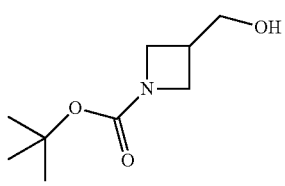

N-Boc-azetidine-3-carboxylic acid (1.94 g, 9.64 mmol) was submitted to Procedure 14 for reduction to the corresponding N-Boc-3-hydroxymethyl-azetidine, which was carried through to the next step without further purification.

N-Boc-azetidine-3-carboxaldehyde

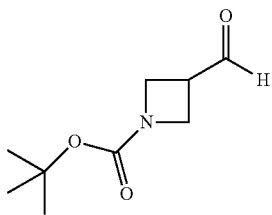

N-Boc-3-hydroxymethyl-azetidine (9.64 mmol) was submitted to Procedure 13 for oxidation to the desired N-Boc-azetidine-3-carboxaldehyde, which was carried through to the next step without further purification.

2-(N-Boc-azetidin-3-yl)-2-hydroxy-acetic acid

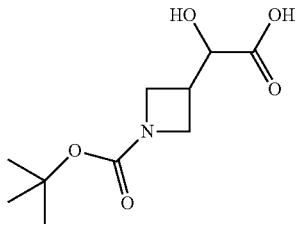 [SMILES: CC(C)(C)OC(=O)N1CC(C(O)C(=O)O)C1]

N-Boc-azetidine-3-carboxaldehyde (1.60 g, 8.64 mmol) was submitted to Procedure 11 to yield the desired 2-(N-Boc-azetidin-3-yl)-2-hydroxy-acetic acid (MS m/e [M+H]$^+$ calcd 232.1, found 231.8).

Synthesis of (2R,3R)-4-azido-2-benzyloxy-3-fluorobutanoic acid (5)

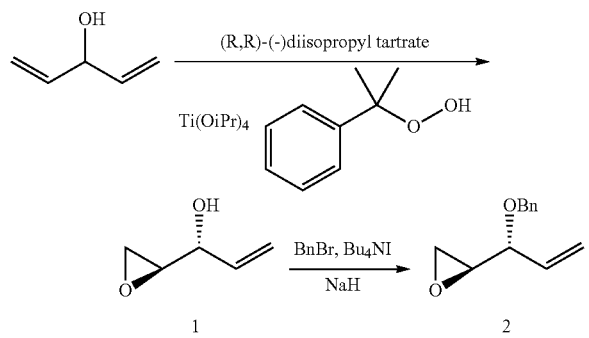

Molecular sieves (4 A, 4 g) were added to a round bottom flask, and were activated by heating with a Bunsen burner under high vacuum. DCM (100 mL) was then added and the flask was cooled to −35° C. with a cryocooler. Titanium tetraisopropoxide (1.75 mL, 5.95 mmol) and (R,R)-(−)-diisopropyl tartrate (1.65 mL, 7.75 mmol) were added and the reaction was stirred for 30 min. Penta-1,4-dienol (5 g, 59.4 mmol) and excess cumene hydroperoxide (80%, 17.5 mL) were added in small portions, and stirring was continued at −35° C. for 48 hr. The reaction was quenched by addition of sat. aq. Na$_2$SO$_4$ (5 mL) immediately followed by Et$_2$O (50 mL) and the reaction was stirred for 2 hr with warming to rt. The reaction mixture was filtered through Celite, and washed with Et$_2$O, Solvent removal under vacuum without heating resulted in approximately 30 mL of a yellow solution. Excess cumene alcohol and hydroperoxide were removed by flash chromatography (silica gel, 40% Et$_2$O/hex). Finally solvent removal under vacuum without heating yielded a mixture of (2S, 3R)-1,2-epoxy-4-penten-3-ol (1) (Rf=0.47, 1:1 EtOAc/hex) and diisopropyl tartrate (Rf=0.6), which was used in the next step without further purification.

To a stirring solution of epoxide (1) in THF (100 mL) under an argon atmosphere was added tetrabutylammonium iodide (2.2 g, 5.96 mmol), followed by benzyl bromide (8.6 mL, 71.9 mmol) and the reaction was cooled to −15° C. Sodium hydride (60% in mineral oil, 2.65 g, 66.1 mmol) was added in small portions and the reaction was stirred overnight with warming to rt. The reaction was quenched with MeOH, filtered through Celite, and washed with Et$_2$O, Solvent removal gave an oily residue which was purified by flash chromatography (silica gel, 5→10% Et$_2$O/hex) to yield (2S, 3R)-1,2-epoxy-3-benzyloxy-4-pentene (2) as a clear non-volatile liquid (5.3 g, 47.6% yield): Rf=0.69 (1:4 EtOAc/hex); [α]$_D$=−36.7° (c 1.52, CHCl$_3$); HRMS (ESI) (M+H)$^+$ calc. for C$_{12}$H$_{14}$O$_2$ 191.1067, obs. 191.1064; $^1$H NMR (CDCl$_3$, 300 MHz) δ 7.38-7.33 (m, 5H), 5.92-5.78 (m, 1H), 5.41-5.39 (m, 1H), 5.37-5.33 (m, 1H), 4.66 (d, J=11.95 Hz, 1H), 4.49 (d, J=11.96 Hz, 1H), 3.83 (dd, J=7.34, 4.20 Hz, 1H), 3.10 (dt, J=4.07, 4.06, 2.70 Hz, 1H), 2.79 (dd, J=5.21, 4.00 Hz, 1H), 2.70 (dd, J=5.23, 2.64 Hz, 1H). $^{13}$C NMR (CDCl$_3$, 100 MHz) δ 138.32, 134.67, 128.56 (2C), 127.87 (2C), 127.82, 119.73, 79.54, 70.83, 53.41, 45.00.

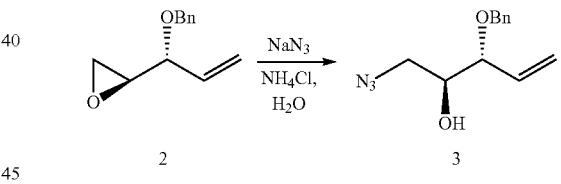

NaN$_3$ (3.38 g, 52 mmol) and NH$_4$Cl (2.78 g, 52 mmol) in H$_2$O (10 mL) were heated until a clear solution was obtained. This solution was then added dropwise to a solution of (2S, 3R)-1,2-epoxy-3-benzyloxy-4-pentene (2) (3.3 g, 17.4 mmol) in MeOH (200 mL) and the reaction mixture was stirred for 4 days. The organic solvent was removed under vacuum, and the aqueous layer was extracted with DCM (3×). The combined organic layers were dried over Na$_2$SO$_4$, filtered and reduced under vacuum to yield a crude, which was purified by flash chromatography (silica gel, 10→20% Et$_2$O/hex) to yield (2S,3R)-1-azido-3-benzyloxy-4-penten-2-ol (3) (2.66 g, 66% yield) as a non-volatile clear liquid: Rf=4.8 (1:4 EtOAc/hex); HRMS (ESI) (M+Na)$^+$ calc. for C$_{12}$H$_{15}$N$_3$O$_2$ 256.1056, obs. 256.1057; [a]p=−46.3° (c 1.50, CHCl$_3$); $^1$H NMR (CDCl$_3$, 300 MHz) δ 7.42-7.28 (m, 5H), 5.91-5.76 (m, 1H), 5.46 (dd, J=17.16, 1.42 Hz, 1H), 5.42 (dd, J=24.00, 1.37 Hz, 1H), 4.65 (d, J=11.67 Hz, 1H), 4.39 (d, J=11.67 Hz, 1H), 3.88-3.80 (m, 2H), 3.44-3.40 (m, 2H), 2.22 (d, J=3.60 Hz, 1H); $^{13}$C NMR (CDCl$_3$, 100 MHz) δ 137.88, 134.60, 128.66 (2C), 128.08 (2C), 128.05, 121.40, 81.39, 72.61, 70.70, 53.0; FTIR (NaCl): 3435, 2870, 2102, 1642, 1454, 1070 cm$^{-1}$.

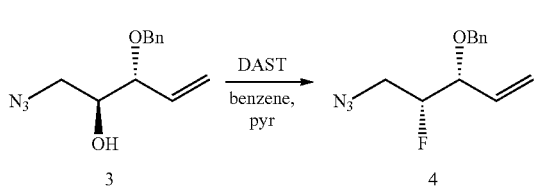

To a stilling solution of DAST (900 μL, 6.87 mmol) in benzene (3.2 mL) and pyridine (400 μL) in a plastic container at −10° C. was added (2S,3R)-1-azido-3-benzyloxy-4-penten-2-ol (3) (750 mg, 3.21 mmol) in small portions, and the reaction was stirred at this temperature for 48 hr followed by 6 hr at rt. The reaction mixture was slowly added to sat. aq. NaHCO$_3$ (20 mL) at 0° C. and was stirred for 10 min. The resulting aqueous mixture was extracted with DCM (3×) and the combined organic layers were washed with 2 N HCl, dried over MgSO$_4$, filtered and reduced under vacuum to yield a crude, which was purified by flash chromatography (silica gel, 1% Et$_2$O/hex) to yield (3R,4R)-5-azido-4-fluoro-3-benzyloxy-pent-1-ene (4) (128 mg, 16.9% yield) as a nonvolatile clear liquid: R$_f$=0.63 (1:9 EtOAC/Hex); [α]$_D$=−11.9° (c 1.50, CHCl$_3$); $^1$H NMR (CDCl$_3$, 400 MHz) δ 7.44-7.29 (m, 5H), 4.63 (dddd, J=47.64, 7.07, 4.99, 3.32 Hz, 1H), 5.49-5.42 (m, 2H), 4.70 (d, J=11.95 Hz, 1H), 4.57 (ddd, J=7.07, 4.99, 3.32 Hz, 1H), 4.44 (d, J=11.90 Hz, 1H), 4.03 (ddd, J=16.87, 7.57, 5.04 Hz, 1H), 3.64-3.52 (m, 1H), 3.45 (ddd, J=27.45, 13.63, 3.27 Hz, 1H). $^{19}$F NMR (CDCl$_3$, 282 MHz)-196.66 (dddd, J=47.27, 27.08, 19.84, 16.89 Hz); $^{13}$C NMR (CDCl$_3$, 100 MHz) δ 137.80, 133.09 (d, J=5.30 Hz), 128.70 (2C), 128.09 (3C), 121.04, 93.33 (d, J=181.54 Hz), 79.08 (d, J=20.39 Hz), 70.92, 51.46 (d, J=22.25 Hz). FTIR (NaCl): 2930, 2104, 1643, 1454, 1281, 1115, 1069 cm$^{-1}$.

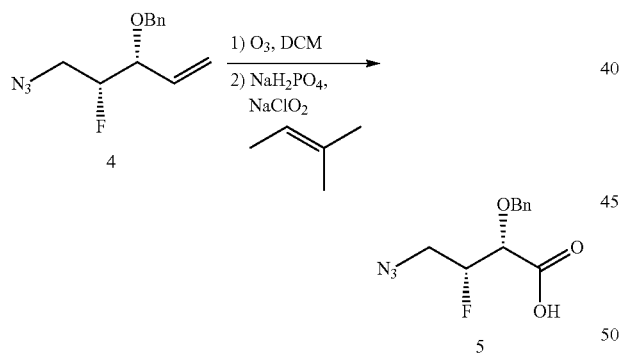

(3R,4R)-5-azido-4-fluoro-3-benzyloxy-pent-1-ene (4) (128 mg, 0.543 mmol) was submitted to Procedure 15, followed by recrystallization from hot hexanes (2×) to yield (2R,3R)-4-azido-2-benzyloxy-3-fluorobutanoic acid (5) (120 mg, 90%): [α]$_D$=−56.9° (c 0.68, CHCl$_3$); HRMS (ESI negative mode) (M−H) calc. for C$_{11}$H$_{12}$FN$_3$O$_3$ 252.0790, obs. 252.0782; $^1$H NMR (CDCl$_3$, 400 MHz), δ 10.55 (s, 1H), 7.46-7.34 (m, 5H), 4.98 (dddd, J=46.40, 7.57, 4.91, 2.92 Hz, 1H), 4.94 (d, J=11.47 Hz, 1H), 4.55 (d, J=11.51 Hz, 1H), 4.17 (dd, J=27.26, 2.86 Hz, 1H), 3.77 (dt, J=13.89, 13.66, 7.27 Hz, 1H), 3.42 (ddd, J=24.28, 13.20, 4.92 Hz, 1H); $^{19}$F NMR (CDCl$_3$, 376 MHz)δ -198.36 (dddd, J=46.28, 27.22, 24.46, 14.15 Hz); $^{13}$C NMR (CDCl$_3$, 100 MHz) δ 174.63 (d, J=4.21 Hz), 136.37, 129.15 (2C), 129.07, 128.98 (2C), 91.53 (d, J=182.59 Hz), 76.40 (d, J=19.90 Hz), 73.96 (s), 50.87 (d, J=25.13 Hz); FTIR (NaCl): 3151, 2098, 1753, 1407, 1283, 1112 cm$^{-1}$.

Synthesis of ent-5

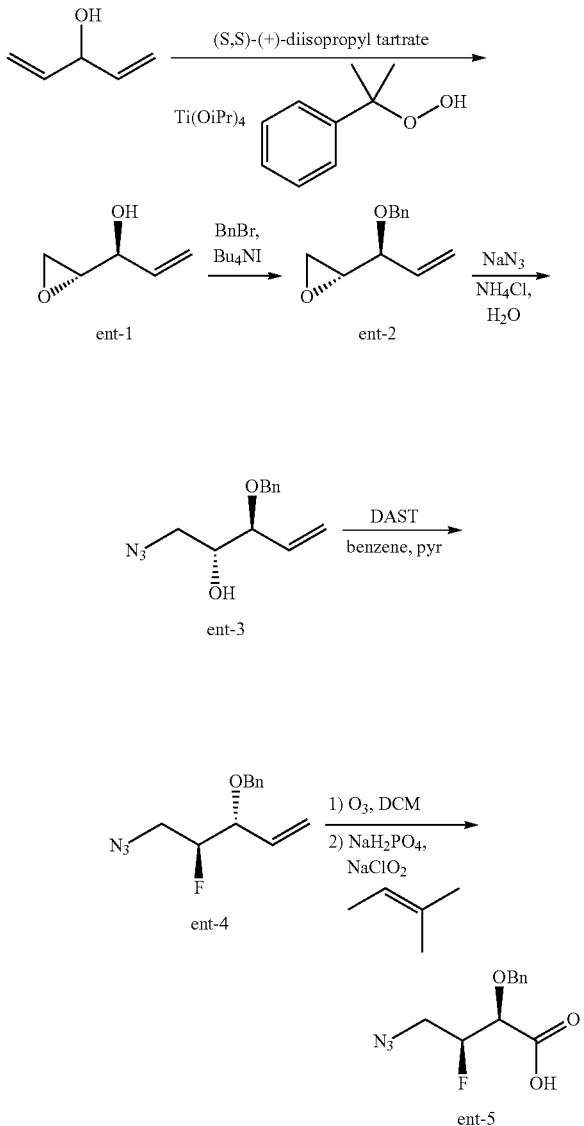

Starting from penta-1,4-dienol (5 g, 59.4 mmol) and using (S,S)-(+)-diisopropyl tartrate under the same reaction conditions as described above the enantiomer ent-2 was obtained (4.9 g, 43% yield): [α]$_D$=+35.7° (c 1.76, CHCl$_3$). (2R, 3S)-1,2-Epoxy-3-benzyloxy-4-pentene (ent-2, 3.9 g, 20.5 mmol) was submitted to the same reaction conditions described above to yield the enantiomer (2R,3S)-1-azido-3-benzyloxy-4-penten-2-ol (ent-3, 2.75 g, 57% yield): [α]$_D$=+47.3° (c 1.30, CHCl$_3$). (2R,3S)-1-Azido-3-benzyloxy-4-penten-2-ol (ent-3) (500 mg, 2.14 mmol) was submitted to the same reactions as described above to yield the enantiomer (3S,4S)-5-azido-4-fluoro-3-benzyloxy-pent-1-ene (ent-4, 75.5 mg, 0.32 mmol, 15% yield, [α]$_D$=+10.7°,c 1.50, CHCl$_3$), which was Synthesis of (R)-4-Azido-3,3-difluoro-2-benzyloxy-butanoic acid (3)

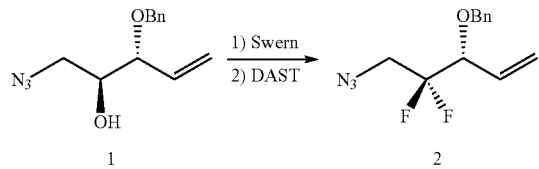

To a stirring solution of DMSO (690 μL, 9.65 mmol) in DCM (25 mL) at −78° C. was added oxalyl chloride (3.21 mL of a 2.0 M solution in DCM, 6.43 mmol) and the reaction was stirred for 1 hr. A solution of (2S,3R)-1-azido-3-benzyloxy-4-penten-2-ol (1) (750 mg, 3.21 mmol) in DCM (1 mL) was added dropwise and the reaction mixture was stirred for 1 hr at −78° C. N-Methyl morpholine (1.41 mL, 12.9 mmol) was added dropwise, and the reaction was stirred at −15° C. for 2 hr. The reaction was quenched with phosphate buffer (0.1 M, pH 6.0) and the aqueous layer was separated. The organic layer was washed with the phosphate buffer (3×), dried over $Na_2SO_4$, filtered and reduced under vacuum to give a brown residue. The residue was dissolved in $Et_2O$, dried over $MgSO_4$, filtered through a cotton plug, and reduced under vacuum to yield the crude ketone, which was dissolved in DCM (1 mL) and was added to a stirring solution of DAST (2 mL, 15.3 mmol) in DCM (3 mL) in a plastic vial at −25° C. The reaction was allowed to slowly warm to rt and was stirred for 48 hr. The reaction mixture was then slowly poured into stirring sat. aq. $NaHCO_3$ (20 mL) at 0° C., and was stirred for 10 min. The resulting aqueous mixture was extracted with DCM (3×), and the combined organic layers were dried over $Na_2SO_4$, filtered and reduced under vacuum to yield a crude, which was purified by flash chromatography (silica gel, 1% $Et_2O$/hex) followed by preparative TLC purification (silica gel, 0.5 mm, 5% $Et_2O$/hex) to yield (R)-5-azido-4,4-difluoro-3-benzyloxy-pent-1-ene (2, 193 mg, 0.76 mmol, 24% yield), as a non-volatile clear liquid: $R_f$=0.72 (1:4 EtOAc/hex); $[\alpha]_b$=−23.8° (c 1.52, $CHCl_3$); $^1H$ NMR ($CDCl_3$, 300 MHz) δ 7.44-7.31 (m, 5H), 5.89 (dddd, J=16.88, 10.61, 7.11, 0.62 Hz, 1H), 5.59-5.56 (m, 1H), 5.53 (d, J=10.74 Hz, 1H), 4.71 (d, J=11.67 Hz, 1H), 4.50 (d, J=11.66 Hz, 1H), 4.14 (td, J=14.25, 7.13, 7.13 Hz, 1H), 3.64 (tq, J=13.67, 13.67, 13.67, 11.19, 11.19 Hz, 2H); $^{19}F$ NMR ($CDCl_3$, 282 MHz) δ −116.63 (dtd, J=257.62, 13.91, 13.90, 8.72 Hz), −111.27 (dtd, J=257.59, 16.18, 16.16, 7.04 Hz); $^{13}C$ NMR ($CDCl_3$, 75 MHz) δ 137.14, 130.33 (t, J=3.06, 3.06 Hz), 128.71 (2C), 128.27, 128.20 (2C), 122.78, 120.69 (dd, J=249.89, 246.83 Hz), 78.87 (dd, J=30.35, 25.35 Hz), 71.48 (d, J=0.48 Hz), 51.47 (dd, J=30.26, 25.92 Hz); FTIR (NaCl): 2928, 2108, 1455, 1292, 1091 cm$^{-1}$.

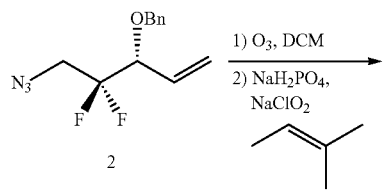

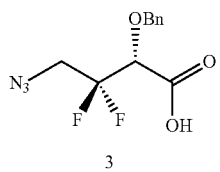

(R)-5-Azido-4,4-difluoro-3-benzyloxy-pent-1-ene (2, 193 mg, 0.76 mmol) was submitted to Procedure 15, followed by washing with cold hexanes (3×) at −20° C. to yield (3) (139 mg, 67.6% yield): $[\alpha]_D$=−32.4° (c 0.80, $CHCl_3$); HRMS (ESI negative mode) (M−H) for $C_{11}H_{11}F_2N_3O_3$ 270.0696, obs. 270.06924; $^1H$ NMR ($CDCl_3$, 400 MHz) δ 7.46-7.32 (m, 5H), 6.48 (s, 1H), 4.84 (d, J=11.30 Hz, 1H), 4.67 (d, J=11.30 Hz, 1H), 4.37 (dd, J=12.23, 9.78 Hz, 1H), 3.75 (dd, J=14.67, 12.35 Hz, 2H); $^{19}F$ NMR ($CDCl_3$, 376 MHz) δ −112.61 (qd, J=260.95, 12.30, 12.29, 12.29 Hz), −109.68 (dtd, J=260.79, 14.75, 14.68, 9.94 Hz); $^{13}C$ NMR ($CDCl_3$, 100 MHz) δ 170.84, 135.48, 129.01, 128.94 (2C), 128.78 (2C), 119.59 (t, J=251.58, 251.58 Hz), 76.56 (dd, J=29.86, 27.24 Hz), 74.34, 51.58 (dd, J=28.94, 26.76 Hz). FI (NaCl): 3337, 2929, 2112, 1738, 1455, 1292, 1210, 1119 cm$^{-1}$.

Synthesis of ent-3

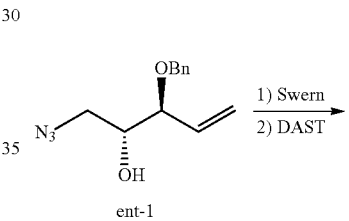

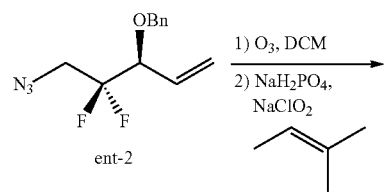

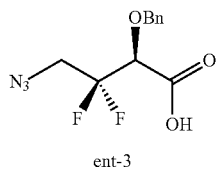

(2R,3S)-1-Azido-3-benzyloxy-4-penten-2-ol (ent-1, 500 mg, 2.14 mmol) was submitted to the same reaction conditions described above to yield (S)-5-azido-4,4-difluoro-3-benzyloxy-pent-1-ene (ent-2, 114 mg, 21% yield, $[\alpha]_D$=+27.9° (c 3.14, $CHCl_3$)). Ent-2 (75.5 mg, 0.32 mmol) was submitted to Procedure 15 to yield (S)-4-azido-2-benzyloxy-3,3-difluorobutanoic acid (ent-3, 34.8 mg, 43% yield, $[\alpha]_D$=+36.4° (c 0.80, CHCl$_3$).

Synthesis of (2S,3S)-4-azido-2,3-bis-benzyloxybutanoic acid (3)

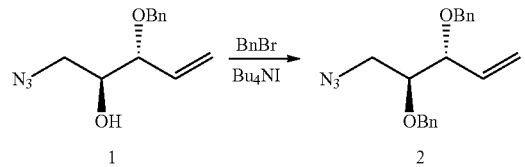

To a stirring solution of (2S,3R)-1-azido-3-benzyloxy-4-penten-2-ol (1) (250 μL, 1.07 mmol) in THF (50 mL) under argon was added tetrabutylammonium iodide (42 mg, 0.11 mmol) followed by benzyl bromide (155 μL, 1.27 mmol) and the reaction was cooled to 0° C. Sodium hydride (60% in mineral oil, 47 mg, 1.18 mmol) was added in small portions and the reaction was stirred overnight with warming to rt. The reaction was quenched with MeOH, filtered through Celite, and washed with Et$_2$O. The organic solvent was removed under vacuum to give an oily residue, which was purified by flash chromatography (silica gel, 2% Et$_2$O/hex) to yield (3R, 4S)-5-azido-3,4-bisbenzyloxy-pent-1-ene (2, 237 mg, 65% yield) as a clear non-volatile liquid: Rf=0.62 (1:4 EtOAc/hex); $[\alpha]_D$=−6.1° (c 1.50, CHCl$_3$); $^1$H NMR (CDCl$_3$, 300 MHz) δ 7.35-7.24 (m, 10H), 5.81 (ddd, J=17.15, 10.58, 7.45 Hz, 1H), 5.37 (ddd, J=5.70, 1.65, 0.86 Hz, 1H), 5.33 (ddd, J=12.07, 1.44, 0.81 Hz, 1H), 4.63 (s, 2H), 4.61 (d, J=11.87 Hz, 1H), 4.35 (d, J=11.78 Hz, 1H), 3.90 (tdd, J=7.37, 5.65, 0.79, 0.79 Hz, 1H), 3.60 (ddd, J=6.39, 5.69, 3.64 Hz, 1H), 3.43 (dd, J=12.93, 6.42 Hz, 1H), 3.35 (dd, J=12.93, 3.60 Hz, 1H); $^{13}$C NMR (CDCl$_3$, 75 MHz) δ 138.25, 138.01, 135.43, 128.60 (4C), 128.29 (2C), 128.02, 127.99 (2C), 127.87, 119.97, 80.76, 80.23, 73.33, 70.79, 51.69; FTIR (NaCl): 2867, 2100, 1606, 1454, 1286, 1095, 1073.

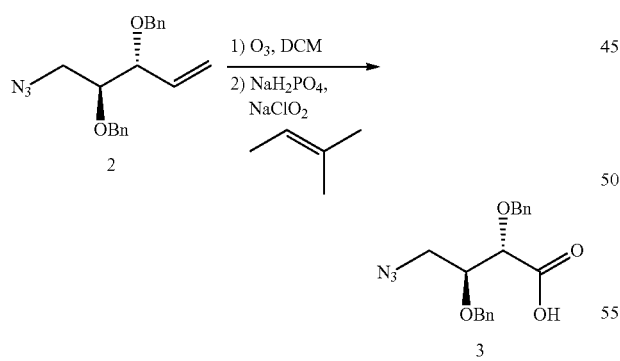

(3R,4S)-5-azido-3,4-bis-benzyloxy-pent-1-ene (2, 237 mg, 0.69 mmol) was submitted to Procedure 15 to yield (2S,3S)-4-azido-2,3-bis-benzyloxybutanoic acid (3, 187.7 mg, 75% yield): $[\alpha]_D$=−15.1° (c 1.05, CHCl$_3$); FIRMS (ESI negative mode) (M−H) calc. for C$_{18}$H$_{19}$N$_3$O$_4$ 340.1303, obs. 340.1296; $^1$H NMR (CDCl$_3$, 300 MHz) δ 7.24 (s, 1H), 7.38-7.33 (m, 10H), 4.79 (d, J=11.61 Hz, 1H), 4.66 (s, 2H), 4.56 (d, J=11.61 Hz, 1H), 4.20 (d, J=4.24 Hz, 1H), 3.98 (td, J=6.56, 4.30, 4.30 Hz, 1H), 3.58 (dd, J=13.04, 6.62 Hz, 1H), 3.42 (dd, J=13.04, 4.31 Hz, 1H); $^{13}$C NMR (CDCl$_3$, 75 MHz) δ 175.57, 137.92, 137.34, 129.44 (2C), 129.36 (2C), 129.15, 129.04 (2C), 128.98 (2C), 128.94, 79.71, 77.651, 74.04, 73.89, 51.65; FTIR (NaCl): 3000, 2918, 2103, 1722, 1455, 1284, 1110 cm$^{-1}$.

Synthesis of ent-3

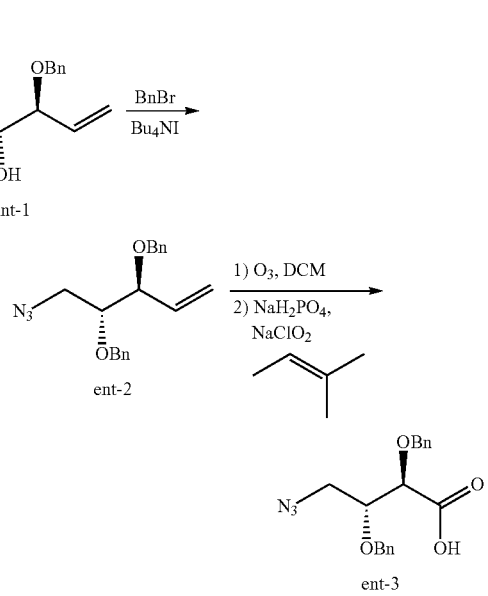

(2R,3S)-1-azido-3-benzyloxy-4-penten-2-ol (ent-1, 250 mg, 1.07 mmol) was submitted to the same reaction conditions as described above to yield (3S,4R)-5-azido-3,4-bis-benzyloxy-pent-1-ene (ent-2, 322 mg, 59% yield): $[\alpha]_D$=+7.9° (c 1.50, CHCl$_3$). Ent-2 (178 mg, 0.55 mmol) was submitted to Procedure 15 to yield ent-3 (144 mg, 77% yield): $[\alpha]_D$=+15.2° (c 0.81, CHCl$_3$).

Synthesis of Compound 9

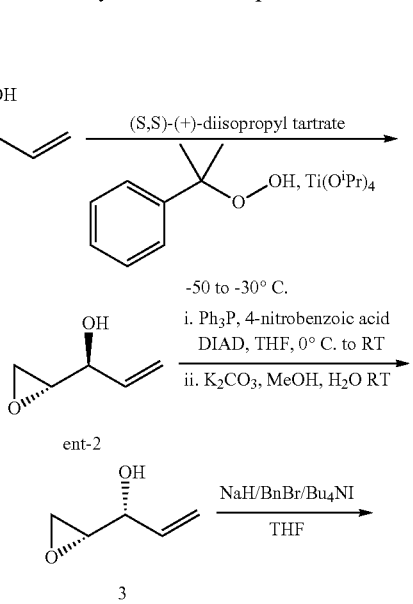

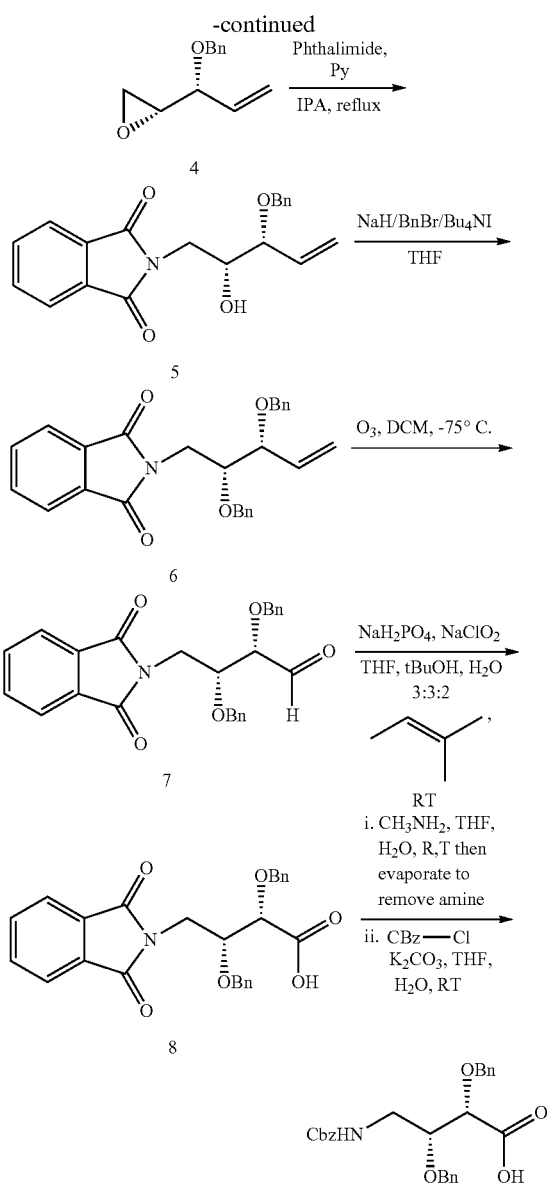

Synthesis of Epoxy Alcohol Ent-2

A 3-neck, 5 liter round bottomed flask equipped with an overhead mechanical stirrer, a thermocouple probe and a nitrogen inlet/outlet was charged with powdered, freshly activated molecular sieves (4 A, 84 g, 0.8 wt. equiv). Anhydrous dichloromethane (2.1 L, 20 vol). The resulting suspension was cooled to approximately −42° C. using an acetonitrile/CO₂ bath, then titanium tetraisopropoxide (37 mL, 0.125 mol, 10 mol %) was charged into the batch, followed by (S,S)-(+)-diisopropyl tartrate (35 mL, 0.166 mol, 13.3 mol %). The reaction mixture was stirred for 30 minutes, then divinyl alcohol 1 (105 g, 1.25 mol, 1.0 equiv) was added over 3 minutes using an addition funnel (minor exotherm, 2° C.). Cumene hydroperoxide (370 mL, 80% titer, 1.99 mol, 1.59 equiv) was then added to the batch over 5 minutes using an addition funnel (10° C. exotherm). The reaction was allowed to proceed for 18 hours, holding the temperature between −45 and −30° C. When complete as determined by TLC analysis ($R_f$ 0.42 for divinyl alcohol, and 0.18 for epoxy alcohol, 50% MTBE in Heptanes), the reaction was quenched with saturated aqueous sodium sulfate (105 mL, 1 vol), diluted with MTBE (1.05 L, 10 vol) and the batch allowed to warm to ambient temperature, with vigorous stirring. Diatomaceous earth, Celite® (105 g, 1 wt. equiv) was added to the batch, which was then filtered through a pad of Celite®. The filter cake was washed with MTBE (0.5 L) and the filtrate concentrated in vacuo on a rotary evaporator (with water bath held at 10-20° C.) to afford a yellow/brownish oil. A portion of the crude product [311 g] was subjected to silica plug (1 kg silica gel) using 0-60% MTBE/petroleum ether. The fractions containing the product were collected and concentrated to obtain a colorless oil (48.3 g). This material was then purified via column chromatography (300 g silica gel, 5-30% MTBE/petroleum ether) to afford ent-2 as a clear liquid [22.6 g, 36% overall mass recovery]: $R_f$=0.59 (1:1 MTBE/petroleum ether); ¹H NMR (CDCl₃, 500 MHz) 5.85 (ddd, J=17.0, 10.5, 6.2 Hz, 1H), 5.40 (dt, J=17.3, 1.3 Hz, 1H), 5.27 (dt, J=10.5, 1.3 Hz, 1 H), 4.36-4.33 (m, 1H), 3.10 (ddd, J=3.8, 3.8, 3.0 Hz, 1H), 2.81 (dd, J=2.9, 5.0 Hz, 1H), 2.76 (dd, 4.1, 5.0 Hz, 1H), 2.07 (d, J=3.0 Hz, 1H).

Synthesis of Compound 3

The reaction was carried out at 20-g scale of alcohol following a literature procedure (*J. Org. Chem.* 2009, 74(15), 5758-5761). A 2-L round-bottomed flask equipped with a mechanical stirrer, a thermocouple probe, and an addition funnel was charged with a solution of epoxy alcohol ent-2 [20 g, 200 mmol, 1 equiv] in tetrahydrofuran (400 mL, 20 vol) along with Ph₃P (105 g, 400 mmol, 2 equiv), and 4-nitrobenzoic acid (67 g, 400 mmol, 2 equiv) under a nitrogen atmosphere. DIAD (81 g, 400 mmol, 2 equiv) was added to the reaction mixture using an addition funnel while maintaining the reaction mixture at 0° C. (ice bath). Once the addition of DIAD was complete, the cold bath was removed and the reaction mixture was allowed to come to ambient temperature (23° C.). The reaction mixture was stirred for 1.5 h (all starting material consumed) and then quenched with aqueous NaHCO₃ solution (100 ml, 5 vol) followed by the addition of MTBE (1000 mL, 50 vol). The resulting solution was transferred into a separatory funnel. Brine (100 mL, 5 vol) was added to obtain phase separation. The organic phase was washed with brine (2×20 vol), dried (MgSO₄), and concentrated under vacuum to obtain an oil (296 g). The oil was passed through a silica plug (1 kg) using 10-20% MTBE/heptanes. The crude solid (46 g) was then dissolved into MTBE (20 vol) and washed with NaHCO₃ (3×5 vol), water (2×2 vol), brine (2×2 vol), dried (MgSO₄), concentrated, and further dried to obtain the benzoate ester as a white solid [29 g, 59%: $R_f$=0.56 (1:1 MTBE/heptanes)]; ¹H NMR (CDCl₃, 500 MHz) δ 8.35 (d, J=10.8 Hz, 2H), 8.25 (d, J=10.8 Hz, 2H), 5.97 (ddd, J=17.2, 10.6, 6.2 Hz, 1H), 5.48 (td, J=17.3, 1.2 Hz, 1H), 5.40 (td, J=10.7, 1.1 Hz, 1H), 5.34 (dd, J=5.0, 1.3 Hz, 1H), 3.31 (ddd, J=6.5, 4.1, 2.6 Hz, 1H), 2.93 (dd, J=4.2, 4.2 Hz, 1H), 2.76 (dd, J=4.8, 2.6 Hz, 1H).

The hydrolysis of the benzoate ester was carried out following the literature procedure (*J. Org. Chem.* 2009, 74(15), 5758-5761). Thus solution of the ester (22.7 g, 91 mmol, 1 equiv) in methanol (340 mL, 15 vol) was treated with an aqueous solution of K₂CO₃ (13.8 g, 100 mmol, 1.1 equiv, in 34 mL, 1.5 vol water) at 10-15° C. The solution immediately turned into a thick slurry. The slurry was stirred at ambient temperature (23° C.) for 3 h (starting material consumed). The reaction mixture was concentrated on a rotary evaporator (at ambient water bath temperature) to ~2 vol (45 mL). The thick solution was then reslurried in DCM (454 mL, 20 vol). The slurry was filtered and the solids were washed with DCM (2×5 vol, 2×114 mL). The combined organic filtrate was dried (MgSO₄), filtered, and concentrated to obtain a solid (31 g).

The crude material was then purified by column chromatography (silica gel, 10-30% MTBE/petroleum ether) to obtain the desired alcohol 3 as a clear oil [9.24 g, quantitative yield, $R_f$=0.31 (1:1 MTBE/heptanes)]; $^1$H NMR (CDCl$_3$, 300 MHz) δ 5.94 (ddd, J=16.2, 10.6, 5.5, 1H), 5.40 (d, J=17.3 Hz, 1H), 5.26 (d, J=10.6 Hz, 1H), 4.0 (t, J=5.3 Hz, 1H), 3.07 (m, 1 H), 2.84 (t, J=4.8 Hz, 1H), 2.77-2.74 (m, 1H), 2.57 (br s, 1H).

Synthesis of Compound 4

A 1-L three-necked round-bottomed flask equipped with an addition funnel, an overhead mechanical stirrer, a nitrogen inlet/outlet, was charged with alcohol 3 [9.24 g, 92.3 mmol, 1 equiv] in anhydrous tetrahydrofuran (166 mL, 18 vol). The solution was cooled to −10 to −15° C. The catalyst Bu$_4$NI (3.41 g, 9.23 mmol, 10 mol %) was charged into the reactor followed by benzyl bromide (19.1 g, 112 mmol, 1.2 equiv). The resulting solution was stirred for 20 min. Sodium hydride (4.1 g, 1.1 equiv, 60% mineral oil dispersion) was then added to the batch in portions such that the batch temperature was maintained at −10 to −15° C. Once the addition of sodium hydride was complete, the reaction mixture was stirred for an additional 30 min and then the cold bath was removed and reaction mixture brought up to ambient temperature and further stirred for 18 h. The reaction was quenched with aqueous NaHCO$_3$ (37 mL, 4 vol) while maintaining the temperature at −5 to 0° C. (ice bath). The resulting solution was diluted with MTBE (185 mL, 20 vol), the organic layer was washed with water (2×18 mL, 2×3 vol), brine (1×18 mL, 1×3 vol), dried (MgSO$_4$), filtered, and concentrated under reduced pressure to obtain crude product as an oil. The synthesis was repeated on 1.98 g scale of alcohol 3. The crude from both the reactions were combined and purified via column chromatography (silica gel column, 2.5-10% MTBE/heptanes) to obtain the desired benzylated product 4 as an oil [13.96 g, 65%: $R_f$=0.61 (3:7 MTBE/heptanes)]; $^1$H NMR (CDCl$_3$, 500 MHz) δ 7.36-7.32 (m, 4H), 7.29-7.26 (m, 1H), 5.83 (ddd, J=17.3, 10.5, 6.7, 1H), 5.36 (td, J=17.3, 1.4 Hz, 1H), 5.31 (td, J=10.5, 1.2 Hz, 1H), 4.63 (ABq, J=12.0 Hz, 2H), 3.62 (ddd, J=, 1H), 3.11-3.08 (m, 1 H), 2.78 (t, J=4.4 Hz, 1H), 2.60 (dd, J=5.0, 2.7 Hz, 1H).

Synthesis of Compound 5

A 250-mL round-bottomed flask equipped with a reflux condenser was charged with alcohol 4 [10 g, 52.5 mmol, 1 equiv], phthalimide (11.6 g, 78.8 mmol, 1.5 equiv), pyridine (0.85 mL, 10.5 mmol, 20 mol %) and IPA (100 mL, 10 vol) and the resulting solution was stirred at 80-82° C. for 8 hrs. The reaction mixture was then cooled to ambient temperature and concentrated on a rotatory evaporator to dryness. The residue was adsorbed on silica gel (20 g), dried under high vacuum and then purified by flash column chromatography on silica gel (10-40% MTBE/heptanes) to afford the desired phthalimide protected amino alcohol 5 as a white tacky solid [15.85 g, 89%]: $R_f$=0.34 (1:1 MTBE/heptanes); $^1$H NMR (DMSO-d$_6$, 500 MHz) δ 7.84-7.82 (m, 4H), 7.36-7.31 (m, 4H), 7.28-7.25 (m, 1H), 5.93 (ddd, J=17.5, 10.5, 10.1 Hz, 1H), 5.38-5.35 (m, 2H), 5.12 (d, J=5.5 Hz, 1H), 4.53 (d, J=11.9 Hz, 1H), 4.40 (d, J=11.9 Hz, 1H), 3.98 (dddd, J=9.0, 4.5, 4.5, 4.5 Hz 1H), 3.86 (dd, J=5.8, 4.6 Hz, 1H), 3.67 (dd, J=13.7, 8.9 Hz, 1H), 3.59 (dd, J=13.7, 4.4 Hz, 1H).

Synthesis of Compound 6

A 1-L three-necked round-bottomed flask equipped with an addition funnel, an overhead mechanical stirrer, and a nitrogen inlet/outlet was charged with a solution of alcohol 5 [15 g, 44.5 mmol, 1 equiv] in anhydrous tetrahydrofuran (270 mL, 18 vol). The solution was cooled to −10 to −15° C., then Bu$_4$NI (1.64 g, 4.45 mmol, 10 mol %) was charged into the reactor followed by benzyl bromide (9.2 g, 53.8 mmol, 1.2 equiv). The resulting solution was stirred for 20 min, then sodium hydride (1.97 g, 1.1 equiv, 60% mineral oil dispersion) was added to the batch in portions such that the batch temperature was maintained at −10 to −15° C. Once the addition of sodium hydride was complete, the reaction mixture was stirred for an additional 30 min and then brought to ambient temperature and further stirred for 18 h. The reaction was quenched with aqueous NaHCO$_3$ (60 mL, 4 vol) while maintaining the reaction mixture at −5 to 0° C. (ice bath). The reaction mixture was then diluted with MTBE (300 mL, 20 vol) and the phases separated. The organic layer was washed with water (2×45 mL, 2×3 vol), brine (1×45 mL, 1×3 vol), dried (MgSO$_4$), filtered, and concentrated to obtain the crude product as an oil. The synthesis was repeated on 1.75 g scale of alcohol 5. The combined crude products from both reactions were purified by flash column chromatography on silica gel (5-25% MTBE/heptanes) to obtain the desired product 6 as a semi solid [15.1 g, 71%: $R_f$=0.61 (1:1 MTBE/heptanes)]; $^1$H NMR (CDCl$_3$, 300 MHz) δ 7.74-7.71 (m, 2H), 7.67-7.64 (m, 2H), 7.37-7.27 (m, 5H), 7.10-7.07 (m, 2H), 6.98-6.93 (m, 3H), 5.97 (ddd, J=17.5, 10.4, 10.0 Hz, 1H), 5.42 (d, J=4.38 Hz, 1H), 5.38 (s, 1H), 4.68 (dd, J=12.3, 12.3 Hz, 2H), 4.45 (d, J=5.37 Hz, 1H), 4.41 (d, J=5.58 Hz, 1H), 3.99-3.82 (m, 3H), 3.65 (dd, J=13.6, 3.2 Hz, 1H).

Synthesis of Aldehyde 7 and Carboxylic Acid 8

A solution of alkene, 6 [1 g, 2.34 mol] in DCM (60 mL, 60 vol) was sparged with ozone at <−70° C. (dry ice-acetone) for 25 min using house air as oxygen source to generate the ozone. Once the reaction was deemed compete (TLC, 1:1 MTBE/heptanes), the solution was sparged with nitrogen for 20 min to remove residual ozone. The reaction was quenched with dimethyl sulfide (1.7 mL, 23.4 mmol, 10 equiv) while maintaining the reaction mixture at <−70° C. (dry ice-acetone). The cold bath was removed and the mixture was allowed to warm to ambient temperature. The reaction mixture was concentrated under reduced pressure and further dried under high vacuum to obtain the crude aldehyde as a thick oil (1.12 g, >99%, $R_f$=0.36, 1:1 MTBE/heptanes). The reaction was repeated at 13 g scale of 6. The two lots of crude aldehyde were combined and subjected to the Pinnick oxidation without further purification.

The crude aldehyde 7 [14.06 g], was taken into a mixture of tetrahydrofuran, tBuOH, and water (105 mL, 105 mL, 70 mL, 3:3:2, 20 vol) along with NaH$_2$PO$_4$ (15.6 g, 130 mmol, 4 equiv) and 2-methyl-2-butene (34.4 mL, 324 mmol, 10 equiv). The solution was cooled (15±5° C., water bath). Sodium chlorite (3.9 g, 43 mmol, 1.33 equiv) was added to the batch and the resulting solution was stirred at ambient temperature for 4 hr. The completion of the reaction was confirmed by TLC analysis (1:1 MTBE/heptanes and 5% MeOH in DCM). The reaction was then quenched with brine (280 mL, 20 vol) and the product extracted into DCM (3×280 mL, 3×20 vol). The organic layers were dried (MgSO$_4$), concentrated under reduced pressure to obtain the crude acid as a thick oil. The crude acid was purified by flash column chromatography over silica (5-100% MTBE/heptanes followed by 5-20% MeOH/DCM). Fractions containing the acid were combined and concentrated under reduced pressure to afford acid 8 as a white solid [2.64 g, 18%: $R_f$=0.33, 5:95 MeOH/DCM)]; $^1$H NMR (CDCl$_3$, 500 MHz) δ 7.78 (dd, J=5.5, 3.0 Hz, 2H), 7.70 (dd, J=5.5, 3.0 Hz, 2H), 7.43-7.40 (m, 2H), 7.37-7.29 (m, 3H), 7.20-7.19 (m, 2H), 7.14-7.11 (m, 2H), 7.09-7.05 (m, 1H), 4.76 (d, J=11 Hz, 1H). 4.65 (dd, J=10.9, 9.4 Hz, 2H), 4.55 (d, J=11.8 Hz, 1H), 4.13 (ddd, J=6.2, 6.2, 3.1 Hz, 1H), 4.1 (d, J=3.0 Hz, 1H), 3.98 (dd, J=14.2, 6.2 Hz, 1H), 3.89 (dd, J=14.2, 6.2 Hz, 1H).

Synthesis of Compound 9

A round bottomed flask equipped with a magnetic stirring bar, and a thermocouple probe was charged with a solution of phthalimide-protected amino acid 8 [2.5 g, 5.61 mmol, 1.0 equiv] in THF (28 mL, 11 vol, bulk solvent grade). To the clear, yellow solution was added deionized water (15 mL, 6 vol) and the resulting mixture cooled to 5° C. Methylamine solution in water (5.0 mL, 40 wt %, 56.1 mmol, 10 equiv) was then added to the batch, which was warmed to ambient temperature (21-23° C.) and stirred for 22.5 hours. Analysis of an aliquot from the reaction mixture by LCMS indicated the reaction was complete. The reaction mixture was then concentrated in vacuo to a yellow solid residue, removing all excess methylamine. The residue was taken up in THF (60 mL, 24 vol) and water (30 mL, 12 vol), cooled to 0-5° C., and to the crude amino acid solution was added potassium carbonate (3.9 g, 28.26 mmol, 5.0 equiv), followed by benzylchloroformate (1.4 mL, 9.81 mmol, 1.75 equiv). The batch was warmed to ambient temperature and the reaction allowed to proceed for 25.5 hours. Analysis of an aliquot at this time point by LCMS indicated a complete conversion of the amino acid to the carbamate. The reaction mixture was concentrated under reduced pressure to remove most of THF, the aqueous residue was diluted with water (30 mL, 12 vol) and the pH adjusted with 2N HCl to approximately pH 5 (pH paper strip). The crude product was extracted with chloroform (3×60 mL), the extracts washed with water (1×60 mL) and with aqueous NaCl (1×60 mL), dried (MgSO$_4$) and concentrated in vacuo to a yellow, mobile oil (3.52 g) which was purified by flash column chromatography on silica gel (50 wt. equiv; elution with 0-5% MeOH in CHCl$_3$) to afford 9 as a yellow oil, which partially solidified upon further drying under high vacuum [2.22 g, 88.1% yield over two steps]. $^1$H NMR (DMSO, 500 MHz) δ 12.92 (s, 1H), 7.43-7.23 (m, 15H), 5.04 (s, 2H), 4.67 (d, J=11.10 Hz, 1H), 4.58 (d, J=11.10 Hz, 1H), 4.48 (d, J=11.05 Hz, 1H), 4.42 (d, J=11.05 Hz, 1H), 4.09 (d, J=2.95 Hz, 1H), 3.96 (ddd, J=6.30, 6.30, 3.15 Hz, 1H), 3.29 (dd, J=6.30, 6.30, 2H).

Synthesis of Cyclopropyl Amino Acids

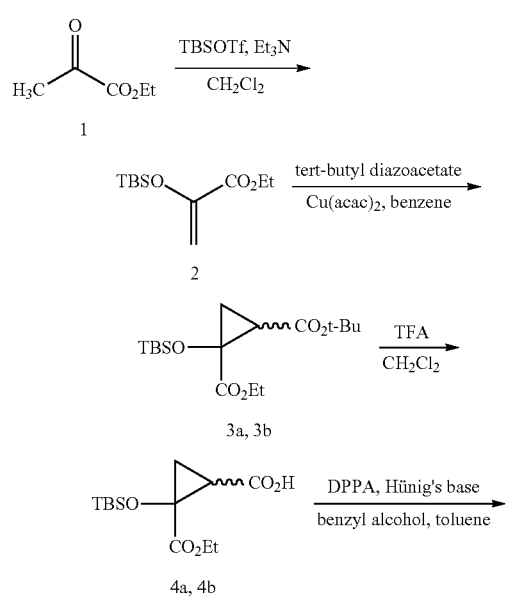

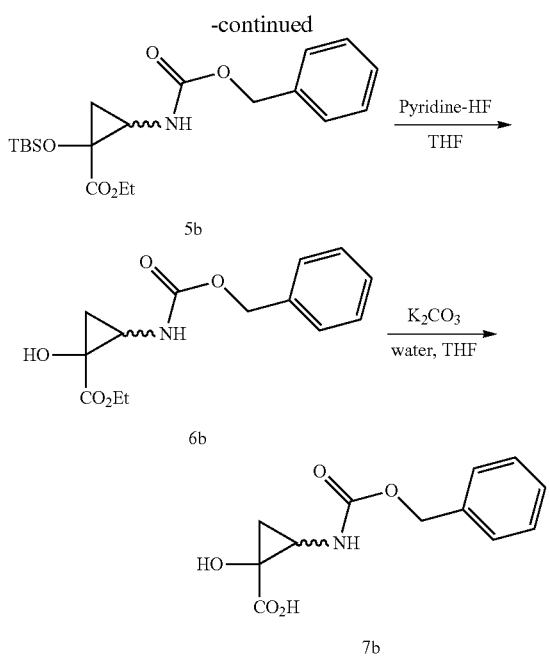

Ethyl-2-(tert-Butyldimethylsilyloxy)acrylate (2)

A solution of ester 1 (4.00 g, 34.4 mmol) and triethylamine (4.79 mL, 34.4 mmol) in anhydrous dichloromethane (170 mL) was cooled to 0° C. under nitrogen and tert-butyldimethylsilyltrifluoromethane sulfonate (8.31 mL, 36.2 mmol) was added dropwise. The resulting solution was stirred vigorously at reflux for 4 h. The solvent was then carefully evaporated, the residue was dissolved in Et$_2$O (170 mL), and the organic phase was washed with water (3×50 mL). The organic phase was dried (Na$_2$SO$_4$), filtered, and concentrated. The residue was purified by silica gel chromatography eluting with 0-20% diethyl ether/hexanes to afford 2 (4.89 g, 62%) as a clear oil: $^1$H NMR (500 MHz, CDCl$_3$) δ 5.50 (d, J=1.0 Hz, 1H), 4.85 (d, J=1.0 Hz, 1H), 4.21 (q, J=7.0 Hz, 2H), 1.31 (t, J=7.0 Hz, 3H), 0.95 (s, 9H), 0.16 (s, 6H).

2-tert-Butyl-1-Ethyl-1-(tert-butyldimethylsilyloxy) cyclopropane-1,2-dicarboxylate (3a and 3b)

A mixture of ethyl-2-(tert-butyldimethylsilyloxy)acrylate (2, 500 mg, 2.17 mmol) and Cu(acac)$_2$ (0.011 g, 0.043 mmol) was heated at 80° C. A solution of text-butyl diazoacetate (463 mg, 3.25 mmol) in benzene (5 mL) was added to the reaction mixture over 2 h. After this time, the reaction mixture was cooled to room temperature and concentrated. The residue was purified by silica gel chromatography eluting with 0-10% diethyl ether/hexanes to afford both diastereomers 3a (0.119 g, 16%) and 3b (0.235 g, 31%) as clear oils. 3a: $^1$H NMR (500 MHz, CDCl$_3$) δ 4.25-4.13 (m, 2H), 2.28 (dd, J=7.5, 2.0 Hz, 1H), 1.73 (dd, J=7.5, 2.0 Hz, 1H), 1.59 (dd, J=9.5, 4.0 Hz, 1H), 1.46 (s, 9H), 1.29 (t, J=7.5 Hz, 3H), 0.90 (s, 9H), 0.18 (s, 3H), 0.12 (s, 3H); ESI MS m/z 367 [M+Na]$^+$; 3b: $^1$H NMR (500 MHz, CDCl$_3$) δ 4.23 (dq, J=11.0, 7.0 Hz, 1H), 4.13 (dq, J=11.0, 7.0 Hz, 1H), 2.11 (dd, J=10.0, 1.5 Hz, 1H), 1.85 (dd, J=5.5, 2.5 Hz, 1H), 1.43 (s, 9H), 1.54 (dd, J=10.0, 4.0 Hz, 1H), 1.28 (t, J=7.5 Hz, 3H), 0.86 (s, 9H), 0.19 (s, 3H), 0.18 (s, 3H); ESI MS m/z 367 [M+Na]$^+$.

2-tert-Butyldimethylsilyloxy)-2-(ethoxycarbonyl) cyclopropanecarboxylic Acid (4a and 4b)

A mixture of dicarboxylate 3a and 3b (0.385 g, 1.12 mmol, 1:2 ratio of 3a/3b), trifluoroacetic acid (0.43 mL), and dichloromethane (0.5 mL) was stirred overnight at room temperature. The solids were filtered, and the filtrate was concentrated. The residue was purified by silica gel chromatography eluting with 0-100% diethyl ether/hexanes to afford both diastereomers 4a (0.050 g, 15%) and 4b (0.078 g, 24%) as off-white solids. 4a: $^1$H NMR (500 MHz, CDCl$_3$) δ 4.25-4.17 (m, 2H), 2.38 (dd, J=7.5, 1.5 Hz, 1H), 1.81-1.76 (m, 2H), 1.30 (t, J=7.0 Hz, 3H), 0.90 (s, 9H), 0.21 (s, 3H), 0.13 (s, 3H); ESI MS m/z 289 [M+H]$^+$; 4b: $^1$H NMR (500 MHz, CDCl$_3$) δ 4.22 (q, J=7.0 Hz, 1H), 2.21 (dd, J=10.0, 1.5 Hz, 1H), 1.93 (dd, J=8.0, 2.0 Hz, 1H), 1.52 (dd, J=6.0, 3.5 Hz, 1H), 1.28 (t, J=7.0 Hz, 3H), 0.87 (s, 9H), 0.19 (s, 3H), 0.17 (s, 3H); ESI MS m/z 287 [M−H]$^-$.

Ethyl-2-(Benzyloxycarbonylamino)-1-(tert-butyldimethylsilyloxy)cyclopropanecarboxylate (5b)

A mixture of 2-(tert-butyldimethylsilyloxy)-2-(ethoxycarbonyl)cyclopropanecarboxylic acid (4b, 0.335 g, 1.16 mmol) in toluene (5 mL) under nitrogen was treated with Hünig's base (0.260 mL, 1.51 mmol) and the mixture was cooled to 0° C. After this time, DPPA (0.324 mL, 1.51 mmol) was added and the mixture was heated at 90° C. for 30 min, followed by the addition of benzyl alcohol (0.155 mL, 1.51 mmol). After 15 h, the mixture was cooled, diluted with ethyl acetate (75 mL), and washed sequentially with 10% citric acid (2×50 mL), water (50 mL), and saturated NaHCO$_3$ (50 mL). The organic phase was dried (MgSO$_4$), filtered, and concentrated. The residue was purified by silica gel chromatography eluting with 10% EtOAc/hexanes to 100% EtOAc to afford the title compound as a clear oil (0.146 g, 30%): $^1$H NMR (300 MHz, CDCl$_3$) δ 7.34-7.30 (m, 5H), 5.40-5.38 (m, 1H), 5.21-5.00 (m, 2H), 4.29-4.18 (m, 2H), 4.16-4.09 (m, 1H), 1.50-1.47 (m, 2H), 1.30 (t, J=7.2 Hz, 3H), 0.88 (s, 9H), 0.26-0.07 (m, 6H); Multimode (APCI+ESI) MS m/z 295 [M+H]$^+$.

Ethyl 2-(Benzyloxycarbonylamino)-1-hydroxycyclopropanecarboxylate (6b)

To a solution of ethyl 2-(benzyloxycarbonylamino)-1-(tert-butyldimethylsilyloxy)cyclopropanecarboxylate (1.45 g, 3.69 mmol) in THF (35 mL) under N$_2$ was added HF•pyridine (1.0 mL, 38 mmol). The reaction mixture was stirred for 5 h. After this time, additional HF•pyridine (1.0 mL, 38 mmol) was added and stirring was continued for 19 h. The reaction mixture was then cooled to 0° C. and diluted with Et$_2$O (150 mL). The mixture was then carefully quenched with saturated aqueous NaHCO$_3$ until gas evolution ceased. At this time, the organic layer was separated and the remaining aqueous layer was extracted with Et$_2$O (300 mL). The combined organic layers were washed with brine (200 mL), dried (Na$_2$SO$_4$), filtered, and concentrated in vacuo. Purification by silica gel chromatography eluting with 20%-50% EtOAc/hexanes afforded the title compound (0.960 g, 93%): $^1$H NMR (300 MHz, CDCl$_3$) δ 7.34-7.30 (m, 5H), 5.11-4.83 (m, 3H), 4.21 (q, J=7.2 Hz, 2H), 3.37-3.25 (m, 2H), 1.73-1.68 (m, 1H), 1.27 (t, J=7.2 Hz, 3H), 1.14-1.06 (m, 1H); ESI MS m/z 280 [M+H]$^+$.

2-(Benzyloxycarbonylamino)-1-hydroxycyclopropanecarboxylic acid (7b)

To a 0° C. solution of ethyl 2-(benzyloxycarbonylamino)-1-hydroxycyclopropanecarboxylate (6b, 12.5 g, 44.7 mmol) in THF (100 mL) was added K$_2$CO$_3$ (24.7 g, 179.0 mmol) as a solution in H$_2$O (300 mL). The reaction was allowed to warm to room temperature and stirred for 4 h and then additional H$_2$O (200 mL) was added. After stirring an additional 18 h at room temperature the reaction was concentrated to remove most of the THF. The remaining aqueous solution was washed with Et$_2$O (2×500 mL), acidified with 2 N HCl to pH 2, and then extracted with EtOAc (5×200 mL). The combined EtOAc layers were washed with brine (500 mL), dried (Na$_2$SO$_4$), filtered and concentrated in vacuo to afford the title compounds (7.75 g, 69%) as a mixture of diastereomers. The mixture was triturated with Et$_2$O to afford a white solid as mostly the major diastereomers. The supernatant was concentrated and then triturated with Et$_2$O to afford a clean mixture of both diastereomers. Major Diastereomer: NMR (300 MHz, MeOD) δ 7.50-7.14 (m, 5H), 5.22-4.96 (m, 2H), 3.23-3.10 (m, 1H), 1.60 (dd, J=8.9, 6.3 Hz, 1H), 1.10 (t, J=6.2 Hz, 1H); Multimode (APCI+ESI) MS m/z 250 [M−H]$^-$. Mixture of Diastereomers: $^1$H NMR (300 MHz, MeOD) δ 7.45-7.14 (m, 5H), 5.24-5.01 (m, 2H), 3.25-3.15 (m, 0.46H), 3.14-3.01 (m, 0.54H), 1.71-1.53 (m, 1H), 1.42 (dd, J=9.1, 6.4 Hz, 0.54H), 1.12 (t, J=6.2 Hz, 0.46H); Multimode (APCI+ESI) MS m/z 250 [M−H]$^-$.

Representative Compounds

The following representative compounds may be prepared according to the foregoing procedures.

Kanamycin B Analogs

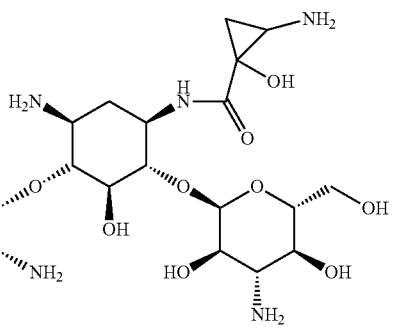

-continued
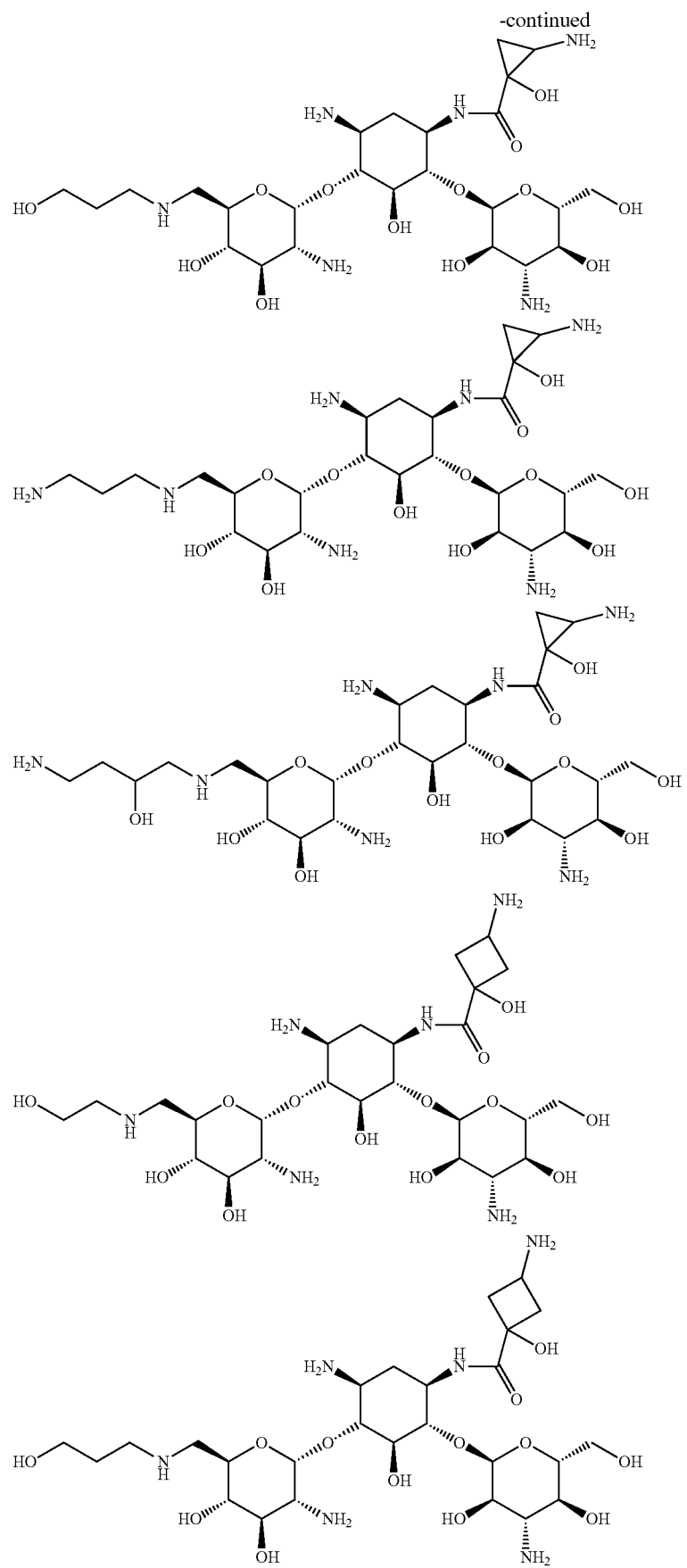

-continued
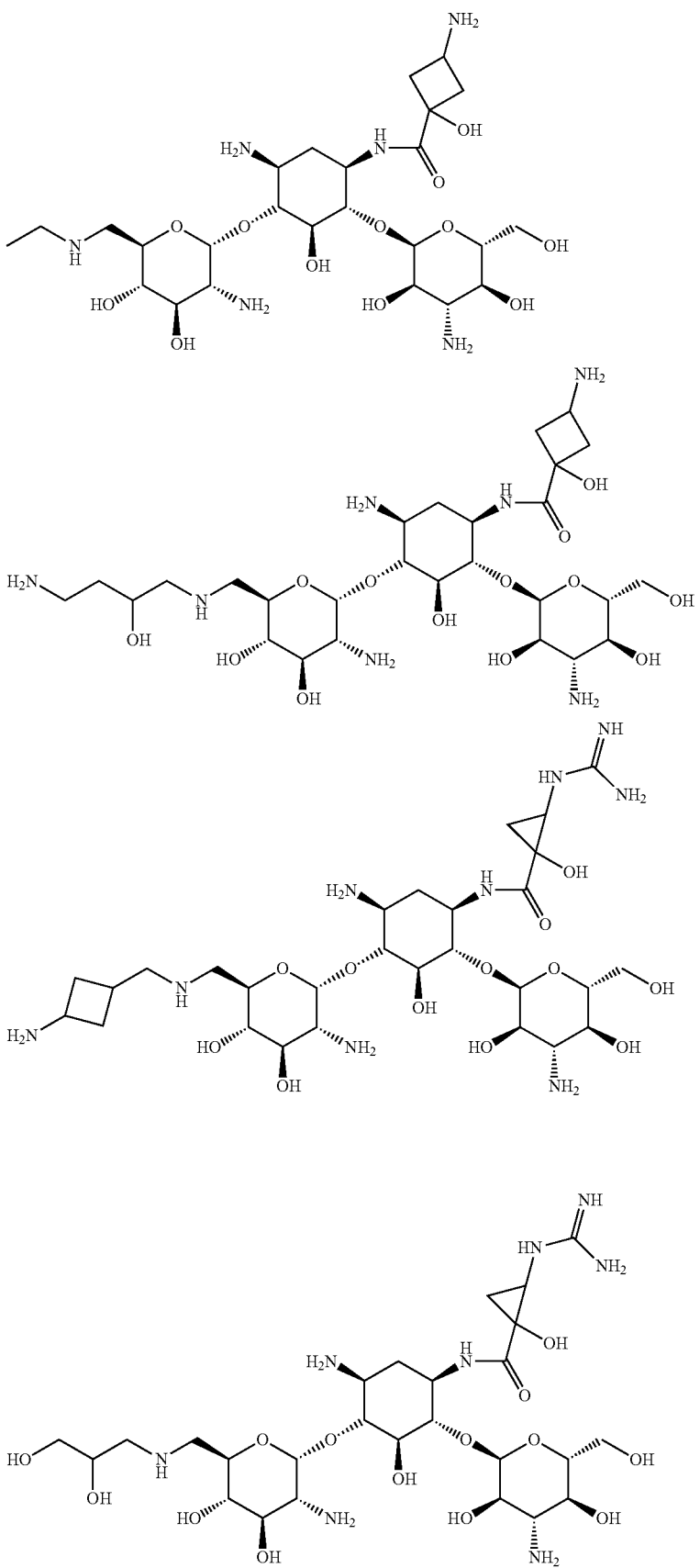

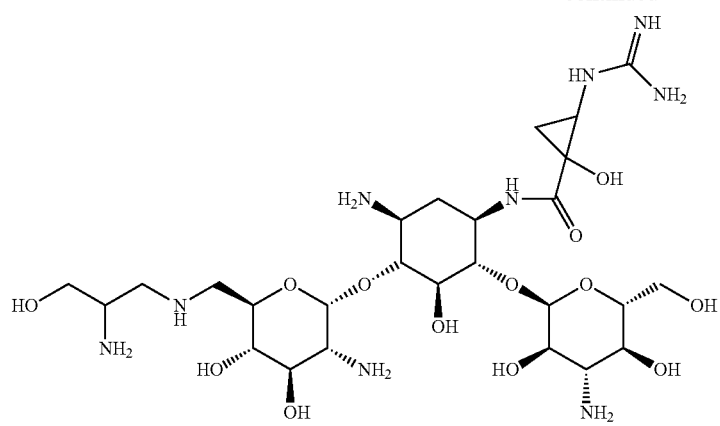
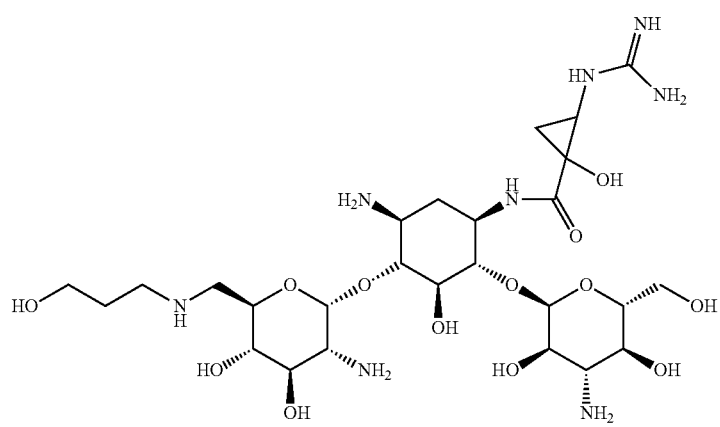
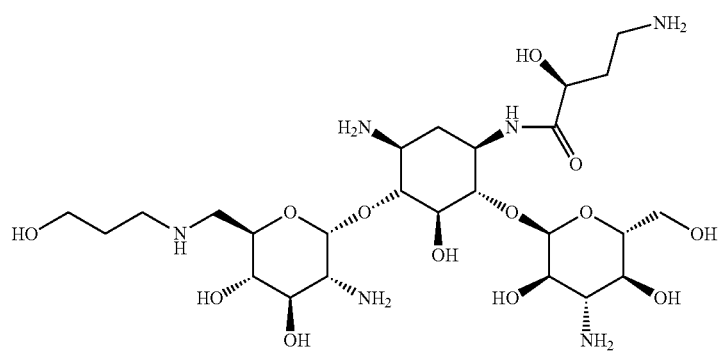
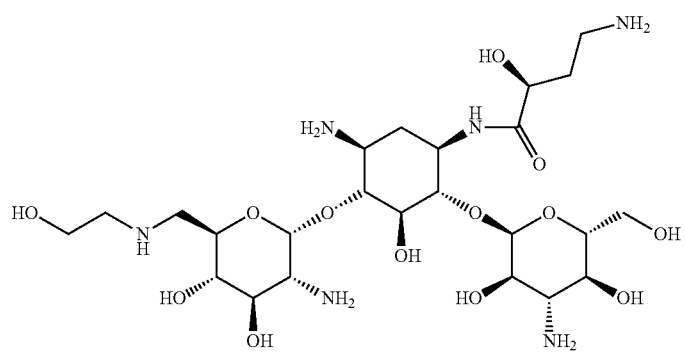

-continued
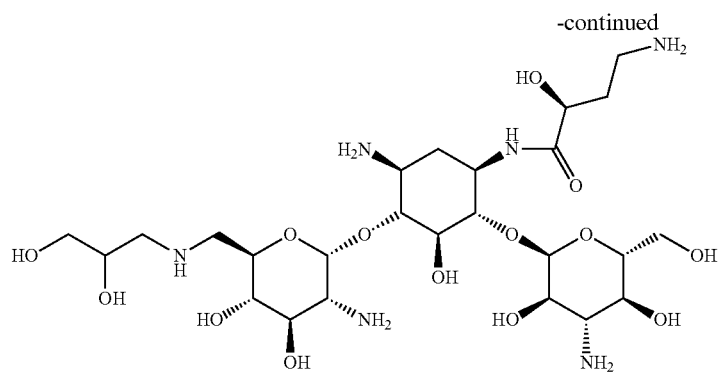
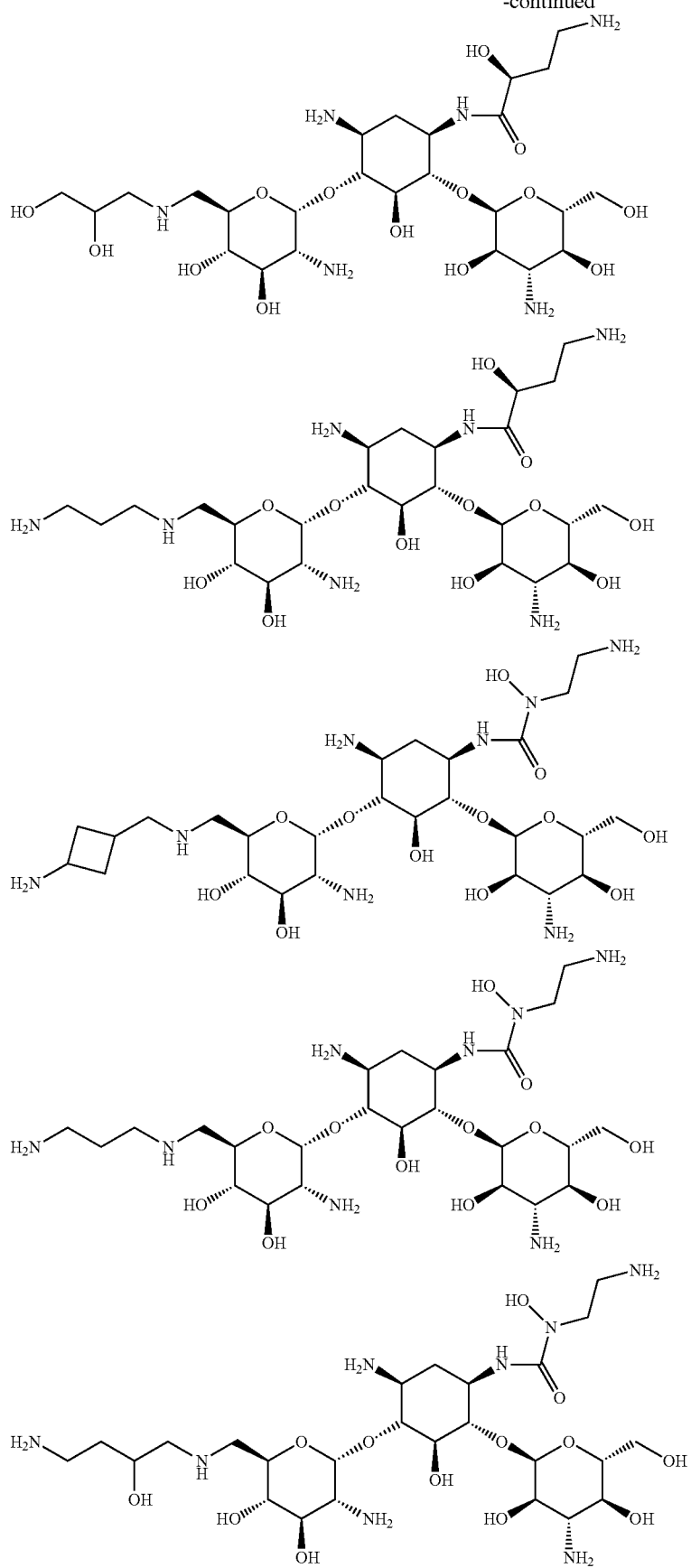

-continued
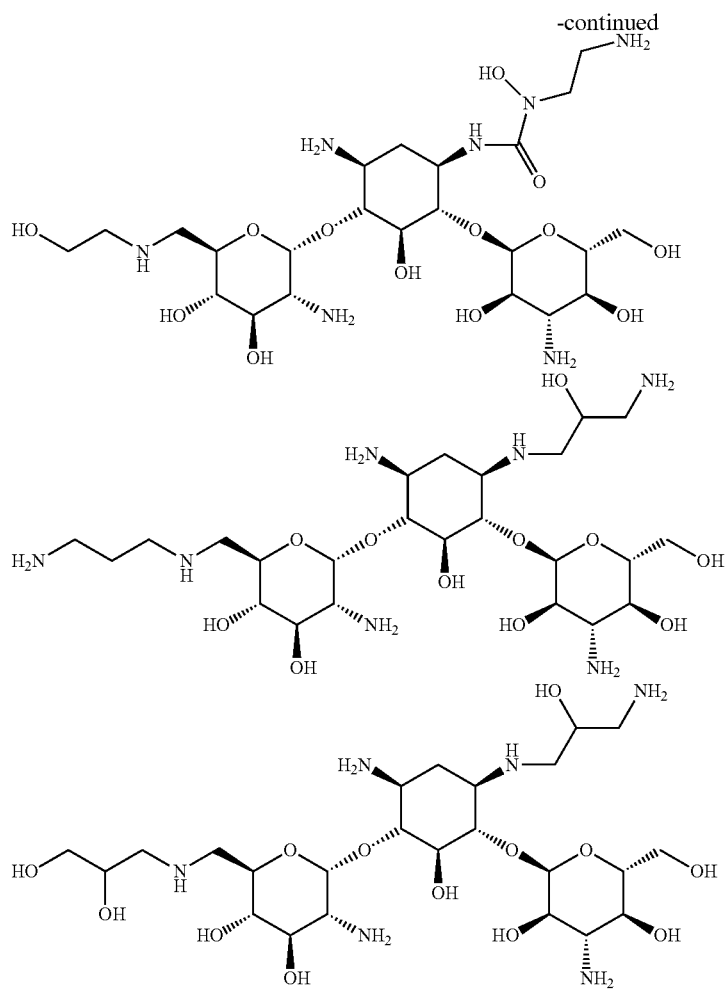
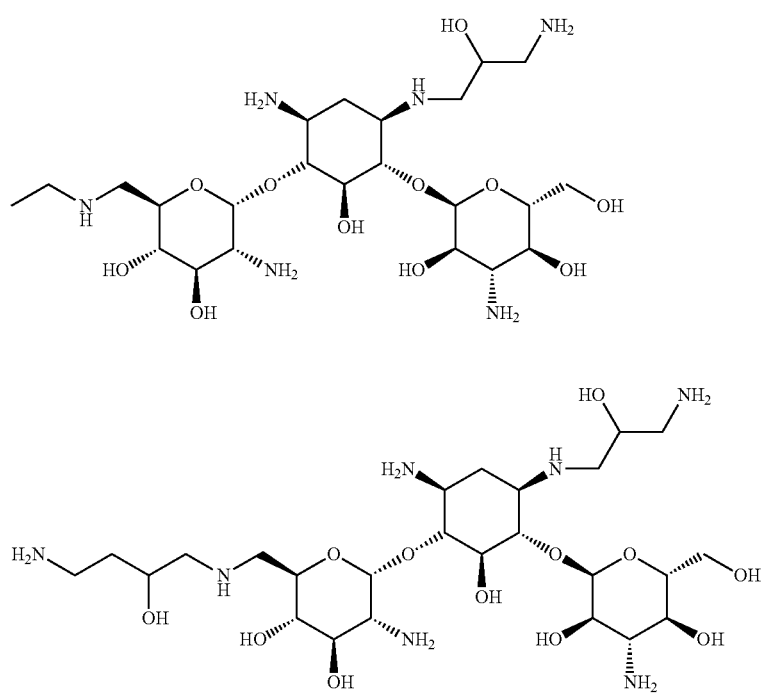

-continued
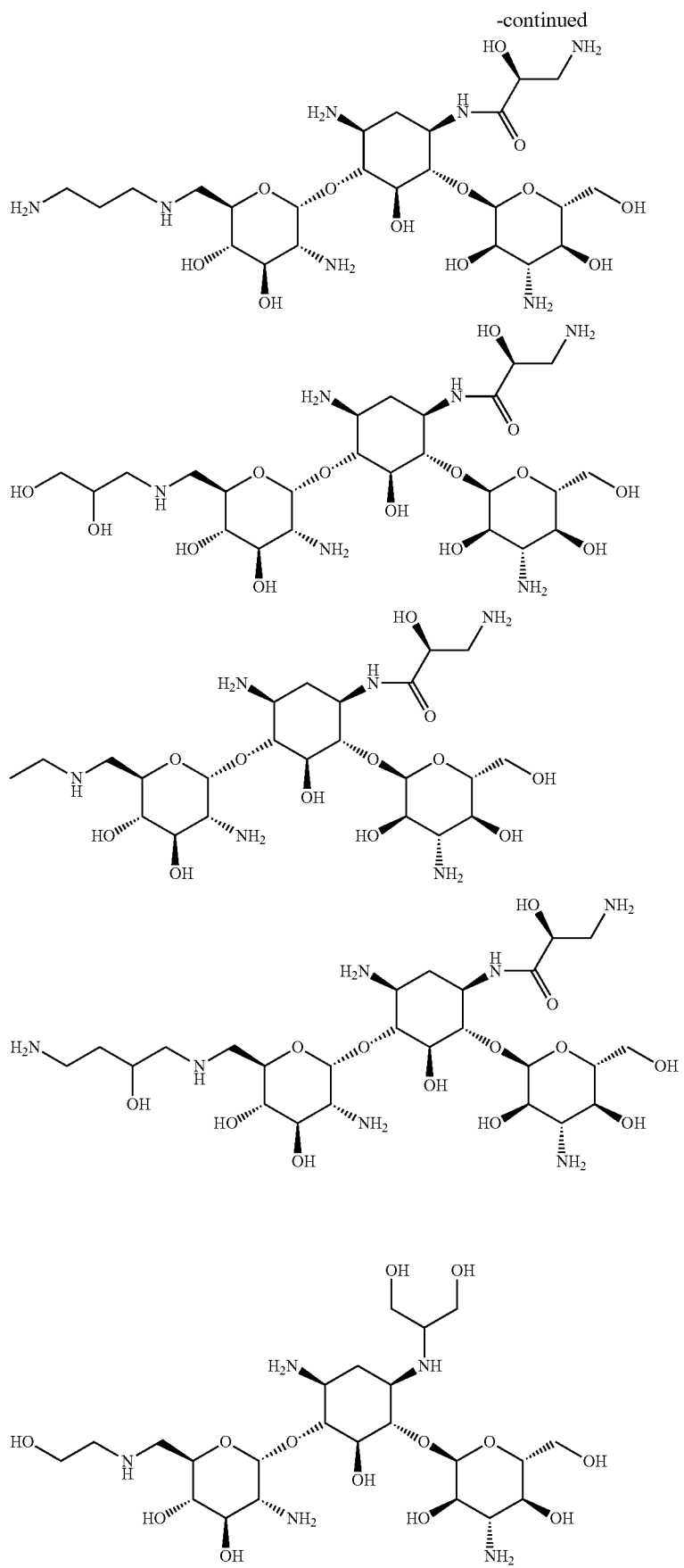

125
-continued
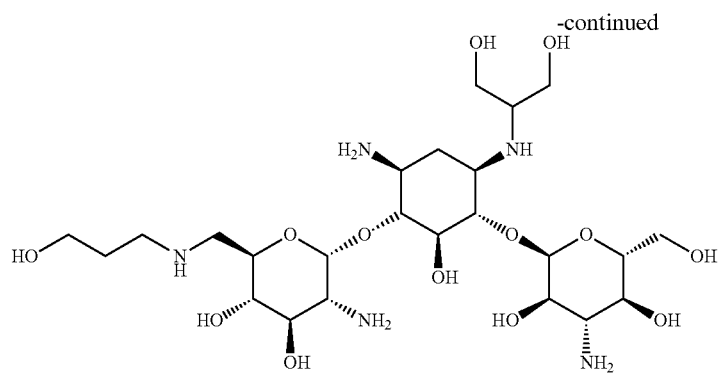
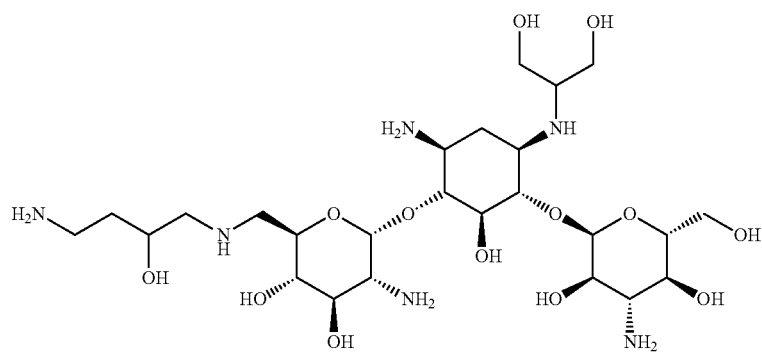
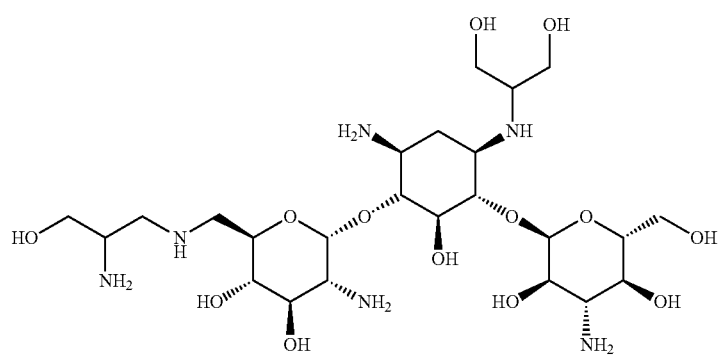
126
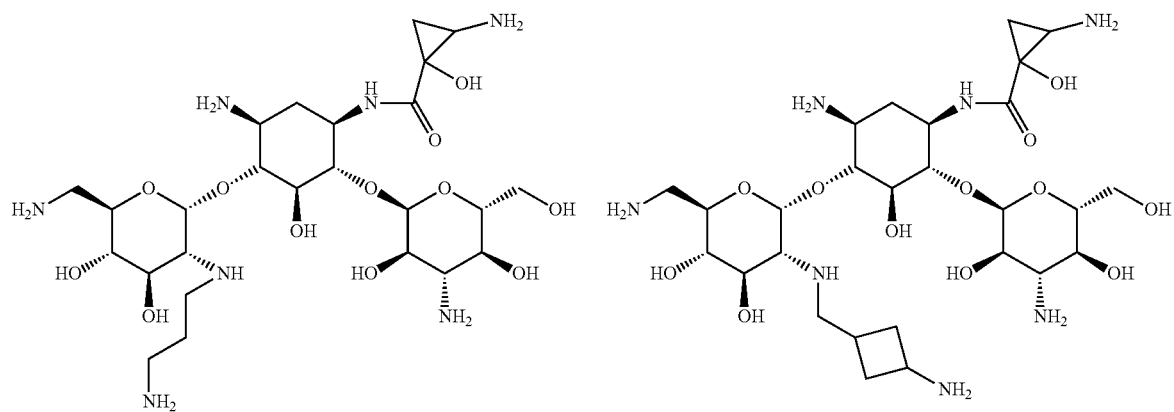

-continued
127
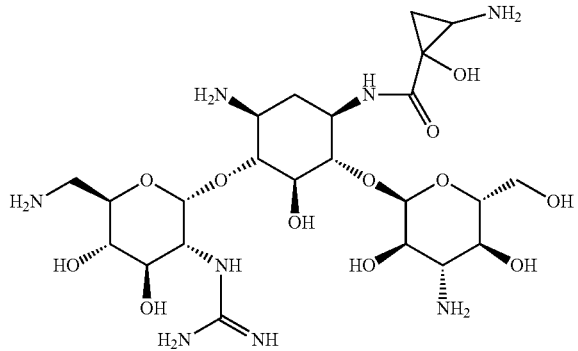
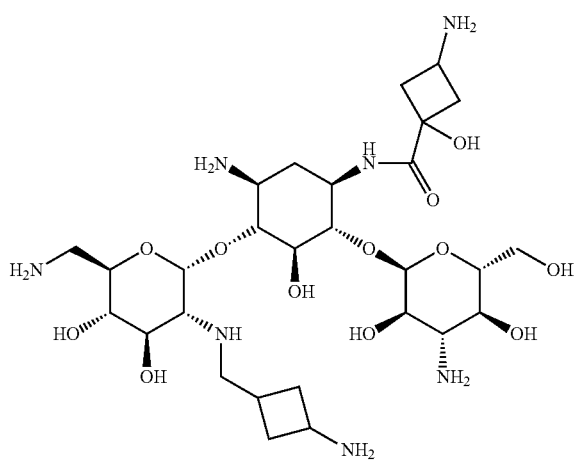
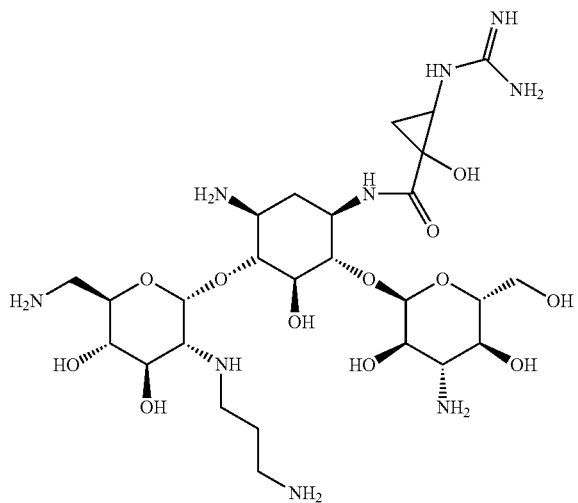
128
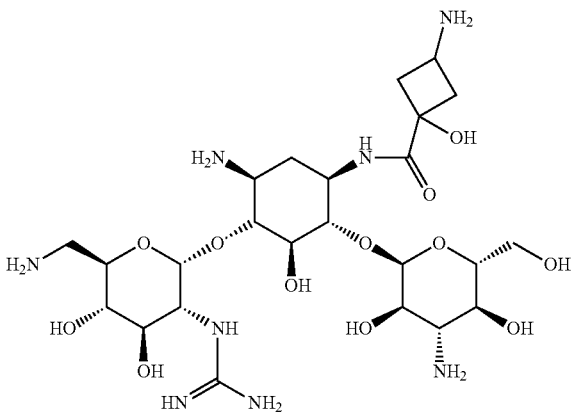
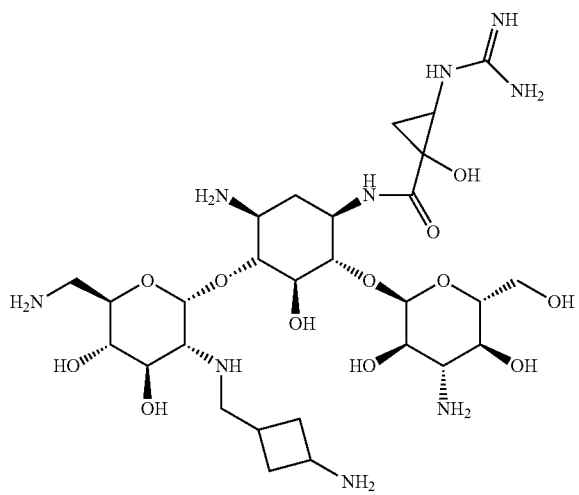
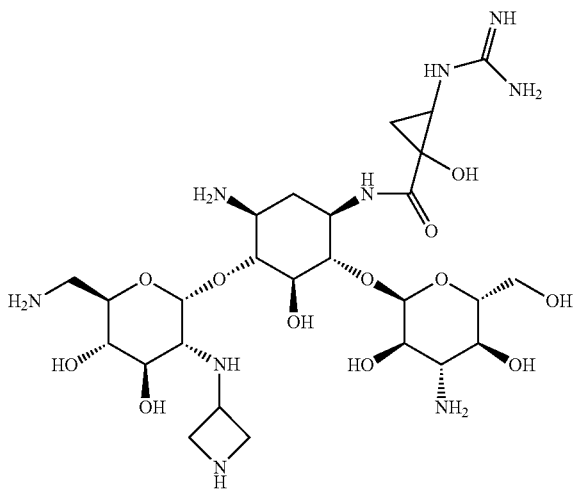

129 130
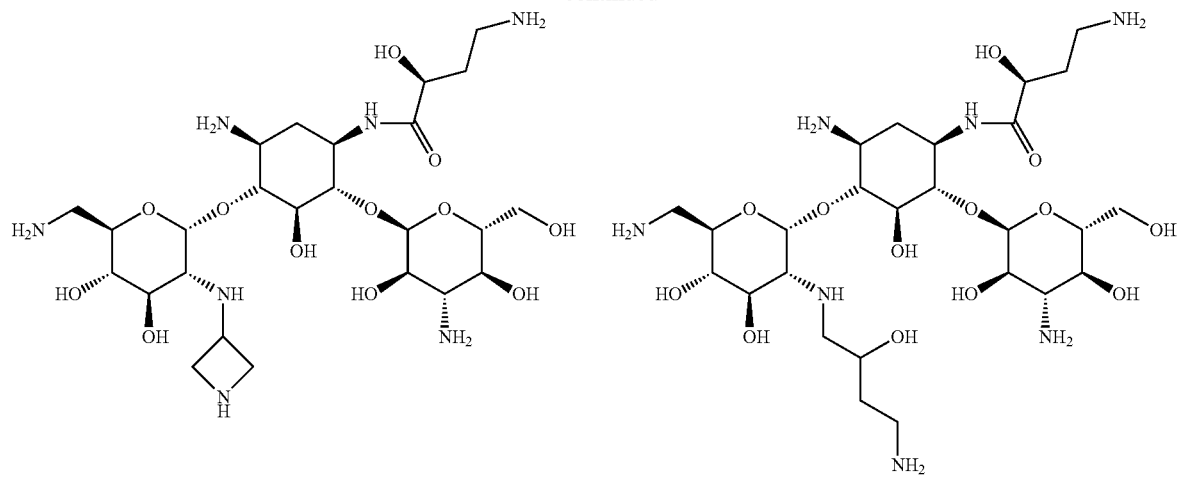
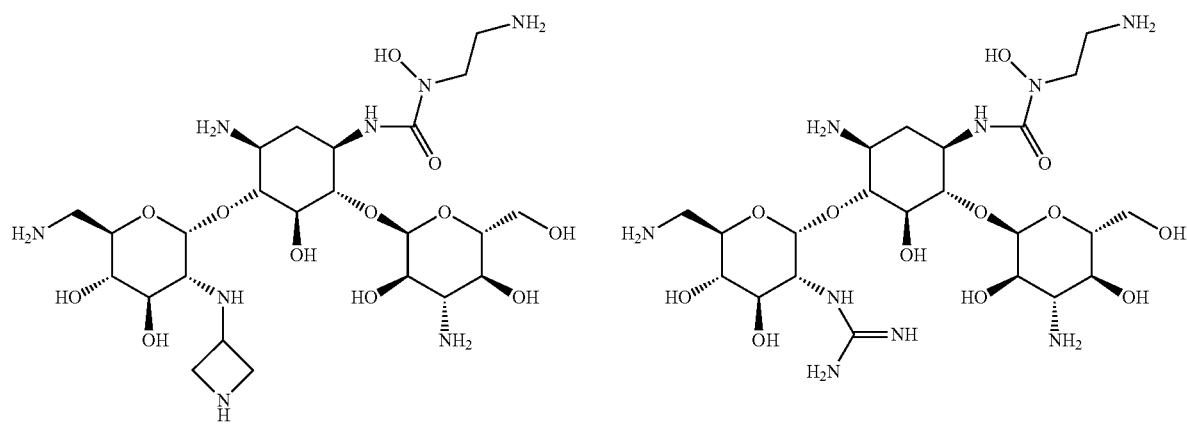
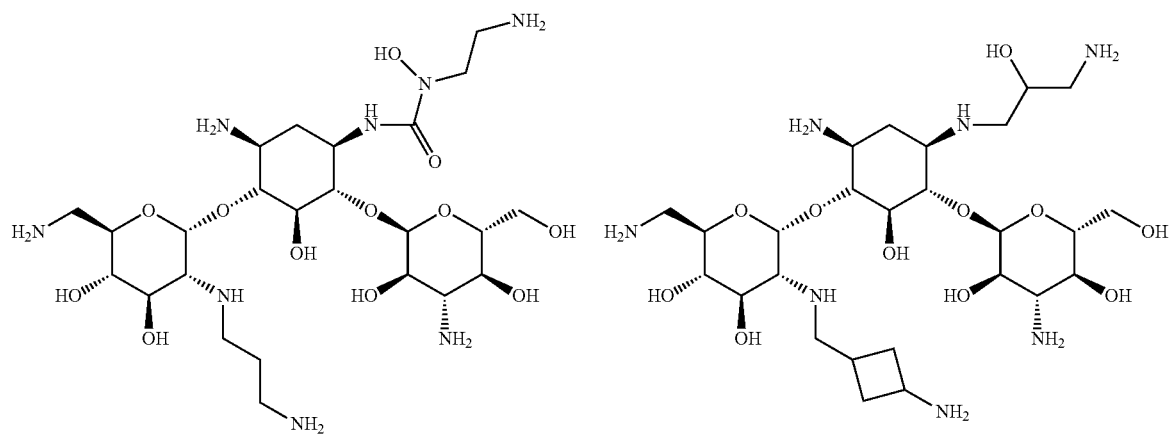

-continued
131                                    132
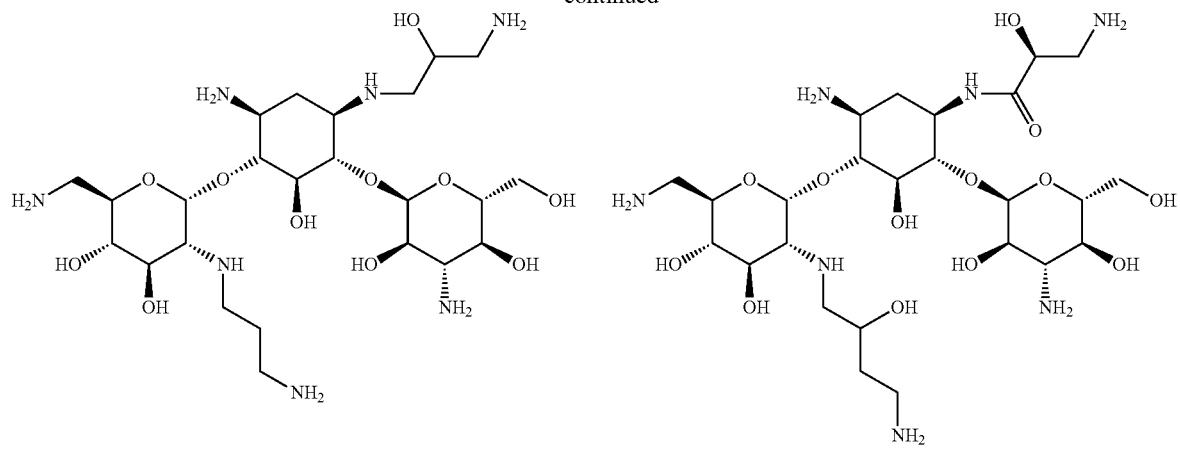
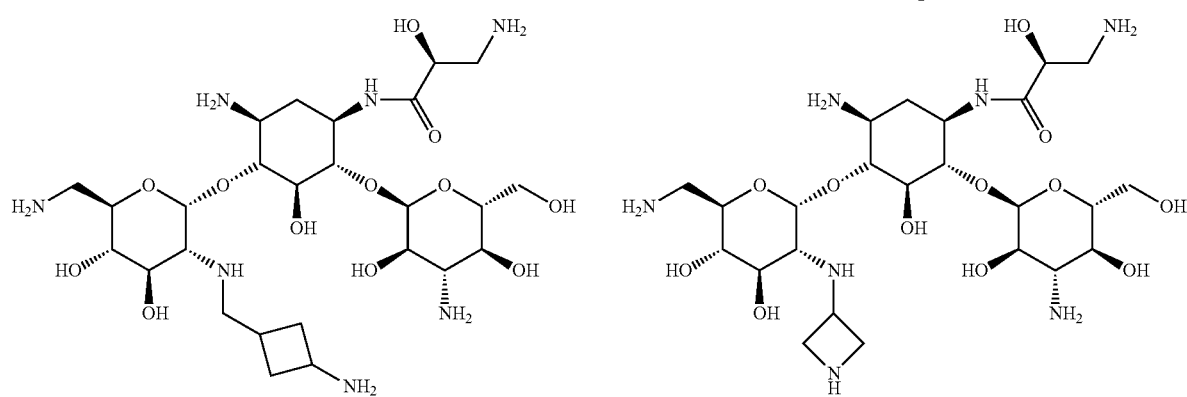
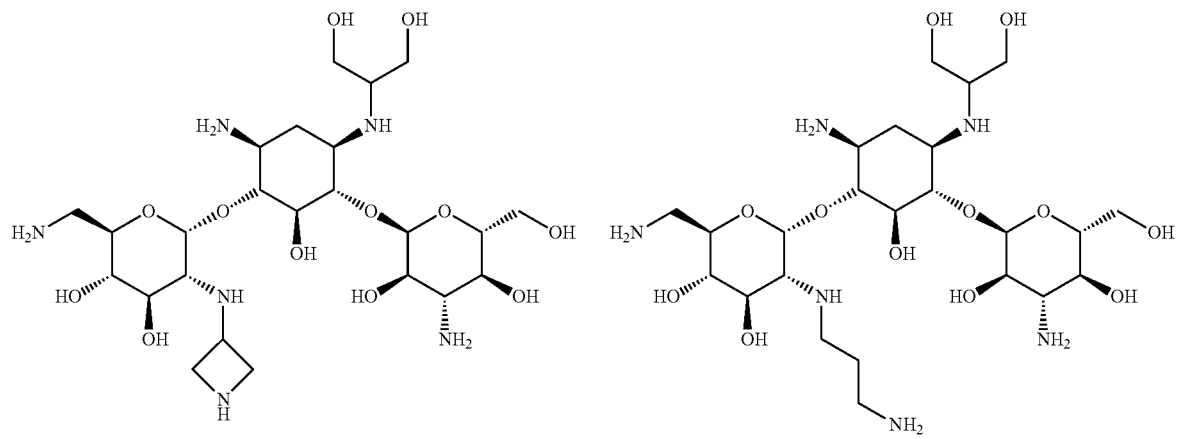
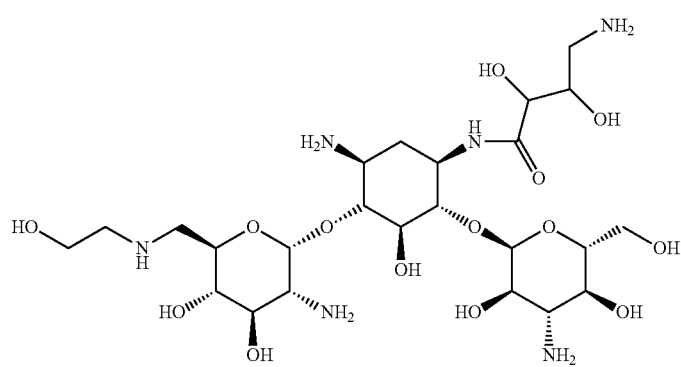

-continued
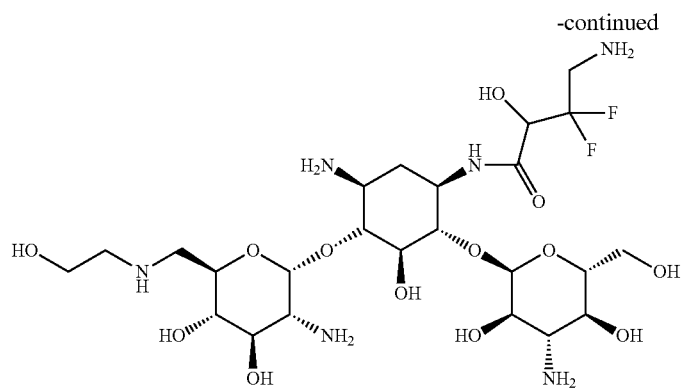
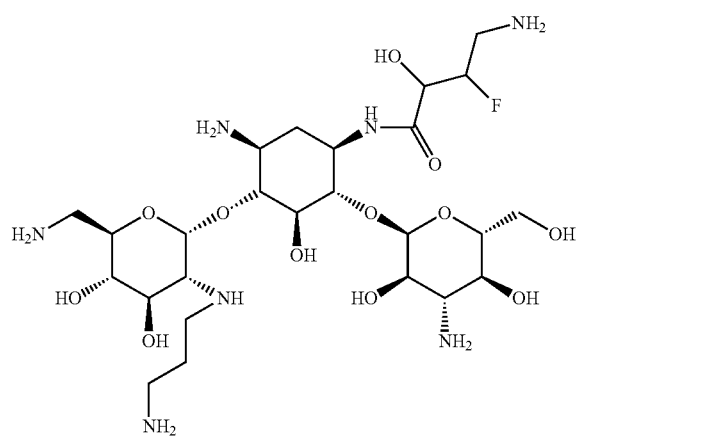
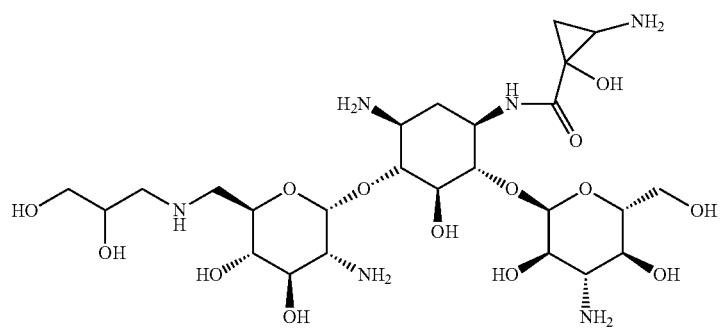
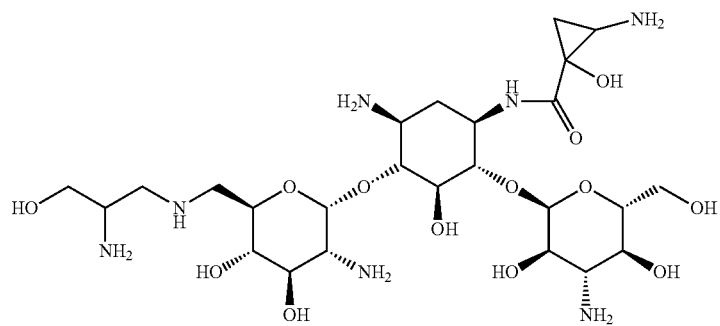

-continued
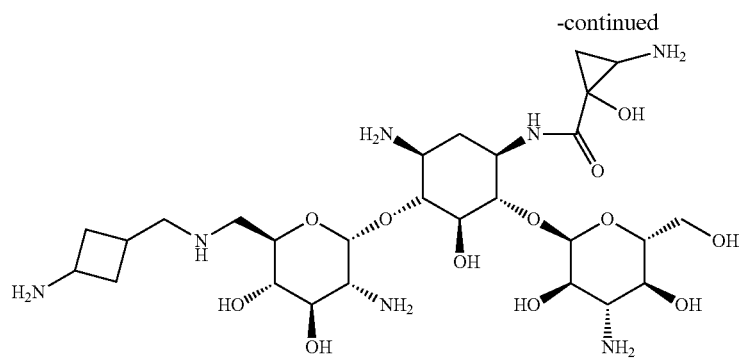
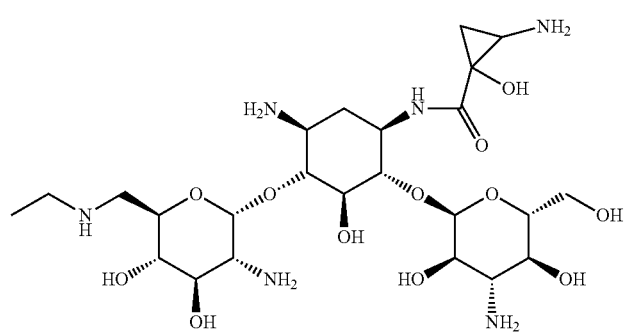
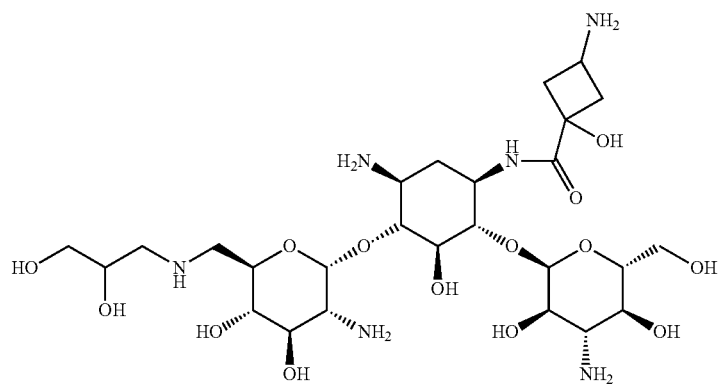
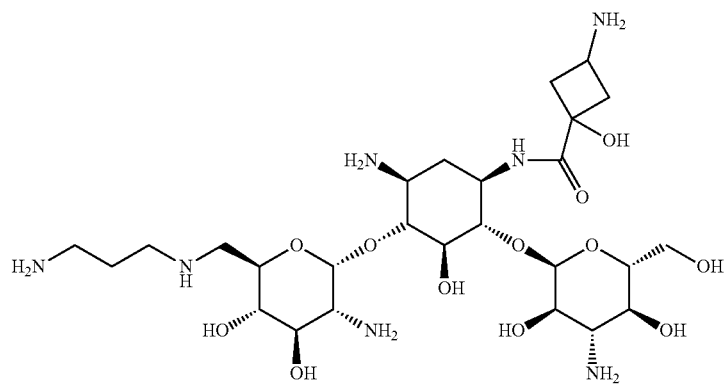

-continued
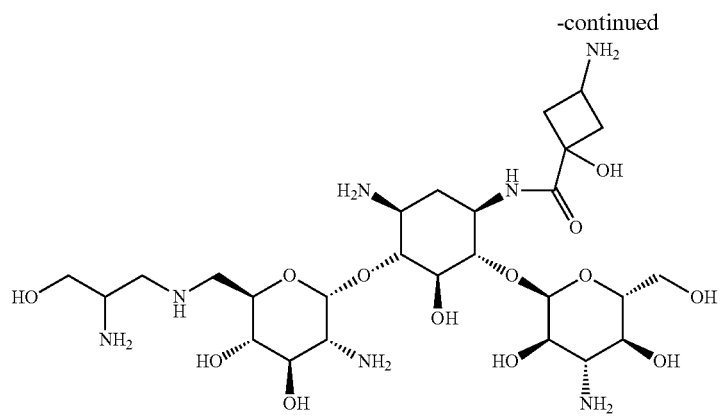
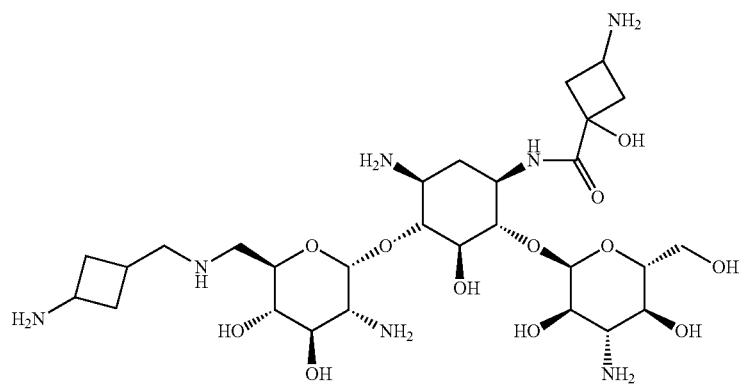
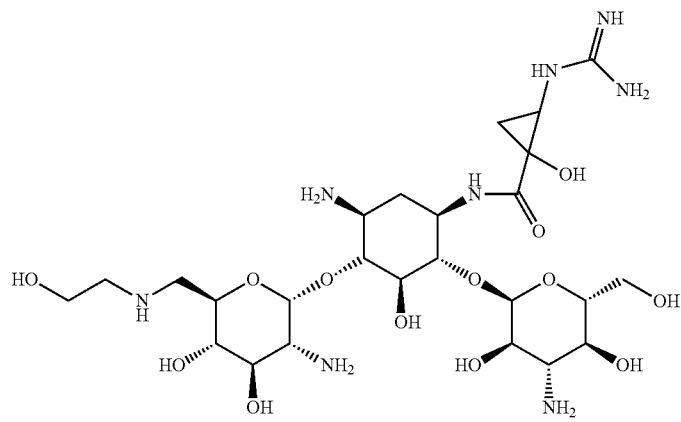
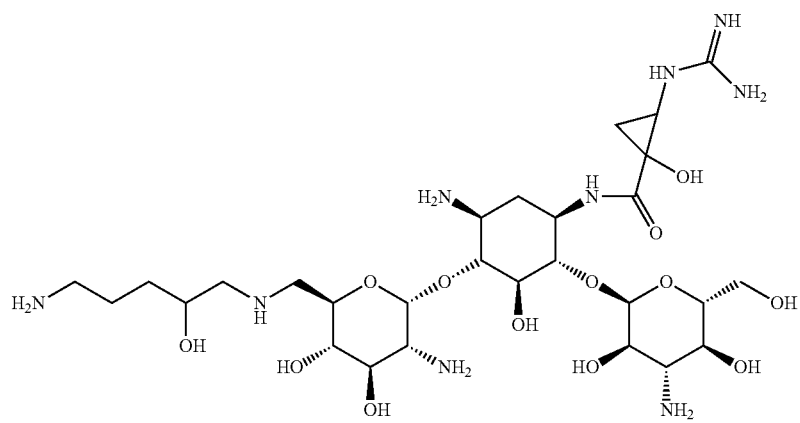

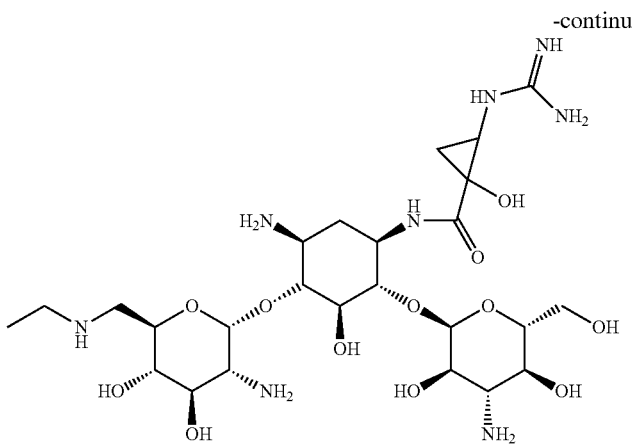
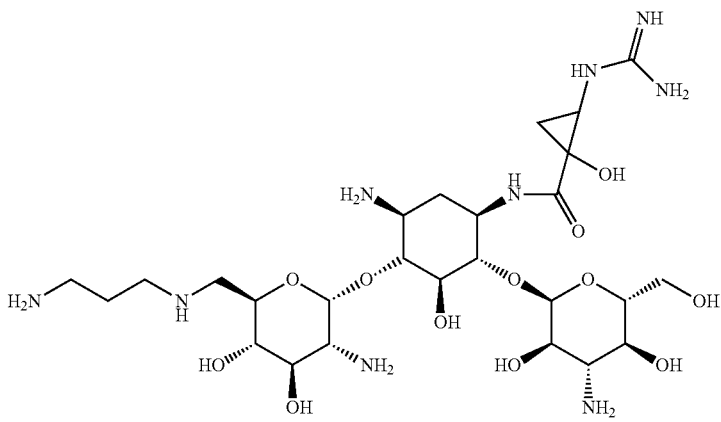
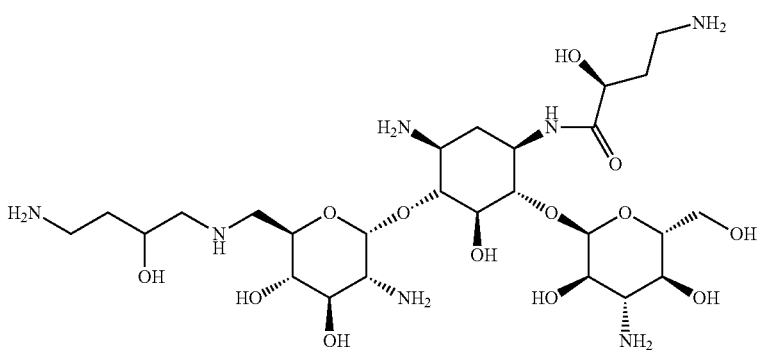
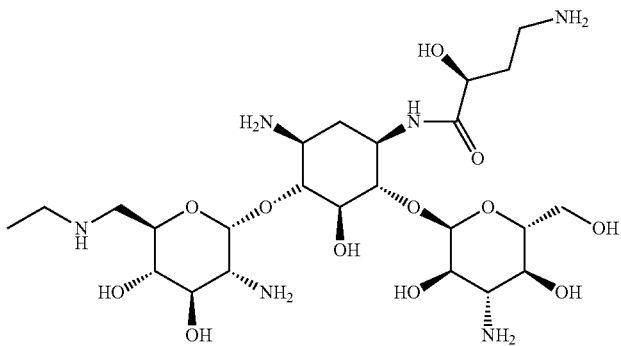

-continued
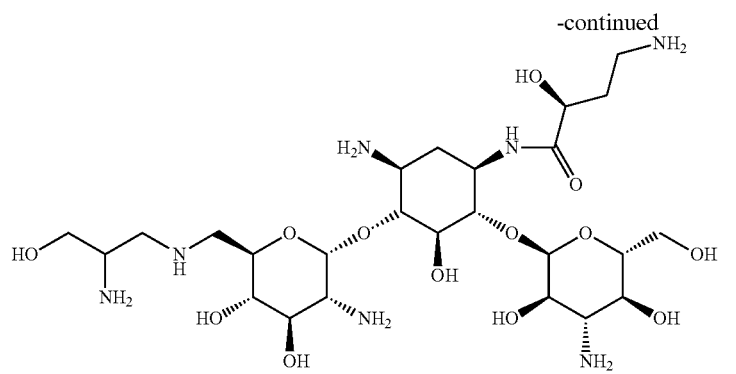
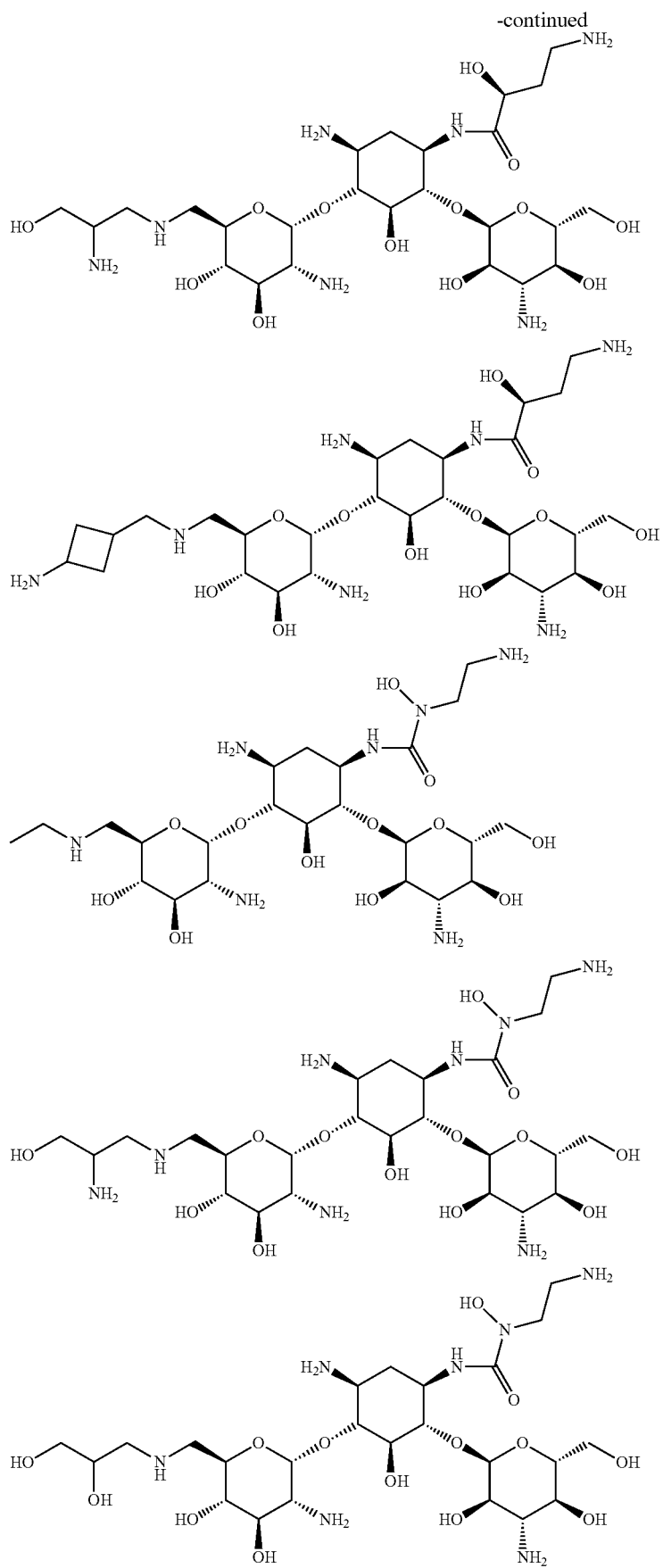

-continued
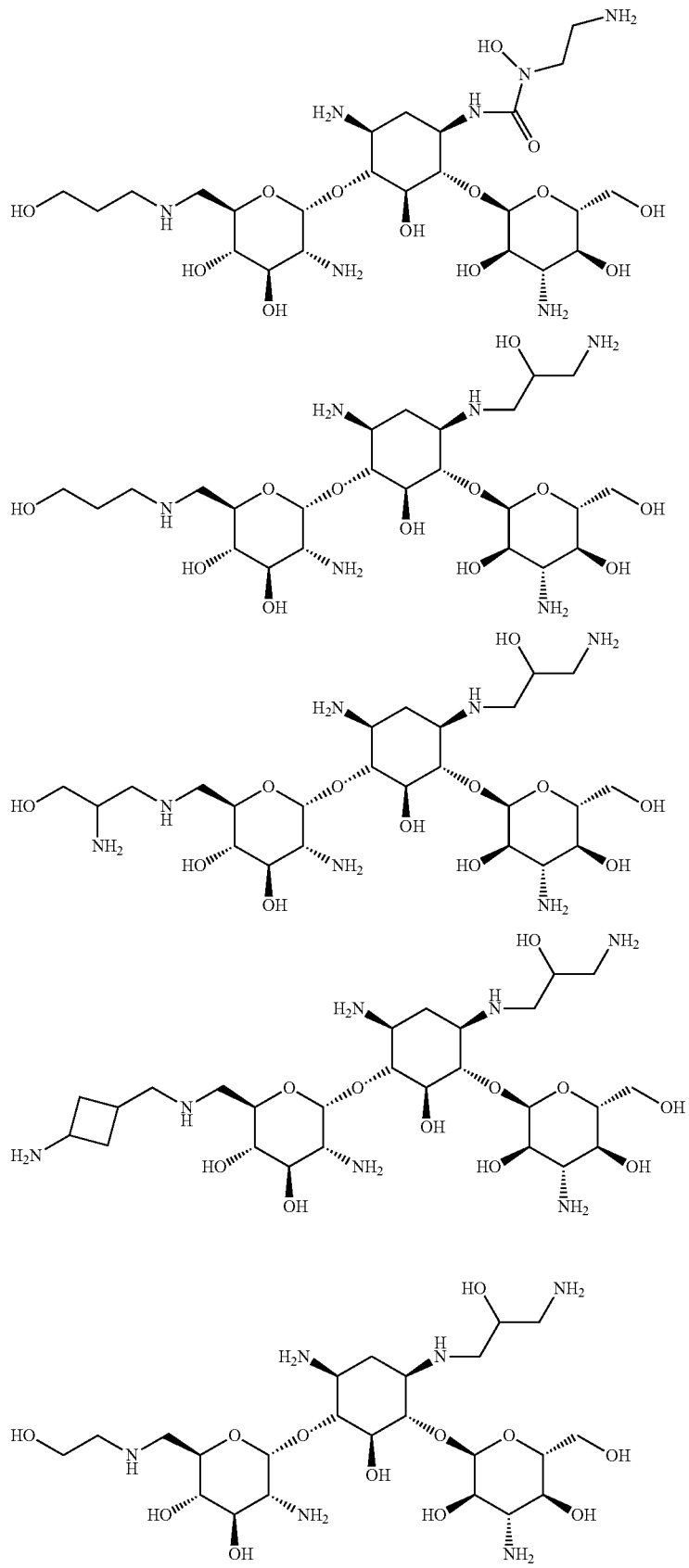

-continued
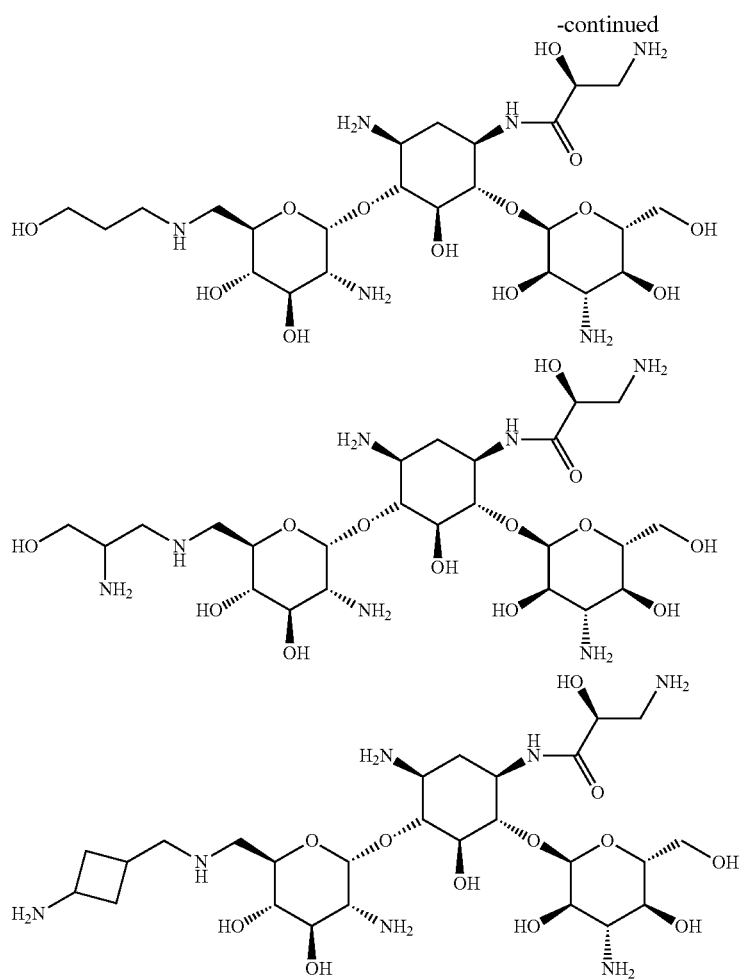
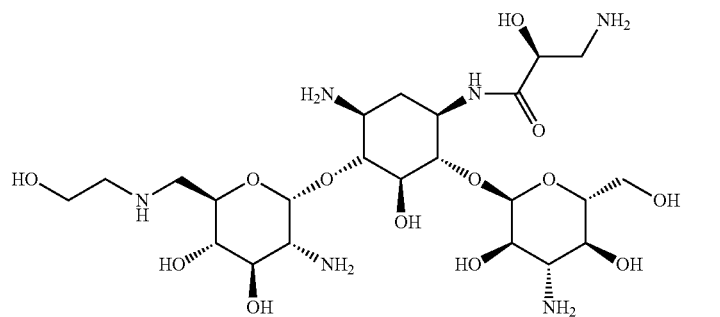
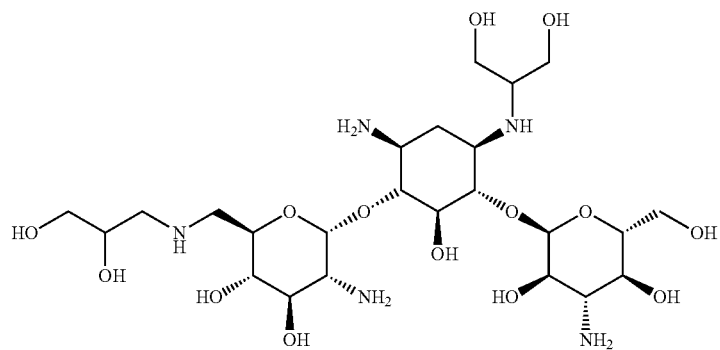

147 148
-continued
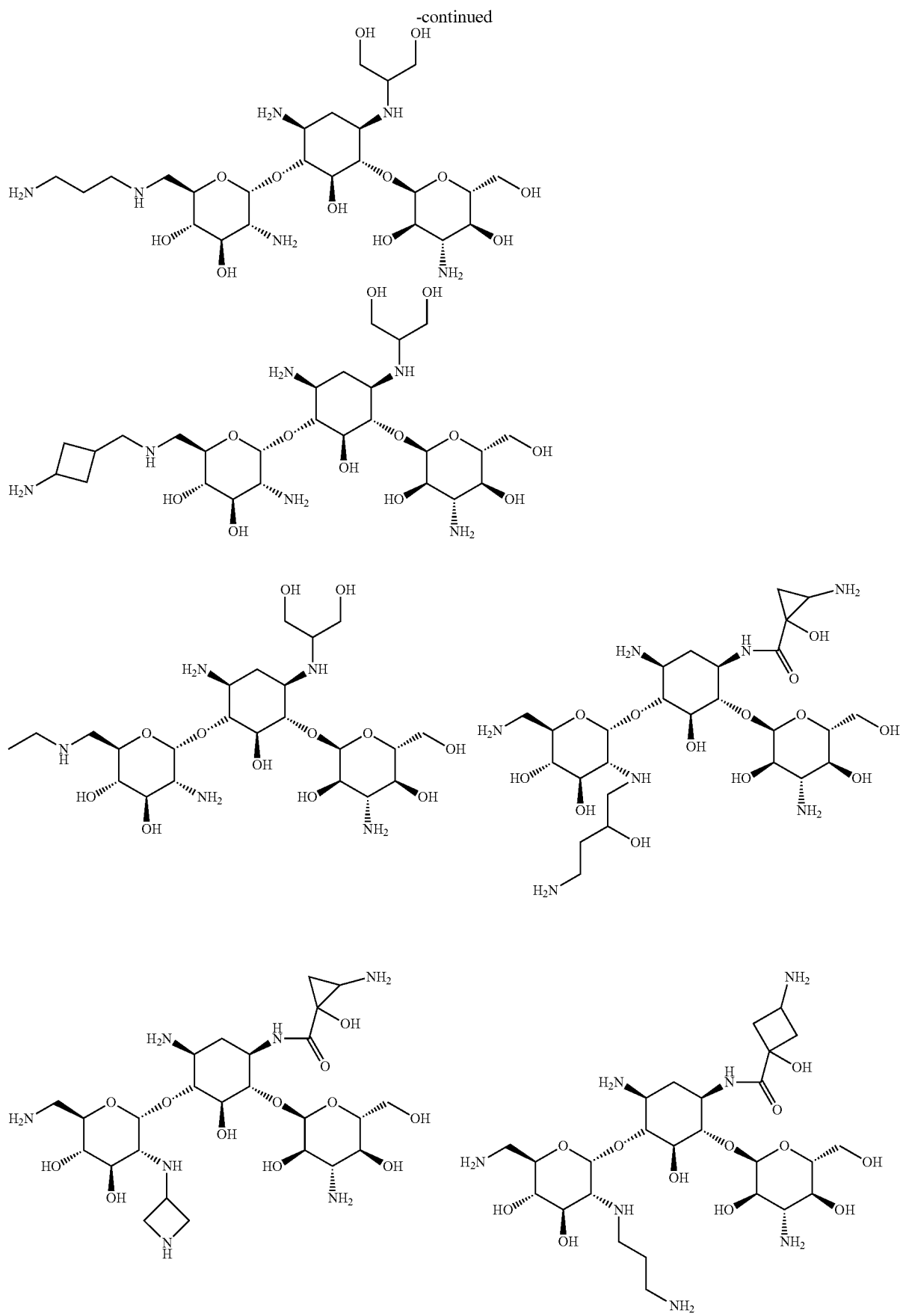

-continued
149
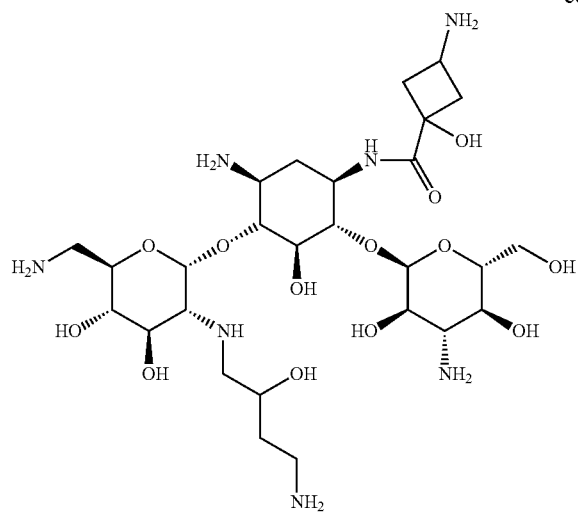
150
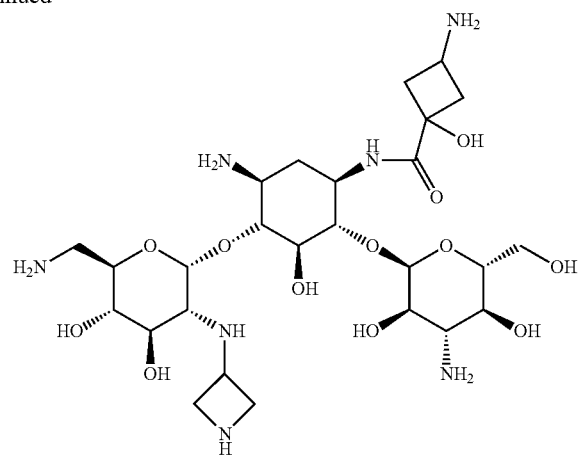
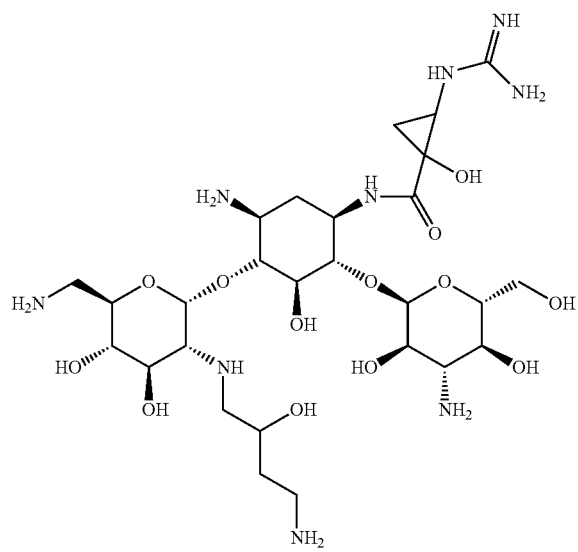
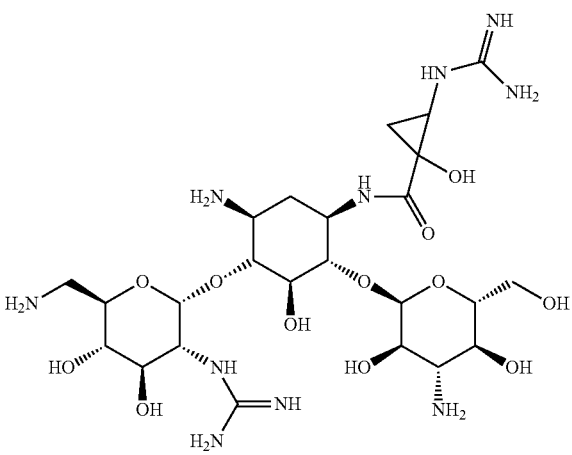
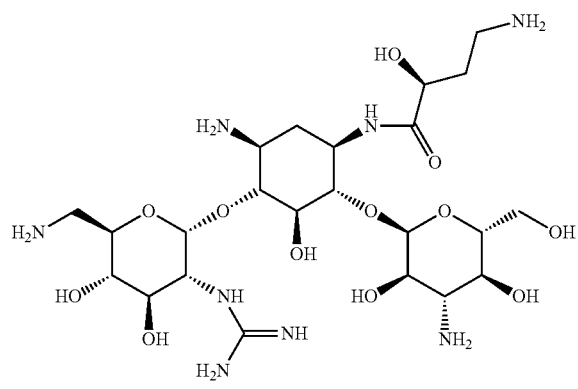
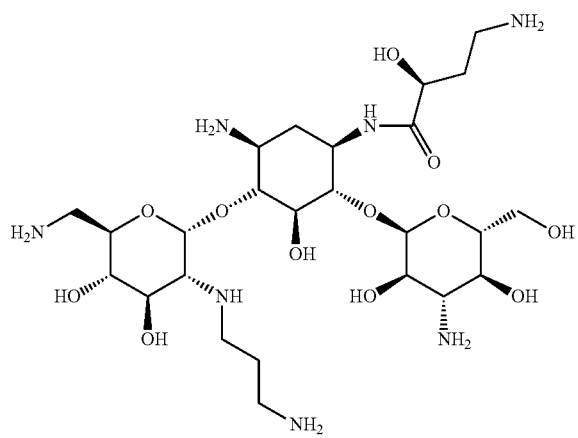

151
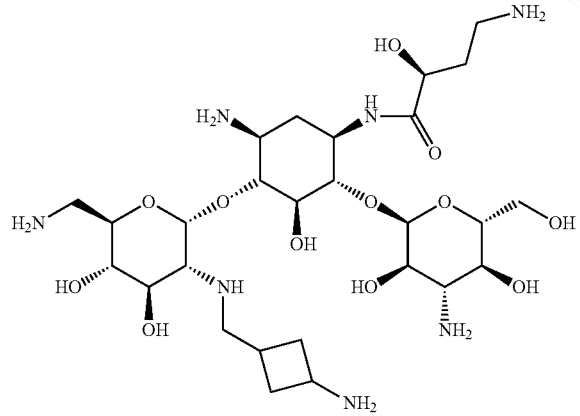
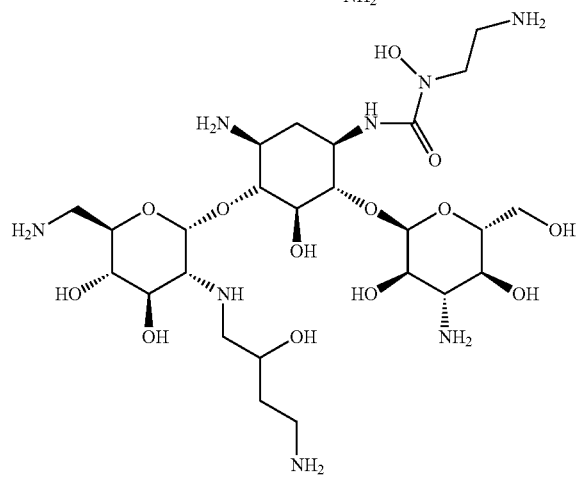
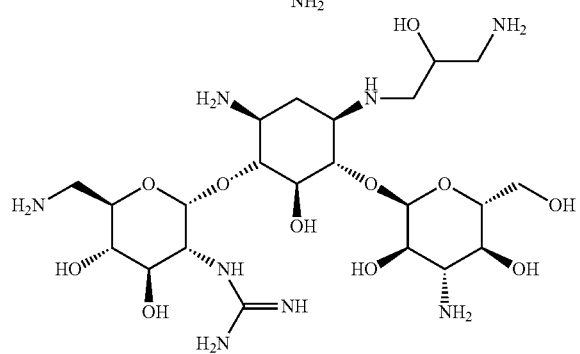
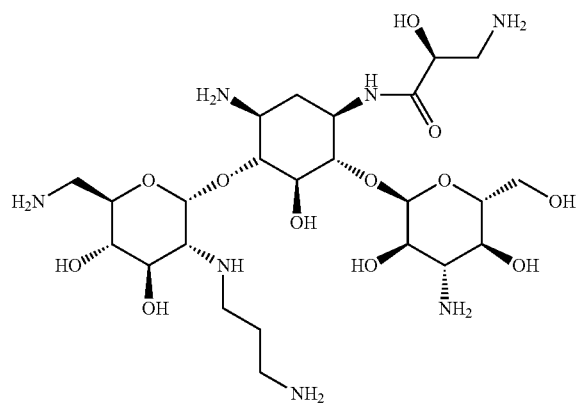
152
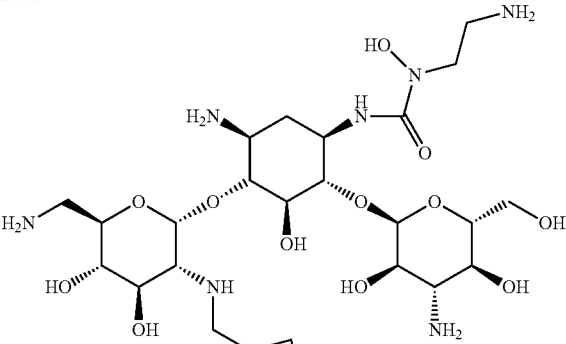
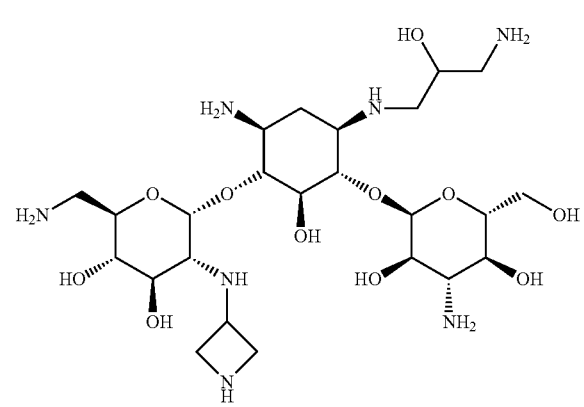
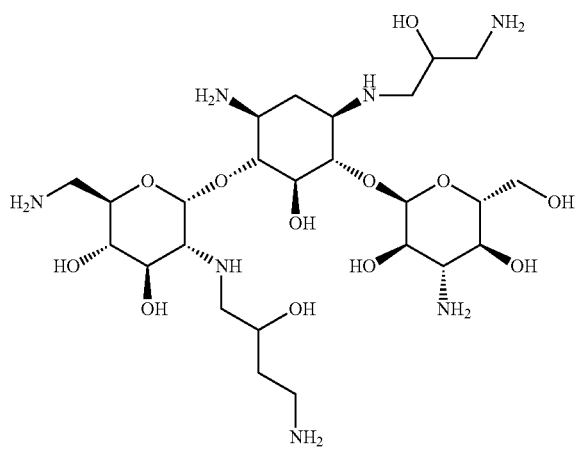
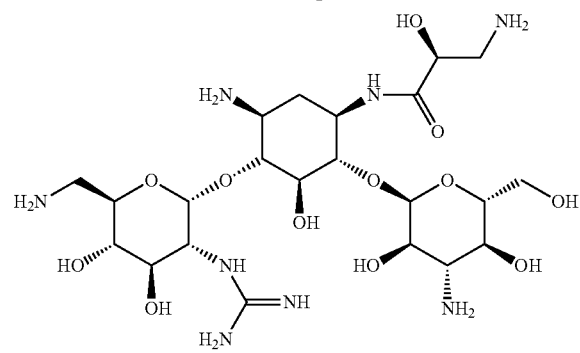

153 154
-continued
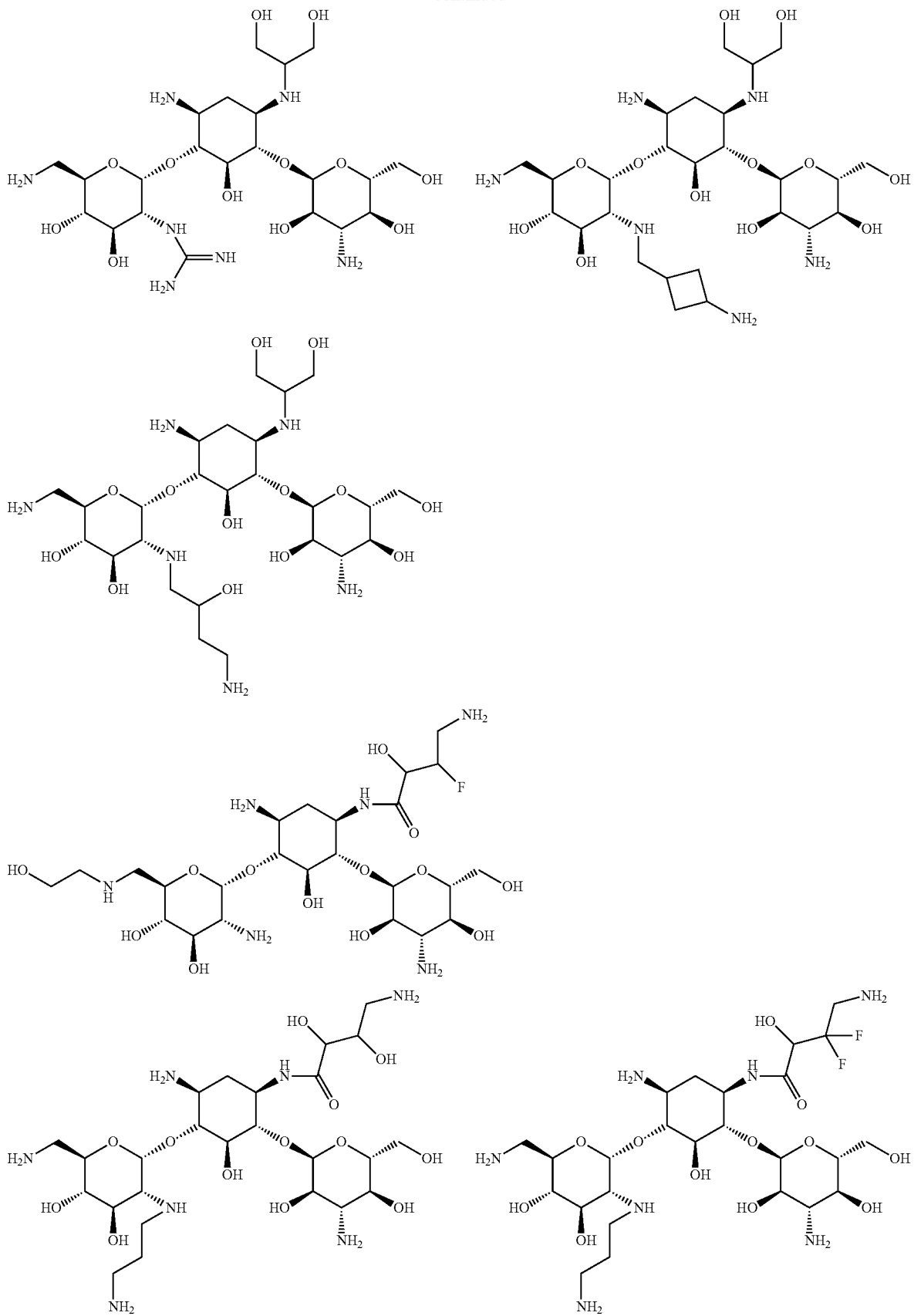

155 156
Kanamycin A Analogs
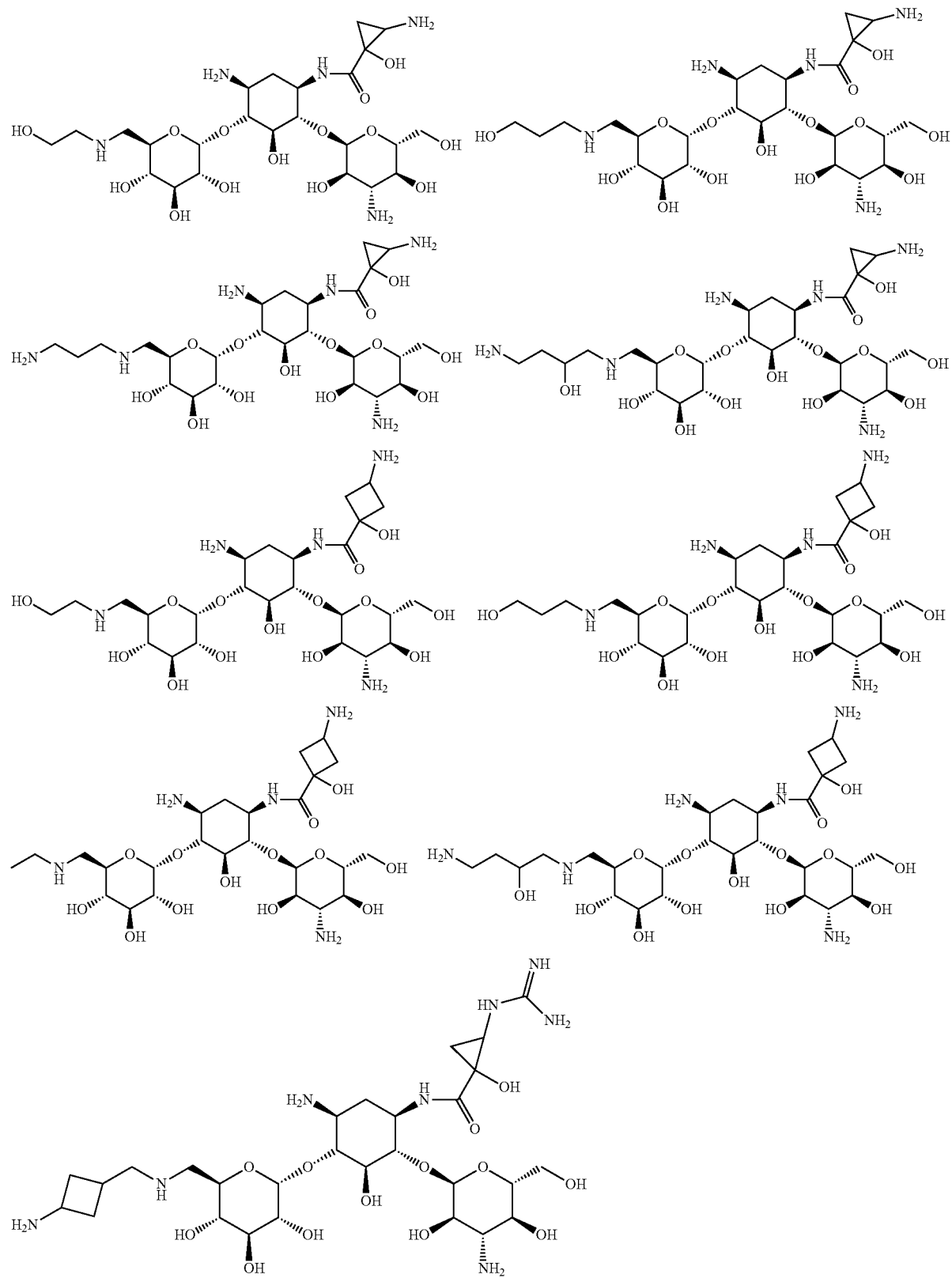

157 158
-continued
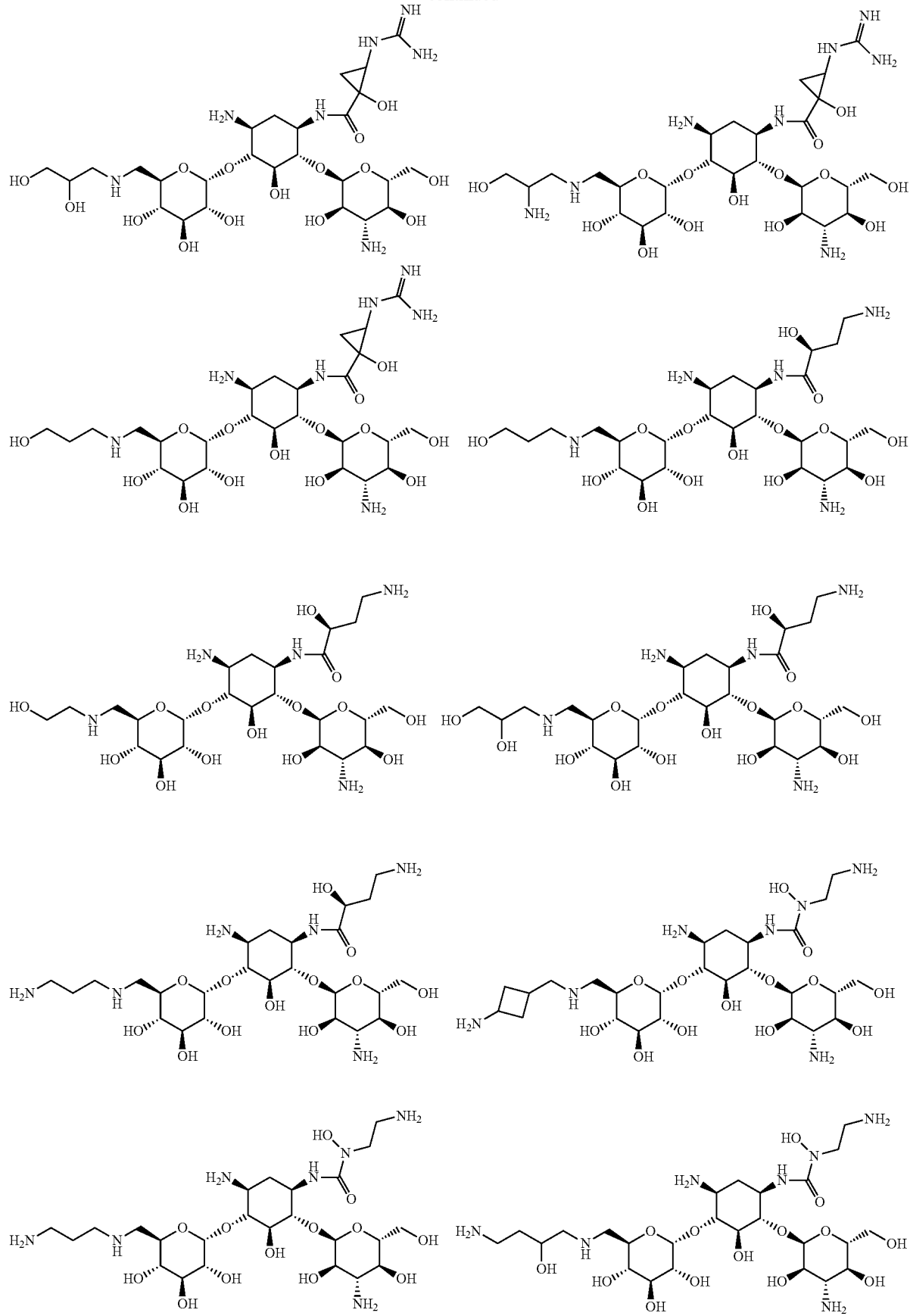

159 160
-continued
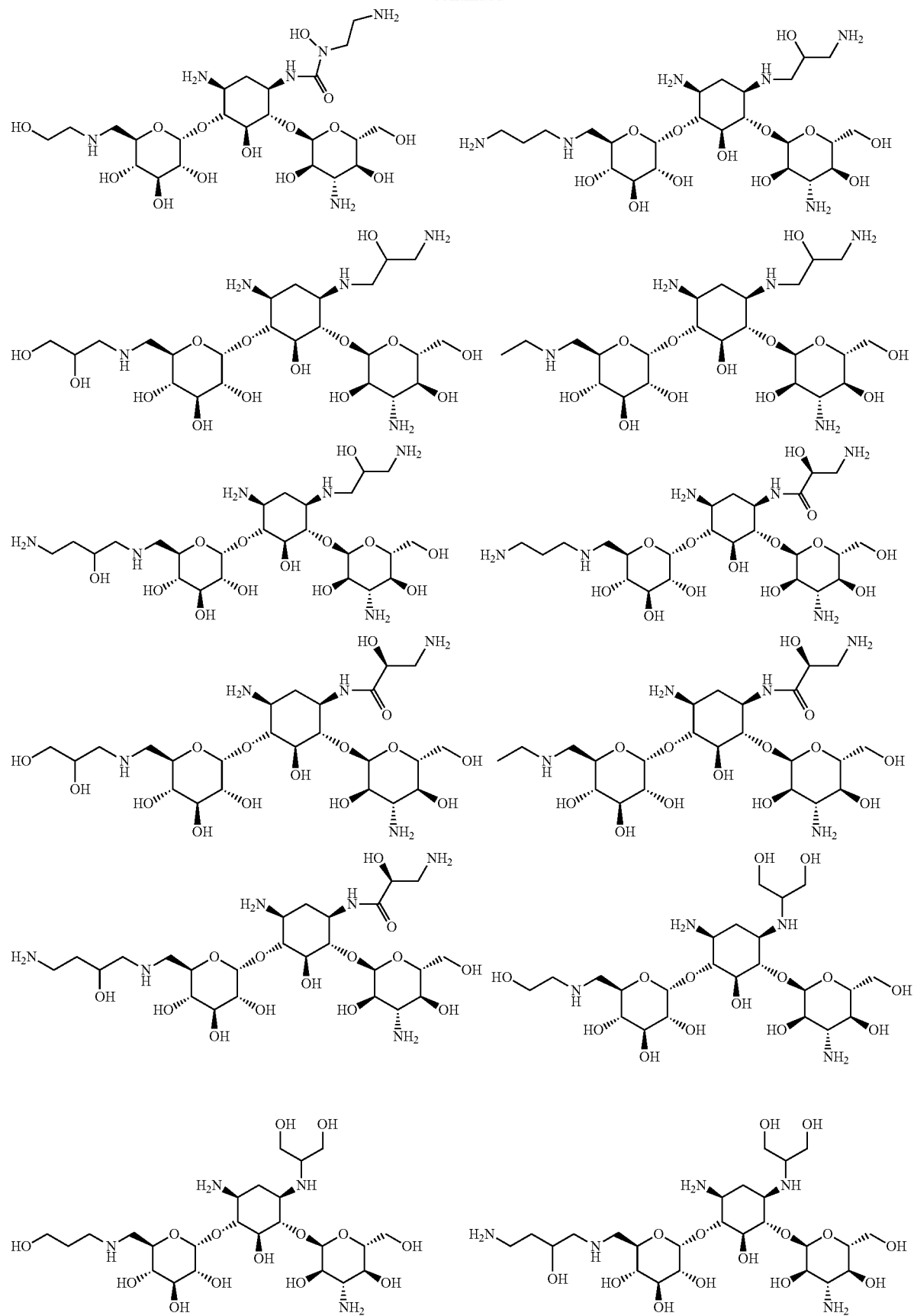

161 162
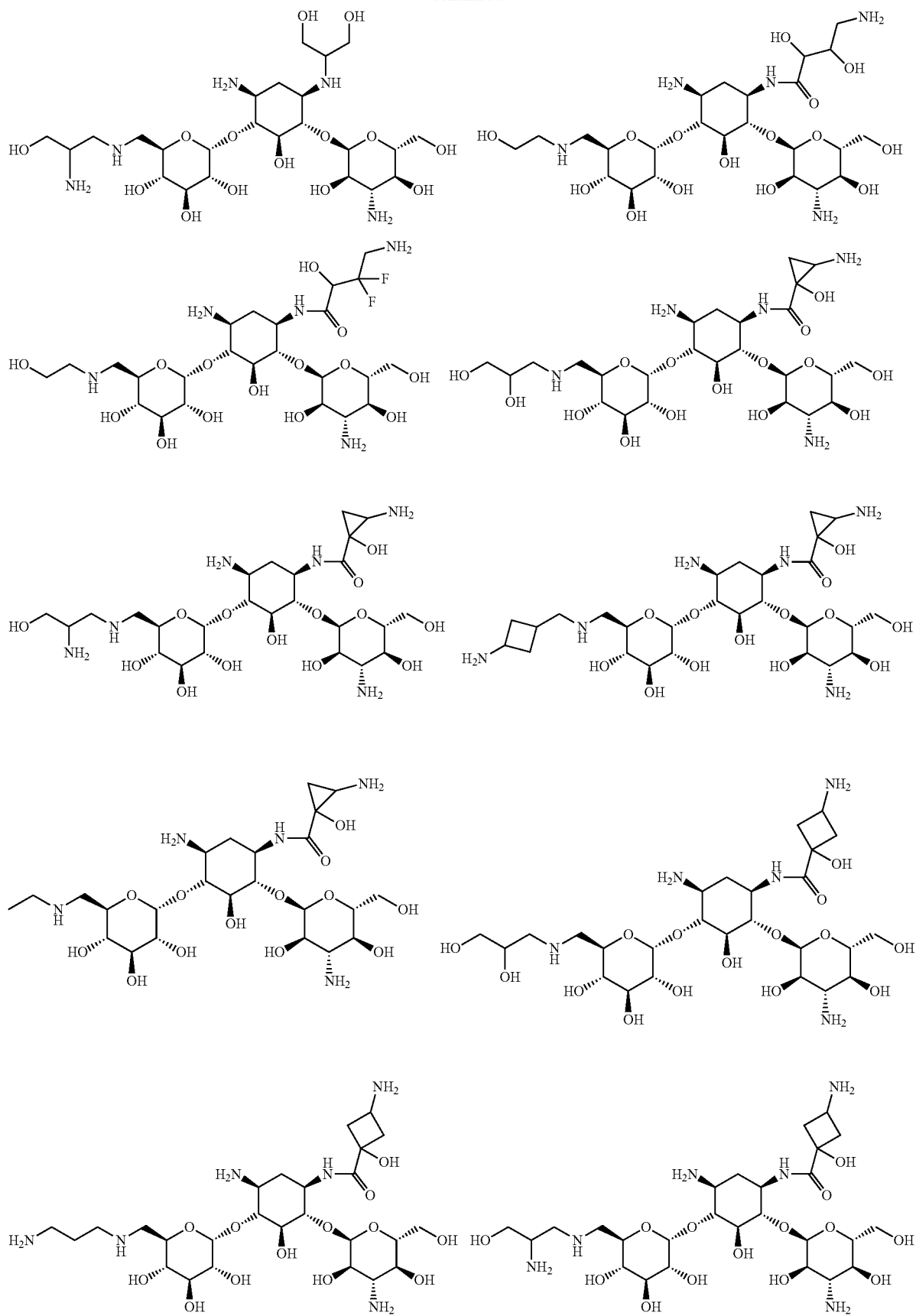
-continued

163    -continued    164
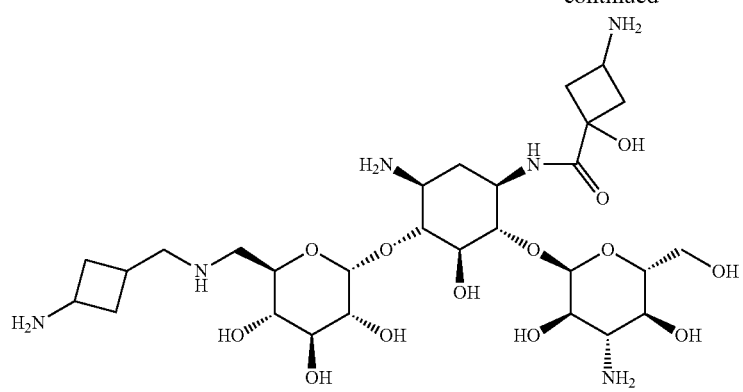
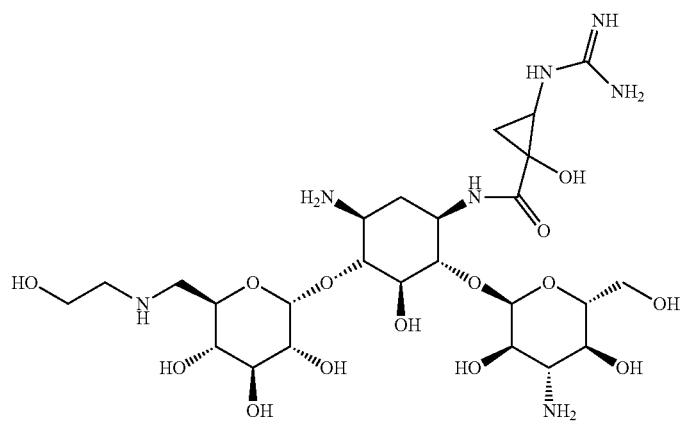
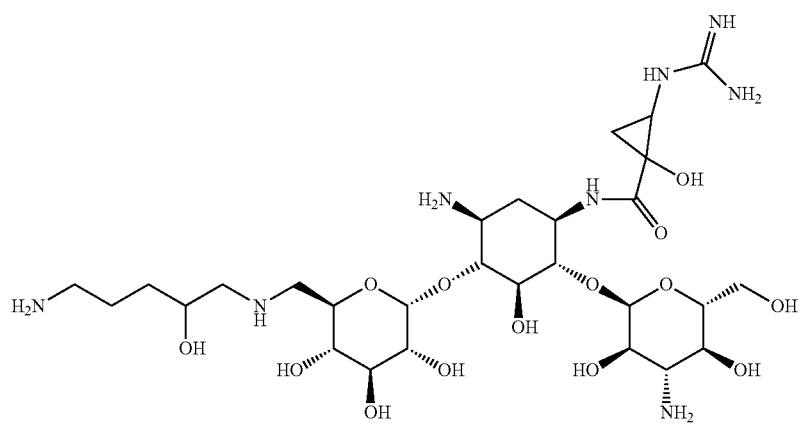
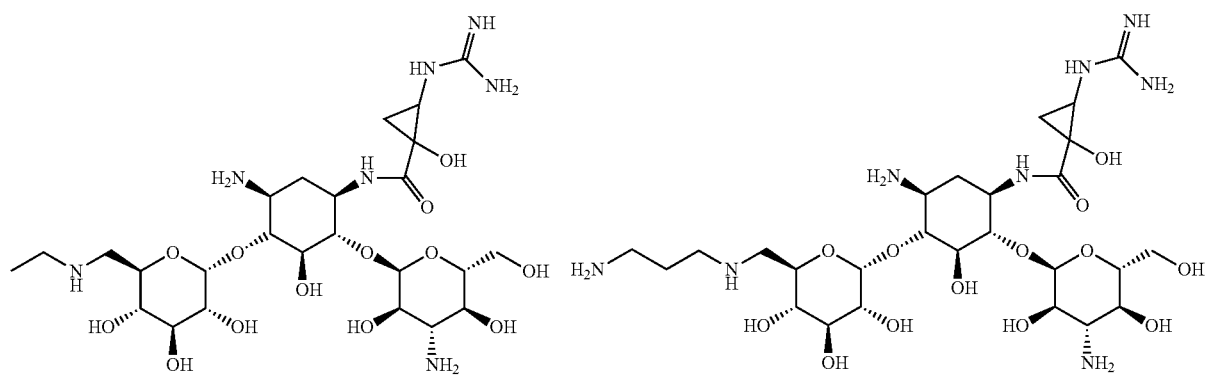

165 166
-continued
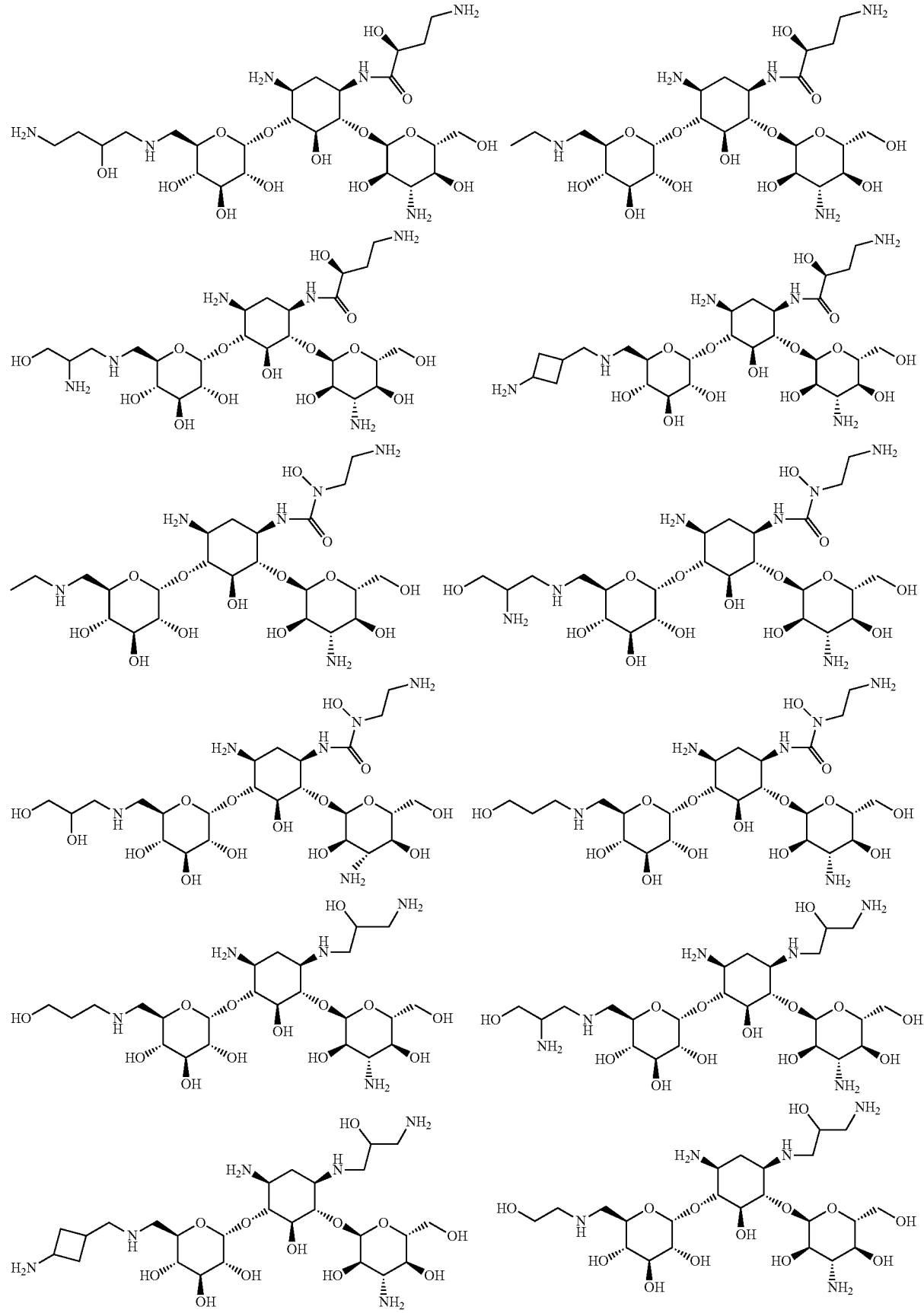

-continued

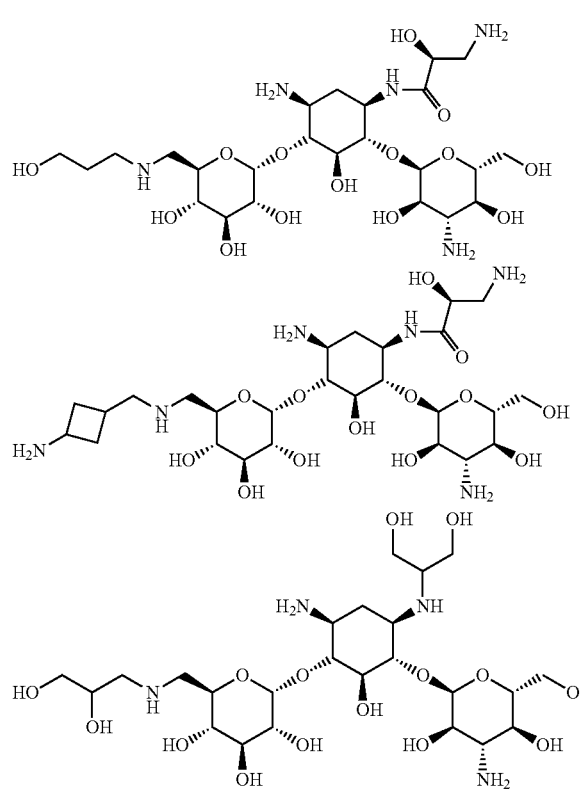

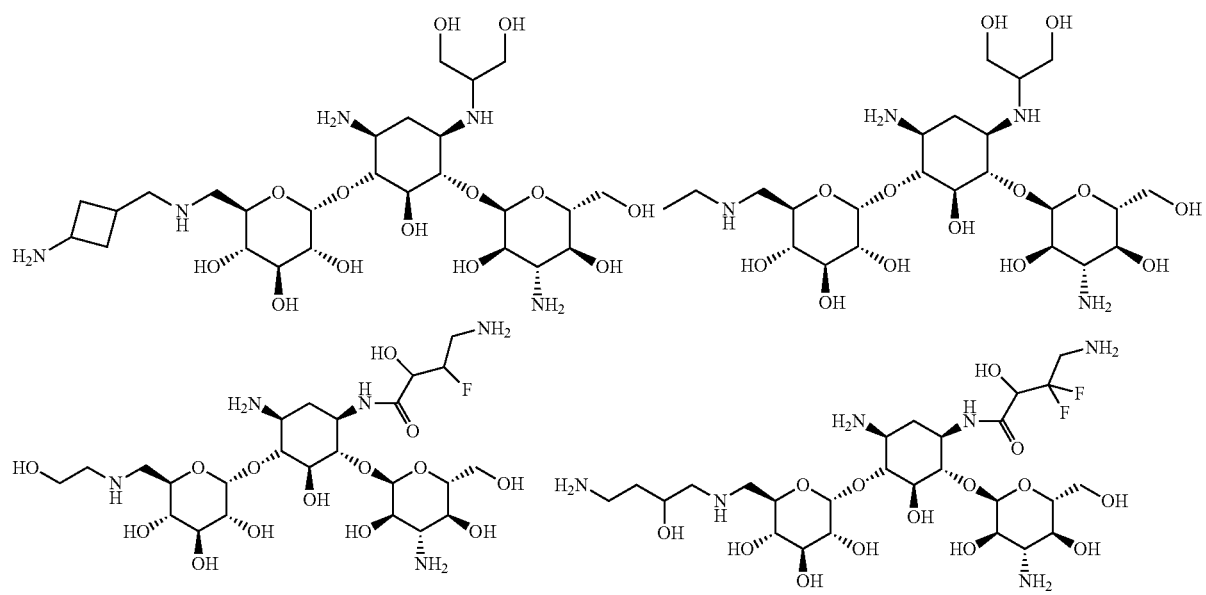

MIC Assay Protocol

Minimum inhibitory concentrations (MIC) are determined by reference Clinical and Laboratory Standards Institute (CLSI) broth microdilution methods per M7-A7 [2006]. Quality control ranges utilizing *E. coli* ATCC 25922, *P. aeruginosa* ATCC 27853 and *S. aureus* ATCC 29213, and interpretive criteria for comparator agents are as published in CLSI M100-S17 [2007]. Briefly, serial two-fold dilutions of the test compounds are prepared at 2× concentration in Mueller Hinton Broth. The compound dilutions are mixed in 96-well assay plates in a 1:1 ratio with bacterial inoculum. The inoculum is prepared by suspension of a colony from an agar plate that is prepared the previous day. Bacteria are suspended in sterile saline and added to each assay plate to obtain a final concentration of $5 \times 10^5$ CFU/mL. The plates are incubated at 35° C. for 20 hours in ambient air. The MIC is determined to be the lowest concentration of the test compound that resulted in no visible bacterial growth as compared to untreated control.

In Vivo Efficacy Models

Compounds are tested for in vivo efficacy in a murine septicemia model of infection. Two models are run on each compound, using E. coli and P. aeruginosa QC bacterial strains. Both studies employ the same design. Male CD-1 (CRL)-derived mice (individual body weight, 24±2 grams) are inoculated IP with the 2×LD90-100 dose of E. coli ATCC 25922 (4.5×10⁵ CFU/mouse) in 0.5 mL of BHI broth containing 5% mucin, or the 2×LD90-100 dose of P. aeruginosa ATCC 27853 (5.8×10⁴ CFU/0.5 mL/mouse) in BHI broth containing 5% mucin. At 1 hour after bacterial challenge, the mice receive a single SC or IV dose of vehicle or test substance to assess in vivo anti-infective activity. Mortality is recorded once daily for 7 days after bacterial inoculation.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure (I):

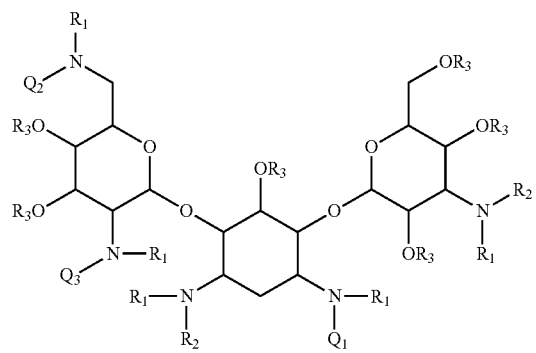

(I)

or a stereoisomer or pharmaceutically acceptable salt thereof, wherein:

$Q_1$ is

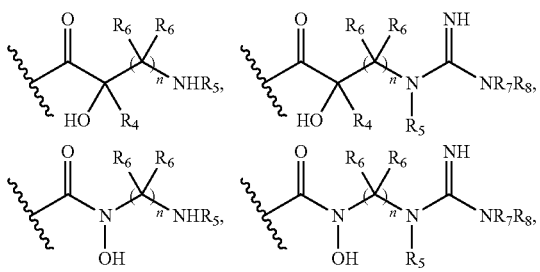

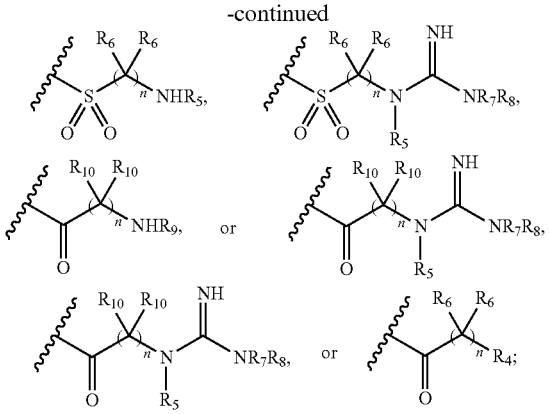

$Q_2$ is hydrogen, optionally substituted alkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_7$R$_8$,

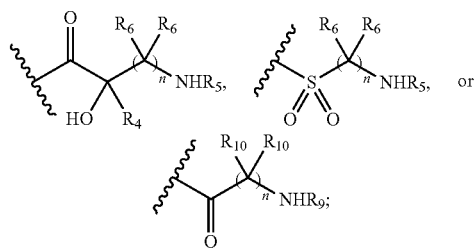

$Q_3$ is hydrogen, optionally substituted alkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR$_7$R$_8$,

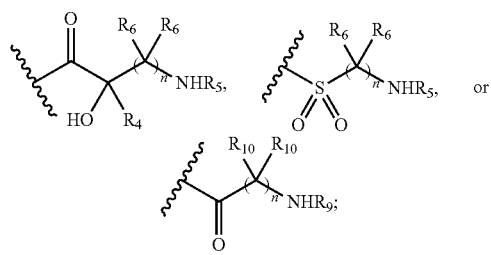

each $R_1$ and $R_2$ is, independently, hydrogen or an amino protecting group;
each $R_3$ is, independently, hydrogen or a hydroxyl protecting group;
each $R_4$, $R_5$, $R_7$ and $R_8$ is, independently, hydrogen or $C_1$-$C_6$ alkyl optionally substituted with one or more halogen, hydroxyl or amino;
each $R_6$ is, independently, hydrogen, halogen, hydroxyl, amino or $C_1$-$C_6$ alkyl;
or $R_4$ and $R_5$ together with the atoms to which they are attached can form a heterocyclic ring having from 4 to 6 ring atoms, or R₅ and one R₆ together with the atoms to which they are attached can form a heterocyclic ring having from 3 to 6 ring atoms, or R₄ and one R₆ together with the atoms to which they are attached can form a carbocyclic ring having from 3 to 6 ring atoms, or R₇ and R₈ together with the atom to which they are attached can form a heterocyclic ring having from 3 to 6 ring atoms;

each R₉ is, independently, hydrogen, hydroxyl, amino or C₁-C₆ alkyl optionally substituted with one or more halogen, hydroxyl or amino;

each R₁₀ is, independently, hydrogen, halogen, hydroxyl, amino or C₁-C₆ alkyl;

or R₉ and one R₁₀ together with the atoms to which they are attached can form a heterocyclic ring having from 3 to 6 ring atoms; and each n is, independently, an integer from 0 to 4, and wherein (i) at least one of Q₂ and Q₃ are other than hydrogen, and (ii) if Q₁ is —C(=O)CH(OH)CH₂NH₂, —C(=O)CH(OH)(CH₂)₂NH₂, or —C(=O)CH(OH)(CH₂)₃NH₂, then Q₂ is not methyl or —C(=O)OC(CH₃)₃, and (iii) if Q₁ is —C(=O)CH(OH)CH₂NH₂ or —C(=O)CH(OH)(CH₂)₂NH₂, then Q₃ is not —C(=O)OC(CH₃)₃, —C(=O)OCH₂Ph, —C(=O)CH(OH)CH₂NH₂ or —C(=O)CH(OH)(CH₂)₂NH₂.

2. A compound of claim 1 wherein Q₁ is:

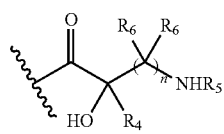

wherein:
R₄ is hydrogen;
R₅ is hydrogen; and
n is an integer from 1 to 4.

3. A compound of claim 2 wherein each R₆ is hydrogen.
4. A compound of claim 3 wherein Q₁ is:

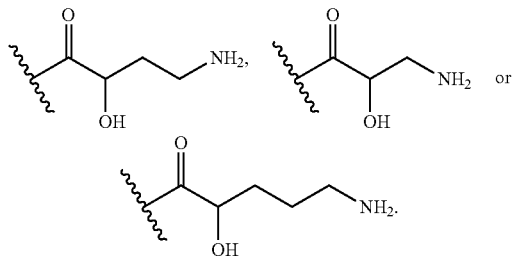

5. A compound of claim 1 wherein Q₂ is other than hydrogen.
6. A compound of claim 5 wherein Q₃ is hydrogen.
7. A compound of claim 5 wherein Q₂ is optionally substituted alkyl.
8. A compound of claim 7 wherein Q₂ is substituted with hydroxyl or amino.
9. A compound of claim 1 wherein each R₁, R₂ and R₃ is hydrogen.
10. A pharmaceutical composition comprising a compound of claim 1, or a stereoisomer, or pharmaceutically acceptable salt thereof, and a pharmaceutically acceptable carrier, diluent or excipient.

11. A method of treating a bacterial infection in a mammal in need thereof, comprising administering to the mammal an effective amount of a compound of claim 1 or a composition of claim 10.

12. A compound having the following structure (II):

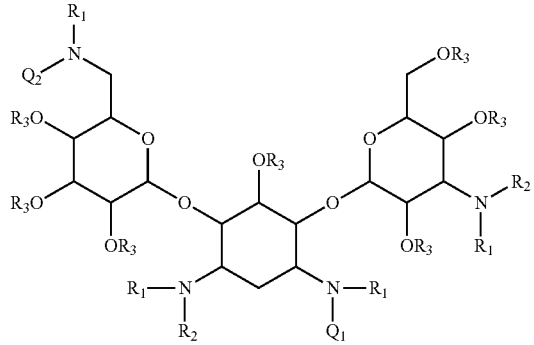

or a stereoisomer or pharmaceutically acceptable salt thereof, wherein:

Q₁ is

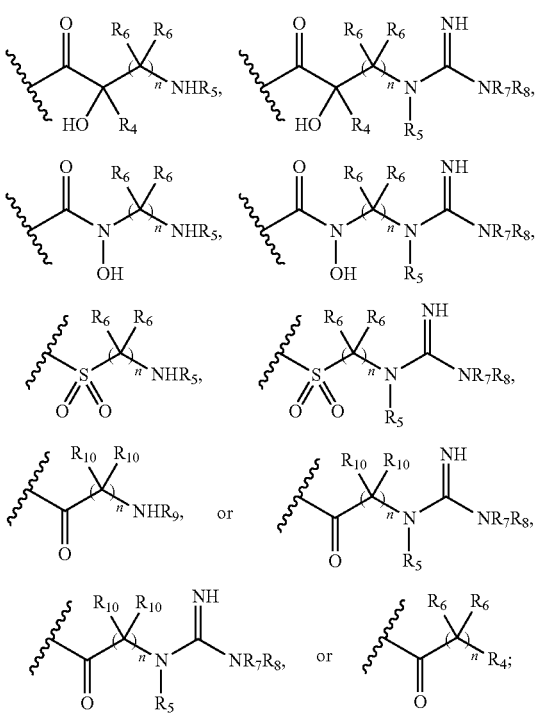

Q₂ is optionally substituted alkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —C(=NH)NR₇R₈,

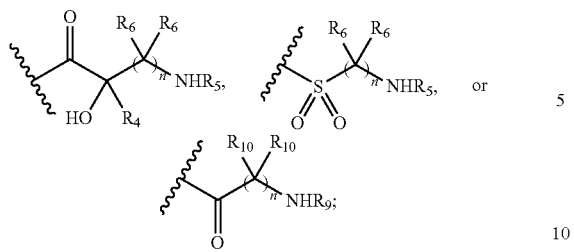
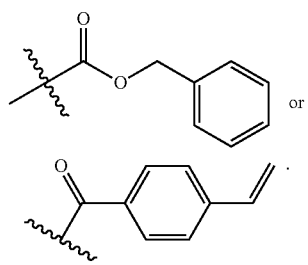
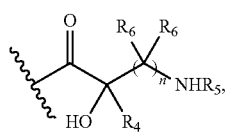

each $R_1$ and $R_2$ is, independently, hydrogen or an amino protecting group;

each $R_3$ is, independently, hydrogen or a hydroxyl protecting group;

each $R_4$, $R_5$, $R_7$ and $R_8$ is, independently, hydrogen or $C_1$-$C_6$ alkyl optionally substituted with one or more halogen, hydroxyl or amino;

each $R_6$ is, independently, hydrogen, halogen, hydroxyl, amino or $C_1$-$C_6$ alkyl;

or $R_4$ and $R_5$ together with the atoms to which they are attached can form a heterocyclic ring having from 4 to 6 ring atoms, or $R_5$ and one $R_6$ together with the atoms to which they are attached can form a heterocyclic ring having from 3 to 6 ring atoms, or $R_4$ and one $R_6$ together with the atoms to which they are attached can form a carbocyclic ring having from 3 to 6 ring atoms, or $R_7$ and $R_8$ together with the atom to which they are attached can form a heterocyclic ring having from 3 to 6 ring atoms;

each $R_9$ is, independently, hydrogen, hydroxyl, amino or $C_1$-$C_6$ alkyl optionally substituted with one or more halogen, hydroxyl or amino;

each $R_{10}$ is, independently, hydrogen, halogen, hydroxyl, amino or $C_1$-$C_6$ alkyl;

or $R_9$ and one $R_{10}$ together with the atoms to which they are attached can form a heterocyclic ring having from 3 to 6 ring atoms; and each n is, independently, an integer from 0 to 4, and wherein (i) if $Q_1$ is —C(=O)CHOH(CH$_2$)$_2$NHR$_5$, then $Q_2$ is not optionally substituted alkyl, and (ii) if $Q_1$ is —C(=O)CH(OH)(CH$_2$)$_2$NHC(=NH)NH$_2$, —C(=O)CH(CH$_3$)CH$_2$NH$_2$, —CH$_2$CH(OH)(CH$_2$)$_2$NH$_2$, —C(=O)CH(OH)CH$_2$NH$_2$, —C(=O)CH(OH)(CH$_2$)$_2$NH$_2$, —C(=O)CH(OH)(CH$_2$)$_3$NH$_2$, or —C(=O)CHF(CH$_2$)$_2$NH$_2$, then $Q_2$ is not methyl, ethyl, —CH(=NH), —C(CH$_3$)(=NH), —C(=NH)NH$_2$, —C(=O)CH$_3$, —C(=O)(CH$_2$)$_2$CO$_2$H, —C(=O)CH(OH)(CH$_2$)$_2$NH$_2$, 13. A compound of claim 12 wherein $Q_1$ is:

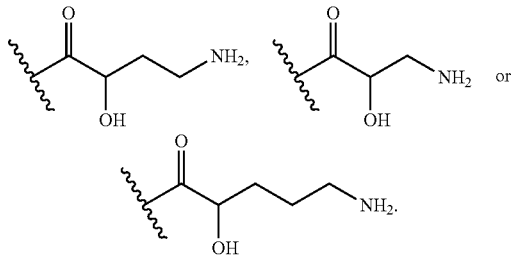

wherein:
  $R_4$ is hydrogen;
  $R_5$ is hydrogen; and
  n is an integer from 1 to 4.

14. A compound of claim 13 wherein each $R_6$ is hydrogen.

15. A compound of claim 14 wherein $Q_1$ is:

16. A compound of claim 12 wherein $Q_2$ is optionally substituted alkyl.

17. A compound of claim 16 wherein $Q_2$ is substituted with hydroxyl or amino.

18. A compound of claim 12 wherein each $R_1$, $R_2$ and $R_3$ is hydrogen.

19. A pharmaceutical composition comprising a compound of claim 12, or a stereoisomer, or pharmaceutically acceptable salt thereof, and a pharmaceutically acceptable carrier, diluent or excipient.

20. A method of treating a bacterial infection in a mammal in need thereof, comprising administering to the mammal an effective amount of a compound of claim 12 or a composition of claim 19.

* * * * *

UNITED STATES PATENT AND TRADEMARK OFFICE
CERTIFICATE OF CORRECTION

PATENT NO. : 8,524,689 B2
APPLICATION NO. : 13/295247
DATED : September 3, 2013
INVENTOR(S) : Adam Aaron Goldblum et al.

It is certified that error appears in the above-identified patent and that said Letters Patent is hereby corrected as shown below:

In the claims,

Issued claim 1, column 170, line 10, please replace "," at the end of the line with -- ; --

Issued claim 1, column 170, lines 12-16, should be deleted:

"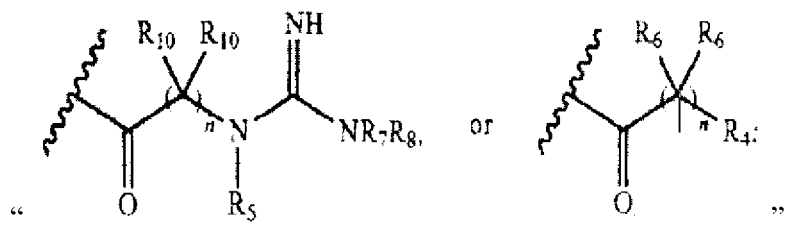"

Issued claim 12, column 172, lines 54-58, should be deleted:

"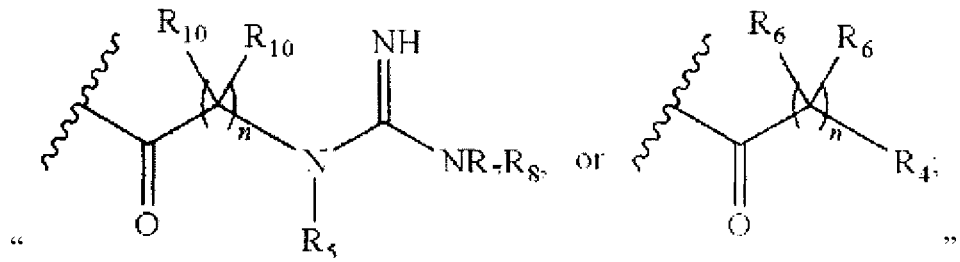"

Issued claim 12, column 172, line 50, please replace "," at the end of the line with -- ; --

Signed and Sealed this
Eleventh Day of August, 2015

Michelle K. Lee
*Director of the United States Patent and Trademark Office*

CERTIFICATE OF CORRECTION (continued)
U.S. Pat. No. 8,524,689 B2

Issued claim 12, column 174, lines 1-6, compound is incorrect.

"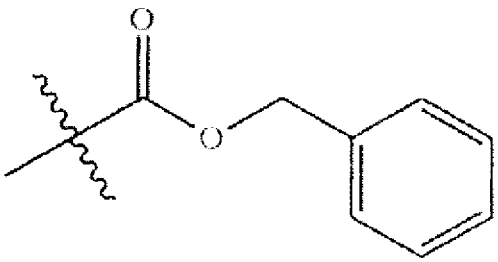 or

"

The correct compound should read:

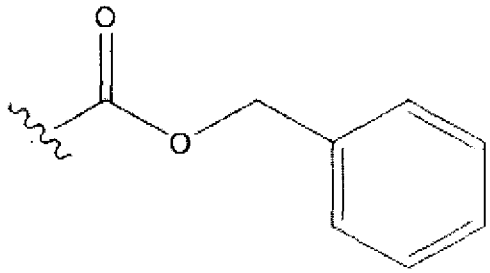 or --